(12) United States Patent
Pinto

(10) Patent No.: US 8,410,155 B2
(45) Date of Patent: Apr. 2, 2013

(54) ARYLPROPIONAMIDE, ARYLACRYLAMIDE, ARYLPROPYNAMIDE, OR ARYLMETHYLUREA ANALOGS AS FACTOR XIA INHIBITORS

(75) Inventor: Donald J. P. Pinto, Churchville, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 880 days.

(21) Appl. No.: 12/518,111

(22) PCT Filed: Dec. 13, 2007

(86) PCT No.: PCT/US2007/087396
§ 371 (c)(1),
(2), (4) Date: Sep. 3, 2009

(87) PCT Pub. No.: WO2008/076805
PCT Pub. Date: Jun. 26, 2008

(65) Prior Publication Data
US 2010/0016316 A1    Jan. 21, 2010

Related U.S. Application Data

(60) Provisional application No. 60/870,110, filed on Dec. 15, 2006.

(51) Int. Cl.
*A61K 31/417* (2006.01)
*A61K 31/4174* (2006.01)
*A61K 31/4412* (2006.01)
*A61K 31/513* (2006.01)
*C07D 233/64* (2006.01)
*C07D 239/28* (2006.01)
*C07D 213/24* (2006.01)
*C07D 213/62* (2006.01)

(52) U.S. Cl. ........ 514/396; 514/269; 514/336; 514/345; 514/397; 544/335; 546/268.1; 546/288; 546/314; 548/300.1; 548/311.1

(58) Field of Classification Search .................. 514/396, 514/397, 269, 336, 345; 548/300.1, 311.1; 544/335; 546/268.1, 288, 314
See application file for complete search history.

(56) References Cited

U.S. PATENT DOCUMENTS

| 7,429,604 | B2 | 9/2008 | Corte et al. |
| 7,453,002 | B2 | 11/2008 | Hangeland et al. |
| 7,459,564 | B2 | 12/2008 | Corte et al. |
| 2004/0132788 | A1 | 7/2004 | Chabrier De Llassauniere et al. |
| 2005/0038087 | A1 | 2/2005 | Chabrier De Llassauniere et al. |
| 2006/0142275 | A1 | 6/2006 | Gordon et al. |
| 2008/0161373 | A1 | 7/2008 | Pinto et al. |
| 2009/0181983 | A1 | 7/2009 | Corte |

FOREIGN PATENT DOCUMENTS

| WO | WO2002/057236 | 7/2002 |
| WO | WO03/089431 | 10/2003 |
| WO | WO2004/017963 | 3/2004 |
| WO | WO2004/087679 A1 | 10/2004 |
| WO | WO2005/097765 A1 | 10/2005 |
| WO | WO2005/123050 A2 | 12/2005 |
| WO | WO2005/123680 A1 | 12/2005 |
| WO | WO2006/063718 A1 | 6/2006 |
| WO | WO2006/076575 A2 | 7/2006 |
| WO | WO2006/114213 A1 | 11/2006 |
| WO | WO-2007/070826 A1 * | 6/2007 |
| WO | WO2007/070826 A1 | 6/2007 |
| WO | WO2007/070816 A2 | 7/2007 |

OTHER PUBLICATIONS

Hoffman, M., "A cell-based model of coagulation and the role of factor VIIa", Blood Reviews, vol. 17, pp. S1-S5 (2003).
Walsh, P.N., "Platelets and Factor XI Bypass the Contact System of Blood Coagulation", Thrombosis and Haemostasis, vol. 82(2), pp. 234-242 (1999).
Mederski W., et al., *Halothiphene benzimidazoles as P1 surrogates of inhibitors of blood coagulation factor Xa*; Bioorganic Medicinal Chemistry Letters, 14, pp. 3763-3769; (2004).

* cited by examiner

*Primary Examiner* — Kamal Saeed
*Assistant Examiner* — Janet L Coppins
(74) *Attorney, Agent, or Firm* — Hong Liu; Jing G. Sun

(57) ABSTRACT

The present invention provides compounds of Formula (I) or (II):

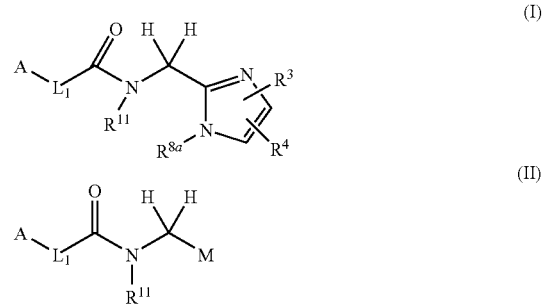

or a stereoisomer, tautomer, pharmaceutically acceptable salt or solvate form thereof, wherein the variables A, $L_1$, $R^3$, $R^4$, $R^{8a}$, $R^{11}$ and M are as defined herein. The compounds of Formula (I) or (II) are selective inhibitors of serine protease enzymes of the coagulation cascade and/or contact activation system; for example thrombin, factor Xa, factor XIa, factor IXa, factor VIIa and/or plasma kallikrein. In particular, it relates to compounds that are selective factor XIa inhibitors or dual inhibitors of fXIa and plasma kallikrein. This invention also relates to pharmaceutical compositions comprising these compounds and methods of treating thromboembolic and/or inflammatory disorders using the same.

15 Claims, No Drawings

US 8,410,155 B2

ARYLPROPIONAMIDE, ARYLACRYLAMIDE, ARYLPROPYNAMIDE, OR ARYLMETHYLUREA ANALOGS AS FACTOR XIA INHIBITORS

CROSS-REFERENCE TO RELATED APPLICATIONS

This application is a 371 application of PCT/US2007/087396 filed Dec. 13, 2007, which claims priority benefit of U.S. provisional application Ser. No. 60/870,110, filed Dec. 15, 2006, which is incorporated by reference herein.

FIELD OF THE INVENTION

The present invention relates generally to novel arylpropionamide, arylacrylamide, arylpropynamide, or arylmethylurea compounds, and analogues thereof, which inhibit factor XIa and/or plasma kallikrein, compositions containing them, and methods of using them, for example, for the treatment or prophylaxis of thromboembolic disorders.

BACKGROUND OF THE INVENTION

Thromboembolic diseases remain the leading cause of death in developed countries despite the availability of anticoagulants such as warfarin (Coumadin®), heparin, low molecular weight heparins (LMWH), and synthetic pentasaccharides and antiplatelet agents such as aspirin and clopidogel (Plavix®). The oral anticoagulant warfarin, inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

One approach is to inhibit thrombin generation by targeting the inhibition of coagulation factor XIa (FXIa). Factor XIa is a plasma serine protease involved in the regulation of blood coagulation, which is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Walsh, P. N. *Thromb. Haemostasis.* 1999, 82, 234-242.) The resulting burst of thrombin converts fibrinogen to fibrin that polymerizes to form the structural framework of a blood clot, and activates platelets, which are a key cellular component of coagulation (Hoffman, M. *Blood Reviews* 2003, 17, S1-55). Therefore, factor XIa plays a key role in propagating this amplification loop and is thus an attractive target for anti-thrombotic therapy.

SUMMARY OF THE INVENTION

The present invention provides novel arylpropionamide, arylacrylamide, arylpropynamide, or arylmethylurea compounds, and analogues thereof, which are useful as selective inhibitors of serine protease enzymes, especially factor XIa and/or plasma kallikrein, or stereoisomers, tautomers, pharmaceutically acceptable salts, solvates, or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for the treatment or prophylaxis of thromboembolic disorders comprising administering to a patient in need of such treatment or prophylaxis a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment or prophylaxis of a thromboembolic disorder.

These and other features of the invention will be set forth in expanded form as the disclosure continues.

DETAILED DESCRIPTION OF THE INVENTION

I. Compounds of the Invention

In a first aspect, the present invention provides, inter alia, compounds of Formula (I):

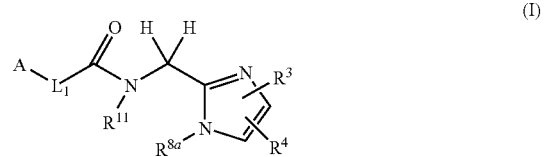

or stereoisomers, tautomers, pharmaceutically acceptable salts, solvates, or prodrugs thereof; wherein, A is a $C_{3-10}$ carbocycle substituted with 0-1 $R^1$ and 0-3 $R^2$, or a 5- to 12-membered heterocycle comprising: carbon atoms and 1-4 heteroatoms selected from N, O, and $S(O)_p$, wherein said heterocycle is substituted with 0-1 $R^1$ and 0-3 $R^2$; provided that when A is a heterocycle containing one or more nitrogen atoms, A is not attached to $L_1$ via any of the nitrogen atoms on the A ring;

$L_1$ is —$CHR^5CH_2$—, —$CH(NR^7R^8)CH_2$—, —$CR^5$=CH—, —C≡C—, —$OCH_2$—, —$C(R^5R^6)NH$—, —$CH_2O$—, —$SCH_2$—, —$S(O)CH_2$—, —$SO_2CH_2$—, —$CH_2NR^{10}$—, or —NHNH—;

provided that when $L_1$ is —$CH_2O$—, then A is other than an unsubstituted phenyl;

$R^1$ is, independently at each occurrence, F, Cl, Br, I, $OCF_3$, $CF_3$, —$(CH_2)_rOR^a$, —$(CH_2)_rSR^a$, CN, —$(CH_2)_rNR^7R^8$, —C(=$NR^8$)$NR^8R^9$, —C(O)$NR^8R^9$, —$S(O)_pNR^8R^9$, or $C_{1-6}$ alkyl substituted with 0-1 $R^{1a}$;

$R^{1a}$ is F, $OCF_3$, $CF_3$, $OR^a$, $SR^a$, CN, —$NR^7R^8$, —C(O)$NR^8R^9$, —$NR^8C(O)R^c$, —$S(O)_pNR^8R^9$, —$NR^8SO_2R^c$, or —$(CF_2)_rCF_3$;

$R^2$ is, independently at each occurrence, =O, F, Cl, Br, $OCF_3$, $CF_3$, $CHF_2$, CN, $NO_2$, —$(CH_2)_rOR^a$, —$(CH_2)_rSR^a$, —$(CH_2)_rC(O)R^a$, —$(CH_2)_rC(O)OR^a$, —$(CH_2)_rOC(O)R^a$, —$(CH_2)_rNR^7R^8$, —$(CH_2)_rC(O)NR^8R^9$, —$(CH_2)_rNR^8C(O)R^c$, —$(CH_2)_rNR^8C(O)OR^c$, —$NR^8C(O)NR^8R^c$, —$S(O)_pNR^8R^9$, —$NR^8S(O)_pR^c$, —$S(O)R^c$, —$S(O)_2R^c$, $C_{1-6}$ alkyl substituted with 0-1 $R^{2a}$, —$(CH_2)_r$-3-7 membered carbocycle optionally substituted with 0-2 $R^{2b}$, or —$(CH_2)_r$-5-7 membered heterocycle comprising carbon atoms and 1-4 heteroatoms selected from N, O, and $S(O)_p$, wherein said heterocycle is substituted with 0-2 $R^{2b}$;

alternately, when $R^1$ and $R^2$ groups are substituents on adjacent atoms they may be taken together with the atoms to which they are attached to form a 5- to 7-membered carbocycle or heterocycle comprising carbon atoms and 0-4 heteroatoms selected from N, O, and $S(O)_p$ and substituted with 0-2 $R^g$;

$R^{2a}$ is F, $OCF_3$, $CF_3$, $OR^a$, $SR^a$, CN, —$NR^7R^8$, —$C(O)NR^8R^9$, —$NR^8C(O)R^c$, —$NR^8C(O)OR^c$, —$NR^8C(O)NR^8R^c$, —$S(O)_pNR^8R^9$, —$NR^8SO_2R^c$, or —$(CF_2)_rCF_3$;

$R^{2b}$ is, independently at each occurrence, =O, F, Br, Cl, $OCF_3$, $CF_3$, —$(CH_2)_rOR^a$, —$(CH_2)_rSR^a$, —$(CH_2)_rCN$, —$(CH_2)_rNR^7R^8$, —$(CH_2)_rC(O)OR^a$, —$(CH_2)_rOC(O)R^a$, —$(CH_2)_rC(O)NR^8R^9$, —$(CH_2)_rNR^8C(O)R^c$, —$(CH_2)_rNR^8C(O)OR^c$, —$(CH_2)_rS(O)_pNR^8R^9$, —$(CH_2)_rNR^8SO_2R^c$, $C_{1-4}$ alkyl or —$(CF_2)_rCF_3$;

$R^3$ is —$(CH_2)_r$—$C_{3-10}$ carbocycle substituted with 0-3 $R^{3a}$ and 0-1 $R^{3d}$, or —$(CH_2)_r$-5- to 12-membered heterocycle comprising: carbon atoms and 1-4 heteroatoms selected from N, O, and $S(O)_p$, wherein said heterocycle is substituted with 0-3 $R^{3a}$ and 0-1 $R^{3d}$;

$R^{3a}$ is, independently at each occurrence, =O, =$NR^8$, F, Cl, Br, I, $OCF_3$, $CF_3$, —$(CH_2)_rCN$, $NO_2$, $(CH_2)_rOR^{3b}$, $(CH_2)_rSR^{3b}$, —$(CH_2)_rNR^7R^8$, —$NHC(O)NR^8R^9$, —$(CH_2)_rC(O)OR^{3b}$, —$C(O)C_{1-4}$ alkyl, —$SO_2NHR^{3b}$, —$SO_2NHCOR^{3c}$, —$SO_2NHCO_2R^{3c}$, —$CONHSO_2R^{3c}$, —$(CH_2)_rNR^8C(O)R^{3b}$, $(CH_2)_rNR^8CO_2R^{3c}$, —$(CH_2)_rS(O)_pNR^8R^9$, —$(CH_2)_rNR^8S(O)_pR^{3c}$, $NHSO_2CF_3$, —$S(O)R^{3c}$, —$S(O)_2R^{3c}$, —$(CH_2)_rOC(O)R^{3b}$, —$(CH_2)_rC(O)NR^8R^9$, —$(CH_2)_rOC(O)NR^8R^9$, —$NHCOCF_3$, —$NHSO_2R^{3c}$, —$CONHOR^{3b}$, $C_{1-4}$ haloalkyl, $C_{1-4}$ haloalkyloxy-, $C_{1-6}$ alkyl substituted by $R^{30}$, $C_{2-6}$ alkenyl substituted by $R^{3e}$, $C_{1-6}$ alkynyl substituted by $R^3$, $C_{3-6}$ cycloalkyl substituted by 0-1 $R^{3d}$, —$(CH_2)_r$—$C_{6-10}$ carbocycle substituted by 0-3 $R^{3d}$ or —$(CH_2)_r$-5- to 10-membered heterocycle comprising: carbon atoms and 14 heteroatoms selected from N, O, and $S(O)_p$, wherein said heterocycle is substituted with 0-3 $R^{3d}$;

alternately, when two $R^{3a}$ groups are substituted on adjacent atoms, they can be taken together with the atoms to which they are attached to form a $C_{3-10}$ carbocycle substituted with 0-2 $R^{3d}$ or a 5- to 10-membered heterocycle comprising carbon atoms and 1-4 heteroatoms selected from N, O, and $S(O)_p$, wherein said heterocycle is substituted with 0-2 $R^{3d}$;

$R^{3b}$ is, independently at each occurrence, H, $C_{1-6}$ alkyl substituted with 0-2 R-d, $C_{2-6}$ alkenyl substituted with 0-2 $R^{3d}$, $C_{2-6}$ alkynyl substituted with 0-2 $R^{3d}$, —$(CH_2)_r$—$C_{3-10}$ carbocycle substituted with 0-3 $R^{3d}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3c}$ is, independently at each occurrence, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, —$(CH_2)_r$—$C_{3-10}$ carbocycle substituted with 0-3 $R^{3d}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3d}$ is, independently at each occurrence, H, =O, F, Cl, Br, CN, $NO_2$, —$(CH_2)_rNR^7R^8$, —$(CH_2)_rOR^a$, —$C(O)R^a$, —$C(O)OR^a$, —$OC(O)R^a$, —$NR^8C(O)R^c$, —$C(O)NR^8R^9$, —$S(O)_2NR^8R^9$, —$NR^7R^8$, —$NR^8S(O)_2NR^8R^9$, —$NR^8S(O)_2R^c$, —$S(O)_pR^c$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —$(CH_2)_r$—$C_{3-10}$ carbocycle substituted with 0-3 $R^d$, or —$(CH_2)_r$-5- to 10-membered heterocycle comprising: carbon atoms and 1-4 heteroatoms selected from N, O, and S(O), wherein said heterocycle is substituted with 0-3 $R^d$;

$R^{3e}$ is, independently at each occurrence, H, —$(CH_2)_rOR^a$, F, =O, CN, $NO_2$, —$(CH_2)_rNR^7R^8$, —$C(O)R^a$, —$C(O)OR^a$, —$OC(O)R^a$, —$NR^8C(O)R^c$, —$C(O)NR^8R^9$, —$S(O)_2NR^8R^9$, —$NR^8S(O)_2NR^8R^9$, —$NR^8S(O)_2R^c$, —$S(O)_pR^c$, —$(CF_2)_rCF_3$, —$(CH_2)_r$—$C_{3-10}$ carbocycle substituted with 0-3 $R^d$, or —$(CH_2)_r$-5- to 10-membered heterocycle comprising: carbon atoms and 1-4 heteroatoms selected from N, O, and $S(O)_p$, wherein said heterocycle is substituted with 0-3 $R^d$;

$R^4$ is H, F, Cl, Br, I, $OCF_3$, $CF_3$, CN, $NO_2$, $(CH_2)_rOR^a$, —$(CH_2)_rSR^a$, —$(CH_2)_rC(O)R^a$, —$(CH_2)_rC(O)OR^a$, —$OC(O)R^a$, —$(CH_2)_rNR^7R^8$, —$NR^8(CH_2)_rC(O)OR^a$, —$(CH_2)_rC(O)NR^8R^9$, —$(CH_2)_rNR^8C(O)R^c$, $(CH_2)_rNR^cC(O)_2R^b$, —$(CH_2)_rNR^8C(O)NR^8R^9$, —$S(O)_pNR^8R^9$, $NR^8S(O)_pR^c$, —$S(O)_2R^c$, or $C_{1-4}$ alkyl substituted with 0-2 $R^{4a}$;

$R^{4a}$ is, independently at each occurrence, H, F, =O, $C_{1-6}$ alkyl, $OR^a$, $SR^a$, $CF_3$, CN, $NO_2$, $C(O)R^a$, —$C(O)OR^a$, —$NR^7R^8$, —$C(O)NR^8R^9$, —$NR^8C(O)R^c$, —$S(O)_pNR^8R^9$, —$NR^8S(O)_pR^c$, —$S(O)R^c$, or —$S(O)_2R^c$;

$R^5$ is, independently at each occurrence, H, F, $CF_3$, $(CH_2)_rOR^a$, =O, —$(CH_2)_rNR^7R^8$, —$S(O)_pNR^8R^9$, —$(CH_2)_rCO_2R^a$, —$(CH_2)_rCONR^8R^9$, or $C_{1-4}$ alkyl;

$R^6$ is, independently at each occurrence, H, F, or $C_{1-4}$ alkyl;

$R^7$ is, independently at each occurrence, H, $C_{1-6}$ alkyl, —$(CH_2)_n$—$C_{3-10}$ carbocycle, —$(CH_2)_n$-(5- to 10-membered heteroaryl), —$C(O)R^c$, CHO, —$C(O)_2R^c$, —$S(O)_2R^c$, —$CONR^8R^c$, —$OCONHR^c$, —$C(O)O$—$(C_{1-4}$ alkyl)$OC(O)$—$(C_{1-4}$ alkyl), or —$C(O)O$—$(C_{1-4}$ alkyl)$OC(O)$—$(C_{6-10}$ aryl); wherein said alkyl, carbocycle, heteroaryl, and aryl are substituted with 0-2 $R^f$, wherein said heteroaryl comprises: carbon atoms and 1-4 heteroatoms selected from N, O, and $S(O)_p$;

$R^8$ is, independently at each occurrence, H, $C_{1-6}$ alkyl, —$(CH_2)_n$-phenyl, or —$(CH_2)_n$-5- to 10-membered heterocycle comprising: carbon atoms and 1-4 heteroatoms selected from N, O, and $S(O)_p$; wherein said alkyl, phenyl and heterocycle are optionally substituted with 0-2 $R^f$, alternatively, $R^7$ and $R^8$, when attached to the same nitrogen, combine to form a 5- to 10-membered heterocycle comprising: carbon atoms and 0-3 additional heteroatoms selected from N, O, and $S(O)_p$, wherein said heterocycle is substituted with 0-2 $R^f$;

$R^{8a}$ is H or $C_{1-4}$ alkyl;

$R^9$ is, independently at each occurrence, H, $C_{1-6}$ alkyl, or —$(CH_2)_n$-phenyl; wherein said alkyl and phenyl are optionally substituted with 0-2 $R^3$;

alternatively, $R^8$ and $R^9$, when attached to the same nitrogen, combine to form a 5- to 12-membered heterocycle comprising: carbon atoms and 0-2 additional heteroatoms selected from N, O, and $S(O)_p$, wherein said heterocycle is substituted with 0-2 $R^d$;

$R^{10}$ is, independently at each occurrence, H or $C_{1-6}$ alkyl substituted with 0-3 $R^{10a}$;

$R^{10a}$ is, independently at each occurrence, H, =O, $C_{1-4}$ alkyl, $OR^a$, $SR^a$, F, $CF_3$, CN, $NO_2$, —C(O)$R^a$, —C(O)O$R^a$, —C(O)$NR^8R^9$, —$NR^8$C(O)$R^c$, —S(O)$_p$$NR^8R^9$, —$NR^8$S(O)$_pR^c$, or —S(O)$_pR^c$;

$R^{11}$ is H, $C_{1-4}$ alkyl, or benzyl;

$R^a$ is, independently at each occurrence, H, $CF_3$, $C_{1-6}$ alkyl, —(CH$_2$)$_r$—$C_{3-7}$ cycloalkyl, —(CH)$_r$—$C_{6-10}$ aryl, or —(CH$_2$)$_r$-5- to 10-membered heterocycle comprising carbon atoms and 1-4 heteroatoms selected from N, O, and S(O)$_p$, wherein said cycloalkyl, aryl or heterocycle groups are optionally substituted with 0-2 $R^f$;

$R^b$ is, independently at each occurrence, $CF_3$, OH, $C_{1-4}$ alkoxy, $C_{1-6}$ alkyl, —(CH$_2$)$_r$—$C_{3-10}$ carbocycle substituted with 0-2 $R^d$, or —(CH$_2$)$_r$-5- to 10-membered heterocycle comprising: carbon atoms and 1-4 heteroatoms selected from N, O, and S(O)$_p$ and substituted with 0-3 $R^d$;

$R^c$ is, independently at each occurrence, $CF_3$, $C_{1-6}$ alkyl substituted with 0-2 $R^f$, $C_{3-6}$ cycloalkyl substituted with 0-2 $R^f$, $C_{6-10}$ aryl, 5- to 10-membered heteroaryl, ($C_{6-10}$ aryl)-$C_{1-4}$ alkyl, or (5- to 10-membered heteroaryl)-$C_{1-4}$ alkyl, wherein said aryl is substituted with 0-3 $R^f$ and said heteroaryl comprises: carbon atoms and 1-4 heteroatoms selected from N, O, and S(O)$_p$ and substituted with 0-3 $R^f$;

$R^d$ is, independently at each occurrence, H, =O, =$NR^8$, $OR^a$, F, Cl, Br, I, CN, $NO_2$, —$NR^7R^8$, —C(O)$R^a$, —C(O)O$R^a$, OC(O)$R^a$, —$NR^8$C(O)$R^c$, —C(O)$NR^8R^9$, —SO$_2$$NR^8R^9$, —$NR^8$SO$_2$$NR^8R^9$, —$NR^8$SO$_2$—$C_{1-4}$ alkyl, —$NR^8$SO$_2$CF$_3$, —$NR^8$SO$_2$-phenyl, —S(O)$_2$CF$_3$, —S(O)$_p$—$C_{1-4}$ alkyl, —S(O)$_p$-phenyl, —(CF$_2$)$_r$CF$_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$;

$R^e$ is, independently at each occurrence, =O, $OR^a$, F, Cl, Br, I, CN, $NO_2$, —$NR^7R^8$, C(O)$R^a$, —C(O)O$R^a$, —$NR^8$C(O)$R^c$, —C(O)$NR^8R^9$, —SO$_2$$NR^8R^9$, —$NR^8$SO$_2$$NR^8R^9$, —$NR^8$SO$_2$—$C_{1-4}$ alkyl, —$NR^8$SO$_2$CF$_3$, —$NR^8$SO$_2$-phenyl, —S(O)$_2$CF$_3$, —S(O)$_p$—$C_{1-4}$ alkyl, —S(O)$_p$-phenyl, or —(CF$_2$)$_r$CF$_3$;

$R^f$ is, independently at each occurrence, H, =O, —(CH$_2$)O$R^g$, F, Cl, Br, I, CN, $NO_2$, —$NR^gR^g$, —C(O)$R^g$, —C(O)O$R^g$, —$NR^g$C(O)$R^g$, —C(O)$NR^gR^g$, —SO$_2$$NR^gR^g$, —$NR^g$SO$_2$$NR^gR^g$, —$NR^g$SO$_2$—$C_{1-4}$ alkyl, —$NR^g$SO$_2$CF$_3$, —$NR^g$SO$_2$-phenyl, —S(O)$_2$CF$_3$, —S(O)$_p$—$C_{1-4}$ alkyl, —S(O)$_p$-phenyl, —(CF$_2$)$_r$CF$_3$, $C_{1-6}$ alkyl, $C_{2-6}$ alkenyl, $C_{2-6}$ alkynyl, —(CH$_2$)$_n$-phenyl, or —(CH$_2$)$_n$-5- to 10-membered heterocycle comprising carbon atoms and 1-4 heteroatoms selected from N, O, and S(O)$_p$;

$R^g$ is, independently at each occurrence, H, $C_{1-6}$ alkyl, or —(CH$_2$)$_n$-phenyl;

n, at each occurrence, is selected from 0, 1, 2, 3, and 4;

p, at each occurrence, is selected from 0, 1, and 2; and r, at each occurrence, is selected from 0, 1, 2, 3, and 4.

In a second aspect, the present invention includes compounds of Formula (I), or stereoisomers, tautomers, pharmaceutically acceptable salts, solvates, or prodrugs thereof, within the scope of the first aspect wherein:

$R^3$ is phenyl substituted with 0-3 $R^{3a}$ and 0-1 $R^{3d}$, naphthyl substituted with 0-3 $R^{3a}$ and 0-1 $R^{3d}$, or —(CH$_2$)$_r$-5- to 12-membered heterocycle comprising: carbon atoms and 1-4 heteroatoms selected from N, O, and S(O)$_p$, wherein said heterocycle is substituted with 0-3 $R^{3a}$ and 0-1 $R^{3d}$;

$R^4$ is H, Me, Et, Pr, F, Cl, Br, I, OCF$_3$, CF$_3$, CN, NO$_2$, —(CH$_2$)$_r$OH, —(CH$_2$)$_r$C(O)O$R^a$, $OR^a$, $SR^a$, —C(O)$R^a$, —C(O)O$R^a$, —$NR^7R^8$, —(CH$_2$)$_r$NH$_2$, —$NR^8$(CH$_2$)$_r$C(O)O$R^a$, (CH$_2$)$_r$C(O)$NR^8R^9$, —$NR^8$C(O)$R^c$, —$NR^8$C(O)O$R^c$, —$NR^8$C(O)$NR^8R^9$, —S(O)$_p$$NR^8R^9$, —$NR^8$S(O)$_pR^c$, or —S(O)$_pR^c$; and $R^{11}$ is H or benzyl.

In a third aspect, the present invention includes compounds of Formula (I), or stereoisomers, tautomers, pharmaceutically acceptable salts, solvates, or prodrugs thereof, within the scope of the first aspect wherein:

$R^1$ is, independently at each occurrence, F, Cl, Br, I, OCF$_3$, CF$_3$, OCH$_3$, CH$_3$, Et, NH$_2$, —C(=NH)NH$_2$, —C(O)NH$_2$, —CH$_2$NH$_2$ or —SO$_2$NH$_2$;

$R^2$ is, independently at each occurrence, F, Cl, Br, CF$_3$, NO$_2$, —(CH$_2$)$_r$O$R^a$, —(CH$_2$)$_r$S$R^a$, —(CH$_2$)$_r$C(O)$R^a$, —C(O)O$R^a$, —C(O)$NR^8R^9$, —$NR^8$C(O)$R^c$, —$NR^8$C(O)O$R^c$, —$NR^8$C(O)$NR^8R^c$, —S(O)$_p$$NR^8R^9$, —$NR^8$SO$_2R^c$, —$NR^7$, $R^8$, —S(O)$R^c$, —S(O)$_2R^c$, $C_{1-6}$ alkyl substituted with 0-1 $R^{2a}$, or a 5-7 membered heterocycle comprising carbon atoms and 1-4 heteroatoms selected from N, O, and S(O)$_p$, wherein said heterocycle is substituted with 0-2 $R^{2b}$;

alternately, when $R^1$ and $R^2$ groups are substituents on adjacent atoms they may be taken together with the atoms to which they are attached to form a 5- to 7-membered carbocycle or heterocycle comprising carbon atoms and 0-4 heteroatoms selected from N, O, and S(O)$_p$ and substituted with 0-2 $R^g$;

$R^3$ is phenyl substituted with 0-2 $R^{3a}$ and 0-1 $R^{3d}$, naphthyl substituted with 0-2 $R^{3a}$ and 0-1 $R^{3d}$, 1,2,3,4-tetrahydronaphthyl substituted with 0-2 $R^{3a}$ and 0-1 $R^{3d}$, or a 5- to 12-membered heterocycle substituted with 0-2 $R^{3a}$ and 0-1 $R^{3d}$, wherein said heterocycle is selected from: thiophene, furan, thiazole, tetrazole, pyridine, pyridone, pyrimidine, pyrrole, pyrazole, indole, 2-oxindole, isoindoline, indazole, 7-azaindole, benzofuran, benzothiophene, benzimidazole, benzisoxazole, benzoxazole, quinazoline, quinoline, isoquinoline, quinoxaline, phthalazine, dihydrophthalazine, dihydroisoquinoline, dihydroquinoline, dihydroquinolinone, dihydroindole, dihydrobenzimidazole, dihydrobenzoxazine, dihydroquinazoline, dihydroquinoxaline, benzothiazine, benzoxazine, tetrahydrobenzazepine, dihydroazabenzocycloheptene, and tetrahydroquinoline;

$R^{3a}$ is, independently at each occurrence, =O, F, Cl, Br, Me, CN, OH, OMe, —OC(O)(t-Bu), —CH$_2$OMe, CF$_3$, COMe, CO$_2$H, CO$_2$Me, —CH$_2$CO$_2$H, —(CH$_2$)$_2$CO$_2$H, —CH$_2$CO$_2$Me, —CH$_2$CO$_2$Et, —CH$_2$CH$_2$CO$_2$Et, —CH$_2$CN, NH$_2$, —CH$_2$NH$_2$, —CH$_2$NMe$_2$, —NHCOMe, —NHCO$_2$Me, —NHCO$_2$Et, —NHCH$_2$CH$_2$CO$_2$H, —NHCO$_2$(i-Pr), —NHCO$_2$(i-Bu), —NHCO$_2$(t-Bu), —NHCO$_2$Bn, —NHCO$_2$CH$_2$CH$_2$OMe, —NHCO$_2$CH$_2$CH$_2$CH$_2$OMe, —NHCO$_2$CH$_2$CO$_2$H, —NHCO$_2$CH$_2$CH$_2$CO$_2$H, —NHCO$_2$CH$_2$CH$_2$OH, —NHCO$_2$CH$_2$CH$_2$NH$_2$, —NHCO$_2$CH$_2$-tetrahydrofuran-2-yl, —NHCO$_2$CH$_2$CH$_2$CH(Me)OMe, —NHCO$_2$CH$_2$CH$_2$C(O)NH$_2$, —NHC(O)NHCH$_2$CH$_2$-morpholino, —NHC(O)NHCH$_2$-pyrid-4-yl, —NHCO$_2$CH$_2$-pyrid-4-yl, —NHCO$_2$CH$_2$-pyrid-3-yl, —NHCO$_2$CH$_2$-pyrid-2-yl, —NHCO$_2$CH$_2$-(piperidin-4-yl), —NHC(O)NHCH$_2$CH$_2$-pyrid-4-yl, —NHCO$_2$CH$_2$CH$_2$-pyrid-4-yl, —NHCO$_2$CH$_2$CH$_2$-morpholino, —CH$_2$NHCO$_2$Me, —NHC(O)NHMe, —NHC(O)N(Me)$_2$, —NHC(O)NHCH$_2$CH$_2$OMe, 4-[(1-carbamoyl-cyclopropanecarbonyl)-amino]-, —NHSO$_2$Me, —SO$_2$NH$_2$, —SO$_2$NHMe, —SO$_2$NHCH$_2$CH$_2$OH, —SO$_2$NHCH$_2$CH$_2$OMe, —CONH$_2$, —CONHMe, —CON(Me)$_2$, —C(O)NHCH$_2$CH$_2$OMe, —CH$_2$CONH$_2$, —CO(N-morpholino), —NHCH$_2$CH$_2$(N-morpholino), —$NR^7R^8$, —NH(1H-imidazol-2-yl), 1H-tetrazol-5-yl, tetrazol-1-yl, pyrimidin-5-yl, N-morpholino, or —(CH$_2$)$_r$-5- to 6-membered heterocycle comprising: carbon atoms and 1-4 heteroatoms selected from N, O, and S(O)$_p$, wherein said heterocycle is substituted with 0-1 $R^{3d}$;

R⁴ is H, F, Cl, Br, OH, OMe, NH₂, Me, Et, CF₃, —CH₂OH, —C(O)₂H, CO₂Me, CO₂Et, —C(O)NH₂, —C(O)NHMe, —C(O)N(Me)₂, or —CH₂CO₂H; and R¹¹ is H or benzyl.

In a fourth aspect, the present invention includes compounds of Formula (I), or stereoisomers, tautomers, pharmaceutically acceptable salts, solvates, or prodrugs thereof, within the scope of the first, second or third aspect wherein:

A is substituted with 0-1 R¹ and 0-3 R² and selected from: C₃₋₇ cycloalkyl, phenyl, naphthyl, 1,2,3,4-tetrahydronaphthyl, pyrrolidinyl, pyridyl, indazolyl, indolyl, imidazolyl, furanyl, thienyl, benzimidazolyl, benzisoxazolyl, benzothiazolyl, benzothiophenyl, 3,4-methylenedioxy-phenyl, oxazolyl, isoxazolyl, thiazolyl, isothiazolyl, and pyrazolyl;

L₁ is —CH₂CH₂—, —CH(NH₂)CH₂—, —CH(NHCOMe)CH₂—, —CH(NHCOEt)CH₂—, —CH(NHCO₂(t-Bu))CH₂—, —CH═CH—, —C(Me)═CH—, —C≡C—, —CH₂NH—, —CH(CH₂CO₂H)NH—, —CH₂O—, —NHNH—, —SCH₂—, —S(O)CH₂—, —SO₂CH₂— or —OCH₂—;

R¹ is, independently at each occurrence, F, Cl, Br, CF₃, NH₂, —CH₂NH₂, —C(═NH)NH₂, —C(O)NH₂, —SO₂NH₂, SRᵃ, ORᵃ, or C₁₋₆ alkyl substituted with 0-1 R¹ᵃ;

R² is, independently at each occurrence, F, Cl, Br, CF₃, Me, Et, ORᵃ, CN, NO₂, NR⁷R⁸, —CH₂OMe, —SRᵃ, —CH₂SMe, C(O)Rᵃ, —C(O)ORᵃ, —CH₂NR⁷R⁸, —SO₂NH₂, —SO₂Me, —NHSO₂Rᶜ, —CH₂NHSO₂Rᶜ, —C(O)NR⁸R⁹, —NHC(O)Rᶜ, —CH₂NHC(O)Rᶜ, —NHC(O)ORᶜ, —CH₂NHC(O)ORᶜ, —NHC(O)NHRᶜ, —CH₂NHC(O)NHRᶜ, or a 5-7 membered heterocycle substituted with 0-2 R²ᵇ and selected from pyrrolidinyl, 2-oxo-1-pyrrolidinyl, piperidinyl, pyrazolyl, triazolyl, imidazolyl, and tetrazolyl;

alternately, when R¹ and R² groups are substituents on adjacent atoms they may be taken together with the atoms to which they are attached to form a 5- to 6-membered heterocycle comprising carbon atoms and 0-4 heteroatoms selected from N, O, and S(O)ₚ;

R³ is phenyl substituted with 0-2 R³ᵃ, naphthyl substituted with 0-2 R³ᵃ, or a 5- to 12-membered heterocycle comprising: carbon atoms and 1-2 heteroatoms selected from N, O, and S(O)ₚ, wherein said heterocycle is substituted with 0-2 R³ᵃ;

R³ᵃ is, independently at each occurrence, ═O, F, Cl, Br, Me, CN, OH, OMe, —OC(O)(t-Bu), CH₂OMe, CF₃, COMe, CO₂H, CO₂Me, —CH₂CO₂H, —(CH₂)₂CO₂H, —CH₂CO₂Me, —CH₂CO₂Et, —CH₂CH₂CO₂Et, —CH₂CN, NH₂, —CH₂NH₂, —CH₂NMe₂, —NHCOMe, —NHCO₂Me, —NHCO₂Et, —NHCH₂CH₂CO₂H, —NHCO₂(i-Pr), —NHCO₂(i-Bu), —NHCO₂(t-Bu), —NHCO₂Bn, —NHCO₂CH₂CH₂OMe, —NHCO₂CH₂CH₂CH₂OMe, —NHCO₂CH₂CO₂H, —NHCO₂CH₂CH₂CO₂H, —NHCO₂CH₂CH₂OH, —NHCO₂CH₂CH₂NH₂, —NHCO₂CH₂-tetrahydrofuran-2-yl, —NHCO₂CH₂CH₂CH(Me)OMe, —NHCO₂CH₂CH₂C(O)NH₂, —NHC(O)NHCH₂CH₂-morpholino, —NHC(O)NHCH₂-pyrid-4-yl, —NHCO₂CH₂-pyrid-4-yl, —NHCO₂CH₂-pyrid-3-yl, —NHCO₂CH₂-pyrid-2-yl, —NHOC₂CH₂— (piperidin-4-yl), —NHC(O)NHCH₂CH₂-pyrid-4-yl, —NHCO₂CH₂CH₂-pyrid-4-yl, —NHCO₂CH₂CH₂-morpholino, —CH₂NHCO₂Me, —NHC(O)NHMe, —NHC(O)N(Me)₂, —NHC(O)NHCH₂CH₂OMe, 4-[(1-carbamoyl-cyclopropanecarbonyl)-amino]-, —NHSO₂Me, —SO₂NH₂, —SO₂NHMe, —SO₂NHCH₂CH₂OH, —SO₂NHCH₂CH₂OMe, —CONH₂, —CONHMe, —CON(Me)₂, —C(O)NHCH₂CH₂OMe, —CH₂CONH₂, —CO(N-morpholino), —NHCH₂CH₂(N-morpholino), —NR⁷R⁸, —NH(1H-imidazol-2-yl), 1H-tetrazol-5-yl, tetrazol-1-yl, pyrimidin-5-yl, or N-morpholino, or —(CH₂)ᵣ-5- to 6-membered heterocycle comprising: carbon atoms and 1-4 heteroatoms selected from N, O, and S(O)ₚ, wherein said heterocycle is substituted with 0-1 R³ᵈ;

alternatively, two of R³ᵃ groups located on adjacent atoms, they can be taken together with the atoms to which they are attached to form a 5- to 10-membered heterocycle comprising: carbon atoms and 1-4 heteroatoms selected from N, O, and S(O)ₚ>, wherein said heterocycle is substituted with 0-2 R³ᵈ;

R⁴ is H, F, Cl, Br, OMe, NH₂, CF₃, Me, Et, CO₂H, CO₂Me, or CO₂Et; and

R⁸ᵃ is H, Me or Et.

In a fifth aspect, the present invention includes compounds of Formula (I), or stereoisomers, tautomers, pharmaceutically acceptable salts, solvates, or prodrugs thereof, within the scope of the first, second, third or fourth aspect wherein:

A is substituted with 0-2 R² and selected from:

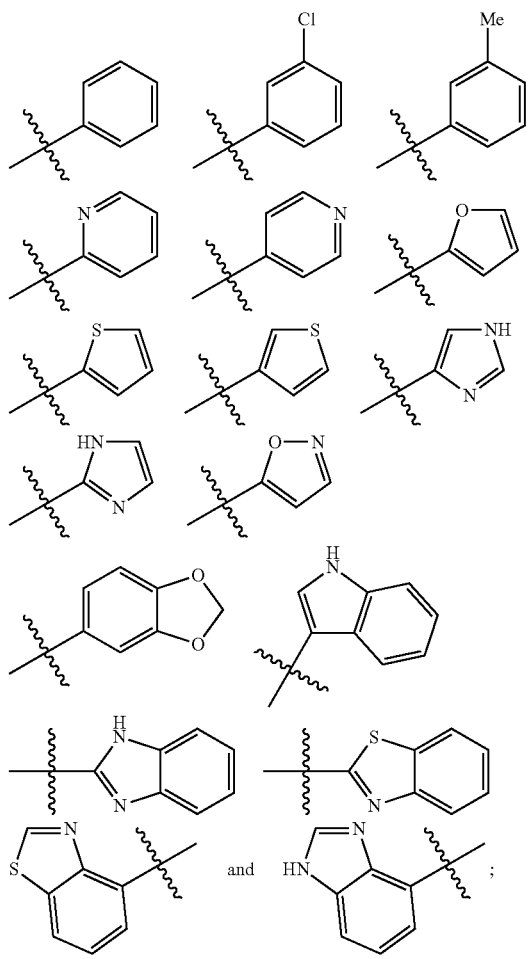

R² is, independently at each occurrence, —O, F, Cl, Br, Me, CF₃, OMe, OEt, OPh, OBn, SMe, SEt, S(n-Pr), SBn, —CH₂SMe, SO₂Me, SO₂NH₂, NH₂, —CH₂NH₂, NO₂, C(O)Me, CO₂H, CO₂Me, CONH₂, CONHMe, —CH₂NHCOPh, —NHCO₂Me, —CH₂NHCO₂Et, —CH₂NHCO₂(i-Pr), —CH₂NHCO₂(t-Bu), —CH₂NHCO₂Bn, —CH₂NHCO(CH₂)₂CO₂, —CONHPh, —NHCONHMe, —CH₂NHCONHEt, —CH₂NHCONH(CH₂)₂CO₂Et, —CH₂NHCONHPh, —CH₂NHCONH(4-Cl-Ph), —CH₂NHCONHBn, —NHSO₂Me, —CH₂NHSO₂Me, —CH₂NHSO₂Et, —CH₂NHSO₂(n-Pr), —CH₂NHSO₂(i-Pr), —CH₂NHSO₂(n-pentyl), —CH₂NHSO₂Pb, —CH₂NHSO₂(4-NHCOMe-Ph), —CH₂NHSO₂(4-Cl-Bn), —CH₂NHSO₂CH₂CH₂Ph, —CH₂NHSO₂CH₂CH₂(2-Cl-Ph), —CH₂NHSO₂CH₂CH₂(3-Cl-Ph), —CH₂NHSO₂CH₂CH₂(4-Cl-Ph), —CH₂NHSO₂(3,4-dimethyl-isoxazol-4-yl), 1-pyrrolidinyl, 2-oxo-1-pyrrolidinyl, 3-carboxy-N-piperidinyl, pyrazol-1-yl, 4-carboxy-pyrazol-1-yl, 1,2,3-triazol-1-yl, 1,2,4-triazol-1-yl, 1,2,3-triazol-2-yl, 4-carboxy-1,2,3-triazol-1-yl, 4-(ethoxycarbonyl)-1,2,3-triazol-1-yl, tetrazol-1-yl, tetrazol-5-yl, 5-Me-tetrazol-1-yl, 5-CF₃-tetrazol-1-yl, or —OCH₂(2-tetrahydrofuranyl);

$R^3$ is phenyl substituted with 0-2 $R^{3a}$, naphthyl substituted with 0-2 $R^{3a}$, 1,2,3,4-tetrahydro-naphthyl substituted with 0-2 $R^{3a}$, or a 5- to 12-membered heterocycle substituted with 0-2 $R^{3a}$ and selected from: thiophene, furan, thiazole, tetrazole, pyridine, pyridinone, pyrimidine, pyrrole, pyrazole, indole, 2-oxindole, isoindolin-1-one, indazole, 1H-indazole-3-one, 7-azaindole, benzofuran, benzothiophene, benzimidazole, benzisoxazole, benzoxazole, quinazoline, quinoline, isoquinoline, 3H-quinazolin-4-one, phthalazine, 2H-phthalazin-1-one, 2H-3,4-dihydrophthalazin-1-one, 1H-quinolin-4-one, 1H-quinolin-2-one, 2H-3,4-dihydroisoquinolin-1-one, 3,4-dihydro-1H-quinolin-2-one, 1,3-dihydroindol-2-one, 3H-benzoxazol-2-one, 1,3-dihydrobenzimidazol-2-one, 1,4-dihydro-3,1-benzoxazin-2-one, 3,4-dihydro-1H-quinazolin-2-one, 1,3-dihydro-quinazoline-2,4-dione, 1,4-dihydro-quinoxaline-2,3-dione, 4H-benzo[1,4]thiazine-3-one, 2H-benzo[1,4]thiazin-3(4H)-one, 4H-1,4-benzoxazin-3-one, 1,3,4,5-tetrahydro-1-benzazepin-2-one, 1,3,4,5-tetrahydro-1,3-benzodiazepin-2-one, 8,9-dihydro-5H-7-oxa-5-aza-benzocyclohepten-6-one, benzimidazol-2-one, 1,3-dihydrobenzimidazol-2-one, 3H-benzoxazol-2-one, 3H-quinazolin-4-one, and 1,2,3,4-tetrahydroquinoline;

$R^4$ is H, Me, F, Br, Cl, CF₃, CO₂H, CO₂Me, or CO₂Et;

$R^{8a}$ is H or Me.

In a sixth aspect, the present invention includes compounds of Formula (I) or its stereoisomers, tautomers, pharmaceutically acceptable salts, solvates, or prodrugs thereof, within the scope of the first aspect wherein:

A is phenyl, 2-fluorophenyl, 3-fluorophenyl, 2-chlorophenyl, 3-chlorophenyl, 2-bromophenyl, 3-bromophenyl, 3-methylphenyl, 2-methoxyphenyl, 3-methoxyphenyl, 3-aminomethylphenyl, 4-aminomethylphenyl, 2-carboxy-5-chlorophenyl, 2-methoxycarbonyl-5-chlorophenyl, 2-(N-(methoxycarbonyl)-amino)-5-chlorophenyl, 2-(N-(ethoxycarbonyl)-aminomethyl)-5-chlorophenyl, 2-(N-(isopropoxycarbonyl)-aminomethyl)-5-chlorophenyl, 2-(N-(tert-butoxycarbonyl)-aminomethyl)-5-chlorophenyl, 2-N-(phenylcarbonyl)-aminomethyl)-5-chlorophenyl, 2-(N-(benzoxycarbonyl)-aminomethyl)-5-chlorophenyl, 2-((N-(3-propanoic acid)carbonyl)-aminomethyl)-5-chlorophenyl, 2-(3-methylureido)-5-chlorophenyl, 2-(3-ethylureidomethyl)-5-chlorophenyl, 2-[3-(2-ethoxycarbonyl-ethyl)-ureidomethyl]-5-chlorophenyl, 2-(3-phenylureido)methyl)-5-chlorophenyl, 2-(3-(4-chlorophenyl)ureido)methyl)-5-chlorophenyl, 2-(3-benzylureido)methyl)-5-chlorophenyl, 2-N-(methylsulfonyl)-amino)-5-chlorophenyl, 2-(N-(methylsulfonyl)-aminomethyl)-5-chlorophenyl, 2-(N-(ethylsulfonyl)-aminomethyl)-5-chlorophenyl, 2-(N-(n-propylsulfonyl)-aminomethyl)-5-chlorophenyl, 2-N(isopropylsulfonyl)-aminomethyl)-5-chlorophenyl, 2-(N-(n-pentylsulfonyl)-aminomethyl)-5-chlorophenyl, 2-N-(phenylsulfonyl)-aminomethyl)-5-chlorophenyl, 2-((N-(4-methylcarbonylaminophenyl)sulfonyl)-aminomethyl)-5-chlorophenyl, 2-(4-chlorobenzylsulfonyl)-aminomethyl)-5-chlorophenyl, 2-N-(phenethylsulfonyl)-aminomethyl)-5-chlorophenyl, 2-N-(2-chlorophen-ethylsulfonyl)-aminomethyl)-5-chlorophenyl, 2-(N-(3-chlorophenethylsulfonyl)-aminomethyl)-5-chlorophenyl, 2-(N-(4-chlorophenethylsulfonyl)-aminomethyl)-5-chlorophenyl, 2-(N-(3,4-dimethyl-isoxazol-4-yl)-aminomethyl)-5-chlorophenyl, 2-(N-(3,4-dimethyl-isoxazol-4-ylsulfonyl)-aminomethyl)-5-chlorophenyl, 3-carbamoyl-phenyl, 2,4-difluorophenyl, 2,5-difluorophenyl, 2,5-dichlorophenyl, 3,5-dichlorophenyl, 5-chloro-2-fluorophenyl, 3-chloro-2-fluorophenyl, 3-chloro-4-methylphenyl, 2-methyl-5-chlorophenyl, 2-methoxy-5-chlorophenyl, 2-ethoxy-5-chlorophenyl, 2-benzyloxy-5-chlorophenyl, 2-methylthio-5-chlorophenyl, 2-ethylthio-5-chlorophenyl, 2-propylthio-5-chlorophenyl, 2-benzylthio-5-chlorophenyl, 2-methylthiomethyl-5-chlorophenyl, 2-(2-oxo-1-pyrrolidinyl)-5-chlorophenyl, 3-trifluoromethyl-2-fluorophenyl, 2-trifluoromethyl-5-chlorophenyl, 5-bromo-2-fluorophenyl, 2-amino-5-chlorophenyl, 2-aminomethyl-5-chlorophenyl, 2-methylsulfonyl-5-chlorophenyl, 2-methylsulfonamide-5-chlorophenyl, 2-phenylcarbamoyl-5-chlorophenyl, 2-(3-carboxy-N-piperidinyl)-5-chlorophenyl, 2,6-difluoro-3-methylphenyl, 2-chloro-6-fluoro-3-methylphenyl, 2-fluoro-6-chloro-3-methylphenyl, 2,6-difluoro-3-chlorophenyl, 2,3-dichloro-6-aminophenyl, 2,3-dichloro-6-nitrophenyl, 2-phenoxyphenyl, 2-phenoxy-5-chlorophenyl, 2-(N-pyrrolidinyl)-5-chlorophenyl, 2-(pyrazol-1-yl)-5-chlorophenyl, 2-(4-carboxy-pyrazol-1-yl)-5-chlorophenyl, 2-(1,2,3-triazol-1-yl)-5-methylphenyl, 2-(1,2,3-triazol-1-yl)-5-chlorophenyl, 2-(1,2,3-triazol-2-yl)-5-chlorophenyl, 2-(1,2,4-triazol-1-yl)-5-chlorophenyl, 2-[(4-carboxy)-1,2,3-triazol-1-yl]-5-methylphenyl, 2-[(4-carboxy)-1,2,3-triazol-1-yl]-5-chlorophenyl, 2-[(4-ethoxycarbonyl)-1,2,3-triazol-1-yl]-5-chlorophenyl, 2-(tetrazol-1-yl)-5-methylphenyl, 2-(tetrazol-1-yl)-5-chlorophenyl, 2-(tetrazol-5-yl)-5-chlorophenyl, 2-(5-methyl-tetrazol-1-yl)-5-chlorophenyl, 2-(tetrazol-1-yl)-3-fluoro-5-chlorophenyl, 2-(tetrazol-1-yl)-3-fluoro-5-methylphenyl, 2-(5-methyltetrazol-1-yl)-5-chlorophenyl, 2-(5-trifluoromethyl-tetrazol-1-yl)-5-chlorophenyl, 2-(2-tetrahydrofuranyl-methoxy)-5-chlorophenyl, 3,4-methylenedioxy-phenyl, cyclopentyl, 2-oxo-1-pyrrolidinyl, 2-furanyl, 2-thienyl, 3-thienyl, 5-chloro-2-thienyl, 5-chloro-3-thienyl, 2,5-dichloro-3-thienyl, 1-imidazolyl, 2-imidazolyl, 4-imidazolyl, 3-chloro-5-isoxazolyl, 4-pyridyl, 3-fluoro-2-pyridyl, 2(1H)-oxo-5-chloropyridin-1-yl, 1-indolyl, 3-indolyl, 2-benzimidazolyl, 6-chlorobenzimidazol-4-yl, 2-methyl-6-chlorobenzothiazol-4-yl or 2,6-dichlorobenzothiazol-4-yl, 2-[(3-carboxy)-pyrazol-1-yl]-5-chlorophenyl, 2-[(3-carboxy)-pyrazol-1-yl]-5-methylphenyl, 2-fluoro-3-chloro-6-(tetrazol-1-yl)phenyl 2-fluoro-3-chloro-6-(methylcarbonyl)phenyl, 2-methylcarbonyl-5-chlorophenyl, 2-(aminocarbonyl)-5-chlorophenyl, 2-(methylaminocarbonyl)-5-chlorophenyl, or 2-(aminosulfonyl)-5-chlorophenyl;

$L_1$ is —CH₂CH₂—, —CH═CH—, —C(Me)═CH—, —C≡C—, —CH₂NH—, —CH₂O—, —NHNH—, —SCH₂—, —S(O)CH₂—, —SO₂CH₂— or —OCH₂—;

$R^3$ is phenyl, 3-biphenyl, 4-biphenyl, 3-aminophenyl, 4-aminophenyl, 3-N,N-dimethylaminophenyl, 4-phenoxyphenyl, 4-benzyloxyphenyl, 4-(t-butoxymethyl)-phenyl, 4-methyl sulfonylphenyl, 3-cyanophenyl, 4-cyanophenyl, 3-fluorophenyl, 4-fluorophenyl, 3-chlorophenyl, 4-chlorophenyl, 3-bromophenyl, 4-bromophenyl, 3-hydroxyphenyl, 4-hydroxyphenyl, 2-methoxyphenyl, 3-methoxyphenyl, 4-methoxyphenyl, 3-trifluoromethylphenyl, 4-trifluoromethylphenyl, 3-carboxyphenyl, 4-carboxyphenyl, 3-methoxycarbonylphenyl, 4-methoxycarbonylphenyl, 3-carboxymethylphenyl, 4-carboxymethylphenyl, 4-methoxycarbonylmethylphenyl, 3-ethoxycarbonylmethylphenyl, 4-ethoxycarbonylmethylphenyl, 4-ethoxycarbonylethylphenyl, 3-carbamoylphenyl, 4-carbamoylphenyl, 3-aminocarbonylmethylphenyl, 4-aminocarbonylmethylphenyl, 4-methylaminocarbonylphenyl, 4-dimethylaminocarbonylmethylphenyl, 4-amidinophenyl, 3-methylcarbonylaminophenyl, 4-methylcarbonylaminophenyl, 4-methoxycarbonylaminophenyl, 4-aminosulfonylphenyl, 3-methylsulfonylaminophenyl, 4-methylsulfonylamino, 2,4-difluorophenyl, 3-fluoro-4-cyanophenyl, 4-amino-3-carboxyphenyl, 4-amino-3-methoxycarbonylphenyl, 2,4-dichlorophenyl, 3-cyano-5-fluorophenyl, 3-fluoro-4-carbamoylphenyl, 3-carboxy-4-cyanophenyl, 3-phenyl-4-carbamoylphenyl, 4-(2-oxo-1-piperidino)-phenyl, thiazol-2-yl, thien-2-yl, 4-methoxycarbonyl-thiazol-2-yl, 4-carbamoyl-thiazol-2-yl, 1-benzyl-pyrazol-4-yl, 5-phenyl-oxazol-2-yl, 5-carbamoyl-thien-2-yl, 5-carboxy-thien-2-yl, pyrid-2-yl, pyrid-3-yl, pyrid-4-yl, 6-amino-pyrid-3-yl, benzimidazol-2-yl, 6-methoxy-pyrid-3-yl, 1-methyl-benzimidazol-2-yl, benzoxazol-2-yl, benzothiazol-2-yl, 3-amino-benzisoxazol-6-yl, 3-amino-benzisoxazol-5-yl, indazol-5-yl, indazol-6-yl, 3-amino-indazol-5-yl, 3-hydroxy-indazol-5-yl, 3-amino-indazol-6-yl, 3-amino-1-methyl-indazol-6-yl, 3-amino-4-fluoro-indazol-6-yl, 3-amino-5-fluoro-indazol-6-yl, 3-amino-7-fluoro-indazol-6-yl, 4-imino-3,4-dihydro-2H-phthalazin-1-on-7-yl, 3-(5-tetrazolyl)-phenyl, 2,3-dihydro-isoindol-1-on-6-yl, quinolin-5-yl, quinolin-6-yl, quinolin-8-yl, isoquinolin-5-yl, 2H-isoquinolin-1-on-6-yl, 2,4-diaminoquinazolin-7-yl, 4-NH$_2$-quinazolin-7-yl,

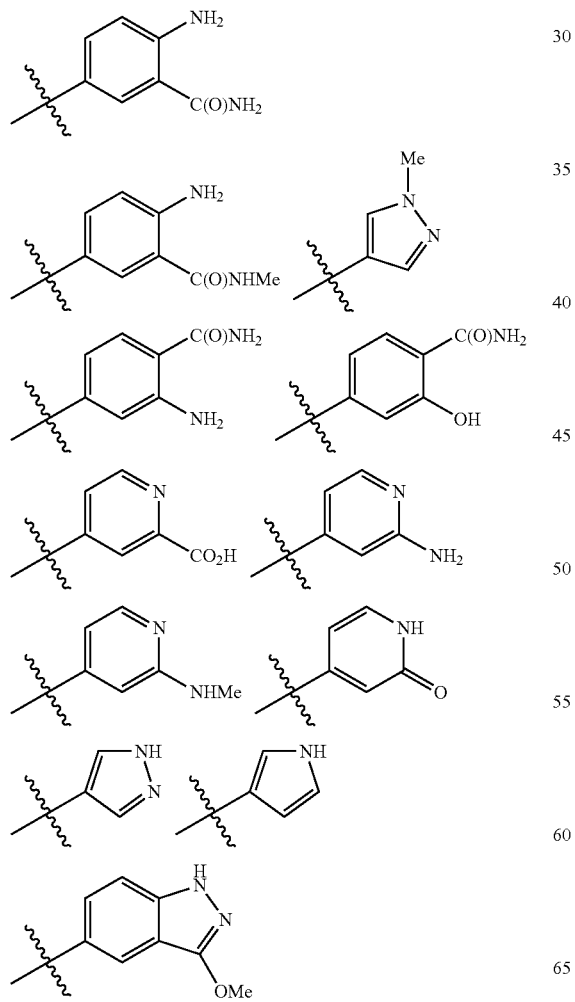

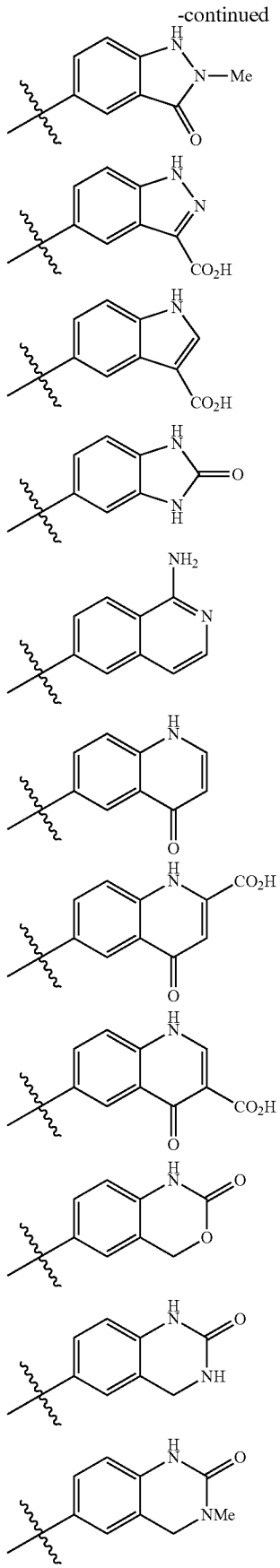

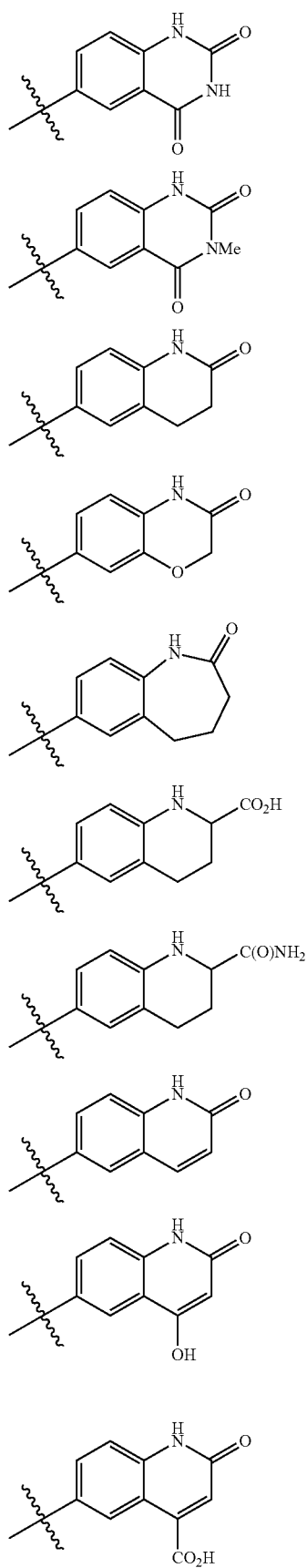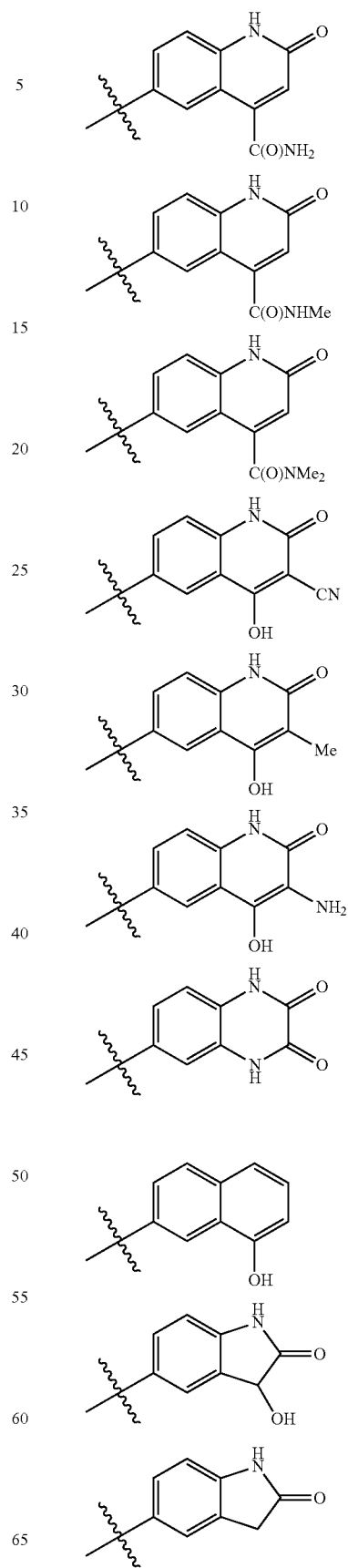

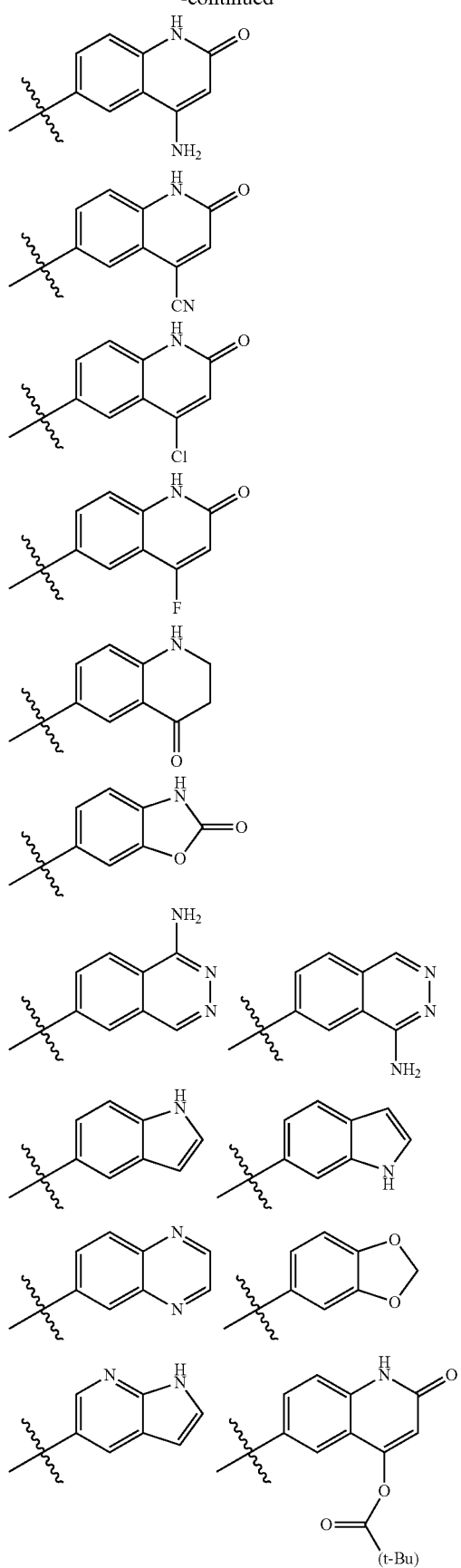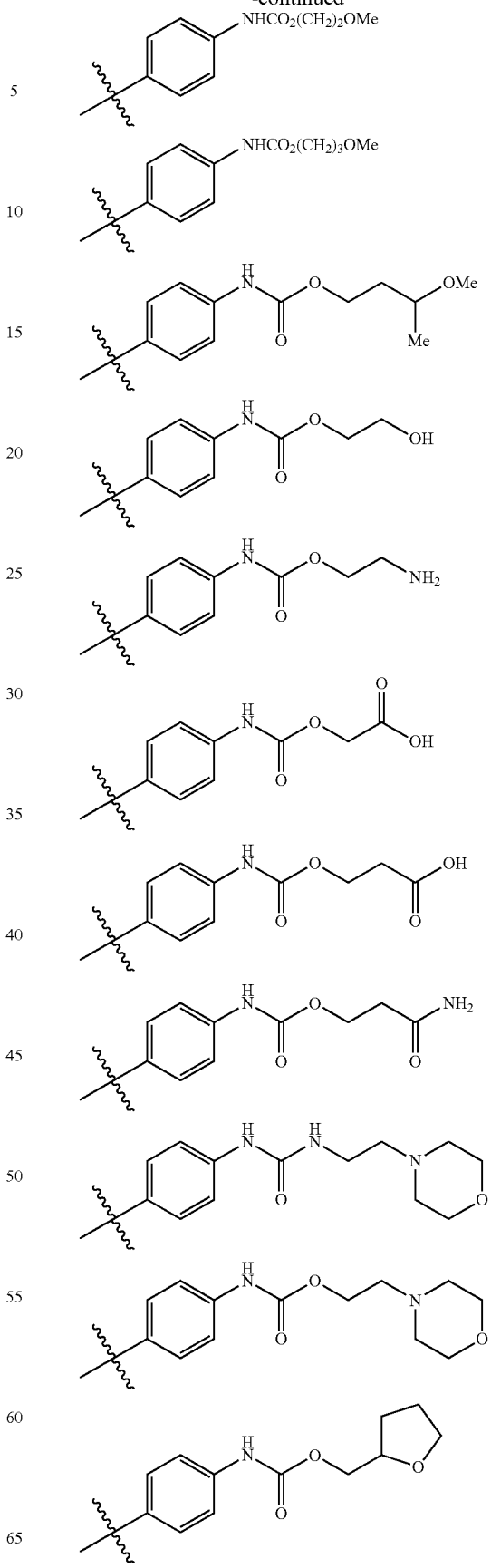

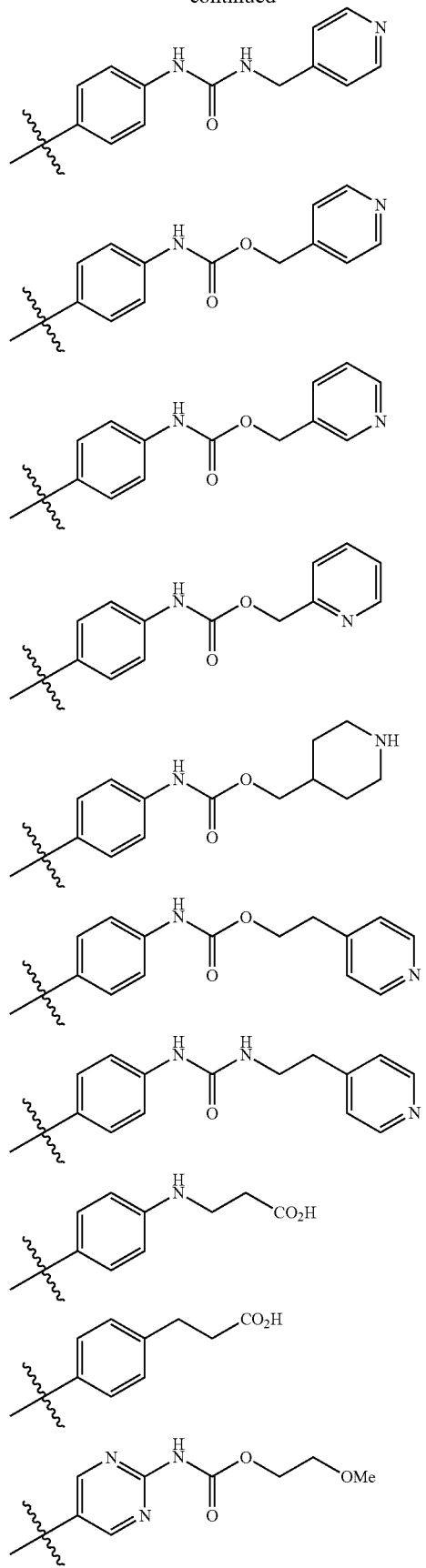
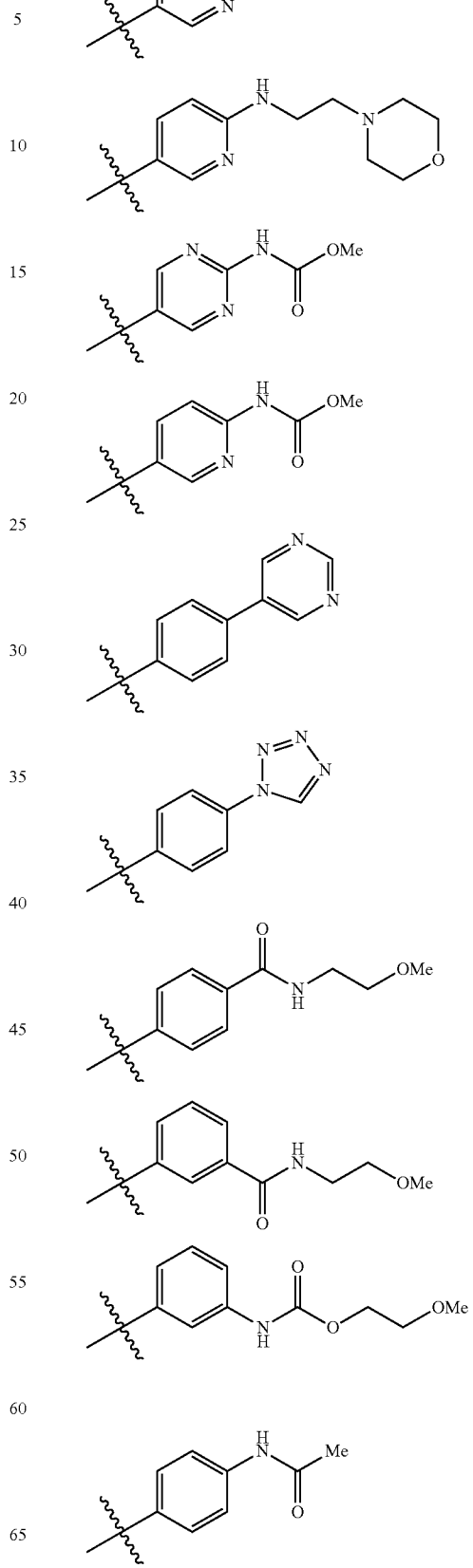

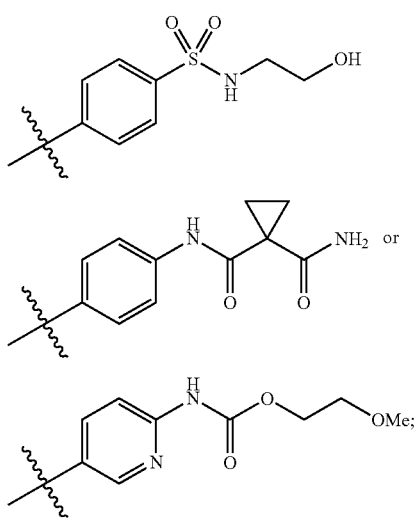

$R^4$ is H, Me, F, Br, C$_1$, CF$_3$, CO$_2$H, CO$_2$Me, or CO$_2$Et; and $R^{8a}$ is H or Me.

In a seventh aspect, the present invention includes compounds of Formula (I) or its stereoisomers, tautomers, pharmaceutically acceptable salts, solvates, or prodrugs thereof, within the scope of the first aspect wherein:

A is 3-chlorophenyl, 3-methylphenyl, 2,5-dichlorophenyl, 5-chloro-2-fluorophenyl, 3-chloro-2-fluorophenyl, 2-methyl-5-chlorophenyl, 2-methoxy-5-chlorophenyl, 2-methylthio-5-chlorophenyl, 2-ethylthio-5-chlorophenyl, 2-propylthio-5-chlorophenyl, 2-benzylthio-5-chlorophenyl, 2-amino-5-chlorophenyl, 2-aminomethyl-5-chlorophenyl, 2,6-difluoro-3-methylphenyl, 2-chloro-6-fluoro-3-methylphenyl, 2-fluoro-6-chloro-3-methylphenyl, 2,6-difluoro-3-chlorophenyl, 2,3-dichloro-6-nitrophenyl, 5-chloro-2-thienyl, 3,4-methylenedioxyphenyl, 2-methoxycarbonyl-5-chlorophenyl, 6-chlorobenzimidazol-4-yl, 2-[(4-carboxy)-pyrazol-1-yl]-5-chlorophenyl, 2-[(4-carboxy)-pyrazol-1-yl]-5-methylphenyl, 2-(1,2,3-triazol-1-yl)-5-methylphenyl, 2-(1,2,3-triazol-1-yl)-5-chlorophenyl, 2-(1,2,4-triazol-1-yl)-5-chlorophenyl, 2-(1,2,3-triazol-2-yl)-5-chlorophenyl, 2-[(4-carboxy)-1,2,3-triazol-1-yl]-5-chlorophenyl, 2-[(4-carboxy)-1,2,3-triazol-1-yl]-5-methylphenyl, 2-[(4-ethoxycarbonyl)-1,2,3-triazol-1-yl]-5-chlorophenyl, 2-(tetrazol-1-yl)-5-methylphenyl, 2-(tetrazol-1-yl)-5-chlorophenyl, 2-(tetrazol-1-yl)-3-fluoro-5-chlorophenyl, 2-(tetrazol-1-yl)-3-fluoro-5-methylphenyl, 2-(5-methyltetrazol-1-yl)-5-chlorophenyl, 2-fluoro-3-chloro-6-(tetrazol-1-yl)phenyl, 2-fluoro-3-chloro-6-(methylcarbonyl)phenyl, or 2-methylcarbonyl-5-chlorophenyl;

L$_1$ is —CH$_2$CH$_2$—, —CH=CH—, —C(Me)=CH—, —C≡C—, or —CH$_2$NH—;

R$^3$ is

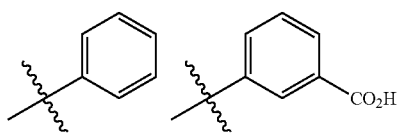

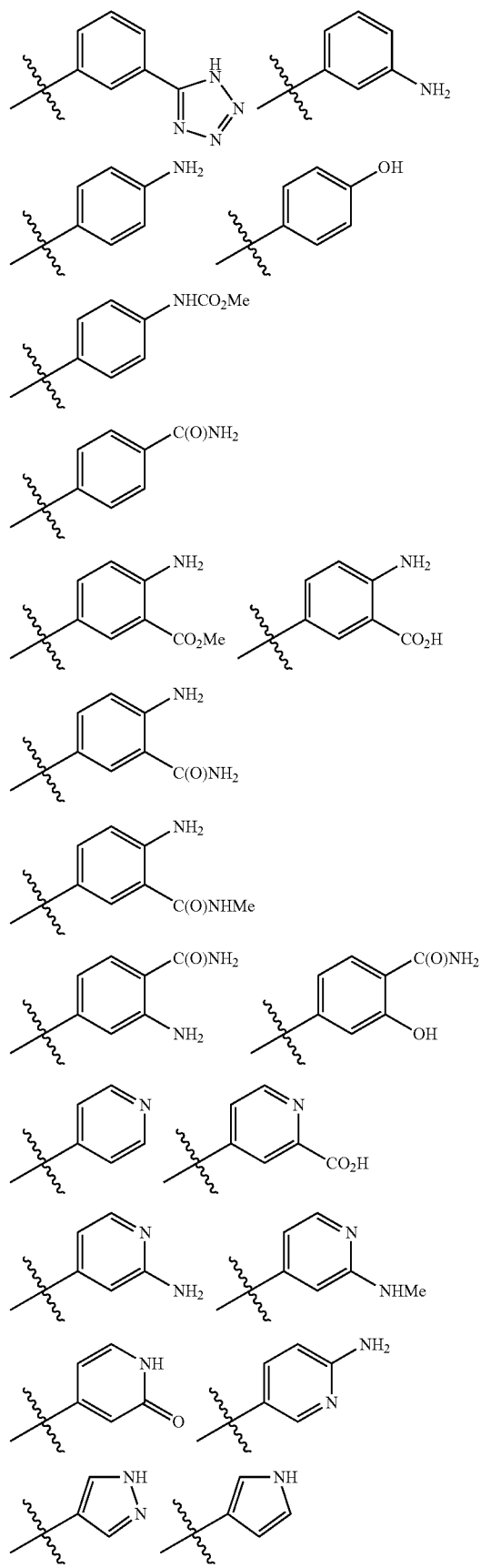

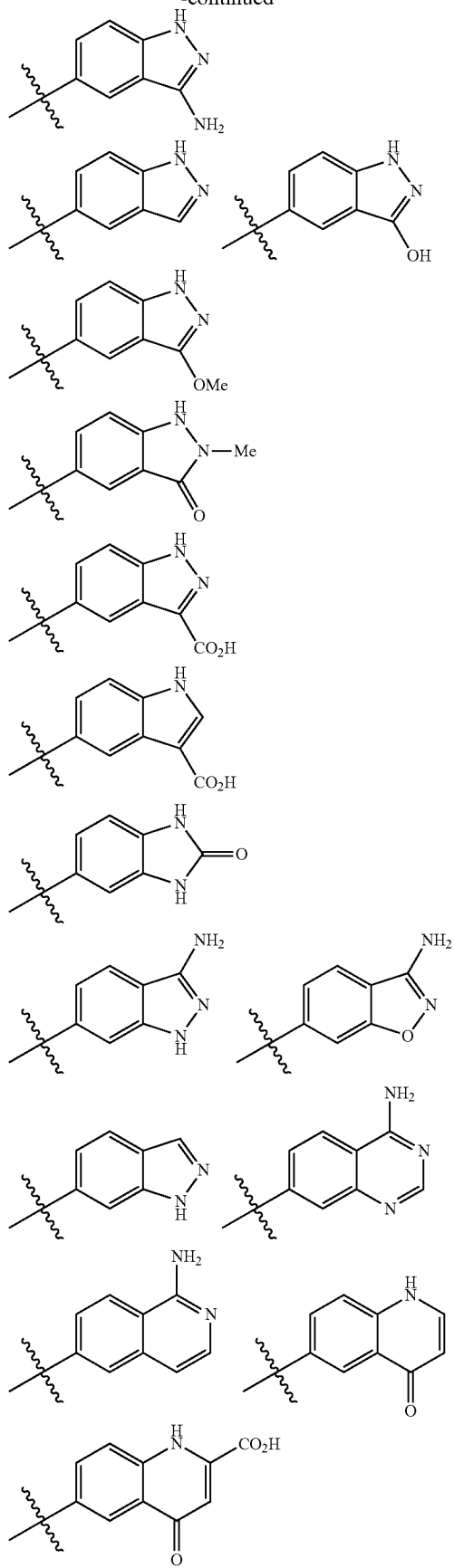
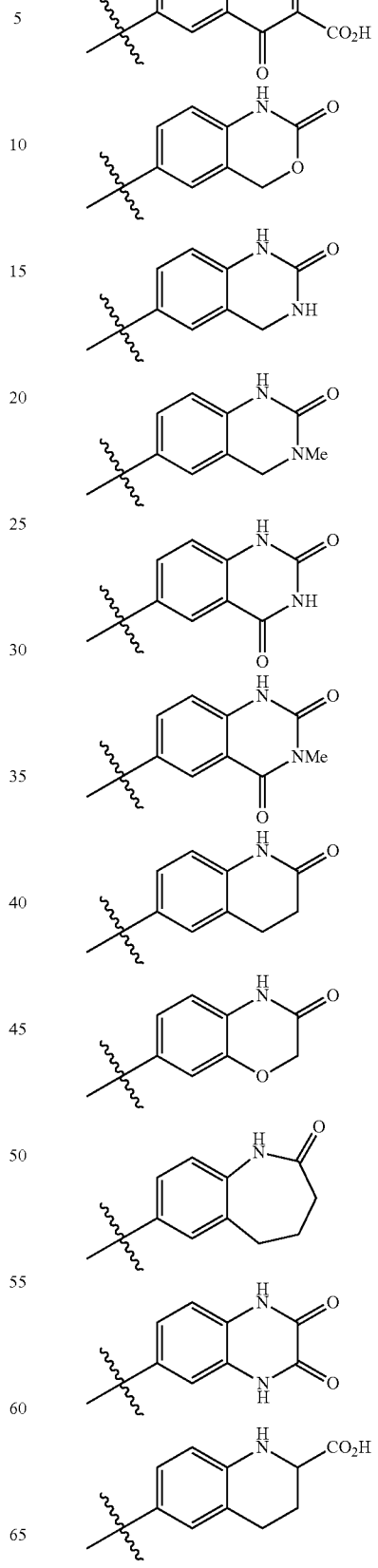

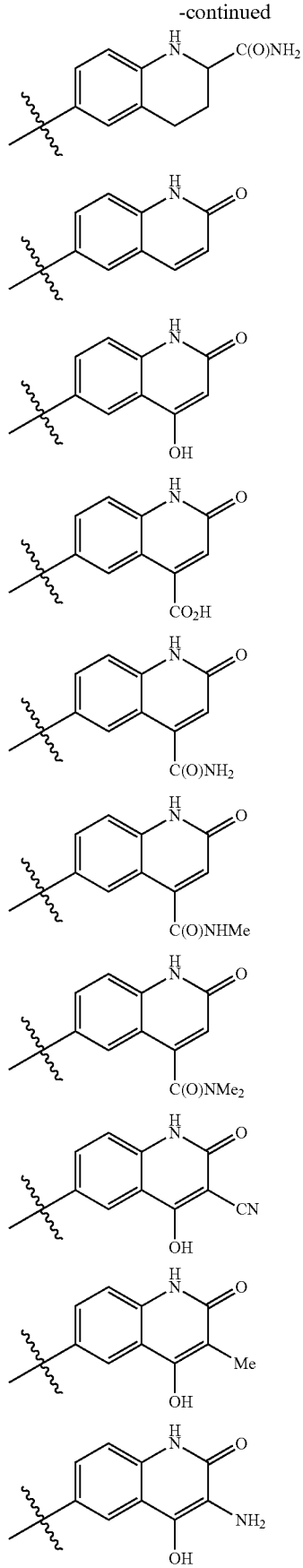
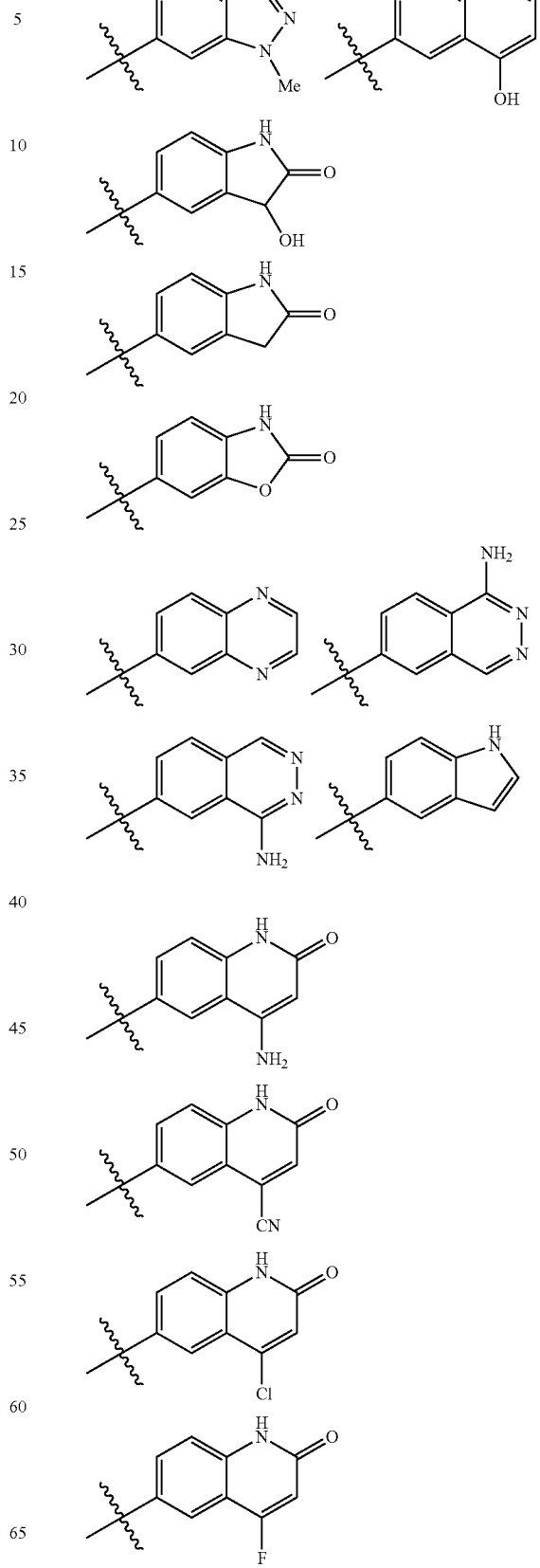

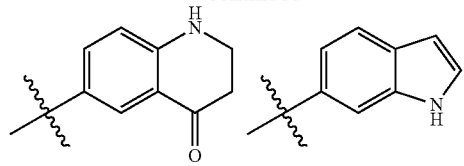
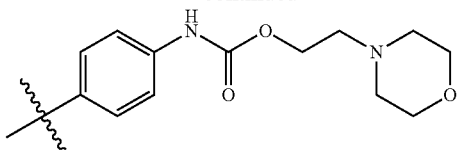
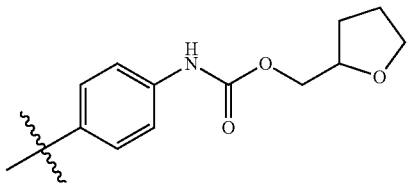
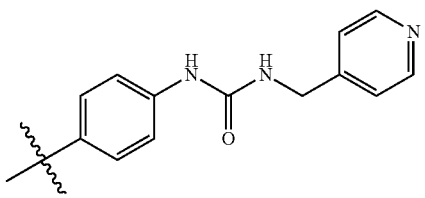
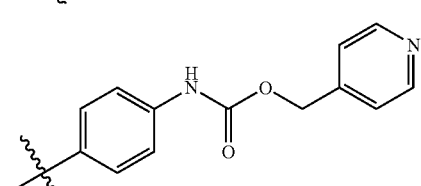
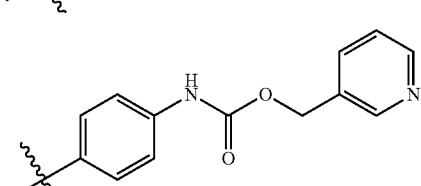
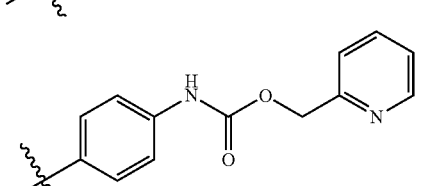
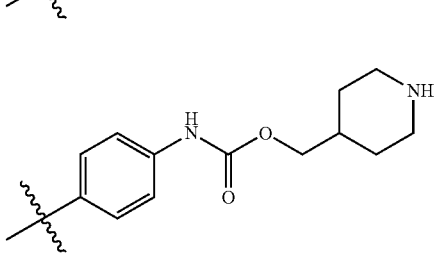
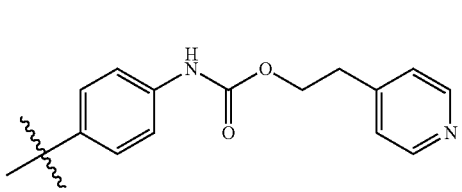
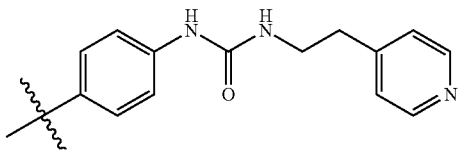

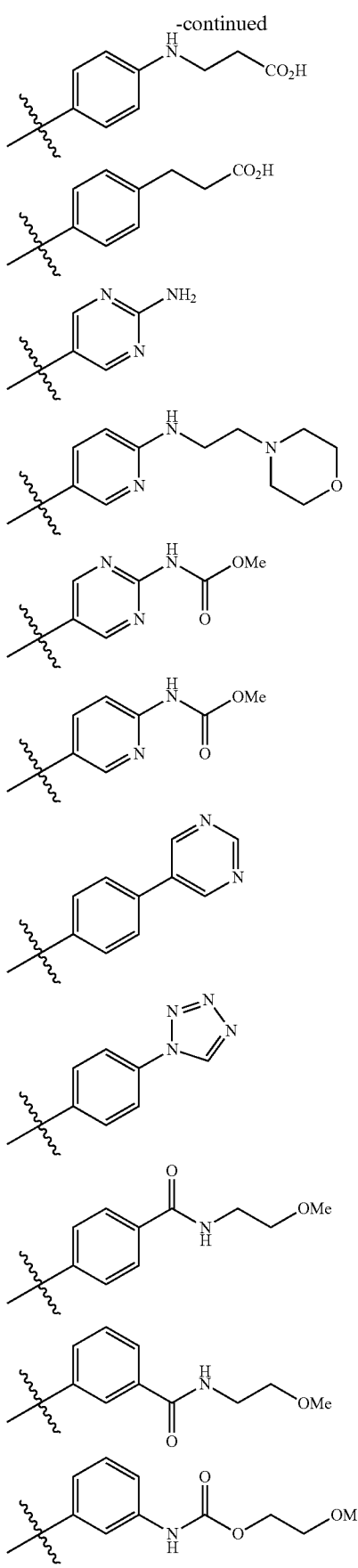
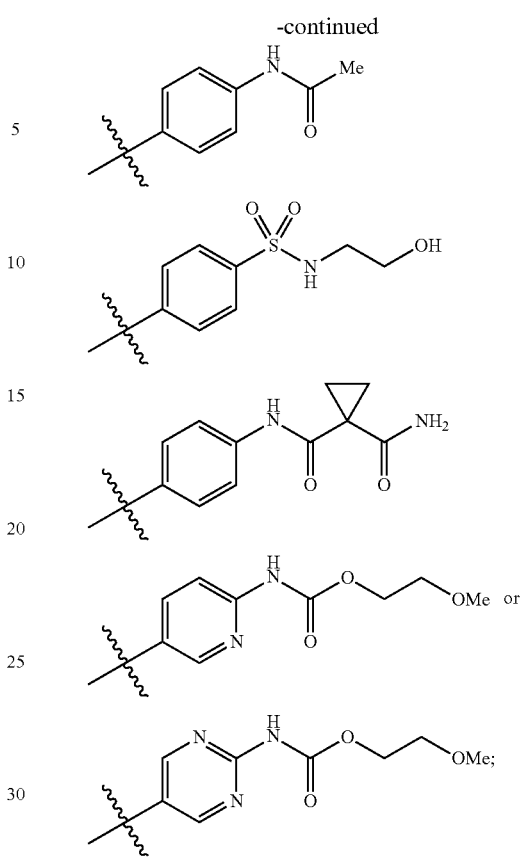
R[4] is H, Me, or Cl;
R[8a] is H or Me; and
R[11] is H or benzyl.
In an eighth aspect, the present invention provides, inter alia, compounds of Formula (II):
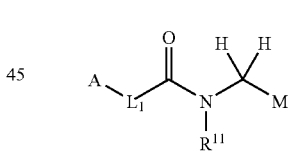
(II)
or stereoisomers, tautomers, pharmaceutically acceptable salts, solvates, or prodrugs thereof, wherein:
M is
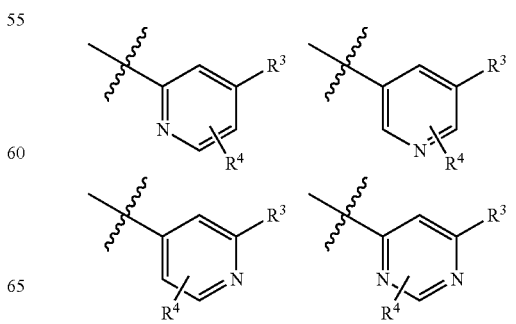

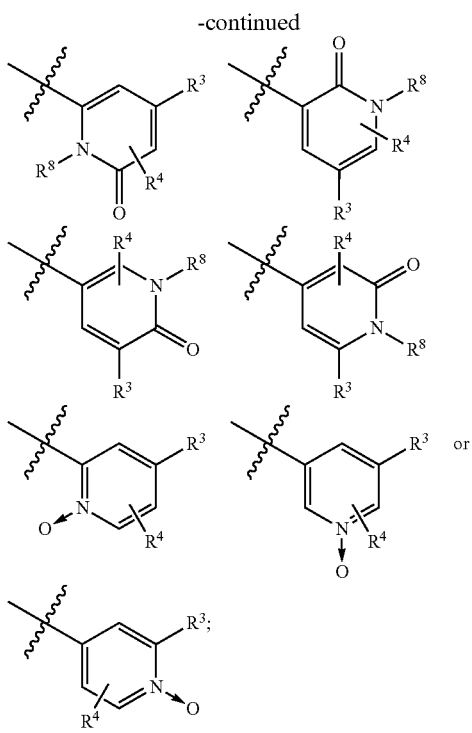

A is a $C_{3-10}$ carbocycle substituted with 0-1 $R^1$ and 0-3 $R^2$, or a 5- to 12-membered heterocycle comprising: carbon atoms and 1-4 heteroatoms selected from N, O, and $S(O)_p$, wherein said heterocycle is substituted with 0-1 $R^1$ and 0-3 $R^2$; provided that when A is a heterocycle containing one or more nitrogen atoms, A is not attached to $L_1$ via any of the nitrogen atoms on the A ring;

$L_1$ is —CHR$^5$CH$_2$—, —CH(NR$^7$R$^8$)CH$_2$—, —CR$^5$=CH—, —C≡C—, —OCH$_2$—, —C(R$^5$R$^6$)NH—, —CH$_2$O—, —SCH$_2$—, —S(O)CH$_2$—, —SO$_2$CH$_2$—, —CH$_2$NR$^{10}$—, or —NHNH—;

provided that when $L_1$ is —CH$_2$O—, then A is other than an unsubstituted phenyl;

$R^1$ is, independently at each occurrence, F, Cl, Br, I, OCF$_3$, CF$_3$, (CH$_2$)$_r$OR$^a$, —(CH$_2$)$_r$SR$^a$, CN, —(CH$_2$)$_r$NR$^7$R$^8$, —C(=NR$^8$)NR$^8$R$^9$, —C(O)NR$^8$R$^9$, —S(O)$_p$NR$^8$R$^9$, or C$_{1-6}$ alkyl substituted with 0-1 $R^{1a}$;

$R^{1a}$ is F, OCF$_3$, CF$_3$, OR$^a$, SR$^a$, CN, —NR$^7$R$^8$, —C(O)NR$^8$R$^9$, NR$^8$C(O)R$^c$, —S(O)$_p$NR$^8$R$^9$, —NR$^8$SO$_2$R$^c$, or —(CF$_2$)$_r$CF$_3$;

$R^2$ is, independently at each occurrence, =O, F, Cl, Br, OCF$_3$, CF$_3$, CHF$_2$, CN, NO$_2$, —(CH$_2$)$_r$OR$^a$, —(CH$_2$)$_r$SR$^a$, —(CH$_2$)$_r$C(O)R$^a$, —(CH$_2$)$_r$C(O)OR$^a$, —(CH$_2$)$_r$OC(O)R$^a$, (CH$_{12}$)$_r$NR$^7$R$^8$, —(CH$_2$)$_r$C(O)NR$^8$R$^9$, —(CH$_2$)$_r$NR$^8$(O)R$^c$, —(CH$_2$)$_r$NR$^8$C(O)OR$^c$, —NR$^8$C(O)NR$^8$R$^9$, —S(O)NR$^8$R$^9$, —NR$^8$S(O)$_p$R$^c$, —S(O)R$^c$, —S(O)$_2$R$^c$, C$_{1-6}$ alkyl substituted with 0-1 $R^{2a}$, —(CH$_2$)$_r$-3-7 membered carbocycle optionally substituted with 0-2 $R^{2b}$, or —(CH$_2$)$_r$-5-7 membered heterocycle comprising carbon atoms and 1-4 heteroatoms selected from N, O, and S(O)P, wherein said heterocycle is substituted with 0-2 $R^{2b}$;

alternately, when $R^1$ and $R^2$ groups are substituents on adjacent atoms they may be taken together with the atoms to which they are attached to form a 5- to 7-membered carbocycle or heterocycle comprising carbon atoms and 0-4 heteroatoms selected from N, O, and $S(O)_p$ and substituted with 0-2 $R^g$;

$R^{2a}$ is F, OCF$_3$, CF$_3$, OR$^a$, SR$^a$, CN, —NR$^7$R$^8$, —C(O)NR$^8$R$^9$, —NR$^8$C(O)R$^c$, —NR$^8$C(O)OR$^c$, —NR$^8$C(O)NR$^8$R$^c$, —S(O)$_p$NR$^8$R$^9$, —NR$^8$SO$_2$R$^c$, or —(CF$_2$)$_r$CF$_3$;

$R^{2b}$ is, independently at each occurrence, =O, F, Br, Cl, OCF$_3$, CF$_3$, —(CH$_2$)$_r$OR$^a$, (CH$_2$)$_r$SR$^a$, (CH$_{12}$)$_r$CN, —(CH$_2$)$_r$NR$^7$R$^8$, —(CH$_2$)$_r$C(O)OR$^a$, —(CH$_2$)$_r$OC(O)R$^a$, —(CH$_2$)$_r$C(O)NR$^8$R$^9$, —(CH$_2$)$_r$NR$^8$C(O)R$^c$, —(CH$_2$)$_r$NR$^8$C(O)OR$^c$, —(CH$_2$)$_r$S(O)$_p$NR$^8$R$^9$, —(CH$_2$)$_r$NR$^8$SO$_2$R$^e$, C$_{1-4}$ alkyl or —(CF$_2$)$_r$CF$_3$;

$R^3$ is, independently at each occurrence, —(CH$_2$)$_r$—C$_{3-10}$ carbocycle substituted with 0-3 $R^{3a}$ and 0-1 $R^{3d}$, or —(CH$_2$)$_r$-5- to 12-membered heterocycle comprising: carbon atoms and 1-4 heteroatoms selected from N, O, and $S(O)_p$, wherein said heterocycle is substituted with 0-3 $R^{3a}$ and 0-1 $R^{3d}$;

$R^{3a}$ is, independently at each occurrence, =O, =NR$^8$, F, Cl, Br, I, OCF$_3$, CF$_3$, —(CH$_2$)$_r$CN, NO$_2$, —(CH$_2$)$_r$OR$^{3b}$, (CH$_2$)$_r$SR$^{3b}$, —(CH$_2$)$_r$NR$^7$R$^8$, —NHC(O)NR$^8$R$^9$, —(CH$_2$)$_r$C(O)OR$^{3b}$, —C(O)C$_{1-4}$ alkyl, SO$_2$NHR$^{3b}$, —SO$_2$NHCOR$^{3c}$, —SO$_2$NHCO$_2$R$^{3c}$, —CONHSO$_2$R$^{3c}$, —(CH$_2$)$_r$NR$^8$C(O)R$^{3b}$, (CH$_2$)$_r$NR$^8$CO$_2$R$^{3c}$, —(CH$_2$)$_r$S(O)$_p$NR$^8$R$^9$, —(CH$_2$)$_r$NR$^8$S(O)$_p$R$^{3c}$, —NHSO$_2$CF$_3$, —S(O)R$^{3c}$, —S(O)$_2$R$^{3c}$, —(CH$_2$)$_r$OC(O)R$^{3b}$, —(CH$_2$)$_r$C(O)NR$^8$R$^9$, —(CH$_2$)$_r$OC(O)NR$^8$R$^9$, —NHCOCF$_3$, —NHSO$_2$R$^{3c}$, CONHOR$^{3b}$, C$_{1-4}$ haloalkyl, C$_{1-4}$ haloalkyloxy-, C$_{1-6}$ alkyl substituted by $R^{3e}$, C$_{2-6}$ alkenyl substituted by $R^{3e}$, C$_{1-6}$ alkynyl substituted by $R^{3e}$, C$_{3-6}$ cycloalkyl substituted by 0-1 $R^{3d}$, —(CH$_2$)$_r$—C$_{6-10}$ carbocycle substituted by 0-3 $R^{3d}$ or —(CH$_2$)$_r$-5- to 10-membered heterocycle comprising: carbon atoms and 1-4 heteroatoms selected from N, O, and $S(O)_p$, wherein said heterocycle is substituted with 0-3 $R^{3d}$;

alternately, when two $R^{3a}$ groups are substituted on adjacent atoms, they can be taken together with the atoms to which they are attached to form a $C_{3-10}$ carbocycle substituted with 0-2 $R^{3d}$, or a 5- to 10-membered heterocycle comprising: carbon atoms and 1-4 heteroatoms selected from N, O, and $S(O)_p$, wherein said heterocycle is substituted with 0-2 $R^{3d}$;

$R^{3b}$ is, independently at each occurrence, H, C$_{1-6}$ alkyl substituted with 0-2 $R^{3d}$, C$_{2-6}$ alkenyl substituted with 0-2 $R^{3d}$, C$_{2-6}$ alkynyl substituted with 0-2 $R^{3d}$, —(CH$_2$)$_r$—C$_{3-10}$ carbocycle substituted with 0-3 $R^{3d}$, or —(CH$_2$)$_r$-5- to 10-membered heterocycle comprising: carbon atoms and 1-4 heteroatoms selected from N, O, and $S(O)_{p7}$ wherein said heterocycle is substituted with 0-3 $R^{3d}$;

$R^{3c}$ is, independently at each occurrence, C$_{1-6}$ alkyl substituted with 0-2 $R^{3d}$, C$_{2-6}$ alkenyl substituted with 0-2 $R^{3d}$, C$_{2-6}$ alkynyl substituted with 0-2 $R^{3d}$, —(CH$_2$)$_r$—C$_{3-10}$ carbocycle substituted with 0-3 $R^{3d}$, or —(CH$_2$)$_r$-5- to 10-membered heterocycle comprising: carbon atoms and 1-4 heteroatoms selected from N, O, and S(O)$_p$, wherein said heterocycle is substituted with 0-3 $R^{3d}$;

$R^{3d}$ is, independently at each occurrence, H, =O, F, Cl, Br, CN, NO$_2$, —(CH$_2$)$_r$NR$^7$R$^8$, —(CH$_2$)$_r$OR$^a$, —C(O)R$^a$, —C(O)OR$^a$, —OC(O)R$^a$, —NR$^8$C(O)R$^c$, —C(O)NR$^8$R$^9$, —S(O)$_2$NR$^8$R$^9$, —NR$^7$R$^8$, —NR$^8$S(O)$_2$NR$^8$R$^9$, —NR$^8$S(O)$_2$R$^c$, —S(O)$_p$R$^c$, —(CF$_2$)$_r$CF$_3$, C$_{1-6}$ alkyl substituted with 0-2 $R^e$, C$_{2-6}$ alkenyl substituted with 0-2 $R^e$, C$_{2-6}$ alkynyl substituted with 0-2 $R^e$, —(CH$_2$)$_r$—C$_{3-10}$ carbocycle substituted with 0-3 $R^d$, or —(CH$_2$)$_r$-5- to 10-membered heterocycle comprising; carbon atoms and 1-4 heteroatoms selected from N, O, and $S(O)_p$, wherein said heterocycle is substituted with 0-3 $R^d$;

$R^{3e}$ is, independently at each occurrence, H, —(CH$_2$)$_r$OR$^a$, F, =O, CN, NO$_2$, —(CH$_2$)$_r$NR$^7$R$^8$, —C(O)R$^a$, —C(O)OR$^a$, —OC(O)R$^a$, —NR$^8$C(O)R$^c$, —C(O)NR$^8$R$^9$, —S(O)$_2$NR$^8$R$^9$, —NR$^8$S(O)$_2$NR$^8$R$^9$, —NR$^8$S(O)$_2$R$^c$, —S(O)$_p$R$^c$, —(CF$_2$)$_r$CF$_3$, —(CH$_2$)$_r$—C$_{3-10}$ carbocycle substituted with 0-3 $R^d$, or (CH$_2$)$_r$-5- to 10-membered heterocycle comprising: carbon atoms and 1-4 heteroatoms selected from N, O, and $S(O)_p$, wherein said heterocycle is substituted with 0-3 $R^d$;

$R^4$ is, independently at each occurrence, H, F, Cl, Br, I, $OCF_3$, $CF_3$, CN, $NO_2$, —$(CH_2)_rOR^a$, —$(CH_2)_rSR^a$, $(CH_2)_rC(O)R^a$, —$(CH_2)_rC(O)OR^a$, —$OC(O)R^a$, —$(CH_2)_rNR^7R^8$, —$NR^8(CO_2)_rO(O)OR^a$, —$(CH_2)_rC(O)NR^8R^9$, $(C_1H_2)_rNR^8C(O)R^c$, —$(CH_2)_rNR^8C(O)_2R^b$, —$(CH_2)_rNR^8C(O)NR^8R^9$, —$S(O)_pNR^8R^9$, —$NR^8S(O)_pR^c$, —$S(O)_2R^c$, or $C_{1-4}$ alkyl substituted with 0-2 $R^{4a}$;

$R^{4a}$ is, independently at each occurrence, H, F, =O, $C_{1-6}$ alkyl, $OR^a$, $SR^a$, $CF_3$, CN, $NO_2$, —$CO)R^a$, —$C(O)OR^a$, —$NR^7R^8$, —$C(O)NR^8R^9$, —$NR^8C(O)R^c$, —$S(O)_pNR^8R^9$, —$NR^8S(O)_pR^c$, —$S(O)R^c$, or —$S(O)_2R^c$;

$R^5$ is, independently at each occurrence, H, F, $CF_3$, —$(CH_2)_rOR^a$, =O, —$(CH_2)_rNR^7R^8$, —$S(O)_pNR^8R^9$, —$(CH_2)_rCO_2R^a$, —$(CH_2)_rCONR^8R^9$, or $C_{1-4}$ alkyl;

$R^6$ is, independently at each occurrence, H, F, or $C_{1-4}$ alkyl;

$R^7$ is, independently at each occurrence, H, $C_{1-6}$ alkyl, —$(CH_2)_n$—$C_{3-10}$ carbocycle, —$(CH_2)_n$-(5- to 10-membered heteroaryl), —$C(O)R^c$, —CHO, —$C(O)_2R^c$, —$S(O)_2R^c$, —$CONR^8R^c$, —$OCONHR^c$, —$C(O)O$—$(C_{1-4}$ alkyl)$OC(O)$—$(C_{1-4}$ alkyl), or —$C(O)O$—$(C_{1-4}$ alkyl)$OC(O)$—$(C_{6-10}$ aryl); wherein said alkyl, carbocycle, heteroaryl, and aryl are substituted with 0-2 $R^f$; wherein said heteroaryl comprises: carbon atoms and 1-4 heteroatoms selected from N, O, and $S(O)_p$;

$R^8$ is, independently at each occurrence, H, $C_{1-6}$ alkyl, —$(CH_2)_n$-phenyl, or —$(CH_2)_n$-5- to 10-membered heterocycle comprising: carbon atoms and 1-4 heteroatoms selected from N, O, and $S(O)_p$; wherein said alkyl, phenyl and heterocycle are optionally substituted with 0-2 $R^f$;

alternatively, $R^7$ and $R^8$, when attached to the same nitrogen, combine to form a 5- to 10-membered heterocycle comprising: carbon atoms and 0-3 additional heteroatoms selected from N, O, and $S(O)_p$, wherein said heterocycle is substituted with 0-2 $R^f$;

$R^9$ is, independently at each occurrence, H, $C_{1-6}$ alkyl, or —$(CH_2)_n$-phenyl;

wherein said alkyl and phenyl are optionally substituted with 0-2 $R^f$;

alternatively, $R^8$ and $R^9$, when attached to the same nitrogen, combine to form a 5- to 12-membered heterocycle comprising: carbon atoms and 0-2 additional heteroatoms selected from N, O, and $S(O)_p$, wherein said heterocycle is substituted with 0-2 $R^d$;

$R^{10}$ is, independently at each occurrence, H or $C_{1-6}$ alkyl substituted with 0-3 $R^{10a}$;

$R^{10a}$ is, independently at each occurrence, H, =O, $C_{1-4}$ alkyl, $OR^a$, $SR^a$, F, $CF_3$, CN, $NO_2$, —$C(O)R^a$, —$C(O)OR^a$, —$C(O)NR^8R^9$, —$NR^8C(O)R^c$, —$S(O)_pNR^8R^9$, —$NR^8S(O)_pR^c$, or —$S(O)_pR^c$;

$R^{11}$ is H, $C_{1-4}$ alkyl, or benzyl;

the variables $R^a$, $R^b$, $R^c$, $R^d$, $R^e$, $R^f$, $R^g$, n, p, and r are, independently at each occurrence, the same as defined in the first aspect;

provided that:
when M is a pyridyl ring, $L_1$ is —CH=CH—, and $R^3$ is unsubstituted phenyl,
then A is other than a substituted phenyl;
when M is a pyridyl ring, $L_1$ is —$CH_2O$—, and $R^3$ is carboxyl substituted pyridyl, then A is other than a 9H-fluoren-9-yl; or
when M is a pyrimidinyl ring, $L_1$ is —$CH_2CH_2$—, A is other than a nitrogen containing heterocycle.

In a ninth aspect, the present invention includes compounds of Formula (II), or stereoisomers, tautomers, pharmaceutically acceptable salts, solvates, or prodrugs thereof, within the scope of the eighth aspect wherein:

$R^3$ is, independently at each occurrence, phenyl substituted with 0-3 $R^{3a}$ and 0-1 $R^{3d}$, naphthyl substituted with 0-3 $R^{3a}$ and 0-1 $R^{3d}$, or —$(CH_2)_r$-5- to 12-membered heterocycle comprising: carbon atoms and 1-4 heteroatoms selected from N, O, and $S(O)_p$, wherein said heterocycle is substituted with 0-3 $R^{3a}$ and 0-1 $R^{3d}$;

$R^4$ is, independently at each occurrence, H, Me, Et, Pr, F, Cl, Br, I, $OCF_3$, $CF_3$, CN, $NO_2$, —$(CH_2)_rOH$, —$(CH_2)_rC(O)OR^a$, $OR^a$, $SR^a$, —$C(O)R^a$, —$C(O)OR^a$, —$NR^7R^8$, —$(CH_2)_rNH_2$, —$NR^8(CH_2)_rC(O)OR^a$, —$(CH_2)_rC(O)NR^8R^9$, —$NR^8C(O)R^c$, —$NR^8C(O)OR^c$, —$NR^8C(O)NR^8R^9$, —$S(O)_pNR^8R^9$, —$NR^8S(O)_pR^c$, or —$S(O)_2R^c$; and $R^{11}$ is H.

In a tenth aspect, the present invention includes compounds of Formula (II), or stereoisomers, tautomers, pharmaceutically acceptable salts, solvates, or prodrugs thereof, within the scope of the eighth aspect wherein:

$R^1$ is, independently at each occurrence, F, Cl, Br, I, $OCF_3$, $CF_3$, $OCH_3$, $CH_3$, Et, $NH_2$, —$C(=NH)NH_2$, —$C(O)NH_2$, —$CH_2NH_2$ or —$SO_2NH_2$;

$R^2$ is, independently at each occurrence, F, Cl, Br, $CF_3$, $NO_2$, —$(CH_2)_rOR^a$, —$(CH_2)_rSR^a$, —$(CH_2)_rC(O)R^a$, —$C(O)OR^a$, —$C(O)NR^8R^9$, —$NR^8C(O)R^c$, —$NR^8C(O)OR^c$, —$NR^8C(O)NR^8R^c$, —$S(O)_pNR^8R^9$, —$NR^8SO_2R^c$, —$NR^7R^8$, $S(O)R^c$, —$S(O)_2R^c$, $C_{1-6}$ alkyl substituted with 0-1 $R^{2a}$, or a 5-7 membered heterocycle comprising carbon atoms and 1-4 heteroatoms selected from N, O, and $S(O)_p$, wherein said heterocycle is substituted with 0-2 $R^{2b}$;

alternately, when $R^1$ and $R^2$ groups are substituents on adjacent atoms they may be taken together with the atoms to which they are attached to form a 5- to 7-membered carbocycle or heterocycle comprising carbon atoms and 0-4 heteroatoms selected from N, O, and $S(O)_p$ and substituted with 0-2 $R^g$;

$R^3$ is, independently at each occurrence, phenyl substituted with 0-2 $R^{3a}$ and 0-1 $R^{3d}$, naphthyl substituted with 0-2 $R^{3a}$ and 0-1 $R^{3d}$, 1,2,3,4-tetrahydronaphthyl substituted with 0-2 $R^{3a}$ and 0-1 $R^{3d}$, or a 5- to 12-membered heterocycle substituted with 0-2 $R^{3a}$ and 0-1 $R^{3d}$, wherein said heterocycle is selected from: thiophene, furan, thiazole, tetrazole, pyridine, pyridone, pyrimidine, pyrrole, pyrazole, indole, 2-oxindole, isoindoline, indazole, 7-azaindole, benzofuran, benzothiophene, benzimidazole, benzisoxazole, benzoxazole, quinazoline, quinoline, isoquinoline, quinoxaline, phthalazine, dihydrophthalazine, dihydroisoquinoline, dihydroquinoline, dihydroquinolinone, dihydroindole, dihydrobenzimidazole, dihydrobenzoxazine, dihydroquinazoline, dihydroquinoxaline, benzothiazine, benzoxazine, tetrahydrobenzazepine, dihydroazabenzocycloheptene, and tetrahydroquinoline;

$R^{3a}$ is, independently at each occurrence, =O, F, Cl, Br, Me, CN, OH, OMe, —OC(O)(t-Bu), —$CH_2OMe$, $CF_3$, COMe, $CO_2H$, $CO_2Me$, —$CH_2CO_2H$, —$(CH_2)_2CO_2H$, —$CH_2CO_2Me$, —$CH_2CO_2Et$, —$CH_2CH_2CO_2Et$, —$CH_{12}CN$, $NH_2$, —$CH_2NH_2$, —$CH_2NMe_2$, —NHCOMe, —$NHCO_2Me$, —$NHCO_2Et$, —$NHCH_2CH_2CO_2H$, —$NHCO_2$(i-Pr), —$NHCO_2$(t-Bu), —$NHCO_2$(t-Bu), —$NHCO_2Bn$, —$NHCO_2CH_2CH_2OMe$, —$NHCO_2CH_2CH_2CH_2OMe$, —$NHCO_2CH_2CO_2H$, —$NHCO_2CH_2CH_2CO_2H$, —$NHCO_2CH_2CH_2OH$, —$NHCO_2CH_2CH_2NH_2$, —$NHCO_2CH_2$-tetrahydrofuran-2-yl, —$NHCO_2CH_2CH_2CH(Me)OMe$, —$NHCO_2CH_2C(O)NH_2$, —NHC(O)NHCH_2CH_2$-morpholino, —NHC(O)NHCH_2$-pyrid-4-yl, —$NHCO_2CH_2$-pyrid-4-yl, —$NHCO_2CH_2$-pyrid-3-yl, —$NHCO_2CH_2$-pyrid-2-yl, —NHCO₂CH₂-(piperidin-4-yl), —NHC(O)NHCH₂CH₂-pyrid-4-yl, —NHCO₂CH₂CH₂-pyrid-4-yl, —NHCO₂CH₂CH₂-morpholino, —CH₂NHCO₂Me, —NHC(O)NHMe, —NHC(O)N(Me)₂, —NHC(O)NHCH₂CH₂OMe, 4-[(1-carbamoyl-cyclopropanecarbonyl)-amino]-, —NHSO₂Me, —SO₂NH₂, —SO₂NHMe, —SO₂NHCH₂CH₂OH, —SO₂NHCH₂CH₂OMe, —CONH₂, —CONHMe, —CON(Me)₂, —C(O)NHCH₂CH₂OMe, —CH₂CONH₂, —CO(N-morpholino), —NHCH₂CH₂(N-morpholino), —NR⁷R⁸, —NH(1H-imidazol-2-yl), 1H-tetrazol-5-yl, tetrazol-1-yl, pyrimidin-5-yl, N-morpholino, or —(CH₂)ᵣ-5- to 6-membered heterocycle comprising: carbon atoms and 1-4 heteroatoms selected from N, O, and S(O)ₚ, wherein said heterocycle is substituted with 0-1 R³;

R⁴ is, independently at each occurrence, H, F, Cl, Br, OH, OMe, NH₂, Me, Et, CF₃, —CH₂OH, —C(O)₂H, CO₂Me, CO₂Et, —C(O)NH₂, —C(O)NHMe, —C(O)N(Me)₂, or —CH₂CO₂H;

R⁸ is, independently at each occurrence, H, C₁₋₆ alkyl or —(CH₂)ₙ-phenyl; and

R¹¹ is H

In an eleventh aspect, the present invention includes compounds of Formula (II), or stereoisomers, tautomers, pharmaceutically acceptable salts, solvates, or prodrugs thereof, within the scope of the eighth, ninth or tenth aspect wherein:

A is substituted with 0-1 R¹ and 0-3 R² and selected from: C₃₋₇ cycloalkyl, phenyl, naphthyl, 1,2,3,4-tetrahydronaphthyl, pyrrolidinyl, pyridyl, indazolyl, indolyl, imidazolyl furanyl, thienyl, benzimidazolyl, benzisoxazolyl, benzothiazolyl, benzothiophenyl, 3,4-methylenedioxy-phenyl, oxazolyl, isoxazolyl, thiazolyl, isothiazolyl, and pyrazolyl;

L₁ is —CH₂CH₂—, —CHNH₂)CH₂—, —CH(NHCOMe)CH₂—, —CH(NHCOEt)CH₂—, —CH(NHCO₂(t-Bu))CH₂—, —CH═CH—, —C(Me)═CH—, —C≡C—, —CH₂NH—, —CH(CH₂CO₂H)NH—, —CH₂O—, —NHNH—, —SCH₂—, —S(O)CH₂—, —SO₂CH₂— or —OCH₂—;

R¹ is, independently at each occurrence, F, Cl, Br, CF₃, NH₂, —CH₂NH₂, —C(═NH)NH₂, —C(O)NH₂, —SO₂NH₂, SRᵃ, ORᵃ, or C₁₋₆ alkyl substituted with 0-1 R¹ᵃ;

R² is, independently at each occurrence, ═O, F, Cl, Br, CF₃, Me, Et, ORᵃ, CN, NO₂, NR⁷R⁸, —CH₂OMe, SRᵃ, —CH₂SMe, —C(O)Rᵃ, —C(O)ORᵃ, —CH₂NR⁷R⁸, —SO₂NH₂, —SO₂Me, —NHSO₂Rᶜ, —CH₂NHSO₂Rᶜ, —C(O)NR⁸R⁹, —NHC(O)Rᶜ, —CH₂NHC(O)Rᶜ, —NHC(O)ORᶜ, —CH₂NHC(O)ORᶜ, —NHC(O)NHRᶜ, —CH₂NHC(O)NHRᶜ, or a 5-7 membered heterocycle substituted with 0-2 R²ᵇ and selected from: pyrrolidinyl, 2-oxo-1-pyrrolidinyl, piperidinyl, pyrazolyl, triazolyl, imidazolyl, and tetrazolyl;

alternately, when R¹ and R² groups are substituents on adjacent atoms they may be taken together with the atoms to which they are attached to form a 5- to 6-membered heterocycle comprising carbon atoms and 0-4 heteroatoms selected from N, O, and S(O)ₚ; —R³ is, independently at each occurrence, phenyl substituted with 0-2 R³ᵃ, naphthyl substituted with 0-2 R³ᵃ, or a 5- to 12-membered heterocycle comprising: carbon atoms and 1-2 heteroatoms selected from N, O, and S(O)ₚ, wherein said heterocycle is substituted with 0-2 R³ᵃ;

R³ᵃ is, independently at each occurrence, ═O, F, Cl, Br, Me, CN, OH, OMe, —OC(O)(t-Bu), CH₂OMe, CF₃, COMe, CO₂H, CO₂Me, —CH₂CO₂H, —(CH₂)₂CO₂H, —CH₂CO₂Me, —CH₂CO₂Et, —CH₂CO₂Et, —CH₂CN, NH₂, —CH₂NH₂, —CH₂NMe₂, —NHCOMe, —NHCO₂Me, —NHCO₂Et, —NHCH₂CH₂CO₂H, —NHCO₂(i-Pr), —NHCO₂(i-Bu), —NHCO₂(t-Bu), —NHCO₂Bn, —NHCO₂CH₂CH₂OMe, —NHCO₂CH₂CH₂CH₂OMe, —NHCO₂CH₂CO₂H, —NHCO₂CH₂CH₂CO₂H, —NHCO₂CH₂CH₂OH, —NHCO₂CH₂CH₂NH₂, —NHCO₂CH₂-tetrahydrofuran-2-yl, —NHCO₂CH₂CH₂CH(Me)OMe, —NHCO₂CH₂CH₂C(O)NH₂, —NHC(O)NHCH₂CH₂-morpholino, —NHC(O)NHCH₂-pyrid-4-yl, —NHCO₂CH₂-pyrid-4-yl, —NHCO₂CH₂-pyrid-3-yl, —NHCO₂CH₂-pyrid-2-yl, —NHCO₂CH₂-(piperidin-4-yl), —NHC(O)NHCH₂CH₂-pyrid-4-yl, —NHCO₂CH₂CH₂-pyrid-4-yl, —NHCO₂CH₂CH₂-morpholino, —CH₂NHCO₂Me, —NHC(O)NHMe, —NHC(O)N(Me)₂, —NHC(O)NHCH₂CH₂OMe, 4-[(1-carbamoyl-cyclopropanecarbonyl)-amino]-, —NHSO₂Me, —SO₂NH₂, —SO₂NHMe, —SO₂NHCH₂CH₂OH, —SO₂NHCH₂CH₂OMe, —CONH₂, —CONHMe, —CON(Me)₂, —C(O)NHCH₂CH₂OMe, —CH₂CONH₂, —CO(N-morpholino), —NHCH₂CH₂(N-morpholino), —NR⁷R⁸, —NH(1H-imidazol-2-yl), 1H-tetrazol-5-yl, tetrazol-1-yl, pyrimidin-5-yl, or N-morpholino, or —(CH₂)ᵣ-5- to 6-membered heterocycle comprising: carbon atoms and 1-4 heteroatoms selected from N, O, and S(O)ₚ, wherein said heterocycle is substituted with 0-1 R³ᵈ;

alternatively, two of R³ᵃ groups located on adjacent atoms, they can be taken together with the atoms to which they are attached to form a 5- to 10-membered heterocycle comprising: carbon atoms and 1-4 heteroatoms selected from N, O, and S(O)ₚ, wherein said heterocycle is substituted with 0-2 R³ᵈ;

R⁴ is, independently at each occurrence, H, F, Cl, Br, OMe, NH₂, CF₃, Me, Et, CO₂H, CO₂Me, or CO₂Et; and R⁸ is, independently at each occurrence, H or C₁₋₄ alkyl.

In a twelfth aspect, the present invention includes compounds of Formula (II), or stereoisomers, tautomers, pharmaceutically acceptable salts, solvates, or prodrugs thereof, within the scope of the eighth, ninth, tenth or eleventh aspect wherein;

A is substituted with 0-2 R² and selected from:

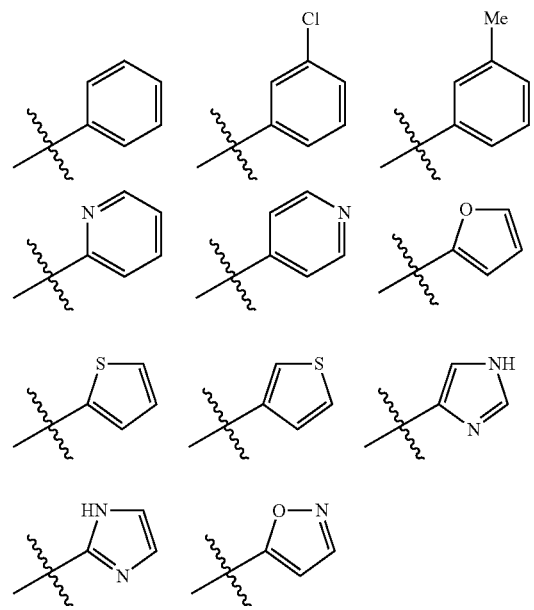

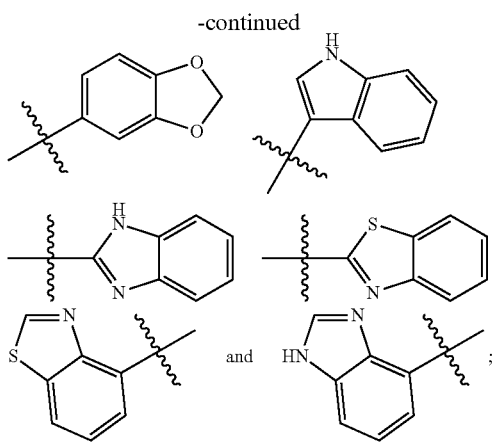

R² is, independently at each occurrence, =O, F, Cl, Br, Me, CF₃, OMe, OEt, OPh, OBn, SMe, SEt, S(n-Pr), SBn, —CH₂SMe, SO₂Me, SO₂NH₂, NH₂, —CH₂NH₂, NO₂, C(O)Me, CO₂H, CO₂Me, CONH₂, CONHMe, —CH₂NHCOPh, —NHCO₂Me, —CH₂NHCO₂Et, —CH₂NHCO₂(i-Pr), —CH₂NHCO₂(t-Bu), —CH₂NHCO₂Bn, —CH₂NHCO(CH₂)₂CO₂H, —CONHPh, —NHCONHMe, —CH₂NHCONHEt, —CH₂NHCONH(CH₂)₂CO₂Et, —CH₂NHCONHPh, —CH₂NHCONH(4-Cl-Ph), —CH₂NHCONHBn, —NHSO₂Me, —CH₂NHSO₂Me, —CH₂NHSO₂Et, —CH₂NHSO₂(n-Pr), —CH₂NHSO₂(i-Pr), —CH₂NHSO₂(n-pentyl), —C₁₋₂NHSO₂Ph, —CH₂NHSO₂(4-NHCOMe-Ph), —CH₂NHSO₂(4-Cl-Bn), —CH₂NHSO₂CH₂CH₂Ph, —CH₂NHSO₂CH₂CH₂(2-Cl-Ph), —CH₂NHSO₂CH₂CH₂(3-Cl-Ph), —CH₂NHSO₂CH₂CH₂(4-Cl-Ph), —CH₂NHSO₂(3,4-dimethyl-isoxazol-4-yl), 1-pyrrolidinyl, 2-oxo-1-pyrrolidinyl, 3-carboxy-N-piperidinyl, pyrazol-1-yl, 4-carboxy-pyrazol-1-yl, 1,2,3-triazol-1-yl, 1,2,4-triazol-1-yl, 1,2,3-triazol-2-yl, 4-carboxy-1,2,3-triazol-1-yl, 4-(ethoxycarbonyl)-1,2,3-triazol-1-yl, tetrazol-1-yl, tetrazol-5-yl, 5-Me-tetrazol-1-yl, 5-CF₃-tetrazol-1-yl, or —OCH₂(2-tetrahydrofuranyl);

R³ is, independently at each occurrence, phenyl substituted with 0-2 R³ᵃ, naphthyl substituted with 0-2 R³ᵃ, 1,2,3,4-tetrahydro-naphthyl substituted with 0-2 R³ᵃ, or a 5- to 12-membered heterocycle substituted with 0-2 R³ᵃ and selected from: thiophene, furan, thiazole, tetrazole, pyridine, pyridinone, pyrimidine, pyrrole, pyrazole, indole, 2-oxindole, isoindolin-1-one, indazole, 1H-indazole-3-one, 7-azaindole, benzofuran, benzothiophene, benzimidazole, benzisoxazole, benzoxazole, quinazoline, quinoline, isoquinoline, 3H-quinazolin-4-one, phthalazine, 2H-phthalazin-1-one, 2H-3,4-dihydrophthalazin-1-one, 1H-quinolin-4-one, 1H-quinolin-2-one, 2H-3,4-dihydroisoquinolin-1-one, 3,4-dihydro-1H-quinolin-2-one, 1,3-dihydroindol-2-one, 3H-benzoxazol-2-one, 1,3-dihydrobenzimidazol-2-one, 1,4-dihydro-3,1-benzoxazin-2-one, 3,4-dihydro-1H-quinazolin-2-one, 1,3-dihydro-quinazoline-2,4-dione, 1,4-dihydro-quinoxaline-2,3-dione, 4H-benzo[1,4]thiazine-3-one, 2H-benzo[1,4]thiazin-3(4H)-one, 4H-1,4-benzoxazin-3-one, 1,3,4,5-tetrahydro-1-benzazepin-2-one, 1,3,4,5-tetrahydro-1,3-benzodiazepin-2-one, 8,9-dihydro-5H-7-oxa-5-aza-benzocyclohepten-6-one, benzimidazol-2-one, 1,3-dihydrobenzimidazol-2-one, 3H-benzoxazol-2-one, 3H-quinazolin-4-one, and 1,2,3,4-tetrahydroquinoline;

R⁴ is, independently at each occurrence, H, Me, F, Br, Cl, CF₃, CO₂H, CO₂Me, or CO₂Et; and R⁸ is, independently at each occurrence, H or Me.

In a thirteenth aspect, the present invention includes compounds of Formula (II) or its stereoisomers, tautomers, pharmaceutically acceptable salts, solvates, or prodrugs thereof, within the scope of the eighth aspect wherein:

A is phenyl, 2-fluorophenyl, 3-fluorophenyl, 2-chlorophenyl, 3-chlorophenyl, 2-bromophenyl, 3-bromophenyl, 3-methylphenyl, 2-methoxyphenyl, 3-methoxyphenyl, 3-aminomethylphenyl, 4-aminomethylphenyl, 2-carboxy-5-chlorophenyl, 2-methoxycarbonyl-5-chlorophenyl, 2-N-(methoxycarbonyl)-amino)-5-chlorophenyl, 2-(N-(ethoxycarbonyl)-aminomethyl)-5-chlorophenyl, 2-(N-(isopropoxycarbonyl)-aminomethyl)-5-chlorophenyl, 2-(N-(tert-butoxycarbonyl)-aminomethyl)-5-chlorophenyl, 2-(phenylcarbonyl)-aminomethyl)-5-chlorophenyl, 2-N-(benzoxycarbonyl)-aminomethyl)-5-chlorophenyl, 2-((N-(3-propanoic acid)carbonyl)-aminomethyl)-5-chlorophenyl, 2-(3-methylureido)-5-chlorophenyl, 2-(3-ethylureidomethyl)-5-chlorophenyl, 2-[3-(2-ethoxycarbonyl-ethyl)-ureidomethyl]-5-chlorophenyl, 2-(3-phenylureido)methyl)-5-chlorophenyl, 2-(3-(4-chlorophenyl)ureido)methyl)-5-chlorophenyl, 2-(3-benzylureido)methyl)-5-chlorophenyl, 2-(N-(methylsulfonyl)-amino)-5-chlorophenyl, 2-(N-(methylsulfonyl)-aminomethyl)-5-chlorophenyl, 2-(N-(ethylsulfonyl)-aminomethyl)-5-chlorophenyl, 2-(N-(n-propylsulfonyl)-aminomethyl)-5-chlorophenyl, 2-(N-(isopropylsulfonyl)-aminomethyl)-5-chlorophenyl, 2-(N-(n-pentylsulfonyl)-aminomethyl)-5-chlorophenyl, 2-N-(phenylsulfonyl)-aminomethyl)-5-chlorophenyl, 2-((N-(4 methylcarbonylaminophenyl)sulfonyl)-aminomethyl)-5-chlorophenyl, 2-(N-(4-chlorobenzylsulfonyl)-aminomethyl)-5-chlorophenyl, 2-(N-(phenethylsulfonyl)-aminomethyl)-5-chlorophenyl, 2-(N-(2-chlorophenethylsulfonyl)-aminomethyl)-5-chlorophenyl, 2-(N-(3-chlorophenethylsulfoniyl)-aminomethyl)-S-chlorophenyl, 2-(N-(4-chlorophenethylsulfonyl)-aminomethyl)-5-chlorophenyl, 2-(N-3,4-dimethyl-isoxazol-4-yl)-aminomethyl)-5-chlorophenyl, 2-(N-(3,4-dimethyl-isoxazol-4-ylsulfonyl)-aminomethyl)-5-chlorophenyl, 3-carbamoyl-phenyl, 2,4-difluorophenyl, 2,5-difluorophenyl, 2,5-dichlorophenyl, 3,5-dichlorophenyl, 5-chloro-2-fluorophenyl, 3-chloro-2-fluorophenyl, 3-chloro-4-methylphenyl, 2-methyl-5-chlorophenyl, 2-methoxy-5-chlorophenyl, 2-ethoxy-5-chlorophenyl, 2-benzyloxy-5-chlorophenyl, 2-methylthio-5-chlorophenyl, 2-ethylthio-5-chlorophenyl, 2-propylthio-5-chlorophenyl, 2-benzylthio-5-chlorophenyl, 2-methylthiomethyl-5-chlorophenyl, 2-(2-oxo-1-pyrrolidinyl)-5-chlorophenyl, 3-trifluoromethyl-2-fluorophenyl, 2-trifluoromethyl-5-chlorophenyl, 5-bromo-2-fluorophenyl, 2-amino-5-chlorophenyl, 2-aminomethyl-5-chlorophenyl, 2-methylsulfonyl-5-chlorophenyl, 2-methylsulfonamide-5-chlorophenyl, 2-phenylcarbamoyl-5-chlorophenyl, 2-(3-carboxy-N-piperidinyl)-5-chlorophenyl, 2,6-difluoro-3-methylphenyl, 2-chloro-6-fluoro-3-methylphenyl, 2-fluoro-6-chloro-3-methylphenyl, 2,6-difluoro-3-chlorophenyl, 2,3-dichloro-6-aminophenyl, 2,3-dichloro-6-nitrophenyl, 2-phenoxyphenyl, 2-phenoxy-5-chlorophenyl, 2-(N-pyrrolidinyl)-5-chlorophenyl, 2-(pyrazol-1-yl)-5-chlorophenyl, 2-(4-carboxy-pyrazol-1-yl)-5-chlorophenyl, 2-(1,2,3-triazol-1-yl)-5-methylphenyl, 2-(1,2,3-triazol-1-yl)-5-chlorophenyl, 2-(1,2,3-triazol-2-yl)-5-chlorophenyl, 2-(1,2,4-triazol-1-yl)-5-chlorophenyl, 2-[(4-carboxy)-1,2,3-triazol-1-yl]-5-methylphenyl, 2-[(4-carboxy)-1,2,3-triazol-1-yl]-5-chlorophenyl, 2-[(4-ethoxycarbonyl)-1,2,3-triazol-1-yl]-5-chlorophenyl, 2-(tetrazol-1-yl)-5-methylphenyl, 2-(tetrazol-1-yl)-5-chlorophenyl, 2-(tetrazol-5-yl)-5-chlorophenyl, 2-(5-methyl-tetrazol-1-yl)-5-chlorophenyl, 2-(tetrazol-1-yl)-3-fluoro-5-chlorophenyl, 2-(tetrazol-1-yl)-3-fluoro-5-methylphenyl, 2-(5-methyltetrazol-1-yl)-5-chlorophenyl, 2-(5-trifluoromethyl-tetrazol-1-yl)-5-chlorophenyl, 2-(2-tetrahydrofuranyl-methoxy)-5-chlorophenyl, 3,4-methylenedioxy-phenyl, cyclopentyl, 2-oxo-1-pyrrolidinyl, 2-furanyl, 2-thienyl, 3-thienyl, 5-chloro-2-thienyl, 5-chloro- 3-thienyl, 2,5-dichloro-3-thienyl, 1-imidazolyl, 2-imidazolyl, 4-imidazolyl, 3-chloro-5-isoxazolyl, 4-pyridyl, 3-fluoro-2-pyridyl, 2(1H)-oxo-5-chloropyridin-1-yl, 1-indolyl, 3-indolyl, 2-benzimidazolyl, 6-chlorobenzimidazol-4-yl, 2-methyl-6-chlorobenzothiazol-4-yl or 2,6-dichlorobenzothiazol-4-yl, 2-[(3-carboxy)-pyrazol-1-yl]-5-chlorophenyl, 2-[(3-carboxy)-pyrazol-1-yl]-5-methylphenyl, 2-fluoro-3-chloro-6-(tetrazol-1-ylphenyl, 2-fluoro-3-chloro-6-(methylcarbonyl)phenyl, 2-methylcarbonyl-5-chlorophenyl, 2-(aminocarbonyl)-5-chlorophenyl, 2-(methylaminocarbonyl)-5-chlorophenyl, or 2-(aminosulfonyl)-5-chlorophenyl;

$L_1$ is —CH$_2$CH$_2$—, —CH=CH—, —C(Me)=CH—, —C≡C—, —CH$_2$NH—, —CH$_2$O—, —NHNH—, —SCH$_2$—, —S(O)CH$_2$—, —SO$_2$CH$_2$— or —OCH$_2$—;

$R^3$ is, independently at each occurrence, phenyl, 3-biphenyl, 4-biphenyl, 3-aminophenyl, 4-aminophenyl, 3-N,N-dimethylaminophenyl, 4-phenoxyphenyl, 4-benzyloxyphenyl, 4-(t-butoxymethyl)-phenyl, 4-methylsulfonylphenyl, 3-cyanophenyl, 4-cyanophenyl, 3-fluorophenyl, 4-fluorophenyl, 3-chlorophenyl, 4-chlorophenyl, 3-bromophenyl, 4-bromophenyl, 3-hydroxyphenyl, 4-hydroxyphenyl, 2-methoxyphenyl, 3-methoxyphenyl, 4-methoxyphenyl, 3-trifluoromethylphenyl, 4-trifluoromethylphenyl, 3-carboxyphenyl, 4-carboxyphenyl, 3-methoxycarbonylphenyl, 4-methoxycarbonylphenyl, 3-carboxymethylphenyl, 4-carboxymethylphenyl, 4-methoxycarbonylmethylphenyl, 3-ethoxycarbonylmethylphenyl 4-ethoxycarbonylmethylphenyl, 4-ethoxycarbonylethylphenyl, 3-carbamoylphenyl, 4-carbamoylphenyl, 3-aminocarbonylmethylphenyl, 4-aminocarbonylmethylphenyl, 4-methylaminocarbonylphenyl, 4-dimethylaminocarbonylmethylphenyl, 4-amidinophenyl, 3-methylcarbonylaminophenyl, 4-methylcarbonylaminophenyl, 4-methoxycarbonylaminophenyl, 4-aminosulfonylphenyl, 3-methylsulfonylaminophenyl, 4-methylsulfonylamino, 2,4-difluorophenyl, 3-fluoro-4-cyanophenyl, 4-amino-3-carboxyphenyl, 4-amino-3-methoxycarbonylphenyl, 2,4-dichlorophenyl, 3-cyano-5-fluorophenyl, 3-fluoro-4-carbamoylphenyl, 3-carboxy-4-cyanophenyl, 3-phenyl-4-carbamoylphenyl, 4-(2-oxo-1-piperidino)-phenyl, thiazol-2-yl, thien-2-yl, 4-methoxycarbonyl-thiazol-2-yl, 4-carbamoyl-thiazol-2-yl, 1-benzyl-pyazol-4-yl, 5-phenyl-oxazol-2-yl, 5-carbamoyl-thien-2-yl, 5-carboxy-thien-2-yl, pyrid-2-yl, pyrid-3-yl, pyrid-4-yl, 6-amino-pyrid-3-yl, benzimidazol-2-yl, 6-methoxy-pyrid-3-yl, 1-methyl-benzimidazol-2-yl, benzoxazol-2-yl, benzothiazol-2-yl, 3-aminobenzisoxazol-6-yl, 3-amino-benzisoxazol-5-yl, indazol-5-yl, indazol-6-yl, 3-amino-indazol-5-yl, 3-hydroxy-indazol-5-yl, 3-amino-indazol-6-yl, 3-amino-1-methyl-indazol-6-yl, 3-amino-4-fluoro-indazol-6-yl, 3-amino-5-fluoro-indazol-6-yl, 3-amino-7-fluoro-indazol-6-yl, 4-imino-3,4-dihydro-2H-phthalazin-1-on-7-yl, 3-(5-tetrazolyl)-phenyl, 2,3-dihydro-isoindol-1-on-6-yl, quinolin-5-yl, quinolin-6-yl, quinolin-8-yl, isoquinolin-5-yl, 2H-isoquinolin-1-on-6-yl, 2,4-diaminoquinazolin-7-yl, 4-NH$_2$-quinazolin-7-yl,

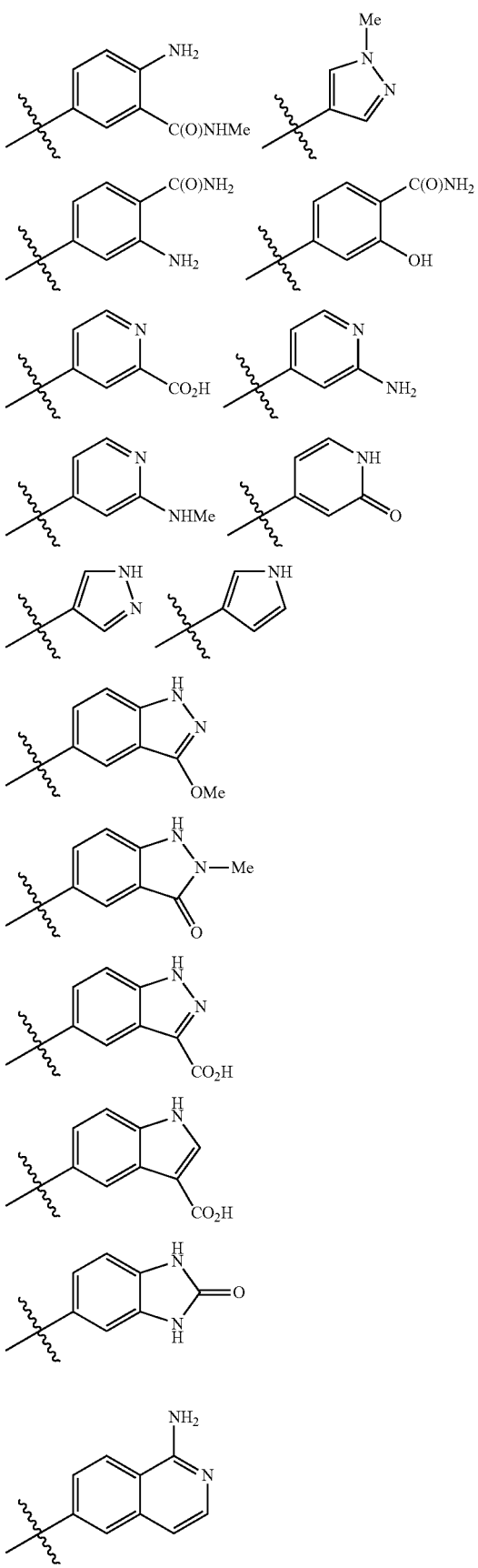

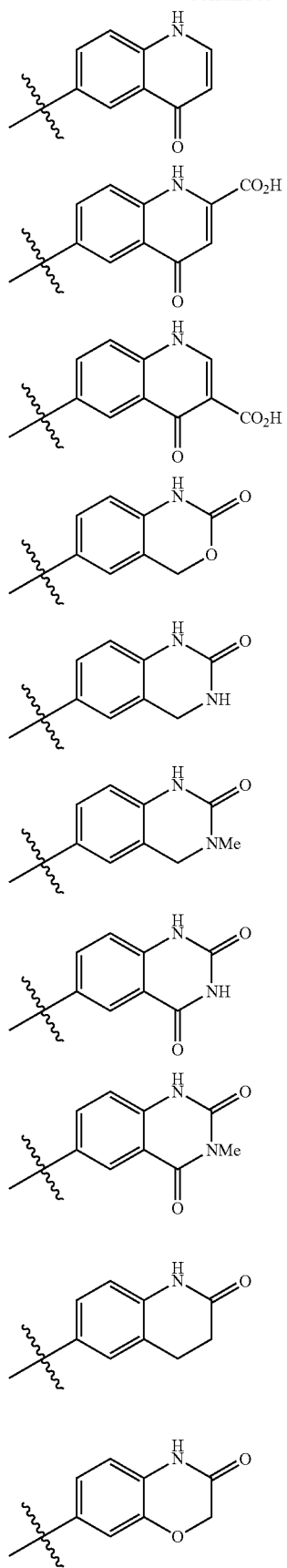
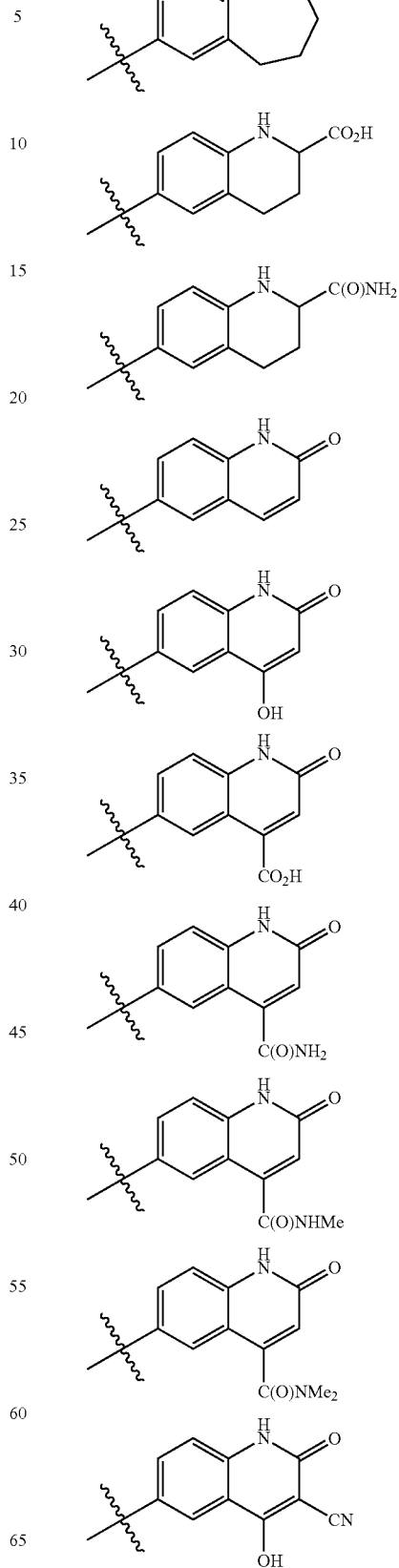

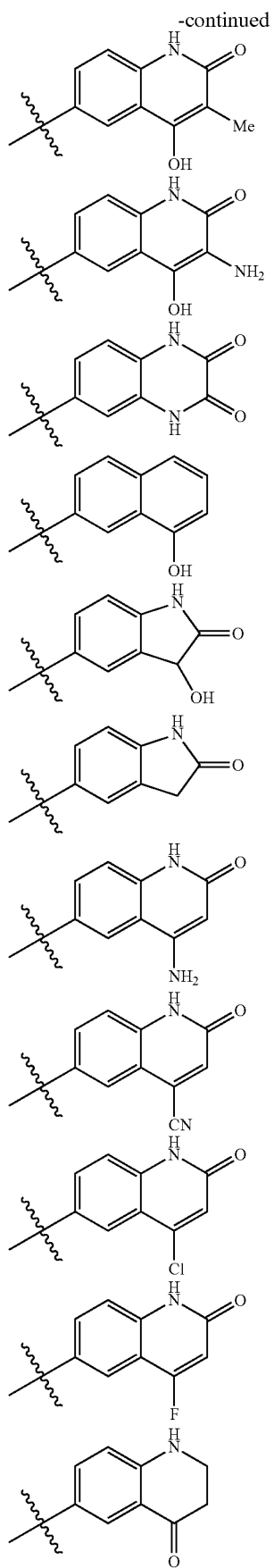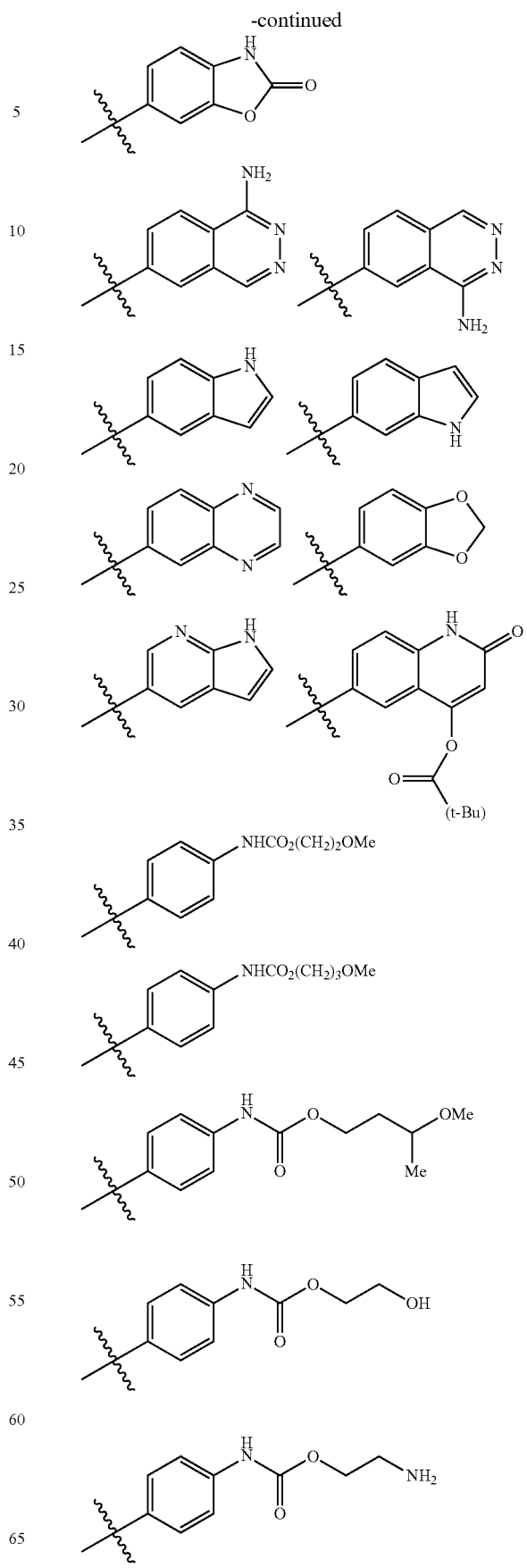

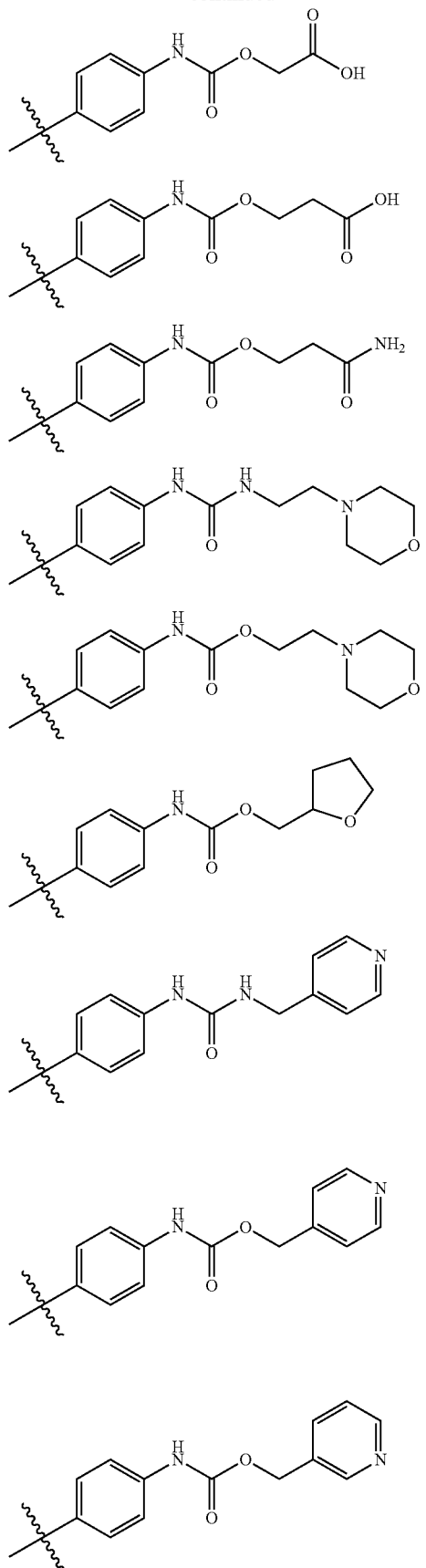
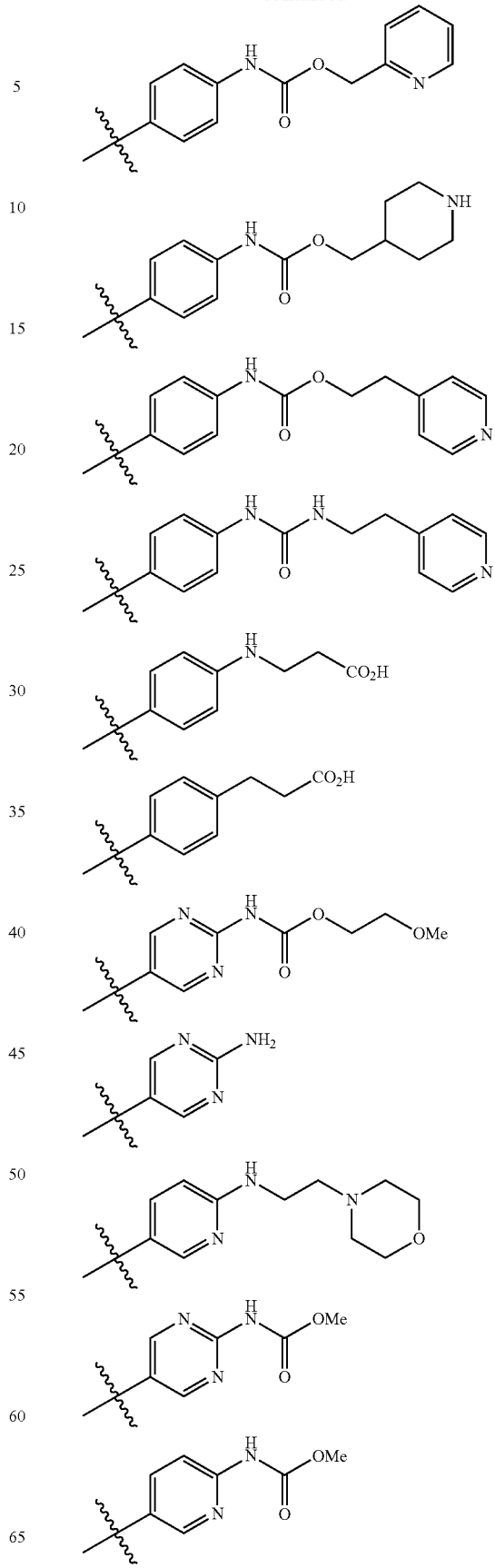

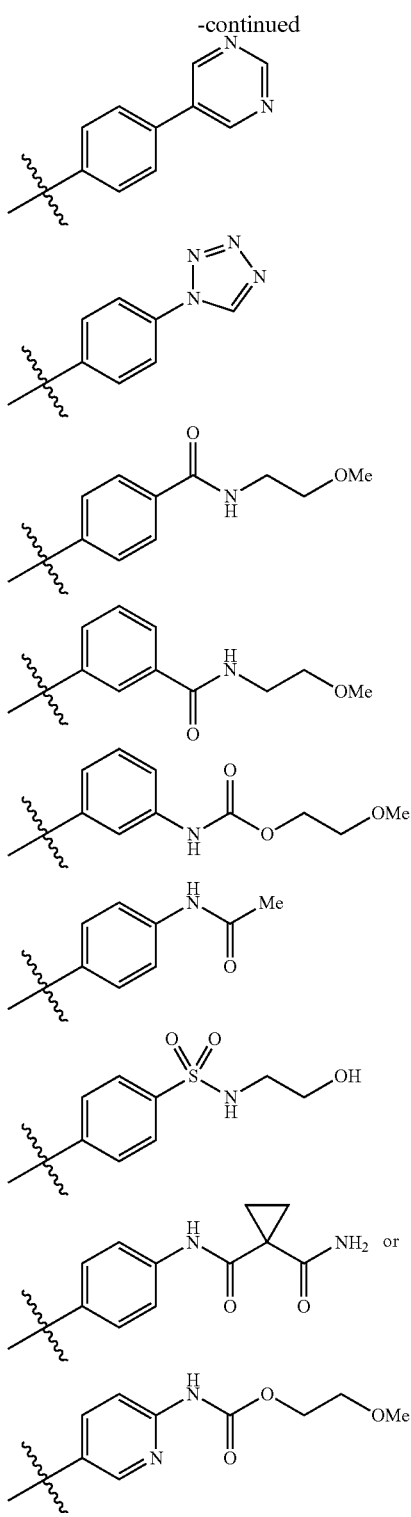

$R^4$ is, independently at each occurrence, H, Me, F, Br, Cl, $CF_3$, $CO_2H$, $CO_2Me$, or $CO_2Et$; and
$R^8$ is, independently at each occurrence, H or Me.

In a fourteenth aspect, the present invention includes compounds of Formula (II) or its stereoisomers, tautomers, pharmaceutically acceptable salts, solvates, or prodrugs thereof, within the scope of the eighth aspect wherein:

A is 3-chlorophenyl, 3-methylphenyl, 2,5-dichlorophenyl, 5-chloro-2-fluorophenyl, 3-chloro-2-fluorophenyl, 2-methyl-5-chlorophenyl, 2-methoxy-5-chlorophenyl, 2-methylthio-5-chlorophenyl, 2-ethylthio-5-chlorophenyl, 2-propylthio-5-chlorophenyl, 2-benzylthio-5-chlorophenyl, 2-amino-5-chlorophenyl, 2-aminomethyl-5-chlorophenyl, 2,6-difluoro-3-methylphenyl, 2-chloro-6-fluoro-3-methylphenyl, 2-fluoro-6-chloro-3-methylphenyl, 2,6-difluoro-3-chlorophenyl, 2,3-dichloro-6-nitrophenyl, 5-chloro-2-thienyl, 3,4-methylenedioxyphenyl, 2-methoxycarbonyl-5-chlorophenyl, 6-chlorobenzimidazol-4-yl, 2-[(4-carboxy)-pyrazol-1-yl]-5-chlorophenyl, 2-[(4-carboxy)-pyrazol-1-yl]-5-methylphenyl, 2-(1,2,3-triazol-1-yl)-5-methylphenyl, 2-(1,2,3-triazol-1-yl)-5-chlorophenyl, 2-(1,2,4-triazol-1-yl)-5-chlorophenyl, 2-(1,2,3-triazol-2-yl)-5-chlorophenyl, 2-[(4-carboxy)-1,2,3-triazol-1-yl]-5-chlorophenyl, 2-[(4-carboxy)-1,2,3-triazol-1-yl]-5-methylphenyl, 2-[(4-ethoxycarbonyl)-1,2,3-triazol-1-yl]-5-chlorophenyl, 2-(tetrazol-1-yl)-5-methylphenyl, 2-(tetrazol-1-yl)-5-chlorophenyl, 2-(tetrazol 1-yl)-3-fluoro-5-chlorophenyl, 2-(tetrazol-1-yl)-3-fluoro-5-methylphenyl, 2-(5-methyltetrazol-1-yl)-5-chlorophenyl, 2-fluoro-3-chloro-6-(tetrazol-1-yl)phenyl, 2-fluoro-3-chloro-6-(methylcarbonyl)phenyl, or 2-methylcarbonyl-5-chlorophenyl;

$L_1$ is —$CH_2CH_2$—, —CH=CH—, —C(Me)=CH—, —C≡C—, or —$CH_2NH$—;

$R^3$ is, independently at each occurrence,

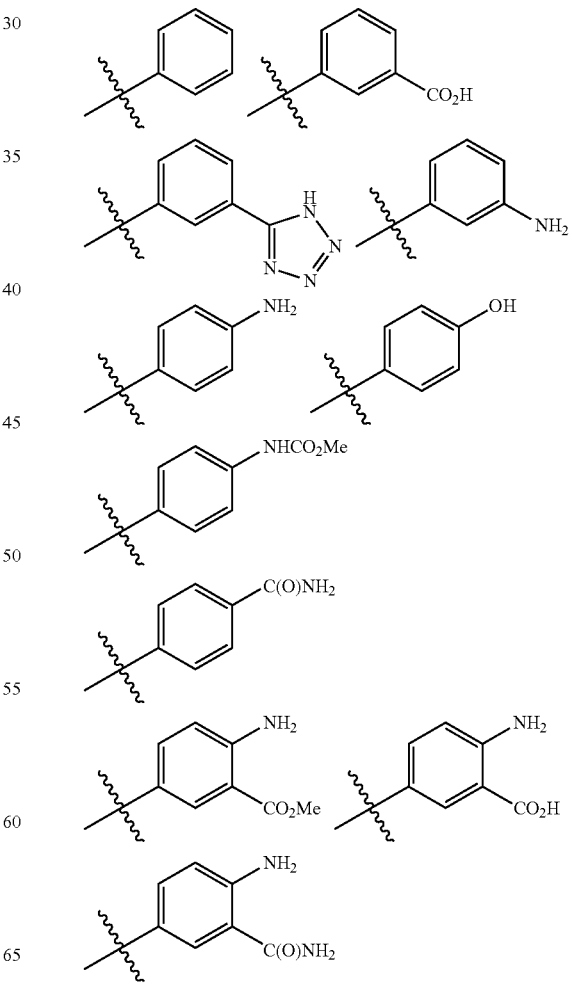

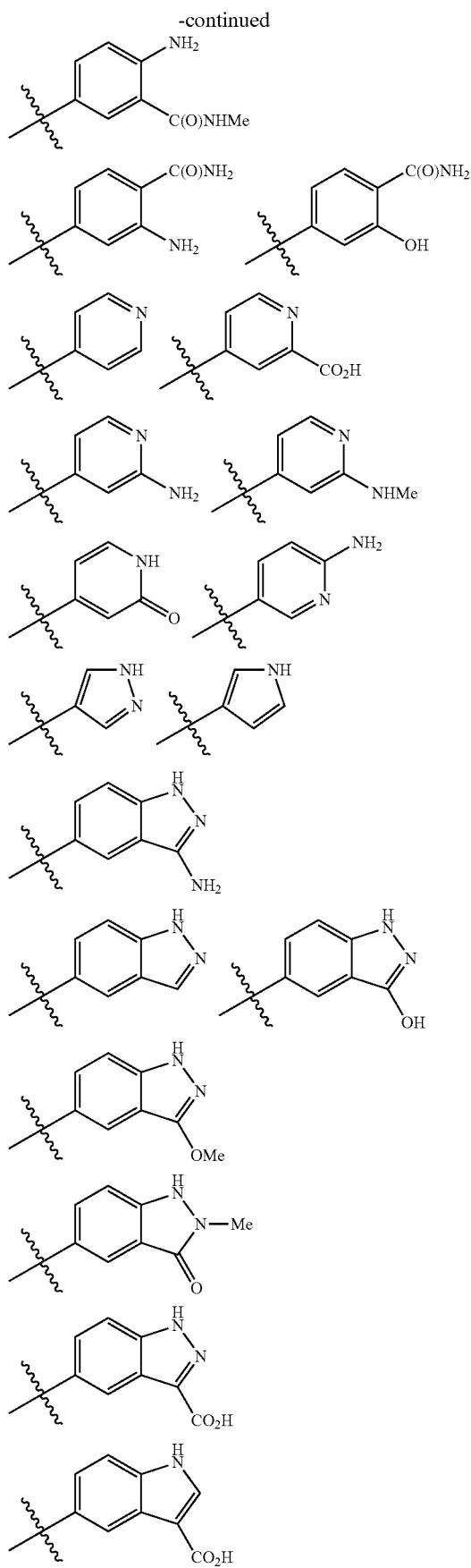
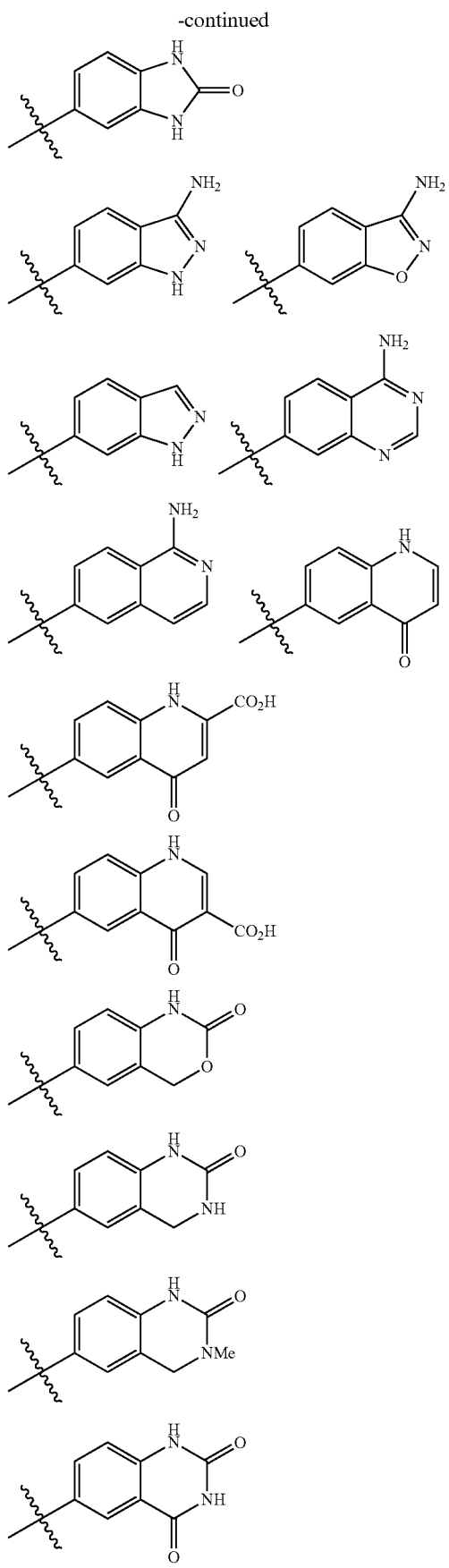

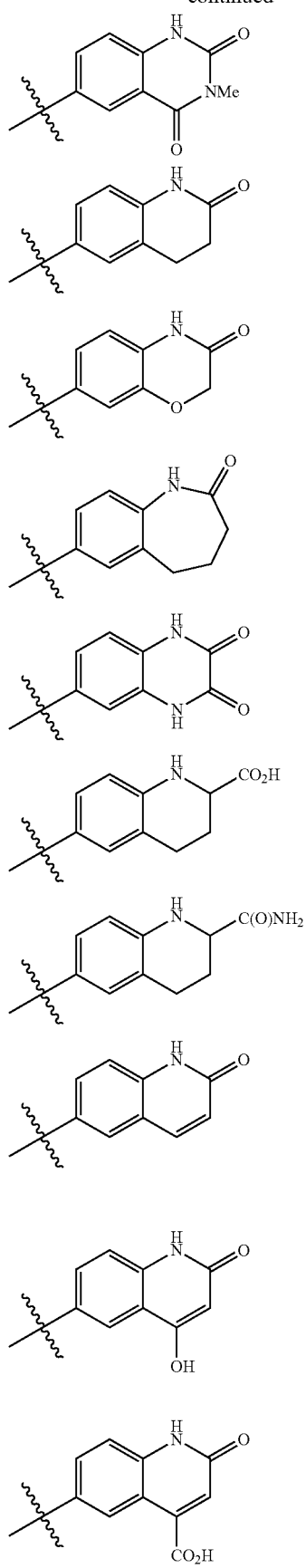
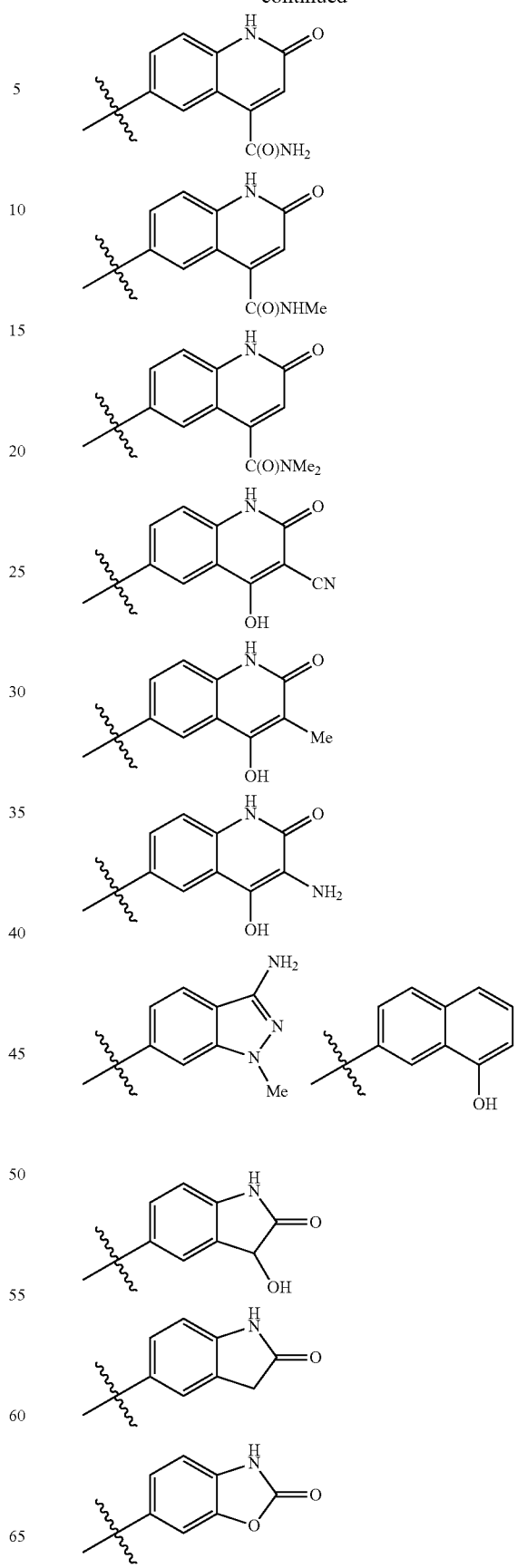

-continued
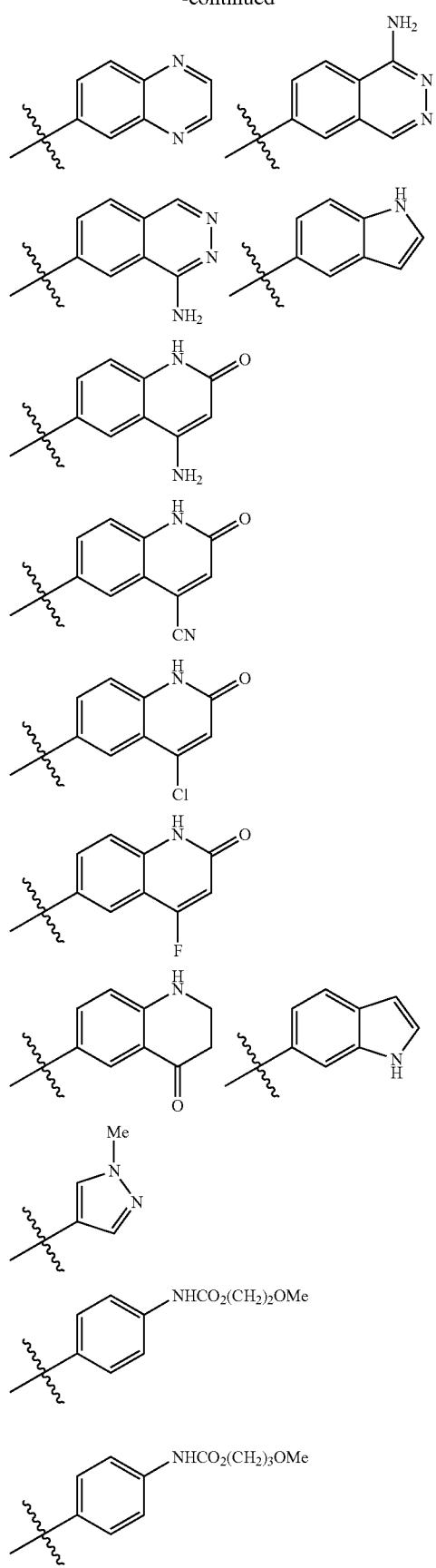
-continued
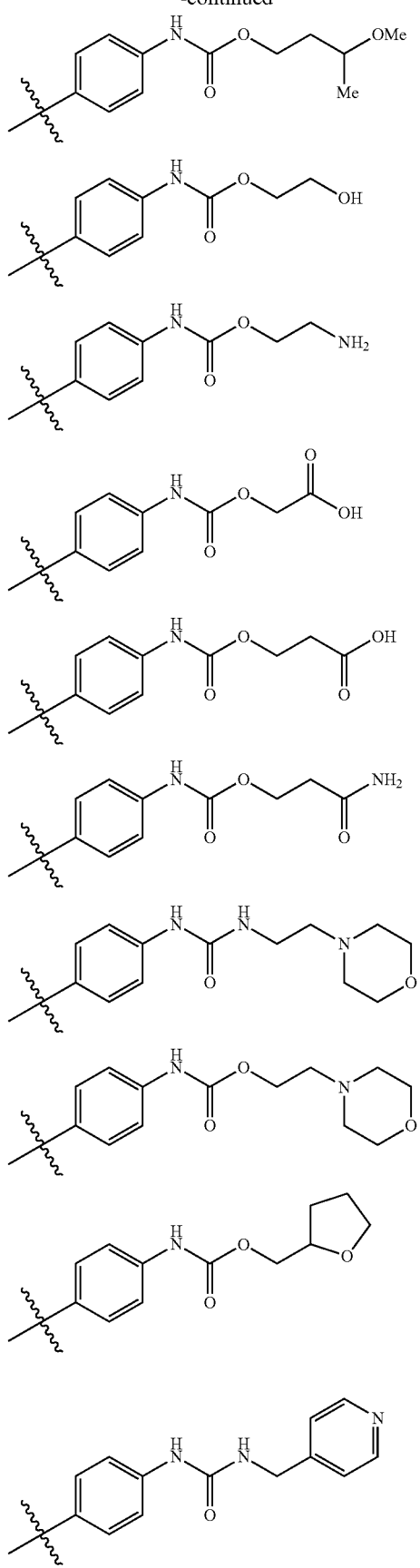

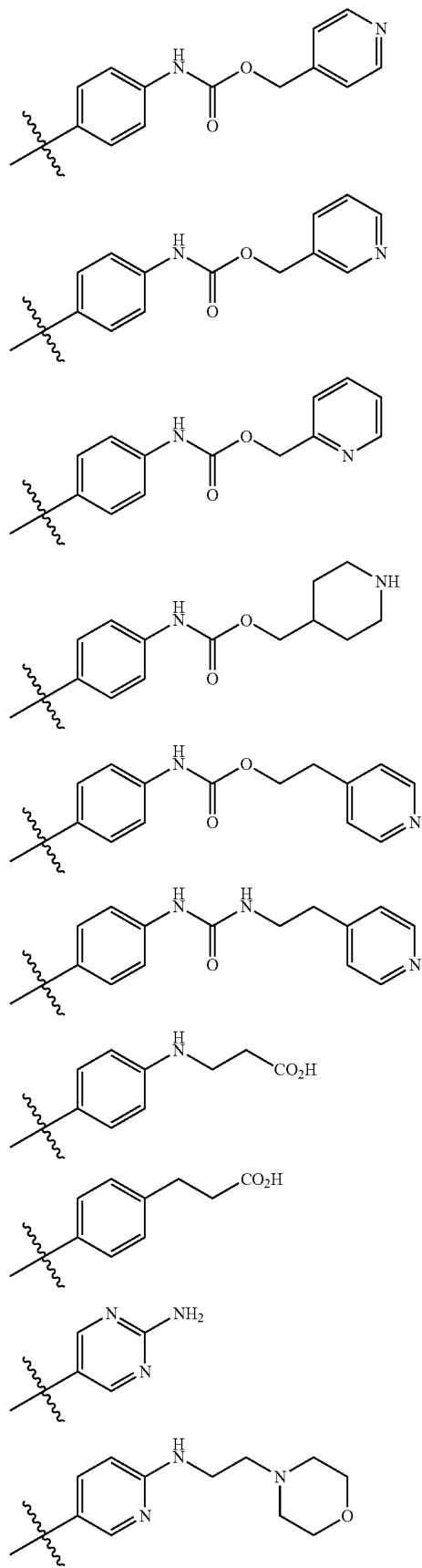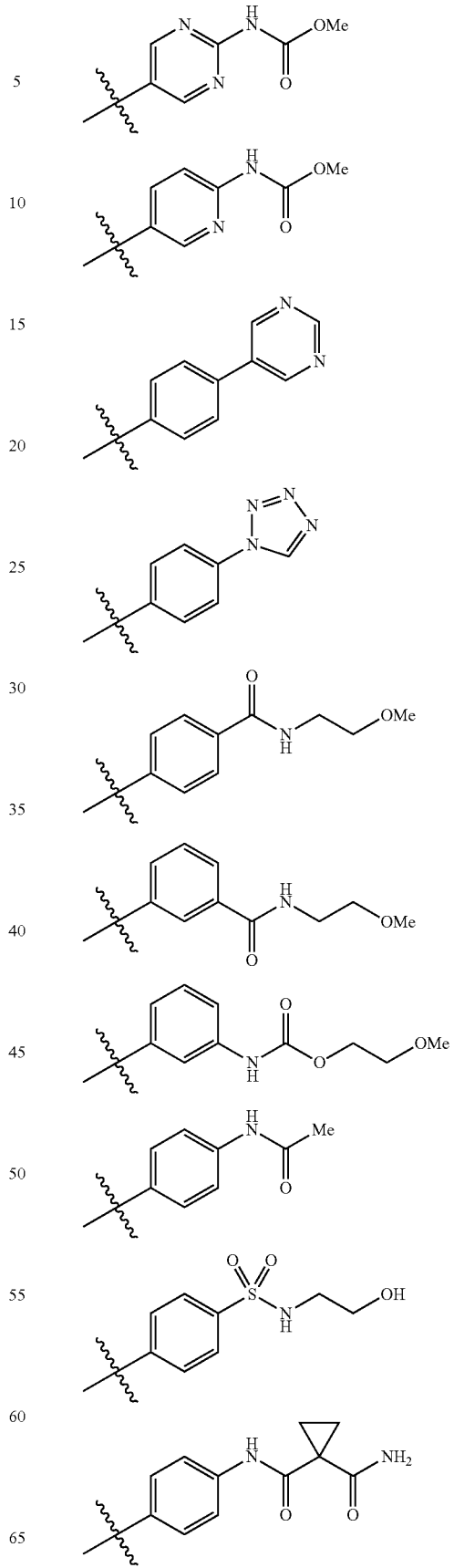

-continued
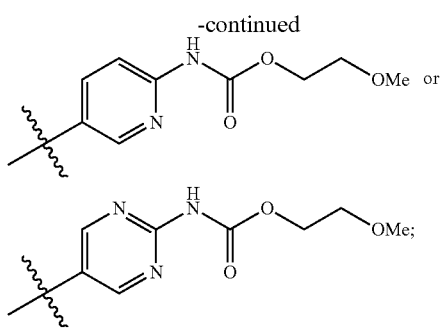
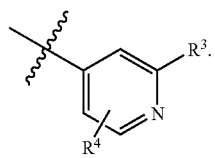
$R^4$ is, independently at each occurrence, H, Me, or Cl;
$R^8$ is, independently at each occurrence, H or Me; and
$R^{11}$ is H.
In another embodiment, M is
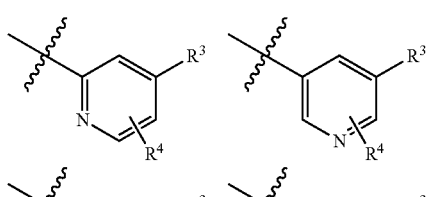
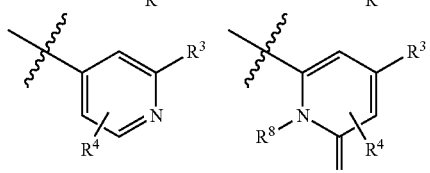
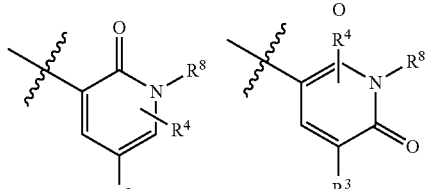
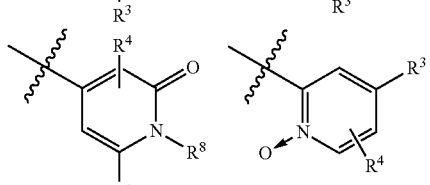
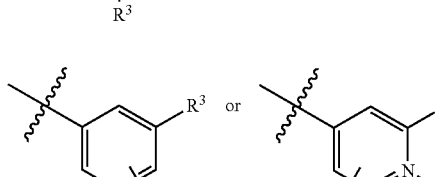
In another embodiment, M is
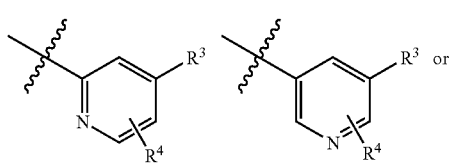
In another embodiment, M is
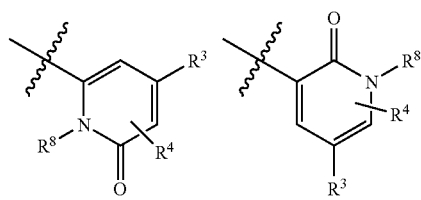
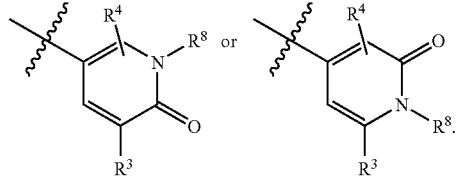
In another embodiment, M is
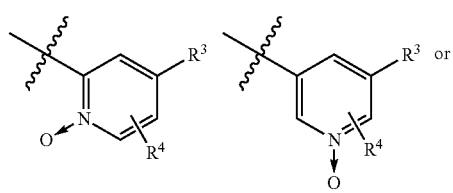
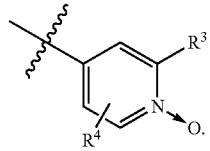
In another embodiment, M is
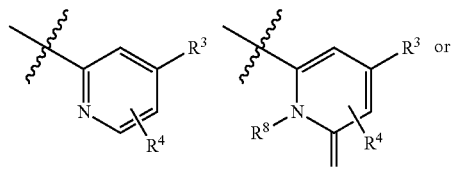
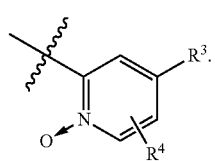

In another embodiment, M is

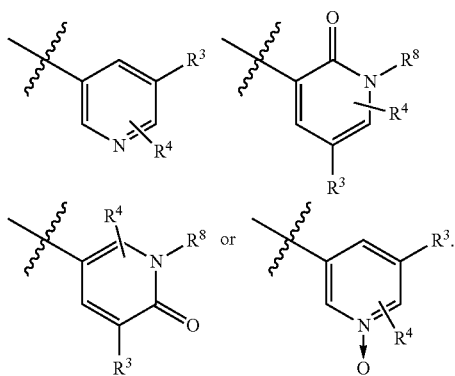

In another embodiment, M is

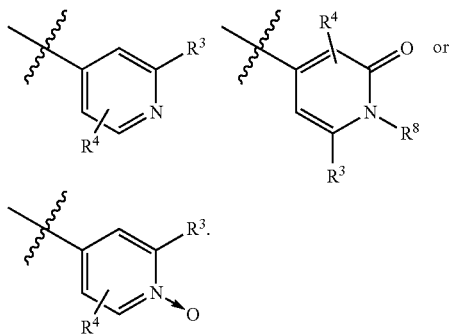

In another embodiment, M is

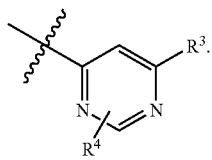

II. Other Embodiments of the Invention

In another embodiment, the present invention provides a composition comprising at least one of the compounds of the present invention or a stereoisomer, tautomer, pharmaceutically acceptable salt, solvate, or prodrug thereof.

In another embodiment, the present invention provides a pharmaceutical composition comprising a pharmaceutically acceptable carrier and at least one of the compounds of the present invention or a stereoisomer, tautomer, pharmaceutically acceptable salt, solvate, or prodrug thereof.

In another embodiment, the present invention provides a pharmaceutical composition, comprising: a pharmaceutically acceptable carrier and a therapeutically effective amount of at least one of the compounds of the present invention or a stereoisomer, tautomer, pharmaceutically acceptable salt, solvate or prodrug thereof.

In another embodiment, the present invention provides a process for making a compound of the present invention or a stereoisomer, tautomer, pharmaceutically acceptable salt, solvate or prodrug thereof.

In another embodiment, the present invention provides an intermediate for making a compound of the present invention or a stereoisomer, tautomer, pharmaceutically acceptable salt, solvate or prodrug thereof.

In another embodiment, the present invention provides a pharmaceutical composition further comprising additional therapeutic agents). In a preferred embodiment, the present invention provides pharmaceutical composition, wherein the additional therapeutic agents) are an anti-platelet agent or a combination thereof. Preferably, the anti-platelet agent(s) are clopidogrel and/or aspirin, or a combination thereof.

In another embodiment, the present invention provides a method for the treatment or prophylaxis of a thromboembolic disorder comprising administering to a patient in need of such treatment or prophylaxis a therapeutically effective amount of at least one of the compounds of the present invention or stereoisomers, tautomers, pharmaceutically acceptable salts, solvates, or prodrugs thereof. Preferably, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders. Preferably, the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a compound of the present invention or stereoisomers, tautomers, pharmaceutically acceptable salts, solvates, or prodrugs thereof, for use in therapy.

In another embodiment, the present invention provides a compound of the present invention or stereoisomers, tautomers, pharmaceutically acceptable salts, solvates, or prodrugs thereof, for use in therapy for the treatment or prophylaxis of a thromboembolic disorder. Preferably, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders. Preferably, the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention also provides the use of a compound of the present invention or stereoisomers, tautomers, pharmaceutically acceptable salts, solvates, or prodrugs thereof, for the manufacture of a medicament for the treatment or prophylaxis of a thromboembolic disorder.

In another embodiment, the present invention provides a method for treating a thromboembolic disorder, comprising: administering to a patient in need thereof a therapeutically effective amount of a first and second therapeutic agent, wherein the first therapeutic agent is a compound of the present invention or a stereoisomer, tautomer, pharmaceutically acceptable salt, solvate or prodrug thereof, and the second therapeutic agent is at least one agent selected from a second factor Xa inhibitor, an anti-coagulant agent, an anti-platelet agent, a thrombin inhibiting agent, a thrombolytic agent, and a fibrinolytic agent. Preferably, the second therapeutic agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof.

In another embodiment, the present invention provides a method for the treatment or prophylaxis of an inflamatory disorder comprising: administering to a patient in need of such treatment or prophylaxis a therapeutically effective amount of at least one of the compounds of the present invention or a stereoisomer, tautomer, pharmaceutically acceptable salt, solvate or prodrug thereof.

In another embodiment, the present invention provides a method for the treatment or prophylaxis of an inflammatory disorder, wherein the inflammatory disorder is selected from the group consisting of sepsis, acute respiratory distress syndrome, and systemic inflammatory response syndrome.

In another embodiment, the present invention provides a combined preparation of a compound of the present invention and additional therapeutic agents) for simultaneous, separate or sequential use in therapy.

In another embodiment, the present invention provides a combined preparation of a compound of the present invention and additional therapeutic agent(s) for simultaneous, separate or sequential use in treatment or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeiic and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The molecular weight of compounds of the present invention is preferably less than about 800 grams per mole.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1, C_2, C_3, C_4, C_5, C_6, C_7, C_8, C_9$, and $C_{10}$ alkyl groups. Additionally, for example, "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

Alkenyl" or "alkenylene" is intended to include hydrocarbon chains of either straight or branched configuration having the specified number of carbon atoms and one or more carbon-carbon double bonds that may occur in any stable point along the chain. For example, "$C_{2-6}$ alkenyl" (or alkenylene), is intended to include $C_2, C_3, C_4, C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more carbon-carbon triple bonds that may occur in any stable point along the chain. For example, "$C_{2-6}$ alkynyl" (or alkynylene), is intended to include $C_2, C_3, C_4, C_5$, and $C_6$ alkynyl groups; such as ethynyl, propynyl, butynyl, pentynyl, and hexynyl.

The term "alkoxy" or "alkyloxy" refers to an —O-alkyl group. "$C_{1-6}$ alkoxy" (or alkyloxy), is intended to include $C_1, C_2, C_3, C_4, C_5$, and $C_6$ alkoxy groups. Example alkoxy groups include, but are not limited to, m-ethoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2- trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9 or 10-membered carbocyclic ring system that contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in *Hawley's Condensed Chemical Dictionary* (13 ed.), R. J. Lewis, ed., J. Wiley & Sons, Inc., New York (1997). "$C_{6-10}$ aryl" refers to phenyl and naphthyl. Unless otherwise specified, "aryl", "$C_{6-10}$ aryl" or "aromatic residue" may be unsubstituted or substituted with 1 to 3 groups selected from OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., NO and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azocinyl, benzimidazolyl, benzofuranyl, benzothiofuranyl, benzothiophenyl, benzoxazolyl, benzoxazolinyl, benztlhiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolin-yl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzisoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9 or 10-membered heterocyclic ring system which contains two fused rings and consists of carbon atoms and 1, 2, 3, or 4 heteroatoms independently selected from the group consisting of N, O and S. Of the two fused rings, one ring is a 5 or 6-membered monocyclic aromatic ring comprising a 5 membered heteroaryl ring, a 6-membered heteroaryl ring or a benzo ring, each fused to a second ring. The second ring is a 5 or 6 membered monocyclic ring which is saturated, partially unsaturated, or unsaturated, and comprises a 5 membered heterocycle, a 6 membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N—O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases in which there are quarternary carbon atoms in compounds of the present invention, these can be replaced by silicon atoms, provided they do not form Si—N or Si—O bond.

When any variable occurs more than one time in any constituent or formula for a compound, its definition at each occurrence is independent of its definition at every other occurrence. Thus, for example, if a group is shown to be substituted with 0-3 $R^{3a}$, then said group may optionally be substituted with up to three $R^{3a}$ groups, and at each occurrence $R^{3a}$ is selected independently from the definition of $R^{3a}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional nontoxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18$^{th}$ Edition, Mack Publishing Company, Easton, Pa., 1990, the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see, a) Design of Prodrugs, edited by H. Bundgaard, (Elsevier, 1985), and *Methods in Enzymology*, Vol. 42, at pp. 309-396, edited by K. Widder, et. al. (Academic Press, 1985);

b) A Textbook of Drug Design and Development, edited by Krosgaard-Larsen and H. Bundgaard, Chapter 5, "Design and Application of Prodrugs," by H. Bundgaard, at pp. 113-191 (1991);

c) H. Bundgaard, *Advanced Drug Delivery Reviews*, Vol. 8, p. 1-38 (1992);

d) H. Bundgaard, et al., *Journal of Pharmaceutical Sciences*, Vol. 77, p. 285 (1988); and e) N. Kakeya, et al., *Chem Phar Bull.*, Vol. 32, p. 692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_1$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g. acetoxymethyl, pivaloyloxymethyl or propionyloxymethyl), $C_{1-6}$alkoxycarbonyloxy-$C_{1-6}$alkyl (e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, *Medicinal Chemistry: Principles and Practice*, ed. F. D. King, The Royal Society of Chemistry, Cambridge, UK, 1994.

Isotopically labeled compounds of the present invention, i.e., wherein one or more of the atoms described are replaced by an isotope of that atom (e.g., $^{12}$C replaced by $^{13}$C or by $^{14}$C; and isotopes of hydrogen include tritium and deuterium), are also provided herein. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate", means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "C" for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "th" for hour or hours, "rt" for room temperature, "RT" for retention time, "atm" for atmosphere, "psi" for pounds per square inch, "conie." for concentrate, "saf" or "sat'd" for saturated, "MW" for molecular weight, "imp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "6" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu Bautyl
i-Bu isobutyl
t-Bu tertbutyl
Ph phenyl
Bn benzyl
AcOH acetic acid
MeOH methanol EtOH ethanol
EtOAc ethyl acetate
Et$_2$O diethyl ether
i-PrOH or TPA isopropanol
HOAc acetic acid
BEMP 2-t-butylimino-2-diethylamino-1,3-dimethyl-perhydro-1,3,2-diazaphosphorine
BOP reagent benzotriazol-1-yloxytris(dimethylaminophosphonium hexafluorophosphate
BBr$_3$ boron tribromide
BINAP rac-2,2'-Bis(diphenylphosphino) 1,1'-binaphthyl
Boc tert-butyloxycarbonyl
2MeS-ADP 2 methylthio adenosine diphosphate
cDNA complimentary DNA
CHCl$_2$ dichloromethane
CH$_3$CN acetonitrile
Cs$_2$CO$_3$ cesium carbonate
ACN acetonitrile
CDI 1,1'-carbonyldiimidazole
DABCO 1,4-diazabicyclo[2.2.2]octane
DBAD di-tert-butylazodicarboxylate
DBU 1,8-diazabicyclo[5.4.0]undec-7-ene
DCE 1,2 dichloroethane
DCM dichloromethane
DCC dicyclohexylcarbodiimide
DEAD diethylazodicarboxyalte
DIBAL-H diisobutylaluminum hydride
DIC or DIPCDI diisopropylcarbodiimide
DIFA or DIPEA N,N,-diisopropylethylamine
DMEM Dulbecco's modified Eagle media
DME 1,2-dimethoxyethane
DMF dimethyl formamide
DMSO dimethyl sulfoxide
DPPA diphenyl phosphoryl azide
EDC (or EDC.HCl) or EDCI (or EDCI.HCl) or EDAC 3-ethyl-3'-(dimethylamino)propyl-carbodiimide hydrochloride (or 1-(3-dimethylaminopropyl)-3-ethylcarbodiimide hydrochloride)
EDTA ethylenediaminetetraacetic acid
FBS Fetal Bovine Serum
HATU O-(7-azabenzotriazol-1-yl)-N,N,N',N'-tetramethyluronium hexafluorophosphate
HCl hydrochloric acid
HEPES 4-(2-hydroxyethyl)piperaxine-1-ethanesulfonic acid
Hex hexane
HOBt or HOBT 1-hydroxybenzotriazole monohydrate
Hunig's base N,N-diisopropylethyl amine
LAH lithium aluminum hydride
LDA Lithium diisopropylamide
LiHMDS Lithium bis(trimethylsilyl)amide
mCPBA or m-CPBA meta-chloroperbenzoic acid
NBS N-bromosuccinimide
NCS N-chlorosuccinimide
D-PBS Dulbecco's Phosphate Buffered Saline
Pd/C palladium on carbon
PCy$_3$ tricyclohexyl phosphine
PPA polyphosphoric acid
PPTS pyridinium p-toluenesulfonate
PS polystyrene
PXPd2 bis[di-tert-butyl phosphinous chloride-kP]di-m-chlorodichloro dipalladium
PyBOP (benzotriazol-1-yloxy)tripyrrolidinophosphonium hexafluorophosphate
SCX Strong Cation Exchanger
SEM-Cl 2-(trimethylsilyl)ethoxymethyl chloride
TEA triethylamine
TFA trifluoroacetic acid
THF tetrahydrofuran
TMSBr trimethylsilyl bromide
TRIS tris(hydroxymethyl)aminomethane
KOAc potassium acetate
K$_3$PO$_4$ potassium phosphate
MgSO$_4$ magnesium sulfate
NaCl sodium chloride
NaH sodium hydride
NaHCO$_3$ sodium bicarbonate
NaOH sodium hydroxide
Na$_2$SO$_3$ sodium sulfite
Na$_2$SO$_4$ sodium sulfate
NH$_3$ ammonia
NH$_4$Cl ammonium chloride
NH$_4$OH ammonium hydroxide
OTs tosylate, para-toluenesulfonate
PBr$_3$ phosphorous tribromide
Pd$_2$(dba)$_3$ tris(dibenzylideneacetone)dipalladium (0)
Pd(dppf)Cl$_2$.CH$_2$Cl$_2$ [1,1'-bis(diphenylphosphino)ferrocene]dichloropalladium(II), complex with dichloromethane
Pd(Ph$_3$P)$_4$ tetrakis(triphenylphosphine) palladium (0)
(Ph$_3$P)$_2$PdCl$_2$ bis(triphenylphosphine)palladium dichloride
(S,S)-EtDuPhosRh(I) (+)-1,2-bis((2S,5S)-2,5-diethylphospholanotbenzene (cyclooctadiene)rhodium (I) trifluoromethanesulfonate The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (Protective Groups In Organic Synthesis, Wiley-Interscience, 3$^{rd}$ Edition, 1999).

Imidazole compounds of this invention wherein L$_1$ is —CH$_2$NH— can be prepared as outlined in Scheme 1. Condensation of an appropriately functionalized amine intermediate 1a with a suitably substituted benzylisocyanate 1b in a solvent such as tetrahydrofuran or methylene chloride in the presence of a base such as triethylamine, diisopropylethylamine or potassium carbonate provides ureas of formula 1c. Alternatively, ureas of formula 1c of this invention can be prepared by condensation of an amine intermediate 1a with carbonyl diimidazole in a solvent such as tetrahydrofuran or N,N-dimethylformamide followed by treatment in situ with an suitably substituted benzyl amine 1d. Urea linked compounds of this invention of formula 1c can also be prepared by condensation of amine intermediate 1a with p-nitrophenylchloroformate in the presence of a suitable base such as triethylamine, followed by treatment of the resulting p-nitrophenylcarbamate with an appropriate substituted amine 1d.

Scheme 1

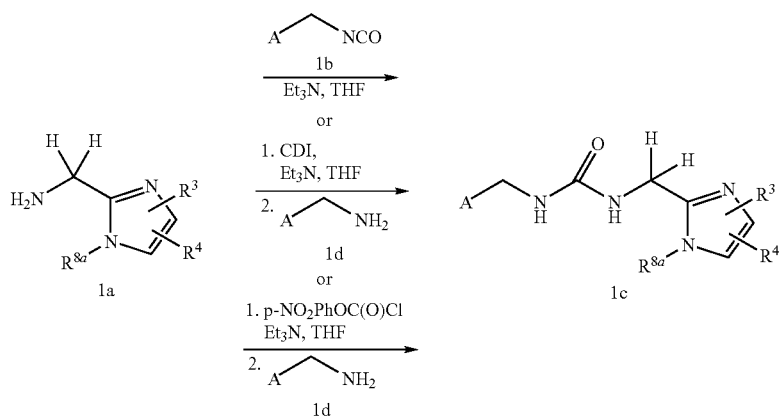

Isocyanates of formula 1b used in Scheme 1 above are either commercially available or can be readily prepared from the corresponding amines 1d by treatment with phosgene or by various other methods known in the art (see for example, H. Eckert & B. Forster, *Angew. Chem. Int. Ed.* 1987, 26, 894; H. Knolker & T. Braxmeier, *Synlett* 1997, 925; S. Porwanski et al. *Tetrahedron Lett,* 2004, 45, 5027). Amines of formula 1d are also available commercially or can be prepared by those knowledgeable in the art from a variety of easily accessible starting materials such as nitriles, aldehydes, alcohols, halides, acids and esters by methods including, but not limited to those outlined in Scheme 2.

Scheme 2

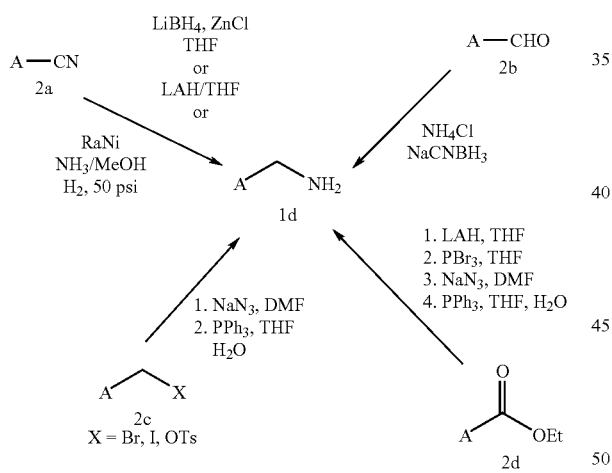

Imidazole compounds of this invention wherein $L_1$ is —NHNH— of formula 3c can be synthesized similarly as outlined in Scheme 3 by treatment of a suitably functionalized amine intermediate 1a with p-nitrochloroformate as described above followed by treatment of the resulting p-nitrophenylcarbamate 3a with a suitably substituted hydrazine of formula 3b.

Scheme 3

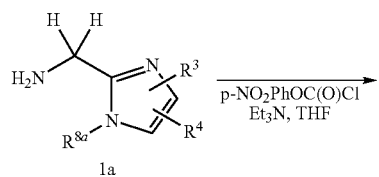

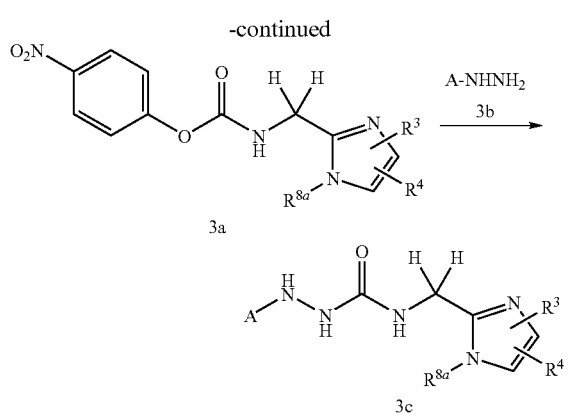

Hydrazine reagents of formula 3b used to prepare compounds of this invention in Scheme 3 are commercially available or can be prepared by those knowledgeable in the art of organic synthesis by other methods. For example, when A is an aryl or heteroaryl group, the requisite hydrazine reagent is readily available via diazotization of a starting aryl or heteroarylamine 4a followed by reduction of the resulting diazonium salt with tin chloride to the corresponding arylhydrazine 4b as illustrated in Scheme 4.

Scheme 4

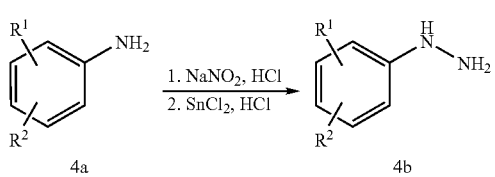

Imidazole compounds of this invention wherein $L_1$ is —(CH$_2$)$_2$—, —CH=CH—, —C≡C—, —OCH$_2$—, or —SCH$_2$— of formula 5b, can be obtained by the condensation of the amine intermediate 1a shown in Scheme 1 with appropriately substituted carboxylic acids 5a using standard amide bond forming conditions known to one skilled in the art as outlined in Scheme 5. Reagent combinations which may be employed for the coupling of amines of formula 1a with suitably substituted carboxylic acids include, but are not limited to: BOP-reagent and triethylamine, EDCI, HOBt, and N-methylmorpholine, or HATU and Hunig's base (DIPEA). Solvents suitable for this transformation include, but are not limited to tetrahydrofuran and dimethylformamide. Coupling of amines of formula 1a with suitably substituted carboxylic acid chlorides or mixed anhydrides derived from carboxylic acids of formula 5a as shown in Scheme 5 can be carried out in solvents such as methylene chloride or tetrahydrofuran in the presence of a base such as triethylamine, N,N-dimethylaminopyridine (DMAP) or potassium carbonate. It should be recognized by one skilled in the art that the choice of amide bond forming method may be influenced by the nature of the substituents on the group A in 5a, or and that it may be necessary to introduce the final $R^1$ and/or $R^2$ groups on to ring A at a later stage in the synthesis if these groups are not compatible with the coupling method to be used for the formation of the amide bond shown in Scheme 5.

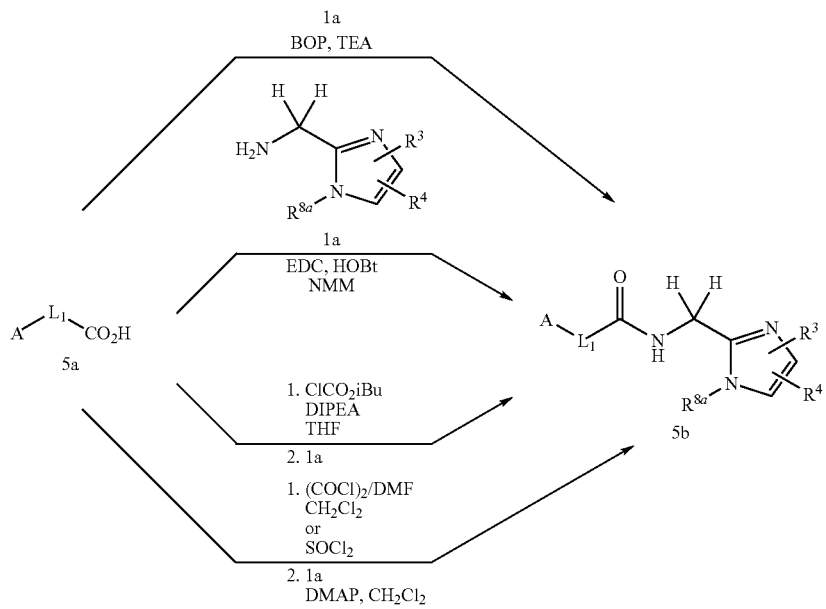

Suitably substituted carboxylic acids 5a where $L_1$ is —$(CH_2)_2$— are either commercially available, or they can be prepared from the corresponding bromides, alcohols, aldehydes, or esters as shown in Scheme 6 using methods known to one skilled in the art.

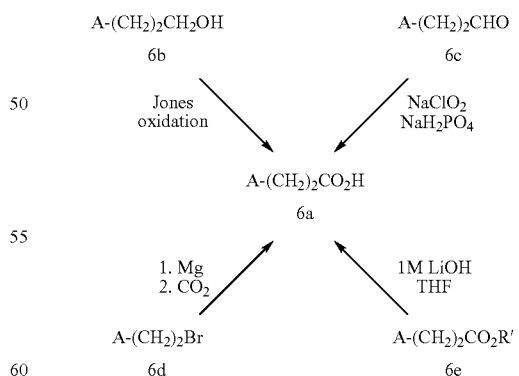

Additional carboxylic acid intermediates of formulae 6f, 6g, 6h, and 6I useful for preparation of amide compounds of this invention can be prepared as outlined in Schemes 6A and 6B.

Scheme 6A

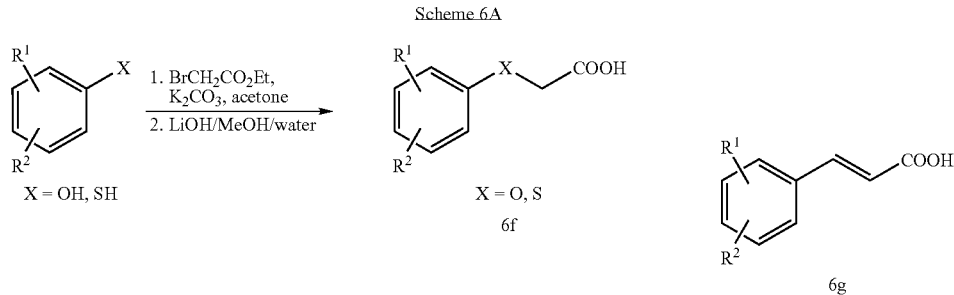

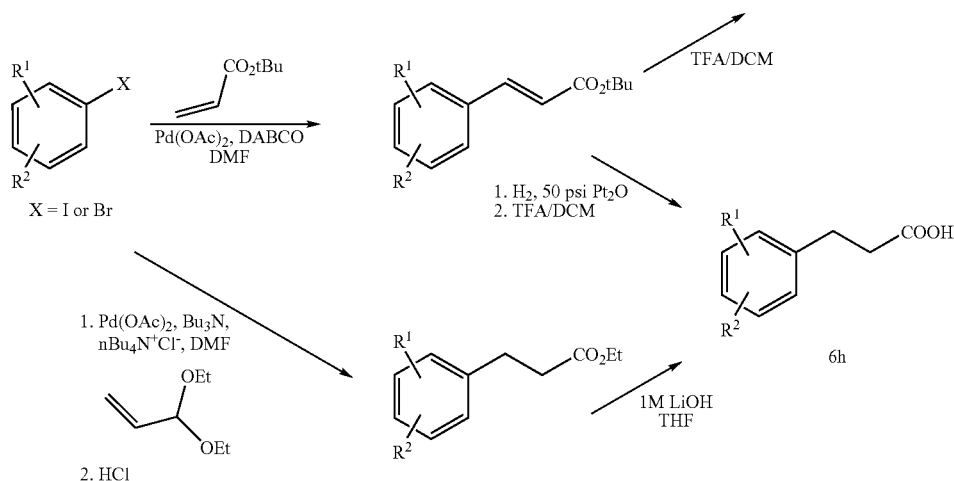

Scheme 6B

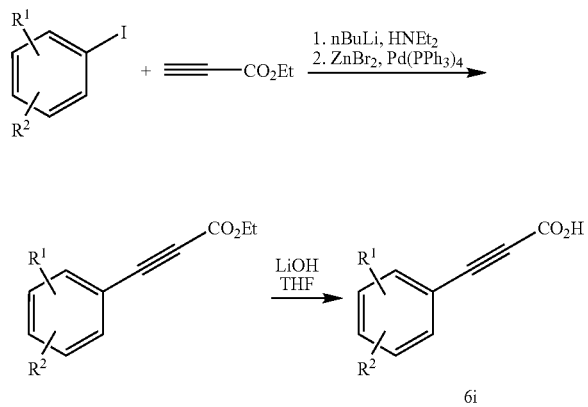

Substitution of suitably substituted heteroaryl alcohols, bromides and iodides for the phenol, bromo and iodobenzene starting materials in Schemes 6A and 6B will provide additional carboxylic acids useful for the preparation of compound of the instant invention wherein A is a heteroaryl moiety, such as, for example, a pyridine, thiophene, indole or benzthiazole moiety.

Imidazole compounds useful for the synthesis of the compounds of this invention may be synthesized according to a modification of the method described by Contour-Galcera et al (*Bioorg. Med. Chem. Lett.* 2001, 11(5), 741-745) as outlined in Scheme 7. An appropriately N-protected glycine derivative 7a is reacted with an alpha-bromoketone 7b in a suitable inert solvent, such as dimethylformamide or tetrahydrofuran in the presence of a base, such as cesium carbonate or potassium bicarbonate to form a ketoester 7c, which when heated in the presence of excess ammonium acetate in a suitable solvent, such as xylene at reflux, with removal of water, provides imidazoles of formula 7d. Imidazole formation can also be carried out by combining the keto ester 7c and ammonium acetate in a suitable solvent, such as xylene or a mixture of xylene and ethanol in a sealed tube using microwave heating. Deprotection then provides aminomethylimidazole compounds 7e. Alternately, treatment of imidazole 7d with a brominating or chlorinating agent, such as N-bromosuccinimide or N-chlorosuccinimide, in a suitable solvent such as acetonitrile or chloroform at a temperature from room temperature to reflux; followed by removal of the amine protecting group provides bromo or chloroimidazoles of formula 7f.

Scheme 7

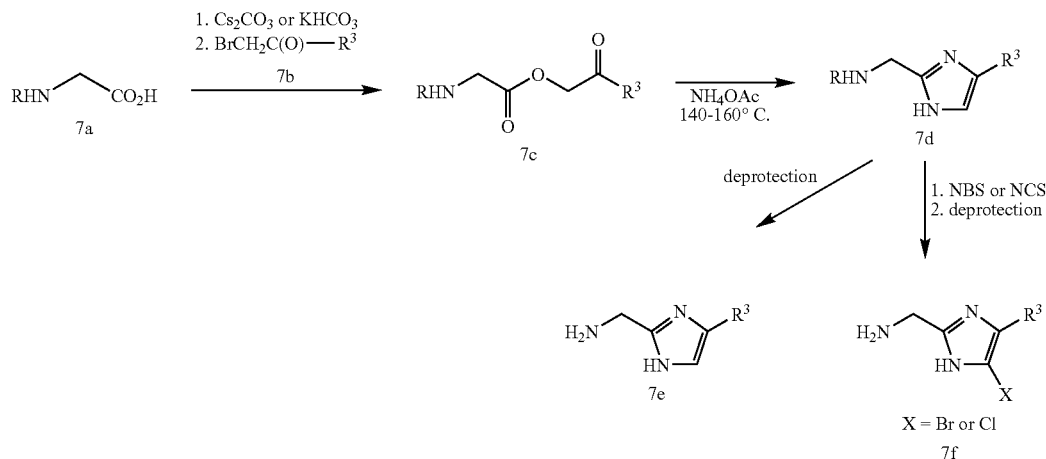

An alternate synthesis of imidazoles compounds useful the preparing of compounds of this invention is shown in Scheme 8. A mixture of a suitably protected amino acetaldehyde 8a, glyoxal trimeric dihydrate and ammonia are combined in a suitable solvent such as methanol and allowed to react with stirring at room temperature. The resulting imidazole 8b is dissolved in a suitable solvent such as chloroform and brominated using, for example, N-bromosuccinimide. Other brominating reagents may be employed, such as bromine, and other solvents suitable for bromination conditions, such as methylene chloride or carbon tetrachloride, may be used. The resulting 4,5-dibromo imidazole 8c is treated with a reducing agent such as sodium hydrogen sulfite utilizing a biphasic solvent system consisting of, for example, 1,4-dioxane and water, and a phase transfer catalyst such as tetrabutylammonium hydrogen sulfate to provide mono-bromoimidazoles 8d. Reaction of this bromo intermediate under Suzuki coupling conditions with a suitably functionalized aryl boronic acid or ester or heteroaryl boronic acid or ester in a suitable solvent such as 1,4-dioxane, dimethoxyethane or toluene, at elevated temperature in the presence of a catalyst, such as palladium (I) tri-tert-butylphosphine bromide dimer and a base such as anhydrous tribasic potassium phosphate according to a modified procedure of Zhong et al. (*Org. Lett.* 2004, 6, 929) and Bellini et al (*Synthesis* 2004, 15, 2419) provides compounds of formula 8e. Other reagent combinations that may be utilized for the Suzuki coupling procedure are palladium tris-(dibenzylidene-acetone) palladium (0), tri-(tert-butyl)-phosphonium tetra-fluoroborate, and tribasic potassium phosphate. Deprotection of 8e provides aminomethylimidazoles of formula 8f. Alternatively imidazoles 8e can be chlorinated or brominated if desired using the procedures described in Scheme 7 prior to removal of the amine protecting group to give compounds 8g.

Scheme 8

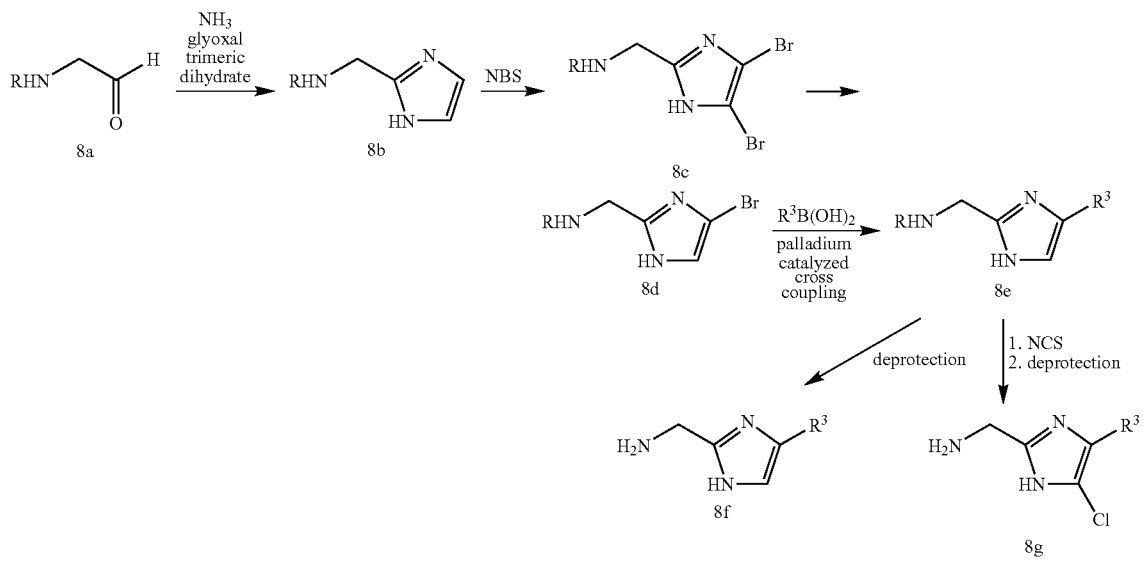

Alternatively, imidazole compounds of this invention can be prepared by introduction of $R^3$ groups via palladium-mediated coupling to an intermediate 4-bromo-5-chloroimidazole intermediate prepared as shown in Scheme 9.

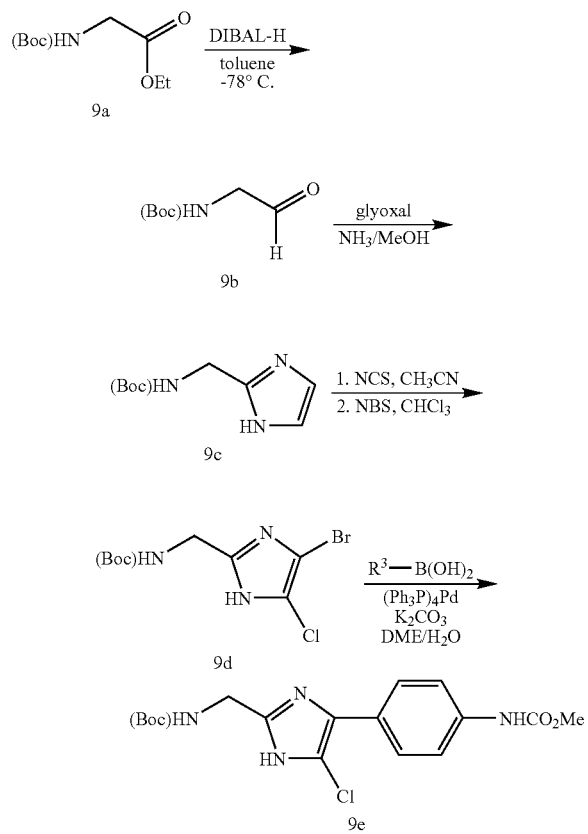

Alternate boronic acid or boronic ester coupling partners that are commercially available or readily synthesized by methods known to one skilled in the art may be employed in this palladium-mediated step to afford additional compounds of this invention. In cases where suitably substituted boronic acids are not commercially available, a modification to this approach may be adopted wherein an aryl halide is subjected to a palladium mediated coupling with a diboron species such as bis(pinacolato) diboron to provide the corresponding 4,4,5,5-tetramethyl-[1,3,2]dioxaborolane intermediate using the method of Ishiyama, T. et al. (*J. Org. Chem.* 1995, 60(23), 7508-7510). Alternately, this same intermediate can be prepared by reaction of the intermediate halide with the corresponding dialkoxyhydroborane as described by Murata et al. (*J. Org. Chem.* 1997, 62(19), 6458-6459). The boron pinacolate intermediates can be used in place of boronic acids for coupling to the aryl/heteroaryl halides or triflates or the boron pinacolate intermediate can be converted to the boronic acids. Alternately, the corresponding boronic acids can be prepared by metal-halogen exchange of the aryl/heteroaryl halide, quenching with a trialkoxyborate reagent, and aqueous workup to provide the boronic acids (Miyaura, N.; Suzuki, A. *Chem. Review,* 1995, 95, 2457).

It is also realized that the scope of intermediate synthesis can be further extended outside the use of Suzuki methodology since the precursor aryl halides or triflates described above are also precursors for Stille, Negishi, Hiyama, and Kumada-type cross coupling methodologies (Tsuji, J. *Transition Metal Reagents and Catalysts: Innovations in Organic Synthesis,* Johm Wiley & Sons, 2000; Tsuji, J. *Palladium Reagents and Catalysts: Innovations in Organic Synthesis,* John Wiley & Sons, 1996.)

As used in Schemes 7, 8 and 9 above, $R^3$ denotes a group as previously defined above, or a suitably functionalized precursor to an $R^3$ group as defined in the detailed description of the invention above. It should be recognized by one skilled in the art that certain functional groups present in the compounds of this invention must, by virtue of incompatibility with the formation of the imidazole shown in Schemes 7-9, be incorporated into the final compounds after the imidazole ring has been formed. Examples of such functional groups include, but are not limited to, carbamoyl, aminoindazolyl, aminobenzisoxazolyl, and 4-hydroxyquinolinyl. An example of modification of the $R^3$ group to introduce a carbamoyl group is illustrated in Scheme 10, wherein hydrolysis of a nitrile precursor 10a using, for example, potassium carbonate, hydrogen peroxide, in DMSO as solvent, according to the method of Katritzky et al. (*Synthesis* 1989, 12, 949-50) provides the corresponding carboxamide 10b.

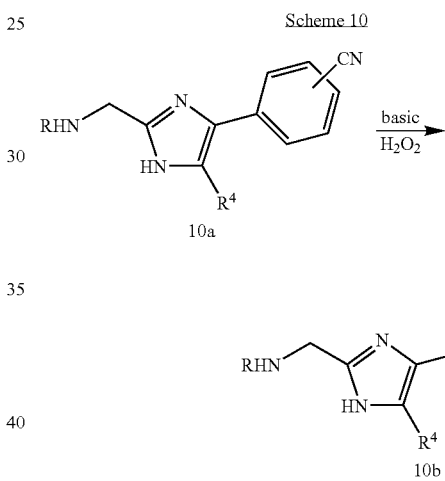

Compounds of this invention where $R^3$ is an 4-aminoquinazoline, 3-aminoindazole or 3-aminobenzisoxazole group can be prepared from a common imidazole precursor 11a bearing an ortho fluorobenzonitrile substituent as shown in Scheme 11. Amino-indazole compounds 11b are obtained by heating 11a with hydrazine or hydrazine monohydrate in a suitable solvent, such as n-butanol or ethanol either conventionally or via microwave irradiation at a temperature between 80 and 160° C. The aminoquinazoline 11c may be prepared by combining 11a with formamidine acetate, or other suitable salt forms, in a suitable solvent such as dimethyl acetamide or dimethyl formamide, and heating to approximately 140° C. Similarly the aminobenzisoxazoles 11d may be prepared from fluoro nitrile precursor 11a by treatment with acetoxyhydroxamic acid in the presence of a base such as potassium carbonate in a suitable solvent such as wet DMF. It is also understood that in some instances it will be advantageous to protect the imidazole NH prior to manipulation of the functionality on $R^3$ in order to avoid potential side reactions or to improve the yields of such transformations. Suitable protecting groups for the imidazole NH include, but are not limited to, 4-methoxybenzyl, methoxymethyl, of trimethylsilylethyoxymethyl groups.

Scheme 11

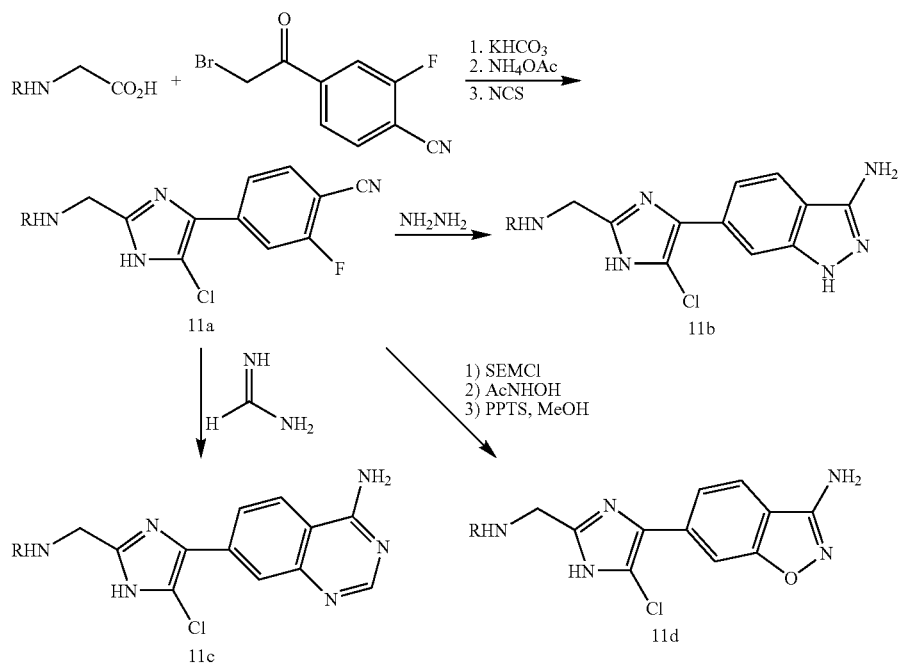

The 2-bromoacetophenone starting materials useful for preparation of imidazole compounds of this invention are either commercially available or may be synthesized from readily available starting materials. For example, a synthesis of 4-(2-bromoacetyl)-2-fluoro-benzonitrile is illustrated in Scheme 12. Palladium catalyzed cyanation of 4-bromo-3-fluorobenzoic acid 12a provides nitrile 12b. The nitrile 12b thus produced is treated sequentially with oxalyl chloride in a suitable solvent, such as dichloromethane, containing a few drops of DMF, then treated with trimethylsilyldiazomethane in a suitable solvent or solvent combination, such as acetonitrile and hexane. The intermediate diazoketone is isolated and treated with hydrobromic acid in acetic acid to provide the alpha bromoketone 12c. Various other methods for displacement of aryl bromides with cyanide reagents and for the conversion of carboxylic acids into the homologated alpha bromoketones are known in the literature and can be applied to prepare additional starting materials useful for the synthesis of compounds of this invention.

-continued

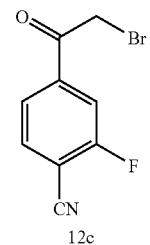

Alternatively, the bromoketone suitable for synthesis of the imidazole compounds of this invention may be prepared by treatment of an appropriately substituted aryl or heteroaryl-bromide such as 13a sequentially with tributyl-(1-ethoxyvinyl)stannane and a palladium catalyst, such as bis-(triphenylphosphine)-dichloro-palladium (II), in a suitable solvent, such as toluene, and heated to reflux, followed by aqueous hydrochloric acid, typically at 5% (w/v) concentration. The resulting methyl ketone 13b is combined with bromine or another suitable brominating reagent in a suitable solvent, such as chloroform or methylene chloride, to produce the bromoketone 13c.

Scheme 12

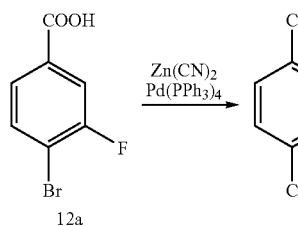

Scheme 13

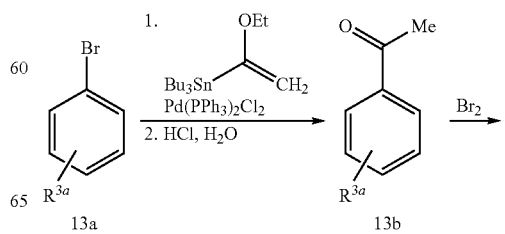

-continued

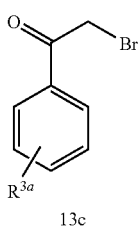
13c

All references cited herein are hereby incorporated in their entirety herein by reference. Methods for synthesis of a large variety of substituted pyridin-e and pyridone compounds useful as starting materials for the preparation of compounds of the present invention are well known in the art and have been extensively reviewed. (For examples of methods useful for the preparation of pyridine and pyridone starting materials see: Krohlue, F. *Synthesis*, 1976, 1.; *Pyridine and Its Derivatives*. In *The Chemistry of Heterocyclic Compounds*, Abramovitch, R. A., Ed.; John Wiley and Sons: New York, 1974; Vol 14; Supplemental 1-4; *Comprehensive Heterocyclic Chemistry*, Vol. 2, Boulton, A. J. and McKillop, A, Eds. Pergamon Press, New York, 1984, pp 165-524; *Comprehensive Heterocyclic Chemistry*, Vol. 5, McKillop, A, Ed. Pergamon Press, New York, 1996, pp 1-300). Methods for synthesis of a large variety of substituted pyrimidine and pyrimidone compounds useful as starting materials for the preparation of compounds of the present invention are well known in the art and have been extensively reviewed. (For examples of methods useful for the preparation of pyrimidine and pyrimidone starting materials see: *The Pyrimidines*. In *The Chemistry of Heterocyclic Compounds*, Taylor, E. C., Ed.; John Wiley and Sons: New York, 1993; Vol 52).

Aminomethyl pyridine compounds useful for the synthesis of pyridine compounds of this invention are either commercially available or are readily prepared from easily obtainable starting materials as shown in Scheme 14 in which Pyr is As outlined in Scheme 15, the amino group of 14f, is then protected, for example as a Boc derivative, and the bromopyridine is subjected to a Suzuki cross coupling reaction with an appropriate boronic acid or boronate derivative to afford aryl or heteroarylpyridine intermediates. Removal of the amine protecting group provides substituted aminomethylpyridine intermediates of formula 15b, 15c or 15d, respectively, which can be used for the synthesis of amides, ureas, carbamates and hydrazides of this invention using the methods described above.

Scheme 15

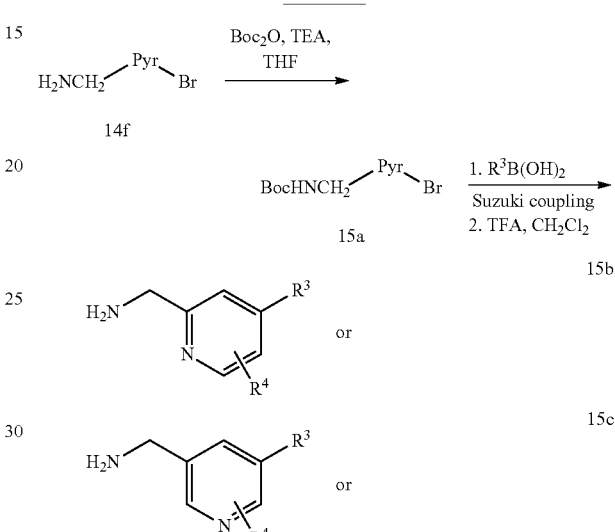

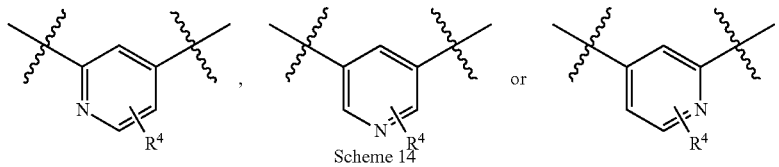

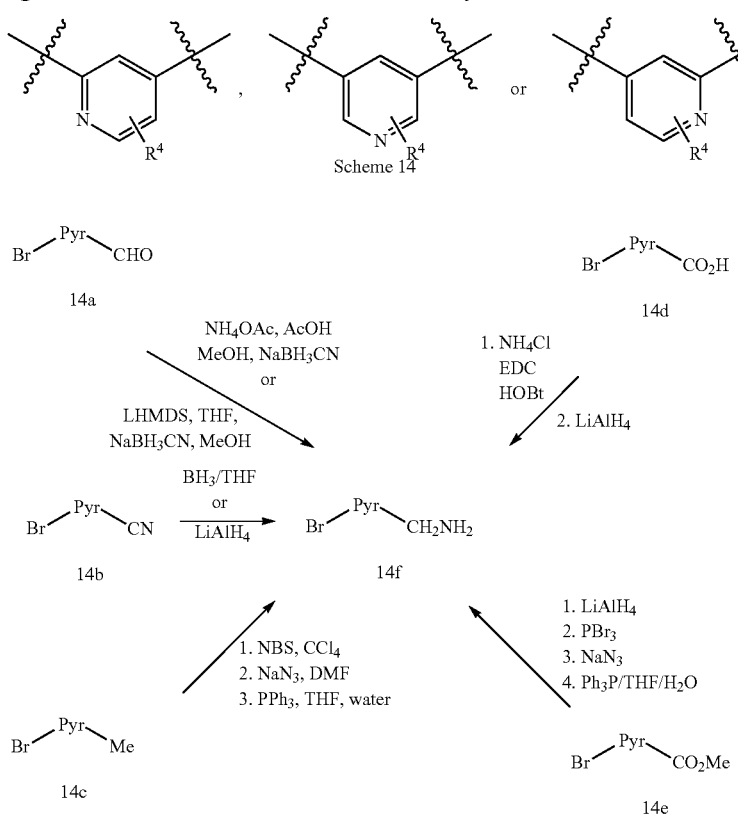

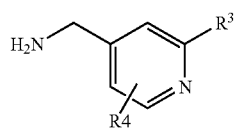

15d

Alternately, the chemistry described in Schemes 14 and 15 can be reversed such that suitably substituted bromopyridine compounds of formulae 14a-e can first be coupled via a Suzuki or similar biaryl coupling method to introduce the appropriate R³ group followed conversion to aminomethylpyridines of formulae 15b-d. Substitution of aminomethylpyridine intermediates of formulae 15b, 15c or 15d for aminomethylimidazole compounds 1a in Schemes 1, 3 and 5 above will then provide pyridine compounds of this invention. These pyridine compounds of this invention can be oxidized with meta-chloroperbenzoic acid, in a solvent such as methylene chloride or chloroform, to give the corresponding pyridine N-oxide compounds of this invention.

Representative aminomethylpyridone compounds of this invention can be prepared as shown in Scheme 16. Compound 16d can be prepared in two steps according to a modified procedure described by Resmini (Resmini, M. et al., *Tetrahedron Asymmetry*, 2004, 15, 1847). A suitably protected amino ester 16a can be converted to the corresponding β-ketophosphonate 16b by treatment with lithium dimethylmethylphosphonate. Horner-Wadsworth-Emmons reaction of 16b and a suitably substituted aldehyde 16c in the presence of base such as potassium carbonate in a solvent such as ethanol or tetrahydrofuran gives the α,β-unsaturated ketone 16d. Condensation of 16d with 1-(ethoxycarbonylmethyl)-pyridinium chloride or 1-(carbamoylmethyl)-pyridinium chloride in the presence of ammonium acetate in a solvent such as ethanol or glacial acetic acid generates the pyridone 16e. Deprotection with TFA yields 16f. Further manipulation of functional groups on R³ using methods known to one skilled in the art of organic synthesis will give additional compounds of the invention.

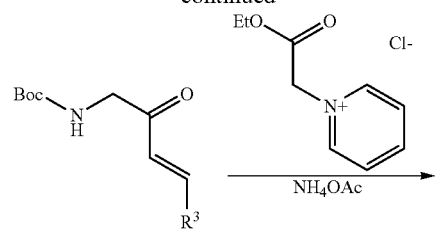

16d

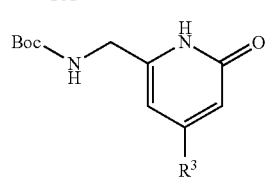

16e

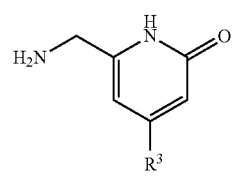

16f

Alternately, representative aminomethylpyridone compounds of this invention can be prepared from either hydroxypyridine or protected hydroxypyridines of formulae 17a, 18a, and 19a as shown in Schemes 17-19. The protecting group R, for example Me or Bn, can be removed with either boron tribromide or HCl to reveal the corresponding pyridone compounds of this invention. The substituted aminomethylpyridone intermediates of formula 16f, 17f, 18f, or 19f can be used for the synthesis of amides, ureas, carbamates and hydrazides of this invention using the methods described above.

Scheme 16

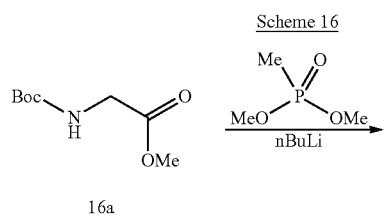

16a

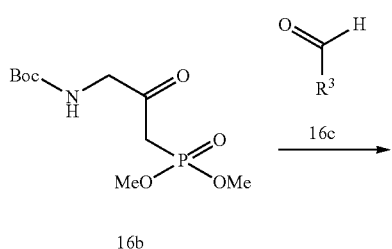

16b

Scheme 17

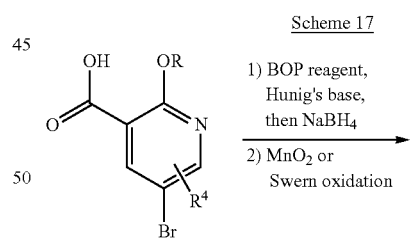

17a
R = Me or Bn

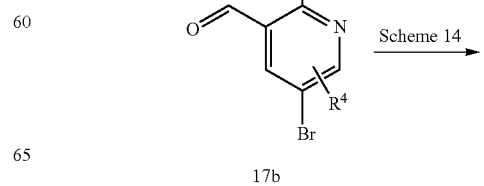

17b

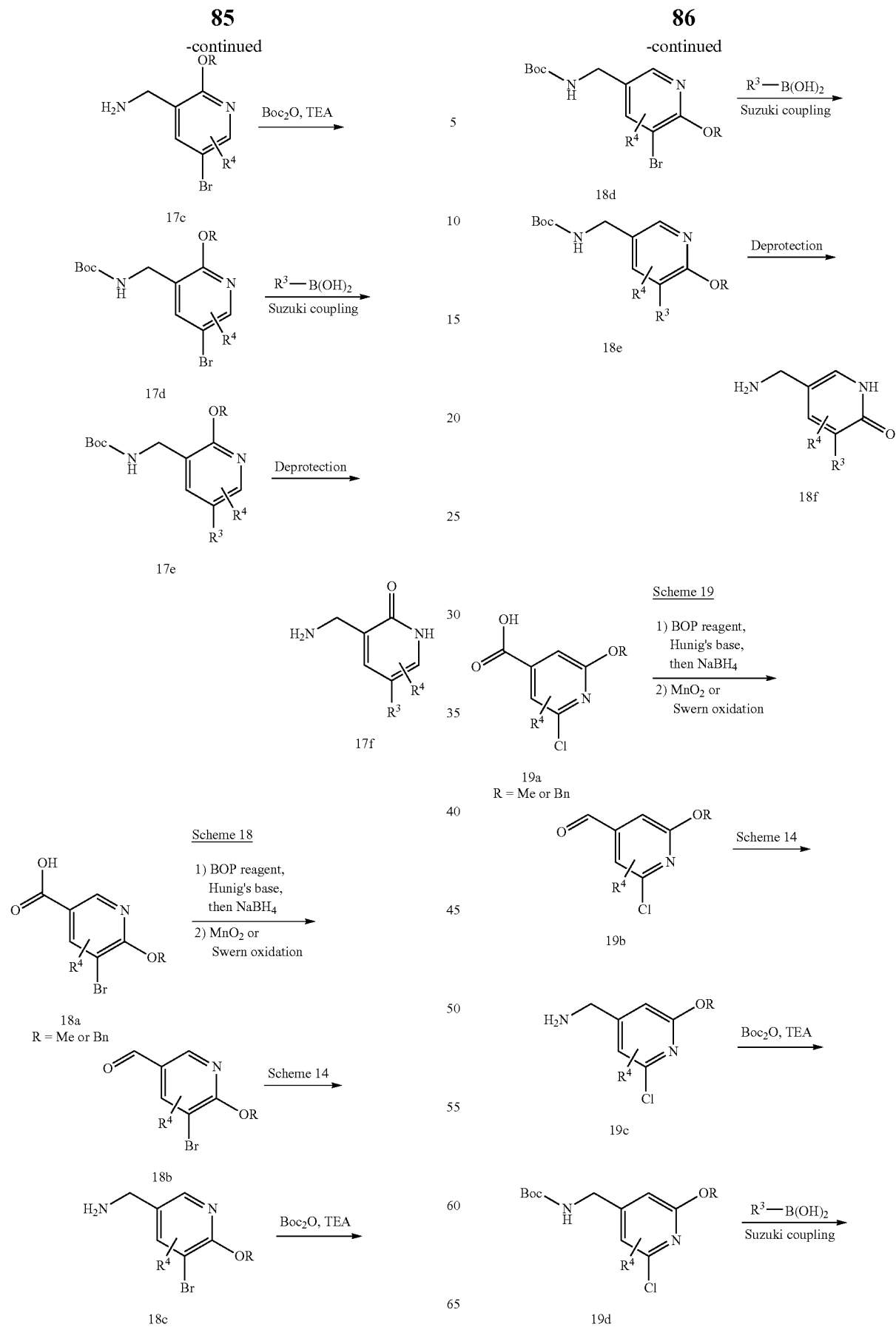

Alternately, the pyrimidone can be converted to the corresponding triflate 21e with sodium hydride and N-phenyltrifluoromethanesulfonimide. Suzuki coupling between an appropriately functionalized pyrimidine 21d/21e and an appropriately substituted aryl or heteroaryl boronic acid or ester provides 21f. Removal of the floc group with TFA yields 21g. The substituted aminomethylpyrimidine intermediates of formula 20d and 21g can be used for the synthesis of amides, ureas, carbamates and hydrazides of this invention using the methods described above. Further manipulation of functional groups on $R^3$, and $R^4$ using methods known to one skilled in the art of organic synthesis will give additional compounds of the invention.

Representative aminomethyl pyrimidine compounds of this invention can be prepared as shown in Scheme 20.

Alternately, representative aminomethylpyrimidine compounds of this invention can be prepared as shown in Scheme 21. Condensation of the β-ketoester 21b, prepared according to a modified procedure of Maibaum (*J. Org. Chem.*, 1988, 53, 869), with an amidine under basic conditions, such as formamidine and sodium methoxide in methanol, yields the pyrimidone 21c. The pyrimidone can be converted to the chloro pyrimidine 21d in two steps with phosphorus oxychloride and then reprotection of the amine with Boc-anhydride.

The synthesis of some additional representative examples of compounds of this invention is depicted in Schemes 22-25.
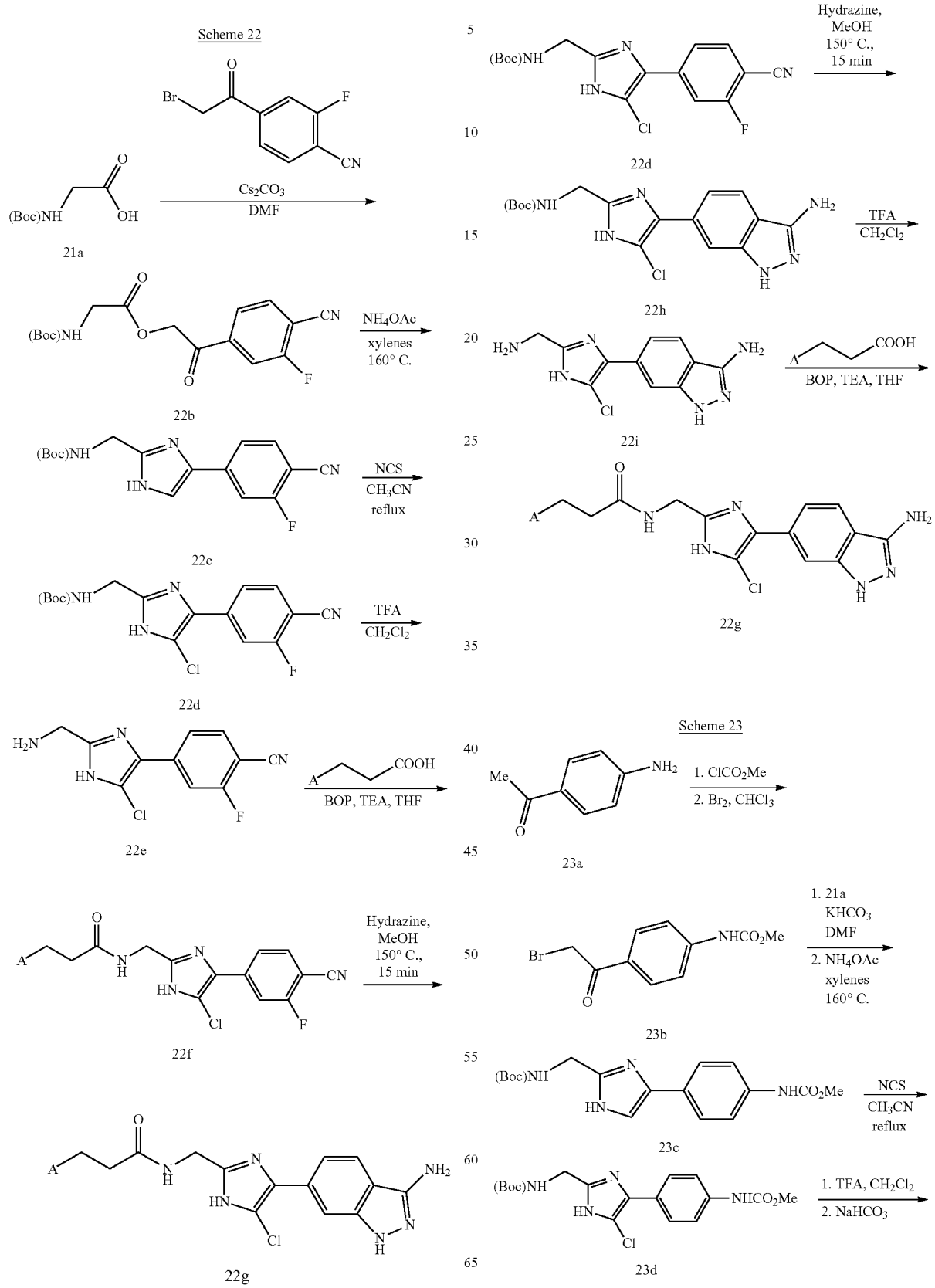
Scheme 22, Scheme 22b (Alternately), Scheme 23

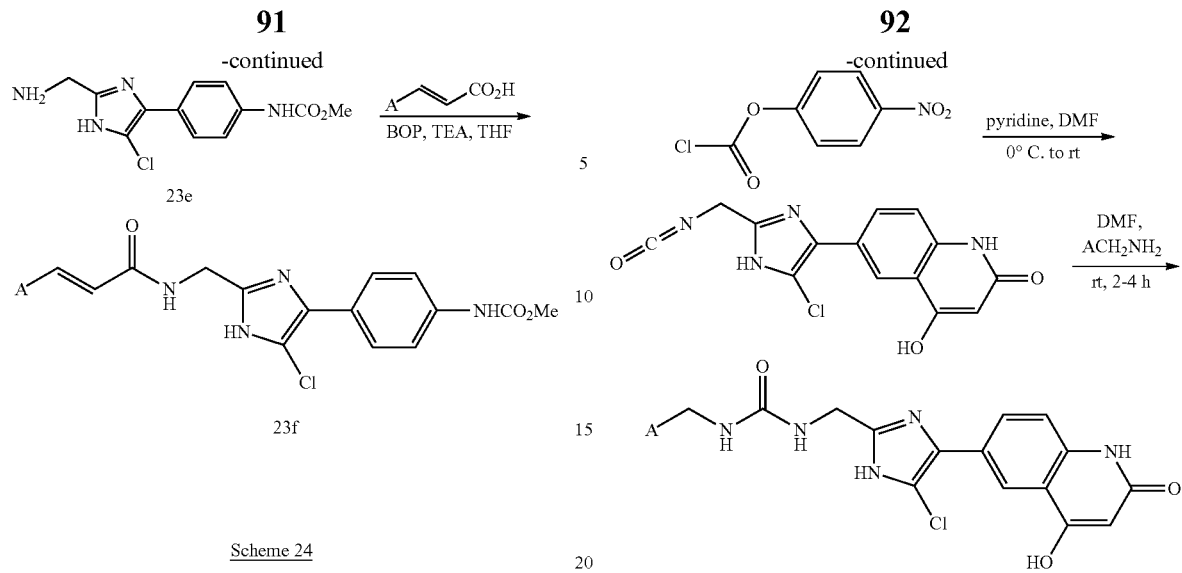

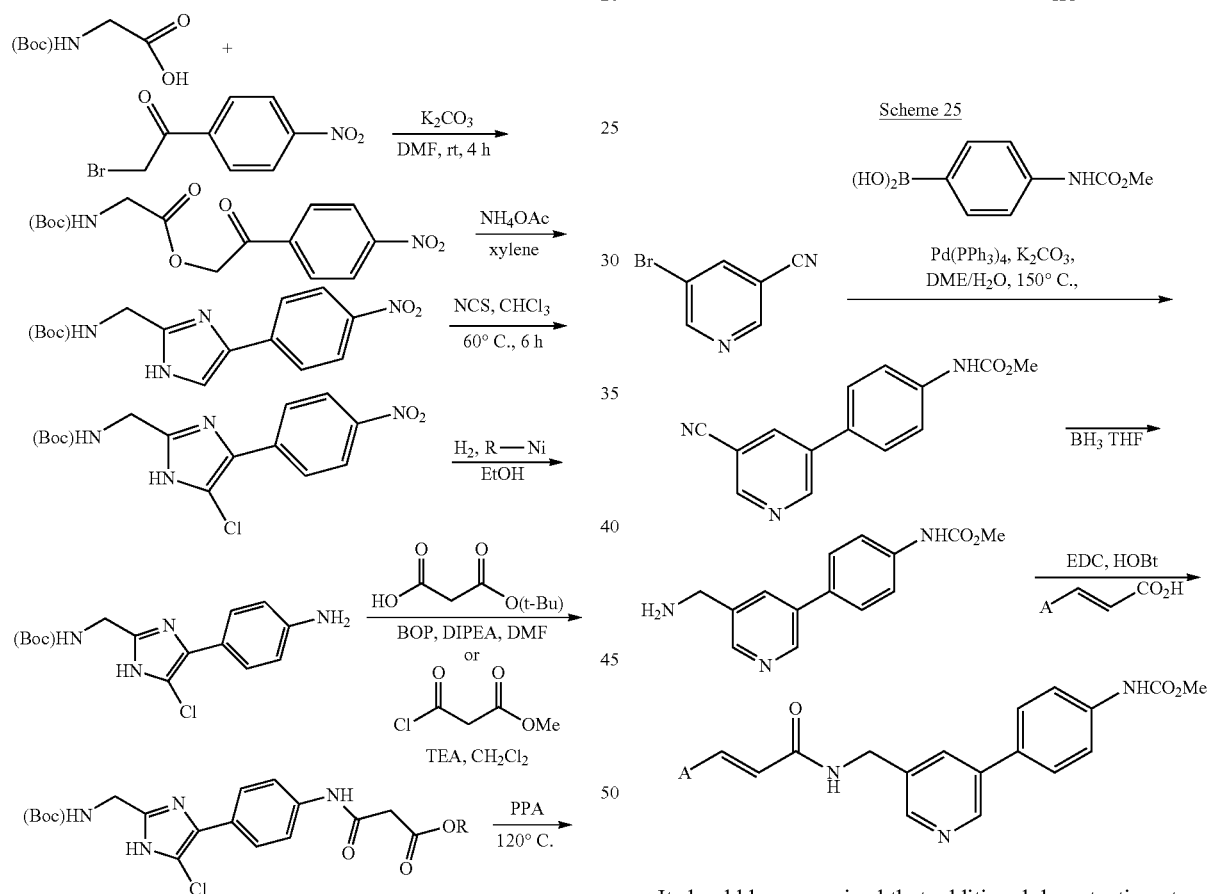

It should be recognized that additional deprotection steps and further functional group manipulations of compounds obtained via Schemes 1-25 above using methods known in the art will then provide additional compounds of this invention.

In the following experimental procedures, solution ratios express a volume relationship, unless stated otherwise. NMR chemical shifts (δ) are reported in parts per million (ppm).

Products were analyzed by reverse phase analytical HPLC carried out on a Shimadzu Analytical HPLC system running DiscoveryVP software using Method A: Phenomenex Luna C18 column (4.6×50 mm or 4.6×75 mm) eluted at 4 mL/min with a 2, 4 or 8 min gradient from 100% A to 100% B (A: 10% methanol, 89.9% water, 0.1% TFA; B: 10% water, 89.9% methanol, 0.1% TFA, UV 220 nm), or Method B: Phenomenex Luna C18 column (4.6×50 mm) eluted at 4 mL/min with a 4 min gradient from 100% A to 100% B (A: 10% acetonitrile, 89.9% water, 0.1% TEA; B: 10% water, 89.9% acetonitrile, 0.1% TFA, UV 220 nm) or Method C: Phenomenex Luna C18 column (4.6×50 mm or 4.6×75 mm) eluted at 4 mL/min with a 2, 4 or 8 min gradient from 100% A to 100% B (A: 10% methanol, 89.9% water, 0.1% $H_3PO_4$; B: 10% water, 89.9% methanol, 0.1% $H_3PO_4$, UV 220 nm).

Purification of intermediates and final products was carried out via either normal or reverse phase chromatography. Normal phase chromatography was carried out using prepacked $SiO_2$ cartridges eluted with gradients of hexanes and ethyl acetate or methylene chloride and methanol. Reverse phase preparative HPLC was carried out using a Shimadzu Preparative HPLC system running DiscoveryVP software using Method A: YMC Sunfire 5 nm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm), Method B: Phenomenex AXIA Luna 5 μm C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), Method C: Phenomenex Luna 5 μm C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), or Method D. Phenomenex Luna 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm). Alternatively, reverse phase preparative HPLC was carried out using a Varian ProStar Preparative HPLC System running Star 6.2 Chromatography Workstation software using Method E: Dynamax 10 μm C18 41.4×250 mm column with a 30 min gradient at 30 mL/min from 10% B to 100% B (A 98% water, 2% acetonitrile, 0.05% TFA; B: 98% acetonitrile, 2% water, 0.05% TFA, NV 254 nm). LCMS chromatograms were obtained on a Shimadzu HPLC system running DiscoveryVP software, coupled with a Waters ZQ mass spectrometer running MassLynx version 3.5 software using the same columns and conditions as utilized for analytical described above.

IV. Biology

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders and include acute coronary syndrome, unstable angina, myocardial infarction, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters, stents, and artificial heart valves;

Some conditions contribute to the risk of developing thrombosis. For example, alterations of the vessel wall, changes in the flow of blood, and alterations in the composition of the vascular compartment. These risk factors are collectively known as Virchow's triad. (Hemostasis and Thrombosis, Basic Principles and Clinical practice, page 853, $5^{th}$ Edition, 2006, edited by Colman, R. W. et al. Published by Lippincott Williams & Wilkins)

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease. Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in factor V (also known as factor V Leiden) and additional risk factors (e.g., pregnancy), are dosed with anticoagulants to prevent the reoccurrence of venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e. heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J. et al. *Blood* 2005, 105, 453-463).

An alternative way of initiation of coagulation is operative when blood is exposed to artificial surfaces (e.g., during hemodialysis, 'on-pump' cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIII has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininiogell in a multiprotein complex formed on the surface of cells and matrices (Shariat- Madar et al. *Blood* 2006, 108, 192-199). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage*, 1998). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Reenne et al. *J. Exp. Medicine* 2005, 202, 271-281; Kleinschmitz et al. *J. Exp. l Medicine,* 2006, 203, 513-518). The fact that factor XI is down-stream from factor XIIa, combined with the identical phenotype of the XII and XI deficient mice suggest that the contact activation system could play a major role in factor XI activation in vivo.

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur oil negatively charged surfaces, most likely on the surface of activated platelets. Platelets contain high affinity (0.8 nM) specific sites (130-500/platelet) for activated factor XT. After activation, factor XIa remains surface bound and recognizes factor IX as its normal macromolecular substrate. (Galiani, D. *Trends Cardiovasc. Med.* 2000, 10, 198-204.)

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al. *Thromb. Res.* 2001, 101, 329-354.) Thus, inhibitors of factor XIa are expected to be anticoagulant and profibrinolytic.

Further evidence for the anti-thromboembolic effects of targeting factor XI is derived from mice deficient in factor XI. It has been demonstrated that complete HCl deficiency protected mice from ferric chloride ($FeCl_3$)-induced carotid artery thrombosis (Rosen et al., *Thromb Haemost* 2002, 87, 774-77; Wang et al., *J Thromb Haemost* 2005, 3, 695-702). Also, factor XI deficiency rescues the perinatal lethal phenotype of complete protein C deficiency (Chan et al., *Amer. J Pathology* 2001, 158, 469-479). Furthermore, baboon cross-reactive, function blocking antibodies to human factor XI protect against baboon arterial—venous shunt thrombosis (Gruber et al., *Blood* 2003, 102, 953-955). Evidence for an antithrombotic effect of small molecule inhibitors of factor XIa is also disclosed in published U.S. Patent Application US20040180855A1. Taken together, these studies suggest that targeting factor XI will reduce the propensity for thrombotic and thromboembolic diseases.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or posttraumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of aPTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The aPTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D. *Frontiers in Bioscience* 2001, 6, 201-207; Gailani, D. et al. *Blood Coagulation and Fibrinolysis* 1997, 8, 134-144.) Taken together, these observations suggest that high levels of inhibition of factor XIa should be well tolerated. This is in contrast to gene targeting experiments with other coagulation factors, excluding factor XII.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al. *Arterioscler. Thromb. Vasc. Biol.* 2000, 20, 2489-2493). A second study establishes a positive correlation between the extent of coronary arteriosclerosis and factor XIa in complex with alpha 1 antitrypsin (Murakami, T. et al. *Arterioscler Thromb Vasc Biol* 1995, 15, 1107-1113.). In another study, Factor XI levels above the $90^{th}$ percentile in patients were associated with a 2.2-fold increased risk for venous thrombosis (Meijers, J. C. M. et al. *N. Engl. J. Med.* 2000, 342, 696-701.)

Plasma kallikrein is a zymogen of a trypsin-like serine protease and is present in plasma at 35 to 50 µg/mL. The gene structure is similar to that of factor XI. Overall, the amino acid sequence of plasma kallikrein has 58% homology to factor XI. Proteolytic activation by factor XIIa at an internal I 389-R390 bond yields a heavy chain (371 amino acids) and a light chain (248 amino acids). The active site of plasma kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage,* 1998).

Also, it is preferred to find new compounds with improved activity in in vitro clotting assays, compared with known serine protease inhibitors, such as the activated partial thromboplastin time (aPTT) or prothrombin time (PT) assay. (for a description of the aPTT and PT assays see, Goodnight, S. H.; Hathaway, W. E. Screening Tests of Hemostasis. *Disorders of*

*Thrombosis and Hemostasis: a clinical guide*, 2$^{nd}$ edition, McGraw-Hill: New York, 2001 pp. 41-51).

It is also desirable and preferable to find compounds with advantageous and improved characteristics compared with known serine protease inhibitors, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility.

Pre-clinical studies demonstrated significant antithrombotic effects of small molecule factor XIa inhibitors in rabbit and rat model of arterial thrombosis, at doses that preserved hemostasis. (Wong P. C. et al. *American Heart Association Scientific Sessions*, Nov. 12-15, 2006, Abstract 6118; Schumacher, W. et al *Journal of Thrombosis and Haemostasis* 2005; Volume 3, Supplement 1: P1228; Schumacher, W. A. et al. *European Journal of Pharmacology*, in press). Furthermore, it was observed that in vitro prolongation of the aPTT by specific XIa inhibitors is a good predictor of efficacy in our thrombosis models. Thus, the in vitro aPTT test can be used as a surrogate for efficacy in vivo.

As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or 'prevention' cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit factor XIa and/or plasma kallikrein and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined vide supra).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to are family history, obesity, physical inactivity, race/ethnicity, previously impaired fasting glucose or glucose tolerance test, history of gestational diabetes mellitus or delivery of a 'big baby', hypertension, low HDL cholesterol, and polycystic ovary syndrome.

Risk factor for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population. (Levitan, N. et al. *Medicine* (Baltimore) 1999, 78(5):285-291; Levine M. et al. *N Engl J Med* 1996, 334(11):677-681; Blom, J. W. et al. *JAMA:* 2005, 293(6):715-722.) Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e. presence of metastases), (ii) the presence of central vein catheters, (iii) surgery and anticancer therapies including chemotherapy, and (iv) hormones and antiangiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al. *British Journal of Surgery* 2001, 88:913-930.)

A. In Vitro Assays

The effectiveness of compounds of the present invention as inhibitors of the coagulation factors XIa, VIIa, IXa, Xa, XIIa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 pM (Haematologic Technologies) and the synthetic substrate S-2366 (pyroGlu-Pro-Arg-pNA; Chromogenix or AnaSpec) at a concentration of 0.0002-0.001 M.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 1-5 nM, recombinant soluble tissue factor at a concentration of 10-40 nM and the synthetic substrate H-D-11e-Pro-Arg-pNA (S-2288; Chromogenix or BMPM-2; AnaSpec) at a concentration of 0.001-0.0075 M.

Factor IXa determinations were made in 0.005 M calcium chloride, 0.1 M sodium chloride, 0.0001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem)

or Pefafluor IXa 3688 (H-D-Leu-Ph'Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; Chromogenix) at a concentration of 0.0002-0.00035 M.

Factor XIIa determinations were made in 50 mM HEPES buffer at pH 7.4 containing 145 mM NaCl, 5 mM KCl, and 0.1% PEG 8000. Determinations were made using purified human Factor XIIa at a final concentration of 4 nM (American Diagnostica) and the synthetic substrate Spectrozyme #312 (pyroGlu-Pro-Arg-pNA; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human kallikrein (Enzyme Research Laboratories) at a final assay concentration of 200 µM and the synthetic substrate S-2302 (H-(D)-Pro-Phe-Arg-pNA; Chromogenix) at a concentration of 0.00008-0.0004 M. The Km value used for calculation of Ki was 0.00005 to 0.00007 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 pyroGlu-Pro-Arg-pNA; Chromogenix) at a concentration of 0.0002-0.00026 M.

The Michaelis constant, $K_m$, for substrate hydrolysis by each protease, was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$$(v_o-v_s)/v_s = I/(K_i(1+S/K_m)) \text{ for a competitive inhibitor with one binding site; or}$$

$$v_s/v_o = A+((B-A)/1+((IC_{50}/(I)^n))) \text{ and}$$

$$K_i = IC_{50}/(1+S/K_m) \text{ for a competitive inhibitor}$$

where:
$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant for the substrate.

The selectivity of a compound may be evaluated by taking the ratio of the $K_i$ value for a given protease with the $K_i$ value for the protease of interest (i.e., selectivity for FXIa versus protease P=$K_i$ for protease P/$K_i$ for FXIa). Compounds with selectivity ratios>20 are considered selective. Compounds with selectivity ratios>100 are preferred, and compounds with selectivity ratios>500 are more preferred.

The effectiveness of compounds of the present invention as inhibitors of coagulation can be determined using a standard or modified clotting assay. All increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5x or IC2x, the inhibitor concentration required to increase the clotting time by 50 or 100 percent, respectively. The IC1.5x or IC2x is found by linear interpolation from relative clotting time versus inhibitor concentration plots using inhibitor concentration that spans the IC1.5x or IC2x.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (Sysmex, Dade-Behring, Ill.). Similarly, clotting times can be determined from laboratory animal species or humans dosed with compounds of the invention.

Activated Partial Thromboplastin Time (aPTT) is determined using Alexin (Trinity Biotech, Ireland) following the directions in the package insert. Plasma (0.05 mL) is warmed to 37° C. for 1 minute. Alexin (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Thromboplastin C Plus, Dade-Behring, Ill.) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

a. In Vivo Electrically-Induced Carotid Artery Thrombosis (ECAT) Model

The rabbit ECAT model, described by Wong et al. (*J Pharmacol Exp Ther* 2000, 295, 212-218), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., S.C., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion.

Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

b. In Vivo Rabbit Arterio-Venous (AV) Shunt Thrombosis Model

The rabbit AV shunt model, described by Wong et al. (Wong, P. C. et al. *J Pharmacol Exp Ther* 2000, 292, 351-357), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length 8 cm; internal diameter 7.9 mm) and an inner piece of tubing (length 2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose that produces 50% inhibition of thrombus formation) are estimated by a nonlinear least square regression program using the Hill sigmoid $E_{max}$ equation (DeltaGraph; SPSS Inc., Chicago, Ill.).

The anti-inflammatory effect of these compounds can be demonstrated in an Evans Blue dye extravasation assay using C1-esterase inhibitor deficient mice. In this model, mice are dosed with a compound of the present invention, Evans Blue dye is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "Pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, $18^{th}$ Edition, 1990.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intra-musculary, or sub-cutaneously. When administered intra-venous or intra-arterial, the dose can be given continuously or intermittend. Furthermore, formulation can be developed for intramusculary and subcutaneous delivery that ensure a gradual release of the active pharmaceutical ingredient.

Compounds of this invention can be administered in intra-nasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 100 milligrams per dosage unit, and the second anti-coagulant in an amount of about 1 to about 50 milligrams per dosage unit.

Where the compounds of the present invention are administered in combination with an anti-platelet agent, by way of general guidance, typically a daily dosage may be about 0.01 to about 25 milligrams of the compound of the present invention and about 50 to about 150 milligrams of the anti-platelet agent, preferably about 0.1 to about 1 milligrams of the compound of the present invention and about 1 to about 3 milligrams of antiplatelet agents, per kilogram of patient body weight.

Where the compounds of the present invention are administered in combination with thrombolytic agent, typically a daily dosage may be about 0.1 to about 1 milligrams of the compound of the present invention, per kilogram of patient body weight and, in the case of the thrombolytic agents, the usual dosage of the thrombolyic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, minieralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin-, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, renin inhibitors (alliskerin) and vasopepsidase inhibitors, an antiarrythmic agent selected from IKur inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) antagonists, thrombin activatable fibrinolysis inhibitor (TAFI) inhibitors, factor VIIa inhibitors, factor IXa inhibitors, and factor Xa inhibitors, or an antiplatelet agent selected from GPIIb/IIIa blockers, GP Ib/IX blockers, protease activated receptor 1 (PAR-1) antagonists, protease activated receptor4 (PAR-4) antagonists, prostaglandin E2 receptor EP3 antagonists, collagen receptor antagonists, phosphodiesterase-III inhibitors, $P2Y_1$ receptor antagonists, $P2Y_{12}$ antagonists, thromboxane receptor antagonists, cyclooxygense-1 inhibitors, and aspirin, or a combination thereof.

In another embodiment, the present invention provides pharmaceutical composition, wherein the additional therapeutic agent(s) are an anti-platelet agent or a combination thereof.

In another embodiment, the present invention provides a pharmaceutical composition, wherein the additional therapeutic agent is the anti-platelet agent clopidogrel.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX™), synthetic pentasaccharide, direct acting thrombin inhibitors including hirudin and argatroban, as well as other factor Vita inhibitors, factor IXa inhibitors, factor Xa inhibitors (e.g., Arixtra™, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDS) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDS, aspirin (acetylsalicylic acid or ASA) and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR-1) antagonists (e.g., E-5555, SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, are ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include clopidogrel, ticlopidine, prasugrel, and AZD-6140, cangrelor, and pharmaceutically acceptable salts or prodrugs thereof. Ticlopidine and clopidogrel are also preferred compounds since they are known to be more gentle than aspirin on the gastrointestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroargininle derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvsatatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., gemfibrozil, clofibrate, fenofibrate and benzafibrate) and other peroxisome proliferator-activated receptors (PPAR) alpha modulators, PPARdelta modulators (e.g., GW-501516), PPAR-gamma modulators (e.g., rosiglitazone), compounds that have multiple functionality for modulating the activities of various combinations of PPARalpha, PPARgamma and PPARdelta, probucol or derivatives thereof (e.g., AGI-1067), cholesterol absorption inhibitors and/or Niemann-Pick C1-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X-receptor (LXR) alpha modulators, LXRbeta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAI derivatives or apoAI peptide mimetics).

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 µM against the target protease and greater than or equal to 0.1 µM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent and selective Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

EXAMPLES

The following Examples have been prepared, isolated and characterized using the methods disclosed herein. The following Examples demonstrate a partial scope of the invention and are not meant to be limiting of the scope of the invention.

Example 1

[4-(5-chloro-2-{[(E)-3-(5-chloro-2-tetrazol-1-yl-phenyl)-acryloylamino]-methyl}-1H-imidazol-4-yl)-phenyl]-carbamic acid methyl ester, trifluoroacetic acid salt 1A. Methyl 4-(2-bromoacetyl)phenylcarbamate: To a suspension of 4-aminoacetophenone in 1:1 dioxane/water (150 mL) was added NaOH (4.4 g, 0.11 mol). The mixture was stirred until the NaOH dissolved, then cooled to 0° C. prior to dropwise addition of methylchloroformate (8.5 mL, 0.11 mol). The resulting mixture was stirred at 0° C. for an additional 10 min then at rt for 2 h, followed by standing overnight. The solvent was removed by evaporation and the residual solids were partitioned between EtOAc and water. The layers were separated and the aqueous layer was extracted with EtOAc. The combined organic extracts were dried over $MgSO_4$, filtered and evaporated to yield a tan powder. The crude product was suspended in EtOAc, washed with 1N HCl, to remove unreacted aniline, washed with brine, dried over $MgSO_4$, filtered and evaporated to provide methyl-4-acetylphenylcarbamate as an orange/tan solid (11.2 g, 53%). A portion of this crude material (3 g, 15.53 mmol) was suspended in $CHCl_3$ (60 mL) and bromine (0.960 mL, 18.63 mmol) was added in small portions. About halfway through the addition, most of the starting material had dissolved in the dark orange reaction mixture. At this point, the mixture quickly decolorized with the formation of a tan precipitate. The remaining bromine was added over ~5 min and the mixture was stirred at rt. After ~30 min, the solid product was collected by filtration and washed with $CHCl_3$ and air-dried overnight to provide 1A (3.25 g, 77%). $^1$HNMR (500 MHz, DMSO-$d_6$) δ: 10.14 (1 H, s), 7.95 (2 H, d, J=8.8 Hz), 7.59 (2 H, d, J=8.8 Hz), 4.83 (2 H, s), 3.57-3.83 (3 H, m).

1B. {4-[2-(tert-butoxycarbonylamino-methyl)-1H-imidazol-4-yl]-phenyl}-carbamic acid methyl ester: To Boc-glycine (0.644 g, 3.68 mmol) and 1A (1 g, 3.68 mmol) was added $Cs_2CO_3$ (1.197 g, 3.68 mmol) and DMF (5 mL) and the mixture was stirred for 24 h at it. The reaction mixture was partitioned with EtOAc/water and extracted with EtOAc (3×25 mL). Combined organic layers were washed with water (20 mL), brine (20 mL) and dried ($MgSO_4$). The crude ester obtained was treated with ammonium acetate (0.95 g, 12.8 mmol) in a mixture of xylene (8 mL) and α,α,α-trifluorotoluene (2 mL) at 160° C. for 15 min in a sealed tube in a microwave reactor. After cooling, the reaction was partitioned between EtOAc/water. The organic layer was washed with water (20 mL), brine (20 mL) and dried ($MgSO_4$). Purification by silica gel chromatography afforded 1B (1.1 g, 73%) as a dark oil. LC/MS m/z 347.4 (M+H)$^+$. $^1$H NMR (400 MHz, $CDCl_3$) δ: 1.46 (s, 9 H) 3.78 (s, 3 H) 4.35 (d, J=6.05 Hz, 2 H) 5.41 (s, 1 H) 6.65 (s, 1 H) 7.17 (s, 1 H) 7.39 (d, J=8.25 Hz, 2 H) 7.61 (d, J=8.25 Hz, 2 H).

1C. [4-(2-aminomethyl-5-chloro-1-imidazol-4-yl)-phenyl]-carbamic acid methyl ester: To 1B (1.1 g, 3.18 mmol) was added NCS (0.445 g, 3.33 mmol) and acetonitrile (20 mL) and the mixture was heated to 60° C. for 1 h. The solvent was removed, and the residue was purified by silica gel chromatography to afford the chloroimidazole derivative (0.79 g, 65.8%) as a tan foam. LC/MS m/z 381.4 (M+H)$^+$. $^1$H NMR (400 MHz, $CDCl_3$) δ: 1.45 (s, 9 H) 3.79 (s, 3 H) 4.23-4.35 (d, J=6.05 Hz, 2 H) 5.57 (t, J=6.05 Hz, 1 H) 6.87 (s, 1 H) 7.44 (d, J=8.24 Hz, 2 H) 7.49-7.67 (d, J=8.24 Hz, 2 H) 8.74 (brd s, 1 H) 10.70 (brd s, 1 H).

This material was treated with TEA in DCM (20 mL) for 24 h, concentrated and quenched with saturated NaHCO$_3$ (100 mL), extracted with EtOAc (3×30 mL). Combined organic layers were washed with water (20 mL), brine (20 mL) and dried (MgSO$_4$) to provide 1C (0.39 g, 43%) as a red oily solid. $^1$HNMR (400 MHz, MeOD) δ: 3.75 (s, 3H), 3.90 (s, 2H), 7.51 (d, J=8.75 Hz, 2H), 7.60 (d, J=8.75 Hz, 2H).

1D. (E)-3-(5-chloro-2-tetrazol-1-yl-phenyl)-acrylic acid methyl ester: To a cooled (0° C.) suspension of NaH. (0.262 g, 6.56 mmol) in THF (27.3 mL) was added dropwise methyl 2-(dimethoxyphosphoryl)-acetate (1.150 mL, 7.10 mmol). The resulting thick, white suspension was diluted with additional THF (15 mL) to facilitate mixing, then allowed to warm to room temperature and stirred at room temperature for 45 min. Next, a slightly cloudy blue solution of 5-chloro-2-tetrazol-1-yl-benzaldehyde (1.14 g, 5.46 mmol), prepared according to a modification of the procedure described by Howard (*J. Med. Chem.*, 2006, 49, 1346.), in THF (8 mL) was added. The yellow/green suspension was stirred vigorously. After 30 min, the reaction was poured into cold sat. ammonium chloride and extracted with EtOAc. The combined organic layers were washed with brine, dried over Na$_2$SO$_4$, filtered and concentrated to give a green/blue solid (1.76 g). The solid was redissolved in EtOAc and filtered through a plug of silica gel and eluted with EtOAc. The filtrate was concentrated to give a greenish solid (1.36 g). Recrystallization from EtOAc gave an off-white solid (0.476 g). Additional product was obtained by concentrating the filtrate, adding methanol, sonicating, and collecting the resulting solid by filtration. A total of 0.829 g (57%) of 1D was obtained. LCMS m/z 265.1 (M+H)$^+$; 287.2 (M+Na)$^+$. $^1$HNMR (500 MHz, CDCl$_3$) δ: 8.80 (s, 1H), 7.78 (d, J=2.2 Hz, 1H), 7.58 (dd, J=8.8, 2.2 Hz, 1H), 7.42 (d, J=8.2 Hz, 1H), 7.25 (d, J=16.0 Hz, 1H), 6.45 (d, J=16.0 Hz, 1H), 3.78 (s, 3H).

1E. (E)-3-(5-chloro-2-tetrazol-1-yl-phenyl)-acrylic acid: To a white suspension of 1D (0.140 g, 0.529 mmol) in MeOH (3.0 mL) was added 1.0 M sodium hydroxide (1.587 ml, 1.587 mmol). The resulting suspension was stirred vigorously at rt for 2.5 h. The yellow suspension was neutralized with 1.0 N HCl (1.60 mL), and concentrated to give a beige solid. The solid was partitioned between 1.0 N HCl and EtOAc, and the layers were separated. The organic layer was washed with brine, dried over Na$_2$SO$_4$, filtered and concentrated to give 0.137 g (100%) of 1E as a white solid. LCMS m/z 251.1 (M+H)$^+$. $^1$HNMR (500 MHz, DMSO-d$_6$) δ: 12.72 (s, 1H), 9.87 (s, 1H), 8.24 (d, J=2.2 Hz, 1H), 7.77 (dd, J=8.8, 2.2 Hz, 1H), 7.73 (d, J=8.2 Hz, 1H), 6.98 (d, J=16.0 Hz, 1H), 6.70 (d, J=16.0 Hz, 1H).

Alternatively, 1E can be prepared as follows. To a cold suspension (0-5° C.) of 4-chloro-2-iodoaniline (10.0 g, 39.5 mmol) and sodium azide (7.95 g, 122 mmol) in trimethyl orthoformate (13.08 mL, 118 mmol) was added acetic acid (150 mL). The resulting clear, slightly brown solution was stirred vigorously at 0-5° C. for 30 min and then warmed to rt. A beige precipitate formed overtime and then redissolved to give a clear brown solution. After 22 h, water (400 mL) was added and the suspension was stirred vigorously for 1 h. The solid was collected by filtration, rinsed with water, air-dried, and dried under vacuum to give 11.16 g (92%) of 1-(4-chloro-2-iodo-phenyl)-1H-tetrazole as a beige solid. LCMS m/z, 307.0. (M+H)$^+$. A flame-dried sealed tube vessel containing this intermediate (0.250 g, 0.816 mmol) and palladium acetate (0.018 g, 0.082 mmol) was purged with argon for several minutes. Next degassed acetonitrile (3.26 mL) was added followed by the addition of ethyl acrylate (0.133 mL, 1.224 mmol) and triethylamine (0.171 mL, 1.224 mmol). The vessel was sealed and the orange brown solution was warmed to 85° C. to give a brown suspension. After 21 h, the reaction was stopped and cooled to rt. The reaction was filtered through a 0.45 micron Glass microfibre (GMF), rinsing with acetonitrile, and the filtrate was concentrated to give a brown residue. Flash chromatography gave 0.098 g (43%) of (E)-3-(5-chloro-2-tetrazol-1-yl-phenyl)-acrylic acid ethyl ester as a pale yellow solid. LCMS m/z 279.1 (M+H)$^+$ and 281 (M+2+H)$^+$. Saponification as described above gave 1E.

1F. Example 1: 1E (71 mg, 0.283 mmol), 1C (80 mg, 0.283 mmol), EDC (81 mg, 0.425 mmol), HOBT (65.1 mg, 0.425 mmol), and diisopropylethyl amine (0.198 mL, 1.133 mmol) were combined in DMF (1 mL) and stirred 24 h. The resulting mixture was partitioned with EtOAc/water and extracted with EtOAc (3×20 mL). Combined organic layers were washed with water (20 mL), brine (20 mL) and dried (MgSO$_4$). Purification by reverse phase HPLC and freeze-drying afforded Example 1 (62.6 mg, 43%). LC/MS m/z 513.3 (M+H)$^+$. $^1$H NMR (400 MHz, CD$_3$OD) δ: 3.75 (s, 3 H) 4.52 (s, 2 H) 6.71 (d, J=15.66 Hz, 1 H) 7.17 (d, J=15.66 Hz, 1 H) 7.49-7.70 (m, 6 H) 7.99 (d, J=2.27 Hz, 1 H) 9.52 (s, 1 H).

Example 2

[4-(5-Chloro-2-{[3-(5-chloro-2-tetrazol-1-yl-phenyl)-propionylamino]-methyl}-1H-imidazol-4-yl)-phenyl]-carbamic acid methyl ester, trifluoroacetic acid salt 2A. 3-(5-chloro-2-tetrazol-1-yl-phenyl)-propionic acid: To a suspension of 1E (0.030 g, 0.120 mmol) in MeOH (5.0 mL) was added platinum oxide (0.005 g, 0.022 mmol). Hydrogen from a balloon was bubbled through the reaction for 1-2 min and then the reaction was stirred vigorously under a hydrogen atmosphere. Additional amounts of platinum oxide (0.010 g, 0.044 mmol) were added over the course of the reaction. After 27 h, the reaction was filtered, and the filtrate was concentrated to give a brown residue. The residue was dissolved in MeOH, refiltered, and the filtrate was concentrated to give 2A (0.025 g, 83%) as a clear colorless residue. LCMS m/z 253.1 (M+H)$^+$. $^1$HNMR (400 MHz, CD$_3$OD) δ: 9.51 (s, 1H), 7.63 (d, J=2.2 Hz, 1H), 7.48 (dd, J=8.8, 2.2 Hz, 1H), 7.43 (d, J=8.8 Hz, 1H), 2.72 (t, J=7.5 Hz, 2H), 2.55 (t, J=7.5 Hz, 2H)).

An alternative synthesis of 2A is as follows. To a clear solution of 1D (0.617 g, 2.331 mmol) in EtOAc (46.6 mL) was added platinum oxide (0.106 g, 0.466 mmol). After a series of vacuum flushes, the vessel was pressurized with hydrogen to 60 psi, and the suspension was stirred vigorously. After 24 h, the reaction was stopped and the pressure was released. The reaction was filtered through a plug of Celite®/silica gel, eluting with EtOAc, to give a pale, green solution. Concentration gave a greenish-black oil weighing 0.705 g. Flash chromatography gave 3-(5-chloro-2-tetrazol-1-yl-phenyl)-propionic acid methyl ester (0.572 g, 92%) as a clear, colorless viscous oil. LCMS m/z 267.1 (M+H)$^+$. Saponification according to the procedure for 1E gave 2A.

2B. Example 2: To a DMF (2 mL) solution of 2A (0.072 g, 0.285 mmol) were added 1C (0.08 g, 0.285 mmol), EDC (0.082 g, 0.427 mmol), HOBT (0.065 g, 0.427 mmol), and Hunig's base (0.199 ml, 1.140 mmol). The reaction mixture was stirred at rt for 24 h. The reaction was quenched with water (10 mL) and extracted with EtOAc (3×10 mL). The combined organic layers were washed with water, brine, and dried (MgSO$_4$). Purification by reverse phase HPLC and freeze-tying of pure fractions afforded the title compound as a white solid (62.5 mg, 34.8%). LC/MS m/z 515.4 (M+H)$^+$. $^1$H NMR (400 MHz, CD$_3$OD) δ 2.53 (t, J=7.33 Hz, 2 H), 2.76 (t, J=7.45 Hz, 2 H), 3.75 (s, 3 H), 4.37 (s, 2 H), 7.34-7.46 (m, 2 H), 7.50-7.63 (m, 5 H) 9.51 (s, 1 H).

Example 3

(E)-N-[5-Chloro-4-(2-oxo-1,2,3,4-tetrahydro-quinolin-6-yl)-1H-imidazol-2-ylmethyl]-3-(5-chloro-2-tetrazol-1-yl-phenyl)-acrylamide, trifluoroacetic acid salt 3A. tert-Butoxycarbonylamino-acetic acid 2-oxo-2-(2-oxo-1,2,3,4-tetrahydro-quinolin-6-yl)-ethyl ester: To Boc-glycine (0.137 g, 0.783 mmol) in dry DMF (5 mL) were added commercially available 7-(2-bromo-acetyl)-3,4-dihydro-1H-quinolin-2-one (0.21 g, 0.783 mmol) and Cs$_2$CO$_3$ (0.255 g, 0.783 mmol), and the reaction mixture was stirred for 24 h at rt. The reaction was quenched with water (100 mL) and extracted with EtOAc (3×20 mL). The combined organic layers were washed with water, brine, and dried over MgSO$_4$, filtered, and concentrated to give 3A. LC/MS m/z 363.3 (M+H)$^+$.

B. [4-(2-Oxo-1,2,3,4-tetrahydro-quinolin-6-yl)-1H-imidazol-2-ylmethyl]-carbamic acid tert-butyl ester: A mixture of the crude product 3A, toluene (8 mL), α,α,α-trifluorotoluene (2 mL), and ammonium acetate (0.423 g, 5.48 mmol) was subjected to microwave heating in a sealed tube at 160° C. for 15 min. The reaction was quenched with water (50 mL) and extracted with EtOAc (3×20 mL). The combined organic layers were washed with water, brine, and dried (MgSO$_4$). Purification by flash chromatography afforded 3B as a tan solid (0.109g, 40.6%). LC/MS m/z 343.3 (M+H)$^+$. $^1$H NMR (400 MHz, CDCl$_3$) δ: 1.47 (s, 9 H), 2.64 (t, J=7.8 Hz, 2 H), 2.99 (t, J=7.3 Hz, 2 H), 4.36 (d, J=6.06 Hz, 2 H), 5.29 (bs, 1 H), 6.74 (d, J=8.08 Hz, 1 H), 7.18 (s, 1 H), 7.52 (d, J=7.08 Hz, 1 H), 7.59 (s, 1 H), 7.76 (bs, 1 H), 10.00 (bs, 1 H).

C. [5-Chloro-4-(2-oxo-1,2,3,4-tetrahydro-quinolin-6-yl)-1H-imidazol-2-ylmethyl]-carbamic acid tert-butyl ester: To 3B (0.1 g, 0.292 mmol) in acetonitrile (5 mL) was added NCS (0.041 g, 0.307 mmol) and the reaction mixture was heated to 60° C. After 2 h the reaction was concentrated and purified by flash chromatography to afford 3C as a yellow solid (52 mg, 47.7%). LC/MS m/z 377.3 (M+H)$^+$. $^1$H NMR (400 MHz, CDCl$_3$) δ: 1.43 (s, 9 H), 2.65 (t, 2 H), 2.98 (t, J=7.45 Hz, 2 H), 4.33 (d, J=5.81 Hz, 2 H), 5.83 (s, 1 H), 6.89 (d, J=8.08 Hz, 1 H), 7.33-7.45 (m, 2 H), 9.09 (s, 1 H), 11.09 (s, 1 H).

3D. 6-(2-aminomethyl-5-chloro-1H-imidazol-4-yl)-3,4-dihydro-1H-quinolin-2-one, bis-hydrochloride salt: To 3C (52 mg) dissolved in dioxane (3 mL) was added 4N HCl (3 mL) and the reaction was stirred 24 h. The reaction was concentrated to afford 3D as a yellow solid (53 mg, 57.9%). LC/MS m/z 277.2 (M+H)$^+$. $^1$H NMR (400 MHz, DMSO-d$_6$) δ: 2.93 (t, J=7.45 Hz, 2 H), 3.46-3.67 (m, 2 H), 3.87-4.14 (m, 2 H), 6.96 (d, J=8.08 Hz, 1 H), 7.47-7.57 (m, 2 H), 8.45 (s, 2 H), 10.24 (s, 1 H).

3E. Example 3: To DMF (3 mL) were added 1E (41.6 mg, 0.166 mmol), 3D (52 mg, 0.166 mmol), EDC (47.7 mg, 0.249 mmol), HOBT (38.1 mg, 0.249 mmol), and Hunig's Base (0, 116 mL, 0.664 mmol). The reaction mixture was stirred at rt for 24 h. The reaction was quenched with water (10 mL) and extracted with EtOAc (3×10 mL). The combined organic layers were washed with water, brine, and dried (MgSO$_4$). The crude product was heated in 3:1 MeOH/DCM (10 mL), cooled and filtered. The solid was re-suspended in CH$_3$CN/H$_2$O and freeze-dried to afford the title compound as a white solid (23.7 mg, 22.9%). LC/MS m/z 509.3 (M+H)$^-$. $^1$H NMR (400 MHz, DMSO-d$_6$) δ: 2.37-2.43 (m, 2 H), 2.85 (t, J=7.58 Hz, 2 H), 4.30 (d, J=5.56 Hz, 2 H), 6.72 (d, J=15.6 Hz, 1 H), 6.81-6.91 (m, 2 H), 7.34-7.46 (m, 2 H), 7.61-7.72 (m, 2 H), 7.89 (d, J=2.02 Hz, 1 H), 8.61 (t, J=5.18 Hz, 1 H), 9.80 (s, 1 H), 10.12 (s, 1 H), 12.54 (s, 1 H).

Example 5

[4-(5-{[(E)-3-(5-Chloro-2-tetrazol-1-yl-phenyl)-acryloylamino]-methyl}-pyridin-3-yl)-phenyl]-carbamic acid methyl ester, trifluoroacetic acid salt 5A. Methyl 4-(5-(aminomethyl)pyridin-3-yl)phenylcarbamate: Tetrakis(triphenylphosphine)palladium(0) (0.063 g, 0.055 mmol) was added to a degassed solution of 4:1 DME/H$_2$O (8 mL) containing 5-bromonicotinonitrile (0.200 g, 1.09 mmol), 4-(methoxycarbonylamino)phenylboronic acid (0.43 g, 2.19 mmol), and potassium carbonate (0.91 g, 6.56 mmol) under argon. The mixture was heated at 150° C. in a microwave reactor for 15 min. The cooled solution was suspended in H$_2$O (20 mL) and extracted with EtOAc (3×10 mL). The combined organic extracts were washed with brine, dried over sodium sulfate, filtered, and concentrated to leave a yellow solid. This residue was dissolve in THF (10 mL), cooled to 0° C., and treated with borane-tetrahydrofuran complex (1639 µL, 1.639 mmol) dropwise under argon. The reaction was allowed to gradually warm to rt and stir under ambient conditions for 16 h. Then, the reaction mixture was cooled to 0° C., treated with 1.0 M HCl (10 mL), and heated at reflux for 30 min. The mixture was cooled back to 0° C. and basified with 1.0 N NaOH. The solution was saturated with NaCl and extracted with THF (3×50 mL). The combined organic extracts were dried over sodium sulfate, filtered and concentrated. The crude product was carried forward to next reaction without purification. LC/MS m/z 258 (M+H)$^+$.

5B. Example 5: 5A (0.13g, 0.50 mmol), 1E (0.19g, 0.75 mmol), HOBt (0.077 g, 0.50 mmol), EDCI (0.096 g, 0.50 mmol), and N-methylmorpholine (0.055 mL, 0.50 mmol) were added to DMF (2.0 mL) and stirred at rt. After 2 h, the reaction mixture was partitioned between EtOAc and H$_2$O/brine (1:1). The organic extract was washed with brine, dried over sodium sulfate, filtered, and concentrated. The crude material was purified by reverse phase HPLC. The product fractions were liberated of organics by rotary evaporation and freeze-dried to give Example 5 as an amber solid (18 mg, 7%). LC/MS m/z 490 (M+H)$^+$. $^1$H NMR (400 MHz, DMSO-d$_6$) δ: 3.68 (s, 3 H), 4.49 (d, J=5.71 Hz, 2 H), 6.72-6.80 (m, 1 H), 6.89-6.96 (m, 1 H), 7.58-7.64 (m, 2 H), 7.67-7.76 (m, 4 H), 8.00 (d, J=1.76 Hz, 1 H), 8.17 (s, 1 H), 8.52 (s, 1 H), 8.79-8.85 (m, 1 H), 8.86 (s, 1 H), 9.87 (s, 1 H), 9.88 (s, 1 H).

Example 6

[4-(5-{[3-(5-Chloro-2-tetrazol-1-yl-phenyl)-propionylamino]-methyl}-pyridin-3-yl)-phenyl]-carbamic acid methyl ester, trifluoroacetic acid salt Example 6 was prepared in the same manner as Example 5 replacing 1E with 2A to give an amber solid (30 mg, 13%). HRMS m/z 492.1542 (M+H)$^+$. $^1$H NMR (400 MHz, DMSO-d$_6$) δ 2.42 (t, J=7.47 Hz, 2 H), 2.63 (t, J=7.47 Hz, 2 H), 3.68 (s, 3 H), 4.35 (d, J=5.71 Hz, 2 H), 7.48-7.57 (m, 2 H), 7.59-7.64 (m, 3 H), 7.66-7.71 (m, 2 H), 8.14 (s, 1 H), 8.45-8.54 (m, 2 H), 8.88 (d, J=1.76 Hz, 1 H), 9.80 (s, 1 H), 9.90 (s, 1 H).

Example 7

[4-(2-{[(E)-3-(5-Chloro-2-tetrazol-1-yl-phenyl)-acryloylamino]-methyl}-pyridin-4-yl)-phenyl]-carbamic acid methyl ester, trifluoroacetic acid salt 7A. [4-(2-Aminomethyl-pyridin-4-yl)-phenyl]-carbamic acid methyl ester: Tetrakis(triphenylphosphine)palladium (0) (0.063 g, 0.055 mmol) was added to a degassed solution of DME/$H_2O$ (4:1, 8 mL) containing, 4-(methoxycarbonylamino)phenylboronic acid (0.32 g, 1.64 mmol), 4-bromopicolinonitrile (0.20 g, 1.09 mmol) and potassium carbonate (0.906 g, 6.56 mmol) under a blanket of argon. The mixture was irradiated at 150° C. microwave conditions for 15 min. The cooled solution was partitioned between EtOAc (20 mL) and $H_2O$ (20 mL). The layers were separated and the aqueous layer was extracted with EtOAc (2×10 mL). The combined organic layers were washed with brine, dried over sodium sulfate, filtered, and concentrated to leave a tan solid. The residue was dissolved 2.0 M $NH_3$/MeOH (20 mL) treated with a slurry of Raney Ni (in water) and stirred under a hydrogen atmosphere (50 psi) for 14 h. The suspension was filtered through a plug of Celite®, the filter-cake was rinsed with MeOH and the combined filtrates were concentrated to give 7A as a tan solid. The crude product was carried forward to the next reaction without purification. LC/MS m/z 258 $(M+H)^+$.

7B. Example 7 was prepared by reacting 7A and 1E according to the procedure described in Example 5B to give a white solid (66 mg, 10% yield). LC/MS m/z 490 $(M+H)^+$. $^1$H NMR (400 MHz, DMSO-$d_6$) δ 3.68 (s, 3 H) 4.57 (d, J=5.50 Hz, 2 H) 6.81-6.88 (m, 1 H) 6.90-6.97 (m, 1 H) 7.63 (d, J=8.79 Hz, 2 H) 7.70-7.85 (m, 6 H) 8.01 (d, J=2.20 Hz, 1 H) 8.61 (d, J=6.05 Hz, 1 H) 8.82 (t, J=5.77 Hz, 1 H) 9.86 (s, 1 H) 9.97 (s, 1 H).

Example 8

[4-(5-{[(E)-3-(5-Chloro-2-tetrazol-1-yl-phenyl)-acryloylamino]-methyl}-6-oxo-1,6-dihydro-pyridin-3-yl)-phenyl]-carbamic acid methyl ester Example 8 was prepared following the procedures described in Example 7 by replacing 5-bromonicotinonitrile with 5-bromo-2-hydroxynicotinonitrile. LC/MS m/z 506 $(M+H)^+$. $^1$H NMR (400 MHz, $CD_3OD$) δ 3.70-3.77 (m, 3 H)$_3$ 4.37 (s, 2 H), 6.75 (d, J=15.39 Hz, 1 H), 7.14 (d, J=15.94 Hz, 1 H), 7.39-7.44 (m, 2 H), 7.49 (d, J=8.79 Hz, 2 H), 7.53-7.59 (m, 2 H), 7.61-7.68 (m, 1 H), 7.81 (s, 1 H), 7.99 (d, J=2.20 Hz, 1 H), 9.52 (s, 1 H).

Example 9

(E)-N-[4-(3-Amino-1H-indazol-6-yl)-5-chloro-1H-imidazol-2-ylmethyl]-3-(5-chloro-2-tetrazol-1-yl-phenyl)-acrylamide, trifluoroacetic acid salt 9A. 4-(2-Bromo-acetyl)-2-fluoro-benzonitrile: To 4-Acetyl-2-fluoro-benzonitrile (2.2 g, 13.48 mmol) in $CHCl_3$ (50 mL) at 70° C. was added a slurry of copper(II)bromide (3.61 g, 16.18 mmol) in EtOAc (50.0 mL) and the reaction was heated 24 h. The reaction was cooled and solid was filtered off. The filtrate was concentrated and purified by flash chromatography to afford 9A (2.2 g, 41%) as a pale yellow solid. 14 NMR (400 MHz, $CDCl_3$) δ 4.40 (s, 2 H) 7.74-7.91 (m, 3 H).

9B. tert-Butoxycarbonylamino-acetic acid 2-(4-cyano-3-fluoro-phenyl)-2-oxo-ethyl ester: To Boc-glycine (0.507 g, 2.89 mmol) in DMF (5 mL) was added $Cs_2CO_3$ (0.942 g, 2.89 mmol) and the reaction was stirred 30 min. 9A (0.7 g, 2.89 mmol) was then added. The reaction was quenched with water (30 mL) and extracted with ethyl acetate (3×40 mL). The combined organic layers were washed with water (10 mL), brine (10 mL) and dried ($Na_2SO_4$). Purification by flash chromatography afforded 1.4 g of 9B as a bright yellow solid. LC/MS m/z 237.2 (M+H-tbutyl)$^+$. The crude material was carried onto the next step.

9C. [4-(4-Cyano-3-fluoro-phenyl)-1H-imidazol-2-ylmethyl]-carbamic acid tert-butyl ester: 9B was placed in xylene (50 mL) with $NH_4OAc$ (1.338 g, 17.35 mmol) and heated to 130° C. for 18 h. The reaction was cooled, quenched with water (30 mL) and extracted with ethyl acetate (3×30 mL). The combined organic layers were washed with water (20 mL), brine (20 mL) and dried ($MgSO_4$). Purification by flash chromatography afforded 9C (0.6 g, 65.6%) as a brown foam. LC/MS m/z 317.3 $(M+H)^+$. $^1$H NMR (400 MHz, $CDDC_3$) δ 1.47 (s, 9 H), 4.34 (d, J=6.05 Hz, 2 H), 5.36 (s, 1 H), 7.38 (s, 1 H), 7.52-7.66 (m, 3 H), 10.22 (s, 1 H).

9D. [5-Chloro-4-(4-cyano-3-fluoro-phenyl)-1-imidazol-2-ylmethyl]-carbamic acid tert-butyl ester: To 9C (0.313 g, 0.989 mmol) in acetonitrile (15 mL) was added NCS (0.145 g, 1.088 mmol) and the reaction was heated at 60° C. for 72 h. The reaction was cooled and concentrated. Purification by flash chromatography afforded 9D (0.144 g, 41.5%) as a brown foam. LC/MS m/z 295.2 (M+H-tbutyl)$^+$. $^1$H NMR (400 MHz, $CDCl_3$) δ 1.43 (s, 9 H), 4.37 (d, J=5.50 Hz, 2 H), 6.23 (t, J=5.50 Hz, 1 H), 7.43 (d, J=8.79 Hz, 2 H), 7.54-7.67 (m, 1 H), 11.74 (s, 1 H).

9E. [4-(3-Amino-1H-indazol-6-yl)-5-chloro-1H-imidazol-2-ylmethyl]-carbamic acid tert-butyl ester: To 9D (0.144 g, 0.411 mmol) in MeOH (10 mL) was added hydrazine hydrate (0.077 mL, 2.463 mmol) and the reaction was heated in the microwave for 11 min. MS showed the reaction to be incomplete. Additional hydrazine was added and the reaction was re-heated for 11 min. The reaction was concentrated and purified by flash chromatography to afford 9E (84 mg, 56.7%) as a clear oil. LC/MS m/z 363.2 $(M+H)^+$.

9F. 6-(2-Aminomethyl-5-chloro-1H-imidazol-4-yl)-1H-indazol-3-ylamine: The product of 9E was placed in dioxane (2 mL) and treated with 4M HCl in dioxane (3 mL) and stirred for 24 h. The solvents were removed to afford 9F (85 mg, 61.7%) as a pale yellow solid. LC/MS m/z 263.2 $(M+H)^+$. $^1$H NMR (400 MHz, DMSO-$d_6$) δ 4.16 (d, J=5.81 Hz, 2 H), 7.59 (d, J=8.59 Hz, 1 H), 7.80 (s, 1 H), 8.04 (d, J=8.59 Hz, 1 H), 8.57 (d, J=2.27 Hz, 2 H).

9G. Example 9: To 9F (63 mg, 0.188 mmol), 1F (47.0 mg, 0.188 mmol), BOP (83 mg, 0.188 mmol) in THF (12 mL) was added Hunig's Base (0.164 ml, 0.939 mmol). After 2 h, the reaction was quenched with water (15 mL) and extracted with ethyl acetate (3×25 mL). The combined organic layers were washed with brine (10 mL) and dried ($MgSO_4$). Purification by reverse phase HPLC and freeze-dried to afford Example 9 (12 mg, 12.9%) as a white solid. LC/MS m/z 495.2 $(M+H)^+$. $^1$H NMR (400 MHz, $CD_3OD$) δ 4.36-4.47 (m, 2 H), 6.63 (d, J=15.66 Hz, 1 H), 7.07 (d, J=15.66 Hz, 1 H), 7.41-7.53 (m, 2 H), 7.56 (d, J=8.59 Hz, 1 H), 7.66 (s, 1 H), 7.85 (d, J=8.59 Hz, 1 H), 7.89 (d, J=2.27 Hz, 1 H), 9.43 (s, 1 H).

Example 10

{4-[2-({Benzyl-[(E)-3-(5-chloro-2-tetrazol-1-yl-phenyl)-acryloyl]-amino}-methyl)-5-chloro-1H-imidazol-4-yl]-phenyl}-carbamic acid methyl ester, trifluoroacetic acid salt 10A. (Benzyl-tert-butoxycarbonyl-amino)-acetic acid: To 2-(benzylamino)acetic acid, HCl (3 g, 14.88 mmol) in DCM (40 mL) was added di-tert-butyl dicarbonate (3.25 g, 14.88 mmol) and TEA (6.22 mL, 44.6 mmol) and stirred for 6 days. The reaction was partitioned with DCM/dil HCl and extracted with DCM (3×20 mL). Combined organic layers were washed with water (20 mL), brine (20 mL) and dried (MgSO$_4$) to afford 10A and containing some triethylamine hydrochloride impurity (5 g, 125%) as a clear colorless oil. $^1$H NMR (400 MHz, CDCl$_3$) δ 1.38-1.46 (d, 9 H), 3.71 (s, 1 H), 3.86 (s, 1 H), 4.54 (d, J=12.38 Hz, 2 H), 7.07-7.37 (m, 5 H). Used without further purification.

10B. (4-{2-[(Benzyl-tert-butoxycarbonyl-amino)-methyl]-1H-imidazol-4-yl}-phenyl)-carbamic acid methyl ester: To 10A (0.244 g, 0.919 mmol) and 1A (0.25 g, 0.919 mmol) in DMF (1 mL) was added cesium carbonate (0.299 g, 0.919 mmol) and the reaction was stirred 24 h. The reaction was quenched with water (10 mL) and extracted with ethyl acetate (3×15 mL). The combined organic layers were washed with brine (10 mL), dried (MgSO$_4$), and concentrated to give the crude ester. The crude ester was heated in a microwave at 160° C. with NH$_4$OAc (0.425 g, 5.51 mmol) in ethanol (5 mL) and toluene (5 mL) for 15 min. The reaction was quenched with water (10 mL) and extracted with ethyl acetate (3×20 mL). The combined organic layers were washed with brine (10 mL), dried (MgSO$_4$), and concentrated. Purification by chromatography afforded 10B (0.337 g, 84%) as a tan solid. LC/MS m/z 437.4 (M+H)$^+$. $^1$H NMR (400 MHz, CDCl$_3$) δ 1.48 (s, 9 H), 3.77 (s, 3 H), 4.41 (s, 2 H), 4.48 (s, 2 H), 6.82 (s, 1 H), 7.17 (s, 1 H), 7.21-7.28 (m, 4 H), 7.29-7.35 (m, 2 H), 7.40 (d, J=7.70 Hz, 2 H), 7.59 (s, 2 H).

10C. Example 10 was prepared according to the procedures described in 1C and 1F by replacing 1B with 10B. LC/MS m/z 603.4 (M+H)$^+$. $^1$H NMR (400 MHz, DMSO-d$_6$) δ 3.69 (s, 3 H), 4.53 (s, 1 H), 4.60 (s, 1 H), 4.76 (s, 1 H), 4.96 (s, 1 H), 7.04 (dd, J=15.16, 4.29 Hz, 1 H), 7.20-7.30 (m, 2 H), 7.29-7.35 (m, 2 H), 7.39 (t J=7.33 Hz, 1 H), 7.50-7.63 (m, 4 H), 7.70-7.78 (m, 2 H), 8.36 (dd, J=22.61, 1.89 Hz, 1 H), 9.79 (d, J=6.32 Hz, 1 H), 9.89 (d, J=7.83 Hz, 1 H).

TABLE 1

| Ex. No. | Structure | MS (M + H)$^+$ |
|---|---|---|
| 1 | 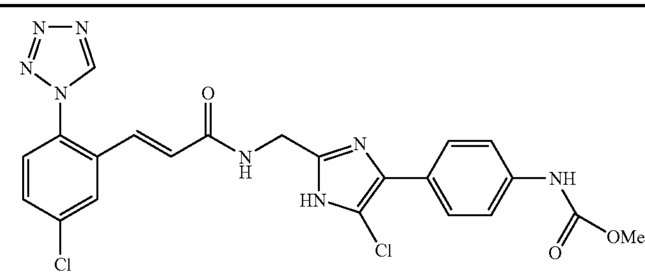 | 513.3 |
| 2 | 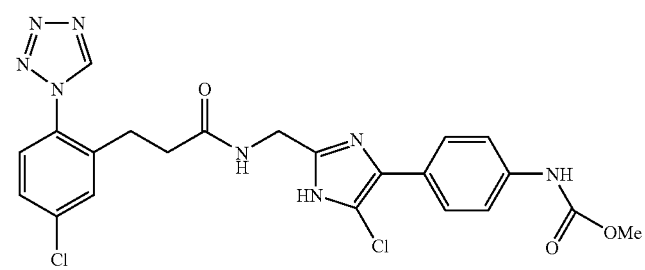 [SMILES: COC(=O)Nc1ccc(-c2nc(CNC(=O)CCc3cc(Cl)ccc3-n3cnnn3)[nH]c2Cl)cc1] | 515.4 |
| 3 | 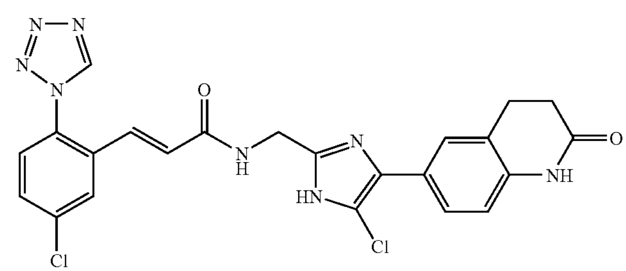 [SMILES: O=C(/C=C/c1cc(Cl)ccc1-n1cnnn1)NCc1nc(-c2ccc3c(c2)CCC(=O)N3)c(Cl)[nH]1] | 509.3 |
| 5 | 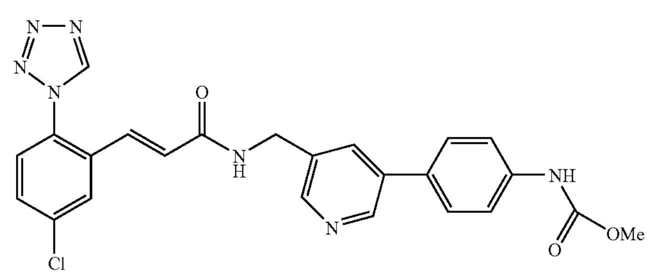 [SMILES: COC(=O)Nc1ccc(-c2cncc(CNC(=O)/C=C/c3cc(Cl)ccc3-n3cnnn3)c2)cc1] | 490 |

TABLE 1-continued

| Ex. No. | Structure | MS (M + H)+ |
|---|---|---|
| 6 | 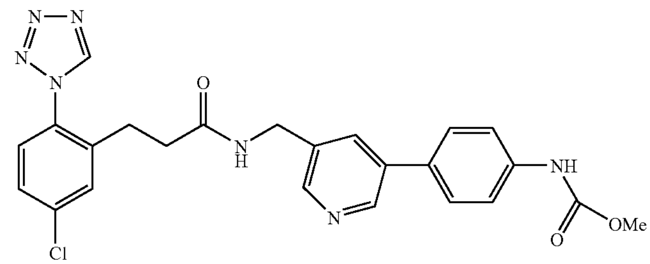 [SMILES: COC(=O)Nc1ccc(-c2cncc(CNC(=O)CCc3cc(Cl)ccc3-n3cnnn3)c2)cc1] | 492.2 |
| 7 | 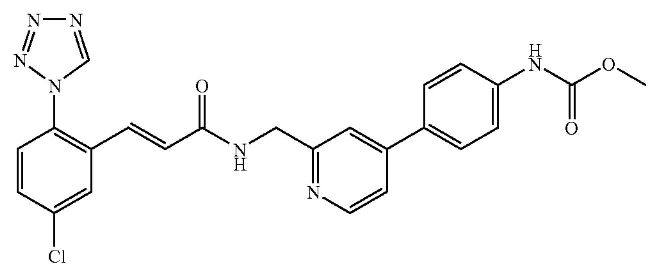 [SMILES: COC(=O)Nc1ccc(-c2ccnc(CNC(=O)/C=C/c3cc(Cl)ccc3-n3cnnn3)c2)cc1] | 490 |
| 8 | 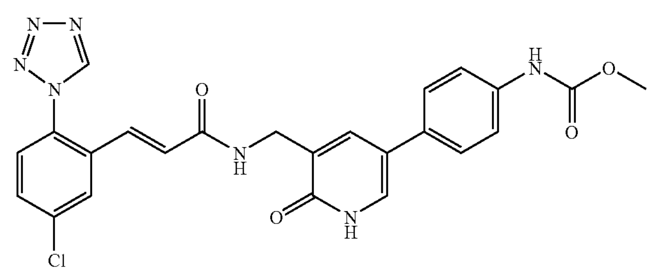 [SMILES: COC(=O)Nc1ccc(-c2c[nH]c(=O)c(CNC(=O)/C=C/c3cc(Cl)ccc3-n3cnnn3)c2)cc1] | 506 |
| 9 | 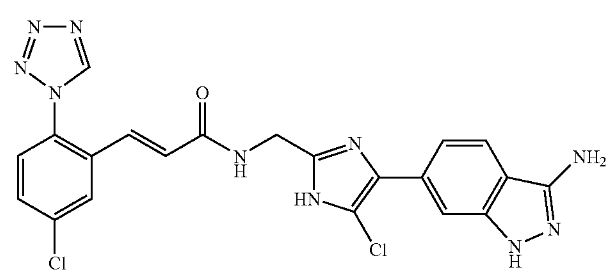 [SMILES: Nc1n[nH]c2cc(-c3nc(CNC(=O)/C=C/c4cc(Cl)ccc4-n4cnnn4)[nH]c3Cl)ccc12] | 495.2 |
| 10 | 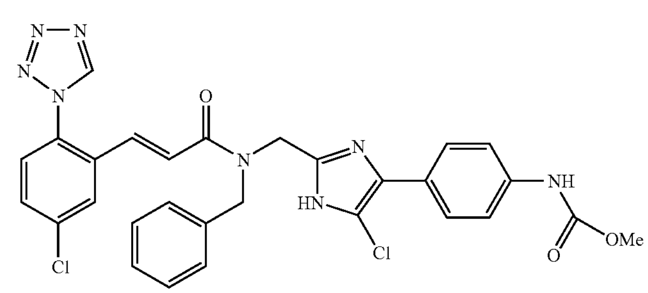 [SMILES: COC(=O)Nc1ccc(-c2nc(CN(Cc3ccccc3)C(=O)/C=C/c3cc(Cl)ccc3-n3cnnn3)[nH]c2Cl)cc1] | 603.4 |

Table 1 below lists Factor XIa Ki values for the above examples measured in the Factor XIa assay described above.

TABLE 1

| Example Number | Factor XIa Ki (nM) |
|---|---|
| 1 | 27.3 |
| 2 | 16.8 |
| 3 | 12.1 |
| 5 | 283 |
| 6 | 1247 |
| 7 | 475 |
| 8 | 277 |
| 9 | 5.5 |
| 10 | 1510 |

While the foregoing specification teaches the principles of the present invention, which examples provided for the purpose of illustration, it will be understood that the practice of the invention encompasses all of the usual variations, adaptations and/or modifications as come within the scope of the following claims and their equivalents.

What is claimed is:
1. A compound of Formula (I):

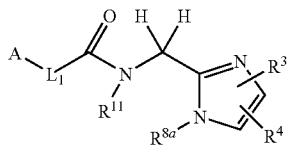

(I)

or stereoisomers, tautomers, or pharmaceutically acceptable salts thereof, wherein:

A is a $C_{3-10}$ carbocycle substituted with 0-1 $R^1$ and 0-3 $R^2$, or a 5- to 12-membered heterocycle comprising: carbon atoms and 1-4 heteroatoms selected from N, O, and $S(O)_p$, wherein said heterocycle is substituted with 0-1 $R^1$ and 0-3 $R^2$; provided that when A is a heterocycle containing one or more nitrogen atoms, A is not attached to $L_1$ via any of the nitrogen atoms on the A ring;

$L_1$ is —CHR$^5$CH$_2$—, —CH(NR$^7$R$^8$)CH$_2$—, —CR$^5$=CH—, —C≡C—, —OCH$_2$—, —C(R$^5$R$^6$)NH—, —CH$_2$O—, —SCH$_2$—, —S(O)CH$_2$—, —SO$_2$CH$_2$—, —CH$_2$NR$^{10}$—, or —NHNH—;

provided that when $L_1$ is —CH$_2$O—, then A is other than an unsubstituted phenyl;

$R^1$ is, independently at each occurrence, F, Cl, Br, I, OCF$_3$, CF$_3$, —(CH$_2$)$_r$OR$^a$, —(CH$_2$)$_r$SR$^a$, CN, —(CH$_2$)$_r$NR$^7$R$^8$, —C(=NR$^8$) NR$^8$R$^9$, —C(O)NR$^8$R$^9$, —S(O)$_p$NR$^8$R$^9$, or $C_{1-6}$ alkyl substituted with 0-1 $R^{1a}$;

$R^{1a}$ is F, OCF$_3$, CF$_3$, OR$^a$, SR$^a$, CN, —NR$^7$R$^8$, —C(O)NR$^8$R$^9$, —NR$^8$C(O)R$^c$, —S(O)$_p$NR$^8$R$^9$, —NR$^8$SO$_2$R$^c$, or —(CF$_2$)$_r$CF$_3$;

$R^2$ is, independently at each occurrence, =O, F, Cl, Br, OCF$_3$, CF$_3$, CHF$_2$, CN, NO$_2$, —(CH$_2$)$_r$OR$^a$, —(CH$_2$)$_r$SR$^a$, —(CH$_2$)$_r$C(O)R$^a$, —(CH$_2$)$_r$C(O)OR$^a$, —(CH$_2$)$_r$OC(O)R$^a$, —(CH$_2$)$_r$NR$^7$R$^8$, —(CH$_2$)$_r$C(O)NR$^8$R$^9$, —(CH$_2$)$_r$NR$^8$C(O)R$^c$, —(CH$_2$)$_r$NR$^8$C(O)OR$^c$, —NR$^8$C(O)NR$^8$R$^c$, —S(O)$_p$NR$^8$R$^9$, —NR$^8$S(O)$_p$R$^c$, —S(O)R$^c$, —S(O)$_2$R$^c$, $C_{1-6}$ alkyl substituted with 0-1 $R^{2a}$, —(CH$_2$)$_r$-3-7 membered carbocycle optionally substituted with 0-2 $R^{2b}$, or —(CH$_2$)$_r$-5-7 membered heterocycle comprising carbon atoms and 1-4 heteroatoms selected from N, O, and $S(O)_p$, wherein said heterocycle is substituted with 0-2 $R^{2b}$;

alternately, when $R^1$ and $R^2$ groups are substituents on adjacent atoms they may be taken together with the atoms to which they are attached to form a 5- to 7-membered carbocycle or heterocycle comprising carbon atoms and 0-4 heteroatoms selected from N, O, and $S(O)_p$ and substituted with 0-2 $R^g$;

$R^{2a}$ is F, OCF$_3$, CF$_3$, OR$^a$, SR$^a$, CN, —NR$^7$R$^8$, —C(O)NR$^8$R$^9$, —NR$^8$C(O)R$^c$, —NR$^8$C(O)OR$^c$, —NR$^8$C(O)NR$^8$R$^c$, —S(O)$_p$NR$^8$R$^9$, —NR$^8$SO$_2$R$^c$, or —(CF$_2$)$_r$CF$_3$;

$R^{2b}$ is, independently at each occurrence, =O, F, Br, Cl, OCF$_3$, CF$_3$, —(CH$_2$)$_r$OR$^a$, —(CH$_2$)$_r$SR$^a$, —(CH$_2$)$_r$CN, —(CH$_2$)$_r$NR$^7$R$^8$, —(CH$_2$)$_r$C(O)OR$^a$, —(CH$_2$)$_r$OC(O)R$^a$, —(CH$_2$)$_r$C(O)NR$^8$R$^9$, —(CH$_2$)$_r$NR$^8$C(O)R$^c$, —(CH$_2$)$_r$NR$^8$C(O)OR$^c$, —(CH$_2$)$_r$S(O)$_p$NR$^8$R$^9$, —(CH$_2$)$_r$NR$^8$SO$_2$R$^c$, $C_{1-4}$ alkyl or —(CF$_2$)$_r$CF$_3$;

$R^3$ is —(CH$_2$)$_r$—$C_{3-10}$ carbocycle substituted with 0-3 $R^{3a}$ and 0-1 $R^{3d}$, or —(CH$_2$)$_r$-5- to 12-membered heterocycle comprising: carbon atoms and 1-4 heteroatoms selected from N, O, and $S(O)_p$, wherein said heterocycle is substituted with 0-3 $R^{3a}$ and 0-1 $R^{3d}$;

$R^{3a}$ is, independently at each occurrence, =O, =NR$^8$, F, Cl, Br, I, OCF$_3$, CF$_3$, —(CH$_2$)$_r$CN, NO$_2$, —(CH$_2$)$_r$OR$^{3b}$, —(CH$_2$)$_r$SR$^{3b}$, —(CH$_2$)$_r$NR$^7$R$^8$, —NHC(O)NR$^8$R$^9$, —(CH$_2$)$_r$C(O)OR$^{3b}$, —C(O)C$_{1-4}$ alkyl, —SO$_2$NHR$^{3b}$, —SO$_2$NHCOR$^{3c}$, —SO$_2$NHCO$_2$R$^{3c}$, —CONHSO$_2$R$^{3c}$, —(CH$_2$)$_r$NR$^8$C(O)R$^{3b}$, —(CH$_2$)$_r$NR$^8$CO$_2$R$^{3c}$, —(CH$_2$)$_r$S(O)$_p$NR$^8$R$^9$, —(CH$_2$)$_r$NR$^8$S(O)$_p$R$^{3c}$, —NHSO$_2$CF$_3$, —S(O)R$^{3c}$, —S(O)$_2$R$^{3c}$, —(CH$_2$)$_r$OC(O)R$^{3b}$, —(CH$_2$)$_r$C(O)NR$^8$R$^9$, —(CH$_2$)$_r$OC(O)NR$^8$R$^9$, —NHCOCF$_3$, —NHSO$_2$R$^{3c}$, —CONHOR$^{3b}$, $C_{1-4}$ haloalkyl, $C_{1-4}$ haloalkyloxy-, $C_{1-6}$ alkyl substituted by $R^{3e}$, $C_{2-6}$ alkenyl substituted by $R^{3e}$, $C_{1-6}$ alkynyl substituted by $R^{3e}$, $C_{3-6}$ cycloalkyl substituted by 0-1 $R^{3d}$, —(CH$_2$)$_r$—$C_{6-10}$ carbocycle substituted by 0-3 $R^{3d}$ or —(CH$_2$)$_r$-5- to 10-membered heterocycle comprising: carbon atoms and 1-4 heteroatoms selected from N, O, and $S(O)_p$, wherein said heterocycle is substituted with 0-3 $R^{3d}$;

alternately, when two $R^{3a}$ groups are substituted on adjacent atoms, they can be taken together with the atoms to which they are attached to form a $C_{3-10}$ carbocycle substituted with 0-2 $R^{3d}$, or a 5- to 10-membered heterocycle comprising: carbon atoms and 1-4 heteroatoms selected from N, O, and $S(O)_p$, wherein said heterocycle is substituted with 0-2 $R^{3d}$;

$R^{3b}$ is, independently at each occurrence, H, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, —(CH$_2$)$_r$—$C_{3-10}$ carbocycle substituted with 0-3 $R^{3d}$, or —(CH$_2$)$_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3c}$ is, independently at each occurrence, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, —(CH$_2$)$_r$—$C_{3-10}$ carbocycle substituted with 0-3 $R^{3d}$, or —(CH$_2$)$_r$-5 to 10-membered heterocycle comprising: carbon atoms and 1-4 heteroatoms selected from N, O, and $S(O)_p$, wherein said heterocycle is substituted with 0-3 $R^{3d}$;

$R^{3d}$ is, independently at each occurrence, H, =O, F, Cl, Br, CN, NO$_2$, —(CH$_2$)$_r$NR$^7$R$^8$, —(CH$_2$)$_r$OR$^a$, —C(O)R$^a$, —C(O)OR$^a$, —OC(O)R$^a$, —NR$^8$C(O)R$^c$, —C(O)NR$^8$R$^9$, —S(O)$_2$NR$^8$R$^9$, —NR$^7$R$^8$, —NR$^8$S(O)$_2$NR$^8$R$^9$, —NR$^8$S(O)$_2$R$^c$, —S(O)$_p$R$^c$, —(CF$_2$)$_r$CF$_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —$(CH_2)_r$—$C_{3-10}$ carbocycle substituted with 0-3 $R^d$, or —$(CH_2)_r$-5- to 10-membered heterocycle comprising: carbon atoms and 1-4 heteroatoms selected from N, O, and $S(O)_p$, wherein said heterocycle is substituted with 0-3 $R^d$;

$R^{3e}$ is, independently at each occurrence, H, —$(CH_2)_rOR^a$, F, =O, CN, $NO_2$, —$(CH_2)_rNR^7R^8$, —$C(O)R^a$, —$C(O)OR^a$, —$OC(O)R^a$, —$NR^8C(O)R^c$, —$C(O)NR^8R^9$, —$S(O)_2NR^8R^9$, —$NR^8S(O)_2NR^8R^9$, $NR^8S(O)_2R^c$, —$S(O)_pR^c$, —$(CF_2)_rCF_3$, —$(CH_2)_r$—$C_{3-10}$ carbocycle substituted with 0-3 $R^d$, or —$(CH_2)_r$-5- to 10-membered heterocycle comprising: carbon atoms and 1-4 heteroatoms selected from N, O, and $S(O)_p$, wherein said heterocycle is substituted with 0-3 $R^d$;

$R^4$ is H, F, Cl, Br, I, $OCF_3$, $CF_3$, CN, $NO_2$, —$(CH_2)_rOR^a$, —$(CH_2)_rSR^a$, —$(CH_2)_rC(O)R^a$, —$(CH_2)_rC(O)OR^a$, —$OC(O)R^a$, —$(CH_2)_rNR^7R^8$, —$NR^8(CH_2)_rC(O)OR^a$, —$(CH_2)_rC(O)NR^8R^9$, —$(CH_2)_rNR^8C(O)R^c$, —$(CH_2)_rNR^8C(O)_2R^b$, —$(CH_2)_rNR^8C(O)NR^8R^9$, —$S(O)_pNR^8R^9$, —$NR^8S(O)_rR^c$, —$S(O)_2R^c$, or $C_{1-4}$ alkyl substituted with 0-2 $R^{4a}$;

$R^{4a}$ is, independently at each occurrence, H, F, =O, $C_{1-6}$ alkyl, $OR^a$, $SR^a$, $CF_3$, CN, $NO_2$, —$C(O)R^a$, —$C(O)OR^a$, —$NR^7R^8$, —$C(O)NR^8R^9$, —$NR^8C(O)R^c$, —$S(O)_pNR^8R^9$, —$NR^8S(O)_pR^c$, —$S(O)R^c$, or —$S(O)_2R^c$;

$R^5$ is, independently at each occurrence, H, F, $CF_3$, —$(CH_2)_rOR^a$, =O, —$(CH_2)_rNR^7R^8$, —$S(O)_pNR^8R^9$, —$(CH_2)_rCO_2R^a$, —$(CH_2)_rCONR^8R^9$, or $C_{1-4}$ alkyl;

$R^6$ is, independently at each occurrence, H, F, or $C_{1-4}$ alkyl;

$R^7$ is, independently at each occurrence, H, $C_{1-6}$ alkyl, —$(CH_2)_n$—$C_{3-10}$ carbocycle, —$(CH_2)_n$-(5- to 10-membered heteroaryl), —$C(O)R^c$, —CHO, —$C(O)_2R^c$, —$S(O)_2R^c$, —$CONR^8R^c$, —$OCONHR^c$, —$C(O)O$—$(C_{1-4}$ alkyl)OC(O)—$(C_{1-4}$ alkyl), or —$C(O)O$—$(C_{1-4}$ alkyl)OC(O)—$(C_{6-10}$ aryl); wherein said alkyl, carbocycle, heteroaryl, and aryl are substituted with 0-2 $R^f$; wherein said heteroaryl comprises, carbon atoms and 1-4 heteroatoms selected from N, O, and $S(O)_p$;

$R^8$ is, independently at each occurrence, H, $C_{1-6}$ alkyl, —$(CH_2)_n$-phenyl, or —$(CH_2)_n$-5- to 10-membered heterocycle comprising: carbon atoms and 1-4 heteroatoms selected from N, O, and $S(O)_p$; wherein said alkyl, phenyl and heterocycle are optionally substituted with 0-2 $R^f$;

alternatively, $R^7$ and $R^8$, when attached to the same nitrogen, combine to form a 5- to 10-membered heterocycle comprising: carbon atoms and 0-3 additional heteroatoms selected from N, O, and $S(O)_p$, wherein said heterocycle is substituted with 0-2 $R^f$;

$R^{8a}$ is H or $C_{1-4}$ alkyl;

$R^9$ is, independently at each occurrence, H, $C_{1-6}$ alkyl, or —$(CH_2)_n$-phenyl; wherein said alkyl and phenyl are optionally substituted with 0-2 $R^f$;

alternatively, $R^8$ and $R^9$, when attached to the same nitrogen, combine to form a 5- to 12-membered heterocycle comprising: carbon atoms and 0-2 additional heteroatoms selected from N, O, and $S(O)_p$, wherein said heterocycle is substituted with 0-2 $R^d$;

$R^{10}$ is, independently at each occurrence, H or $C_{1-6}$ alkyl substituted with 0-3 $R^{10a}$;

$R^{10a}$ is, independently at each occurrence, H, =O, $C_{1-4}$ alkyl, $OR^a$, $SR^a$, F, $CF_3$, CN, $NO_2$, —$C(O)R^a$, —$C(O)OR^a$, —$C(O)NR^8R^9$, —$NR^8C(O)R^c$, —$S(O)_pNR^8R^9$, —$NR^8S(O)_pR^c$, or —$S(O)_pR^c$;

$R^{11}$ is H, $C_{1-4}$ alkyl, or benzyl;

$R^a$ is, independently at each occurrence, H, $CF_3$, $C_{1-6}$ alkyl, —$(CH_2)_r$—$C_{3-7}$ cycloalkyl, —$(CH_2)_r$—$C_{6-10}$ aryl, or —$(CH_2)_r$-5- to 10-membered heterocycle comprising carbon atoms and 1-4 heteroatoms selected from N, O, and $S(O)_p$, wherein said cycloalkyl, aryl or heterocycle groups are optionally substituted with 0-2 $R^f$;

$R^b$ is, independently at each occurrence, $CF_3$, OH, $C_{1-4}$ alkoxy, $C_{1-6}$ alkyl, —$(CH_2)_r$—$C_{3-10}$ carbocycle substituted with 0-2 $R^d$, or —$(CH_2)_r$-5- to 10-membered heterocycle comprising: carbon atoms and 1-4 heteroatoms selected from N, O, and $S(O)_p$ and substituted with 0-3 $R^d$;

$R^c$ is, independently at each occurrence, $CF_3$, $C_{1-6}$ alkyl substituted with 0-2 $R^f$, $C_{3-6}$ cycloalkyl substituted with 0-2 $R^f$, $C_{6-10}$ aryl, 5- to 10-membered heteroaryl, ($C_{6-10}$ aryl)-$C_{1-4}$ alkyl, or (5- to 10-membered heteroaryl)-$C_{1-4}$ alkyl, wherein said aryl is substituted with 0-3 $R^f$ and said heteroaryl comprises: carbon atoms and 1-4 heteroatoms selected from N, O, and $S(O)_p$ and substituted with 0-3 $R^f$;

$R^d$ is, independently at each occurrence, H, =O, =$NR^8$, $OR^a$, F, Cl, Br, I, CN, $NO_2$, —$NR^7R^8$, —$C(O)R^a$, —$C(O)OR^a$, —$OC(O)R^a$, —$NR^8C(O)R^c$, —$C(O)NR^8R^9$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$;

$R^e$ is, independently at each occurrence, =O, $OR^a$, F, Cl, Br, I, CN, $NO_2$, —$NR^7R^8$, —$C(O)R^a$, —$C(O)OR^a$, —$NR^8C(O)R^c$, —$C(O)NR^8R^9$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, or —$(CF_2)_rCF_3$;

$R^f$ is, independently at each occurrence, H, =O, —$(CH_2)_rOR^g$, F, Cl, Br, I, CN, $NO_2$, —$NR^gR^g$, —$C(O)R^g$, —$C(O)OR^g$, —$NR^gC(O)R^g$, —$C(O)NR^gR^g$, —$SO_2NR^gR^g$, —$NR^gSO_2NR^gR^g$, —$NR^gSO_2$—$C_{1-4}$ alkyl, —$NR^gSO_2CF_3$, —$NR^gSO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl, $C_{2-6}$ alkenyl, $C_{2-6}$ alkynyl, —$(CH_2)_n$-phenyl, or —$(CH_2)_n$-5- to 10-membered heterocycle comprising carbon atoms and 1-4 heteroatoms selected from N, O, and $S(O)_p$;

$R^g$ is, independently at each occurrence, H, $C_{1-6}$ alkyl, or —$(CH_2)_n$-phenyl;

n, at each occurrence, is selected from 0, 1, 2, 3, and 4;

p, at each occurrence, is selected from 0, 1, and 2; and r, at each occurrence, is selected from 0, 1, 2, 3, and 4.

2. A compound according to claim 1, wherein:

$R^3$ is phenyl substituted with 0-3 $R^{3a}$ and 0-1 $R^{3d}$, naphthyl substituted with 0-3 $R^{3a}$ and 0-1 $R^{3d}$, or —$(CH_2)_r$-5- to 12-membered heterocycle comprising: carbon atoms and 1-4 heteroatoms selected from N, O, and $S(O)_p$, wherein said heterocycle is substituted with 0-3 $R^{3a}$ and 0-1 $R^{3d}$;

$R^4$ is H, Me Et, Pr, F, Cl, Br, T, $OCF_3$, $CF_3$, CN, $NO_2$, —$(CH_2)_rOH$, —$(CH_2)_rC(O)OR^a$, $OR^a$, $SR^a$, $OC(O)R^a$, $OC(O)OR^a$, —$NR^7R^8$, —$(CH_2)_rNH_2$, —$NR^8(CH_2)_rC(O)OR^a$, —$(CH_2)_rC(O)NR^8R^9$, —$NR^8C(O)R^c$, —$NR^8C(O)OR^c$, —$NR^8C(O)NR^8R^9$, —$S(O)_pNR^8R^9$, —$NR^8S(O)_pR^c$, or —$S(O)_2R^c$; and $R^{11}$ is H or benzyl.

3. A compound according to claim 1, wherein:

$R^1$ is, independently at each occurrence, F, Cl, Br, I, $OCF_3$, $CF_3$, $OCF_3$, $CH_3$, Et, $NH_2$, —C(=NH)$NH_2$, —C(O)$NH_2$, —$CH_2NH_2$ or —$SO_2NH_2$;

$R^2$ is, independently at each occurrence, F, Cl, Br, $CF_3$, $NO_2$, —$(CH_2)_rOR^a$, —$(CH_2)_rSR^a$, —$(CH_2)_rC(O)R^a$, —$C(O)OR^a$, —$C(O)NR^8R^9$, —$NRPC(O)R^c$, —$NR^8C(O)OR^c$, —$NR^8C(O)NR^8R^c$, —$S(O)_pNR^8R^9$, —$NR^8SO_2R^c$, —$NR^7R^8$, —$S(O)R^c$, —$S(O)_2R^c$, $C_{1-6}$ alkyl substituted with 0-1 $R^{2a}$, or a 5-7 membered heterocycle comprising carbon atoms and 1-4 heteroatoms selected from N, O, and $S(O)_p$, wherein said heterocycle is substituted with 0-2 $R^{2b}$;

alternately, when $R^1$ and $R^2$ groups are substituents on adjacent atoms they may be taken together with the atoms to which they are attached to form a 5- to 7-membered carbocycle or heterocycle comprising carbon atoms and 0-4 heteroatoms selected from N, O, and $S(O)_p$ and substituted with 0-2 $R^g$;

$R^3$ is phenyl substituted with 0-2 $R^{3a}$ and 0-1 $R^{3d}$, naphthyl substituted with 0-2 $R^{3a}$ and 0-1 $R^{3d}$, 1,2,3,4-tetrahydronaphthyl substituted with 0-2 $R^{3a}$ and 0-1 $R^{3d}$, or a 5- to 12-membered heterocycle substituted with 0-2 $R^{3a}$ and 0-1 $R^{3d}$, wherein said heterocycle is selected from: thiophene, furan, thiazole, tetrazole, pyridine, pyridone, pyrimidine, pyrrole, pyrazole, indole, 2-oxindole, isoindoline, indazole, 7-azaindole, benzofuran, benzothiophene, benzimidazole, benzisoxazole, benzoxazole, quinazoline, quinoline, isoquinoline, quinoxaline, phthalazine, dihydrophthalazine, dihydroisoquinoline, dihydroquinoline, dihydroquinolinone, dihydroindole, dihydrobenzimidazole, dihydrobenzoxazine, dihydroquinazoline, dihydroquinoxaline, benzothiazine, benzoxazine, tetrahydrobenzazepine, dihydroazabenzocycloheptene, and tetrahydroquinoline;

$R^{3a}$ is, independently at each occurrence, =O, F, Cl, Br, Me, CN, OH, OMe, —OC(O)(t-Bu), —$CH_2$OMe, $CF_3$, COMe, $CO_2H$, $CO_2Me$, —$CH_2CO_2H$, —$(CH_2)_2CO_2H$, —$CH_2CO_2Me$, —$CH_2CO_2Et$, —$CH_2CH_2CO_2Et$, —$CH_2CN$, $NH_2$, —$CH_2NH_2$, —$CH_2NMe_2$, —NHCOMe, —$NHCO_2Me$, —$NHCO_2Et$, —$NHCH_2CH_2CO_2H$, —$NHCO_2$(i-Pr), —$NHCO_2$(i-Bu), —$NHCO_2$(t-Bu), —$NHCO_2Bn$, —$NHCO_2CH_2CH_2OMe$, —$NHCO_2CH_2CH_2CH_2OMe$, —$NHCO_2CH_2CO_2H$, —$NHCO_2CH_2CH_2CO_2H$, —$NHCO_2CH_2CH_2OH$, —$NHCO_2CH_2CH_2NH_2$, $NHCO_2CH_2$-tetrahydrofuran-2-yl, —$NHCO_2CH_2CH_2CH(Me)OMe$, —$NHCO_2CH_2CH_2C(O)NH_2$, —NHC(O)$NHCH_2CH_2$-morpholino, —NHC(O)$NHCH_2$-pyrid-4-yl, —$NHCO_2CH_2$-pyrid-4-yl, —$NHCO_2CH_2$-pyrid-3-yl, —$NHCO_2CH_2$-pyrid-2-yl, —$NHCO_2CH_2$-(piperidin-4-yl), —NHC(O)$NHCH_2CH_2$-pyrid-4-yl, —$NHCO_2CH_2CH_2$-pyrid-4-yl, —$NHCO_2CH_2CH_2$-morpholino, —$CH_2NHCO_2Me$, —NHC(O)NHMe, —NHC(O)N(Me)$_2$, —NHC(O)$NHCH_2CH_2OMe$, 4-[(1-carbamoyl-cyclopropanecarbonyl)-amino]-, —$NHSO_2Me$, —$SO_2NH_2$, —$SO_2NHMe$, —$SO_2NHCH_2CH_2OH$, —$SO_2NHCH_2CH_2OMe$, —$CONH_2$, —CONHMe, —CON(Me)$_2$, —C(O)$NHCH_2CH_2OMe$, —$CH_2CONH_2$, —CO(N-morpholino), —$NHCH_2CH_2$(N-morpholino), —$NR^7R^8$, —NH(1H-imidazol-2-yl), 1H-tetrazol-5-yl, tetrazol-1-yl, pyrimidin-5-yl, N-morpholino, or —$(CH_2)_r$-5- to 6-membered heterocycle comprising: carbon atoms and 1-4 heteroatoms selected from N, O, and $S(O)_p$, wherein said heterocycle is substituted with 0-1 $R^{3d}$;

$R^4$ is H, F, Cl, Br, OH, OMe, $NH_2$, Me, Et, $CF_3$, —$CH_2OH$, —$C(O)_2H$, $CO_2Me$, $CO_2Et$, —$C(O)NH_2$, —$C(O)NHMe$, —$C(O)N(Me)_2$, or —$CH_2CO_2H$; and $R^{11}$ is H or benzyl.

4. A compound according to claim 1, wherein:

A is substituted with 0-1 $R^1$ and 0-3 $R^2$ and selected from: $C_{3-7}$ cycloalkyl, phenyl, naphthyl, 1,2,3,4-tetrahydronaphthyl, pyrrolidinyl, pyridyl, indazolyl, indolyl, imidazolyl, furanyl, thienyl, benzimidazolyl, benzisoxazolyl, benzothiazolyl, benzothiophenyl, 3,4-methylenedioxy-phenyl, oxazolyl, isoxazolyl, thiazolyl, isothiazolyl, and pyrazolyl;

$L_1$ is —$CH_2CH_2$—, —$CH(NH_2)CH_2$—, —CH(NHCOMe)$CH_2$—, —CH(NHCOEt)$CH_2$—, —CH(NHCO$_2$(t-Bu))$CH_2$—, —CH=CH—, —C(Me)=CH—, —C≡C—, —$CH_2NH$—, —CH($CH_2CO_2H$)NH—, —$CH_2O$—, —NHNH—, —$SCH_2$—, —S(O)$CH_2$—, —$SO_2CH_2$— or —$OCH_2$—;

$R^1$ is, independently at each occurrence, F, Cl, Br, $CF_3$, $NH_2$, —$CH_2NH_2$, —C(=NH)$NH_2$, —C(O)$NH_2$, —$SO_2NH_2$, $SR^a$, $OR^a$, or $C_{1-6}$ alkyl substituted with 0-1 $R^{1a}$;

$R^2$ is, independently at each occurrence, =O, F, Cl, Br, $CF_3$, Me, Et, $OR^a$, CN, $NO_2$, $NR^7R^8$, —$CH_2OMe$, —$SR^a$, —$CH_2SMe$, $C(O)R^a$, —$C(O)OR^a$, —$CH_2NR^7R^8$, —$SO_2NH_2$, —$SO_2Me$, —$NHSO_2R^c$, —$CH_2NHSO_2R^c$, —$C(O)NR^8R^9$, —$NHC(O)R^c$, —$CH_2NHC(O)R^c$, —$NHC(O)OR^c$, —$CH_2NHC(O)OR^c$, —$NHC(O)NHR^c$, —$CH_2NHC(O)NHR^c$, or a 5-7 membered heterocycle substituted with 0-2 $R^{2b}$ and selected from: pyrrolidinyl, 2-oxo-1-pyrrolidinyl, piperidinyl, pyrazolyl, triazolyl, imidazolyl, and tetrazolyl;

alternately, when $R^1$ and $R^2$ groups are substituents on adjacent atoms they may be taken together with the atoms to which they are attached to form a 5- to 6-membered heterocycle comprising carbon atoms and 0-4 heteroatoms selected from N, O, and $S(O)_p$;

$R^3$ is phenyl substituted with 0-2 $R^{3a}$, naphthyl substituted with 0-2 $R^{3a}$, or a 5- to 12-membered heterocycle comprising: carbon atoms and 1-2 heteroatoms selected from N, O, and $S(O)_p$, wherein said heterocycle is substituted with 0-2 $R^{3a}$;

$R^{3a}$ is, independently at each occurrence, =O, F, Cl, Br, Me, CN, OH, OMe, —OC(O)(t-Bu), $CH_2OMe$, $CF_3$, COMe, $CO_2H$, $CO_2Me$, —$CH_2CO_2H$, —$(CH_2)_2CO_2H$, —$CH_2CO_2Me$, —$CH_2CO_2Et$, —$CH_2CH_2CO_2Et$, —$CH_2CN$, $NH_2$, —$CH_2NH_2$, —$CH_2NMe_2$, —NHCOMe, —$NHCO_2Me$, —$NHCO_2Et$, —$NHCH_2CH_2CO_2H$, —$NHCO_2$(i-Pr), —$NHCO_2$(i-Bu), —$NHCO_2$(t-Bu), —$NHCO_2Bn$, —$NHCO_2CH_2CH_2OMe$, —$NHCO_2CH_2CH_2CH_2OMe$, —$NHCO_2CH_2CO_2H$, —$NHCO_2CH_2CH_2CO_2H$, —$NHCO_2CH_2CH_2OH$, —$NHCO_2CH_2CH_2NH_2$, —$NHCO_2CH_2$-tetrahydrofuran-2-yl, —$NHC_2OCH_2CH_2CH(Me)OMe$, —$NHCO_2CH_2CH_2C(O)NH_2$, —NHC(O)$NHCH_2CH_2$-morpholino, —NHC(O)$NHCH_2$-pyrid-4-yl, —$NHCO_2CH_2$-pyrid-4-yl, —$NHCO_2CH_2$-pyrid-3-yl, —$NHCO_2CH_2$-pyrid-2-yl, —$NHCO_2CH_2$-piperidin-4-yl), —NHC(O)NH$CH_2CH_2$-pyrid-4-yl, —$NHCO_2CH_2CH_2$-pyrid-4-yl, —$NHCO_2CH_2CH_2$-morpholino, —$CH_2NHCO_2Me$, —NHC(O)NHMe, —NHC(O)N(Me)$_2$, —NHC(O)$NHCH_2CH_2OMe$, 4-[(1-carbamoyl-cyclopropanecarbonyl)-amino]-, —$NHSO_2Me$, —$SO_2NH_2$, —$SO_2NHMe$, —SO$_2$NHCH$_2$CH$_2$OH, —SO$_2$NHCH$_2$CH$_2$OMe, —CONH$_2$, —CONHMe, —CON(Me)$_2$, —C(O)NHCH$_2$CH$_2$OMe, —CH$_2$CONH$_2$, —CO(N-morpholino), —NHCH$_2$CH$_2$(N-morpholino), —NR$^7$R$^8$, —NH(1H-imidazol-2-yl), 1H-tetrazol-5-yl, tetrazol-1-yl, pyrimidin-5-yl, or N-morpholino, or —(CH$_2$)$_r$-5- to 6-membered heterocycle comprising: carbon atoms and 1-4 heteroatoms selected from N, O, and S(O)$_p$, wherein said heterocycle is substituted with 0-1 R$^{3d}$;

alternatively, two of R$^{3a}$ groups located on adjacent atoms, they can be taken together with the atoms to which they are attached to form a 5- to 10-membered heterocycle comprising: carbon atoms and 1-4 heteroatoms selected from N, O, and S(O)$_p$, wherein said heterocycle is substituted with 0-2 R$^{3d}$;

R$^4$ is H, F, Cl, Br, OMe, NH$_2$, CF$_3$, Me, Et, CO$_2$H, CO$_2$Me, or CO$_2$Et; and R$^{8a}$ is H, Me or Et.

5. A compound according to claim 1, wherein:
A is substituted with 0-2 R$^2$ and selected from:

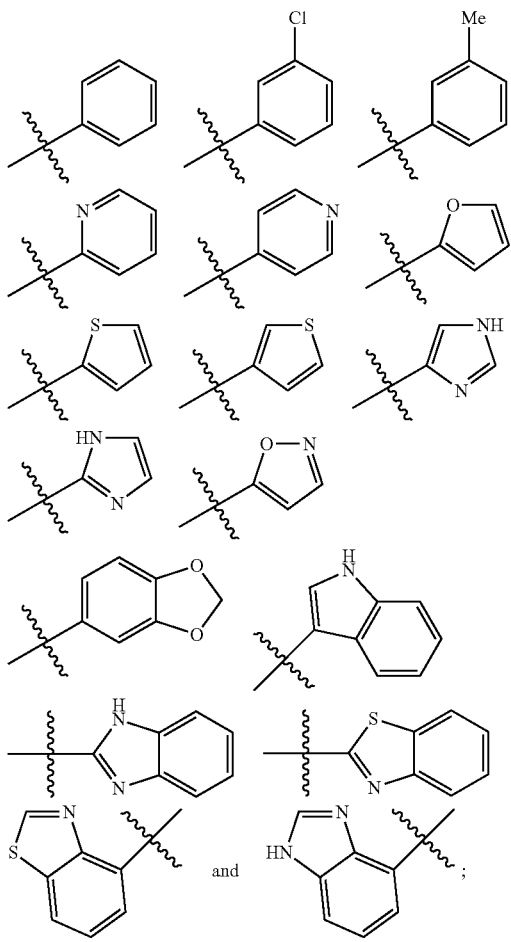

R$^2$ is, independently at each occurrence, =O, F, Cl, Br, Me, CF$_3$, OMe, OEt, OPh, OBn, SMe, SEt, S(n-Pr), SBn, —CH$_2$SMe, SO$_2$Me, SO$_2$NH$_2$, NH$_2$, —CH$_{12}$NH$_{12}$, NO$_2$, C(O)Me, CO$_2$H, CO$_2$Me, CONH$_2$, CONHMe, —CH$_2$NHCOPh, —NHCO$_2$Me, —CH$_2$NHCO$_2$Et, —CH$_2$NHCO$_2$(i-Pr), —CH$_2$NHCO$_2$(t-Bu), —CH$_2$NHCO$_2$Bn, —CH$_2$NHCO(CH$_2$)$_2$CO$_2$H, —CONHPh, —NHCONHME, —CH$_2$NHCONHEt,
—CH$_2$NHCONH(CH$_2$)$_2$CO$_2$Et, —CH$_2$NHCONHPh, —CH$_2$NHCONH(4-Cl-Ph), —CH$_2$NHCONHBn, —NHSO$_2$Me, —CH$_2$NHSO$_2$Me, —CH$_2$NHSO$_2$Et, —CH$_2$NHSO$_2$(n-Pr), —CH$_2$NHSO$_2$(i-Pr), —CH$_2$NHSO$_2$(n-pentyl), —CH$_2$NHSO$_2$Ph, —CH$_2$NHSO$_2$(4-NHCOMe-Ph), —CH$_2$NHSO$_2$(4-Cl-Bn), —CH$_2$NHSO$_2$CH$_2$CH$_2$Ph, —CH$_2$NHSO$_2$CH$_2$CH$_2$(2-Cl-Ph), —CH$_2$NHSO$_2$CH$_2$CH$_2$(3-Cl-Ph), —CH$_2$NHSO$_2$CH$_2$CH$_2$(4-Cl-Ph), —CH$_2$NHSO$_2$(3,4-dimethyl-isoxazol-4-yl), 1-pyrrolidinyl, 2-oxo-1-pyrrolidinyl, 3-carboxy-N-piperidinyl, pyrazol-1-yl, 4-carboxy-pyrazol-1-yl, 1,2,3-triazol-1-yl, 1,2,4-triazol-1-yl, 1,2,3-triazol-2-yl, 4-carboxy-1,2,3-triazol-1-yl, 4-(ethoxycarbonyl)-1,2,3-triazol-1-yl, tetrazol-1-yl, tetrazol-5-yl, 5-Me-tetrazol-1-yl, 5-CF$_3$-tetrazol-1-yl, or —OCH$_2$(2-tetrahydrofuranyl);

R$^3$ is phenyl substituted with 0-2 R$^{3a}$, naphthyl substituted with 0-2 R$^{3a}$, 1,2,3,4-tetrahydro-naphthyl substituted with 0-2 R$^{3a}$, or a 5— to 12-membered heterocycle substituted with 0-2 R$^{3a}$ and selected from: thiophene, furan, thiazole, tetrazole, pyridine, pyridinone, pyrimidine, pyrrole, pyrazole, indole, 2-oxindole, isoindolin-1-one, indazole, 1H-indazole-3-one, 7-azaindole, benzofuran, benzothiophene, benzimidazole, benzisoxazole, benzoxazole, quinazoline, quinoline, isoquinoline, 3H-quinazolin-4-one, phthalazine, 2H-phthalazin-1-one, 2H-3,4-dihydrophthalazin-1-one, 1H-quinolin-4-one, 1H-quinolin-2-one, 2H-3,4-dihydroisoquinolin-1-one, 3,4-dihydro-1H-quinolin-2-one, 1,3-dihydroindol-2-one, 3H-benzoxazol-2-one, 1,3-dihydrobenzimidazol-2-one, 1,4-dihydro-3,1-benzoxazin-2-one, 3,4-dihydro-1H-quinazolin-2-one, 1,3-dihydro-quinazoline-2,4-dione, 1,4-dihydro-quinoxaline-2,3-dione, 4H-benzo[1,4]thiazine-3-one, 2H-benzo[1,4]thiazin-3(4H)-one, 4H-1,4-benzoxazin-3-one, 1,3,4,5-tetrahydro-1-benzazepin-2-one, 1,3,4,5-tetrahydro-1,3-benzodiazepin-2-one, 8,9-dihydro-5H-7-oxa-5-azabenzocyclohepten-6-one, benzimidazol-2-one, 1,3-dihydrobenzimidazol-2-one, 3H-benzoxazol-2-one, 3H-quinazolin-4-one, and 1,2,3,4-tetrahydroquinoline;

R$^4$ is 4, Me, F, Br, C$_1$, CF$_3$, CO$_2$H, CO$_2$Me, or CO$_2$Et;
R$^{8a}$ is H or Me.

6. A compound according to claim 1, wherein:
A is phenyl, 2-fluorophenyl, 3-fluorophenyl, 2-chlorophenyl, 3-chlorophenyl, 2-bromophenyl, 3-bromophenyl, 3-methylphenyl, 2-methoxyphenyl, 3-methoxyphenyl, 3-aminomethylphenyl, 4-aminomethylphenyl, 2-carboxy-5-chlorophenyl, 2-methoxycarbonyl-5-chlorophenyl, 2-(N-(methoxycarbonyl)-amino)-5-chlorophenyl, 2-(N-(ethoxycarbonyl)-aminomethyl)-5-chlorophenyl, 2-(N-(isopropoxycarbonyl)-aminomethyl)-5-chlorophenyl, 2-(N-(tert-butoxycarbonyl)-aminomethyl)-5-chlorophenyl, 2-N-(phenylcarbonyl)-aminomethyl)-5-chlorophenyl, 2-(N-(benzoxycarbonyl)-aminomethyl)-5-chlorophenyl, 2-((N-(3-propanoic acid)carbonyl)-aminomethyl)-5-chlorophenyl, 2-(3-methylureido)-5-chlorophenyl, 2-(3-ethylureidomethyl)-5-chlorophenyl, 2-[3-(2-ethoxycarbonyl-ethyl)-ureidomethyl]-5-chlorophenyl, 2-(3-phenylureido)methyl)-5-chlorophenyl, 2-(3-(4-chlorophenyl)ureido)methyl)-5-chlorophenyl, 2-(3-benzylureido)methyl)-5-chlorophenyl, 2-(N-(methylsulfonyl)-amino)-5-chlorophenyl, 2-(N-(methylsulfonyl)-aminomethyl)-5-chlorophenyl, 2-N-(ethylsulfonyl)-aminomethyl)-5-chlorophenyl, 2-(N-(n-propylsulfonyl)-aminomethyl)-5-chlorophenyl, 2-(N-(isopropylsulfonyl)-aminomethyl)-5-chlorophenyl, 2-(N-(n-pentylsulfonyl)-aminomethyl)-5-chlorophenyl, 2-(N-(phenylsulfonyl)-aminomethyl)-5-chlorophenyl, 2-((N-(4-methylcarbonylaminophenyl)

sulfonyl)-aminomethyl)-5-chlorophenyl, 2-(N-(4-chlorobenzylsulfonyl)-aminomethyl)-5-chlorophenyl, 2-(N-(phenethylsulfonyl)-aminomethyl)-5-chlorophenyl, 2-(N-(2-chlorophenethylsulfonyl)-aminomethyl)-5-chlorophenyl, 2-(N-(3-chlorophenethylsulfonyl)-aminomethyl)-5-chlorophenyl, 2-(N-(4-chlorophenethylsulfonyl)-aminomethyl)-5-chlorophenyl, 2-N-(3,4-dimethyl-isoxazol-4-yl)-aminomethyl)-5-chlorophenyl, 2-(N-(3,4-dimethyl-isoxazol-4-ylsulfonyl)-aminomethyl)-5-chlorophenyl, 3-carbamoyl-phenyl, 2,4-difluorophenyl, 2,5-difluorophenyl, 2,5-dichlorophenyl, 3,5-dichlorophenyl, 5-chloro-2-fluorophenyl, 3-chloro-2-fluorophenyl, 3-chloro-4-methylphenyl, 2-methyl-5-chlorophenyl, 2-methoxy-5-chlorophenyl, 2-ethoxy-5-chlorophenyl, 2-benzyloxy-5-chlorophenyl, 2-methylthio-5-chlorophenyl, 2-ethylthio-5-chlorophenyl, 2-propylthio-5-chlorophenyl, 2-benzylthio-5-chlorophenyl, 2-methylthiomethyl-5-chlorophenyl, 2-(2-oxo-1-pyrrolidinyl)-5-chlorophenyl, 3-trifluoromethyl-2-fluorophenyl, 2-trifluoromethyl-5-chlorophenyl, 5-bromo-2-fluorophenyl, 2-amino-5-chlorophenyl, 2-aminomethyl-5-chlorophenyl, 2-methylsulfonyl-5-chlorophenyl, 2-methylsulfonamide-5-chlorophenyl, 2-phenylcarbamoyl-5-chlorophenyl, 2-(3-carboxy-N-piperidinyl)-5-chlorophenyl, 2,6-difluoro-3-methylphenyl, 2-chloro-6-fluoro-3-methylphenyl, 2-fluoro-6-chloro-3-methylphenyl, 2,6-difluoro-3-chlorophenyl, 2,3-dichloro-6-aminophenyl, 2,3-dichloro-6-nitrophenyl, 2-phenoxyphenyl, 2-phenoxy-5-chlorophenyl, 2-(N-pyrrolidinyl)-5-chlorophenyl, 2-(pyrazol-1-yl)-5-chlorophenyl, 2-(4-carboxy-pyrazol-1-yl)-5-chlorophenyl, 2-(1,2,3-triazol-1-yl)-5-methylphenyl, 2-(1,2,3-triazol-1-yl)-5-chlorophenyl, 2-(1,2,3-triazol-2-yl)-5-chlorophenyl, 2-(1,2,4-triazol-1-yl)-5-chlorophenyl, 2-[(4-carboxy)-1,2,3-triazol-1-yl]-5-methylphenyl, 2-[(4-carboxy)-1,2,3-triazol-1-yl]-5-chlorophenyl, 2-[(4-ethoxycarbonyl)-1,2,3-triazol-1-yl]-5-chlorophenyl, 2-(tetrazol-1-yl)-5-methylphenyl, 2-(tetrazol-1-yl)-5-chlorophenyl, 2-(tetrazol-5-yl)-5-chlorophenyl, 2-(5-methyl-tetrazol-1-yl)-5-chlorophenyl, 2-(tetrazol-1-yl)-3-fluoro-5-chlorophenyl, 2-(tetrazol-1-yl)-3-fluoro-5-methylphenyl, 2-(5-methyltetrazol-1-yl)-5-chlorophenyl, 2-(5-trifluoromethyl-tetrazol-1-yl)-5-chlorophenyl, 2-(2-tetrahydrofuranyl-methoxy)-5-chlorophenyl, 3,4-methylenedioxy-phenyl, cyclopentyl, 2-oxo-1-pyrrolidinyl, 2-furanyl, 2-thienyl, 3-thienyl, 5-chloro-2-thienyl, 5-chloro-3-thienyl, 2,5-dichloro-3-thienyl, 1-imidazolyl, 2-imidazolyl, 4-imidazolyl, 3-chloro-5-isoxazolyl, 4-pyridyl, 3-fluoro-2-pyridyl, 2(1H)-oxo-5-chloropyridin-1-yl, 1-indolyl, 3-indolyl, 2-benzimidazolyl, 6-chlorobenzimidazol-4-yl, 2-methyl-6-chlorobenzothiazol-4-yl or 2,6-dichlorobenzothiazol-4-yl, 2-[(3-carboxy)-pyrazol-1-yl]-5-chlorophenyl, 2-[(3-carboxy)-pyrazol-1-yl]-5-methylphenyl, 2-fluoro-3-chloro-6-(tetrazol-1-yl) phenyl, 2-fluoro-3-chloro-6-(methylcarbonyl)phenyl, 2-methylcarbonyl-5-chlorophenyl, 2-(aminocarbonyl)-5-chlorophenyl, 2-(methylaminocarbonyl)-5-chlorophenyl, or 2-(aminosulfonyl)-5-chlorophenyl;

$L_1$ is —CH$_2$CH$_2$—, —CH=CH—, —C(Me)=CH—, —C≡C—, —CH$_2$NH—, —CH$_2$O—, —NHNH—, —SCH$_2$—, —S(O)CH$_2$—, —SO$_2$CH$_2$— or —OCH$_2$—;

$R^3$ is phenyl, 3-biphenyl, 4-biphenyl, 3-aminophenyl, 4-aminophenyl, 3-N,N-dimethylaminophenyl, 4-phenoxyphenyl, 4-benzyloxyphenyl, 4-(t-butoxymethyl)-phenyl, 4-methylsulfonylphenyl, 3-cyanophenyl, 4-cyanophenyl, 3-fluorophenyl, 4-fluorophenyl, 3-chlorophenyl, 4-chlorophenyl, 3-bromophenyl, 4-bromophenyl, 3-hydroxyphenyl, 4-hydroxyphenyl, 2-methoxyphenyl, 3-methoxyphenyl, 4-methoxyphenyl, 3-trifluoromethylphenyl, 4-trifluoromethylphenyl, 3-carboxyphenyl, 4-carboxyphenyl, 3-methoxycarbonylphenyl, 4-methoxycarbonylphenyl, 3-carboxymethylphenyl, 4-carboxymethylphenyl, 4-methoxycarbonylmethylphenyl, 3-ethoxycarbonylmethylphenyl, 4-ethoxycarbonylmethylphenyl, 4-ethoxycarbonylethylphenyl, 3-carbamoylphenyl, 4-carbamoylphenyl, 3-aminocarbonylmethylphenyl, 4-aminocarbonylmethylphenyl, 4-methylaminocarbonylphenyl, 4-dimethylaminocarbonylmethylphenyl, 4-amidinophenyl 3-methylcarbonylaminophenyl 4-methylcarbonylaminophenyl, 4-methoxycarbonylaminophenyl, 4-aminosulfonylphenyl, 3-methylsulfonylaminophenyl, 4-methylsulfonylamino, 2,4-difluorophenyl, 3-fluoro-4-cyanophenyl, 4-amino-3-carboxyphenyl, 4-amino-3-methoxycarbonylphenyl, 2,4-dichlorophenyl, 3-cyano-5-fluorophenyl, 3-fluoro-4-carbamoylphenyl, 3-carboxy-4-cyanophenyl, 3-phenyl-4-carbamoylphenyl, 4-(2-oxo-1-piperidino)-phenyl, thiazol-2-yl, thien-2-yl, 4-methoxycarbonyl-thiazol-2-yl, 4-carbamoyl-thiazol-2-yl, 1-benzyl-pyrazol-4-yl, 5-phenyl-oxazol-2-yl, 5-carbamoyl-thien-2-yl, 5-carboxy-thien-2-yl, pyrid-2-yl, pyrid-3-yl, pyrid-4-yl, 6-amino-pyrid-3-yl, benzimidazol-2-yl, 6-methoxy-pyrid-3-yl, 1-methyl-benzimidazol-2-yl, benzoxazol-2-yl, benzothiazol-2-yl, 3-amino-benzisoxazol-6-yl, 3-amino-benzisoxazol-5-yl, indazol-5-yl, indazol-6-yl, 3-amino-indazol-5-yl, 3-hydroxy-indazol-5-yl, 3-amino-indazol-6-yl, 3-amino-1-methyl-indazol-6-yl, 3-amino-4-fluoro-indazol-6-yl, 3-amino-5-fluoro-indazol-6-yl, 3-amino-7-fluoro-indazol-6-yl, 4-imino-3,4-dihydro-2H-phthalazin-1-on-7-yl, 3-(5-tetrazolyl)-phenyl, 2,3-dihydro-isoindol-1-on-6-yl, quinolin-5-yl, quinolin-6-yl, quinolin-8-yl, isoquinolin-5-yl, 2H-isoquinolin-1-on-6-yl, 2,4-diaminoquinazolin-7-yl, 4-NH$_2$-quinazolin-7-yl,

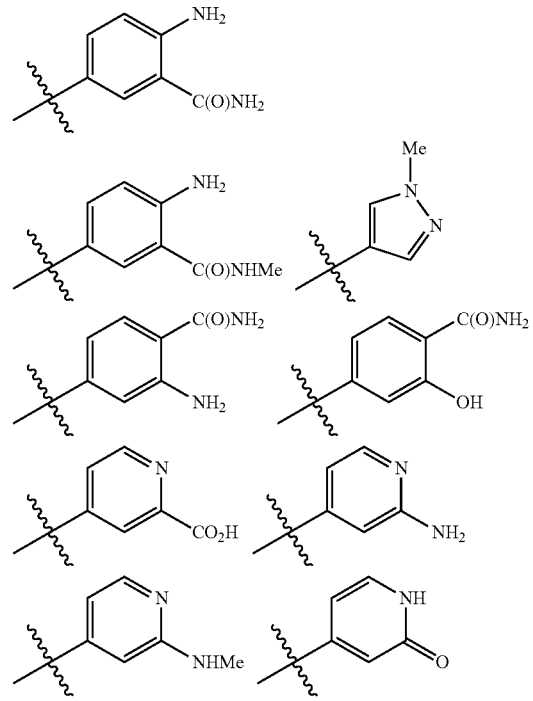

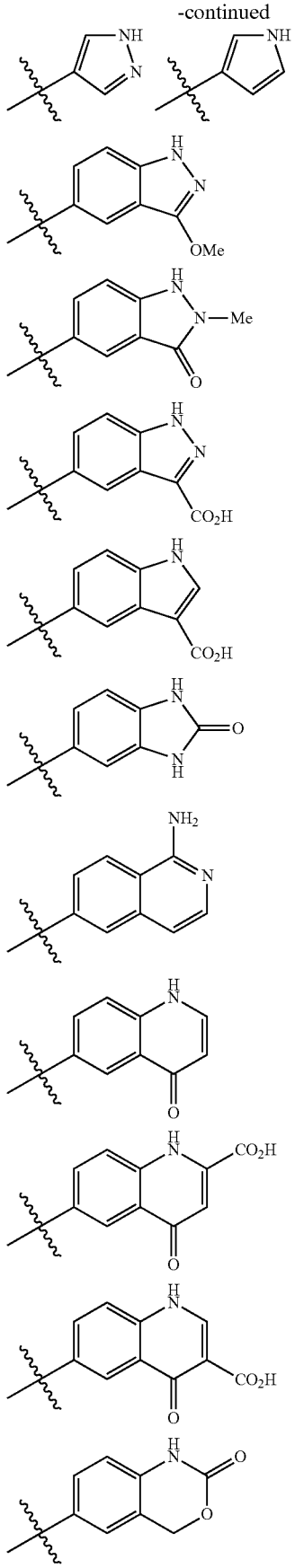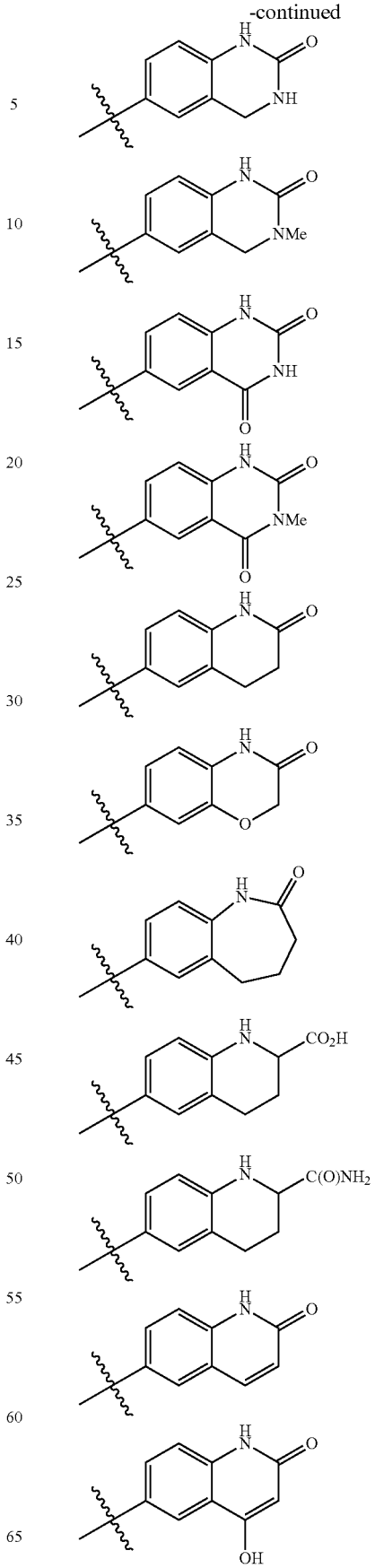

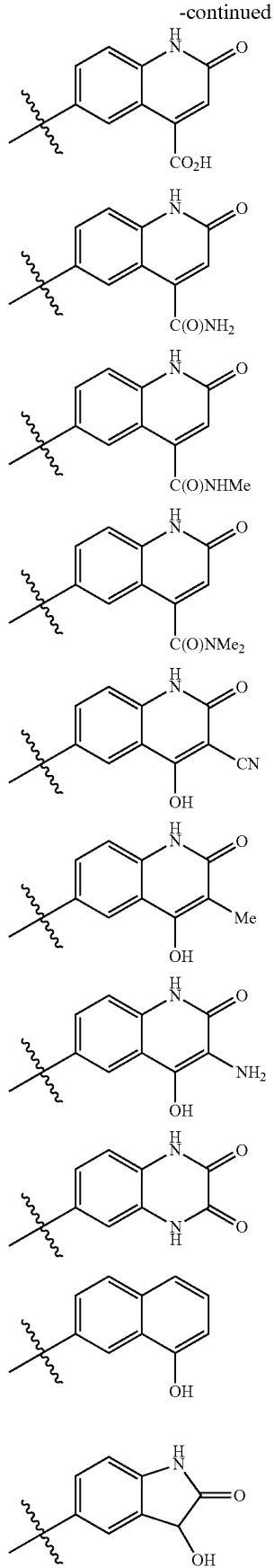
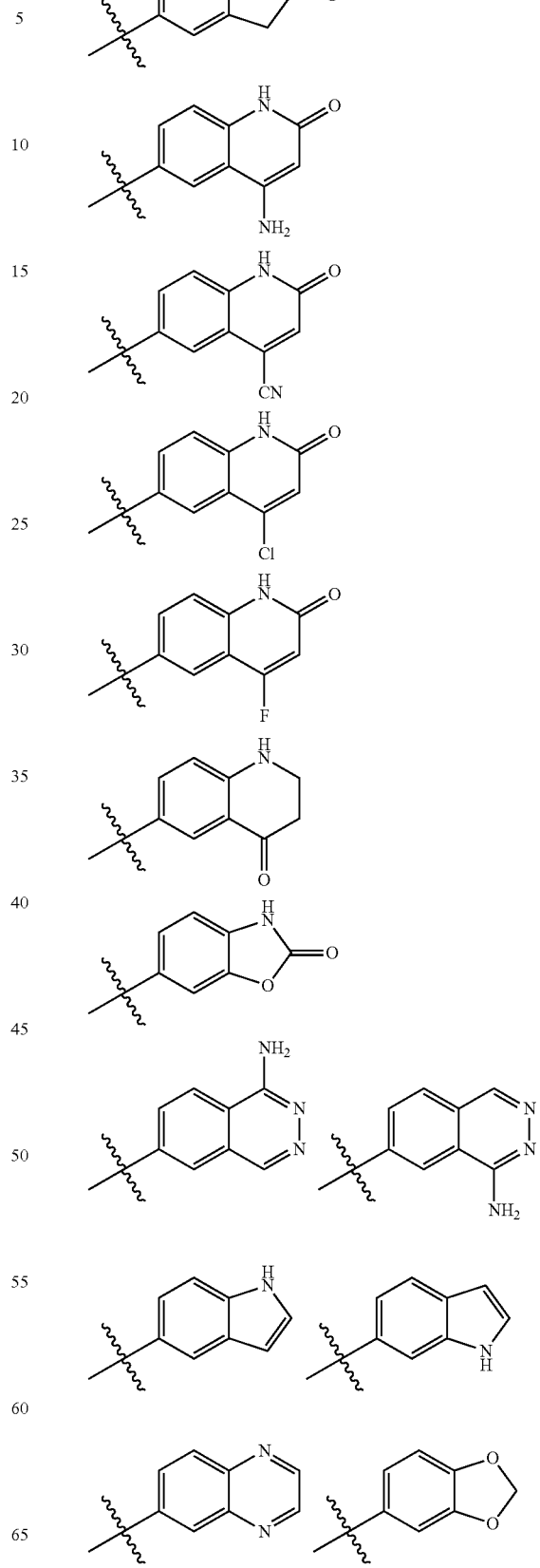

137
-continued
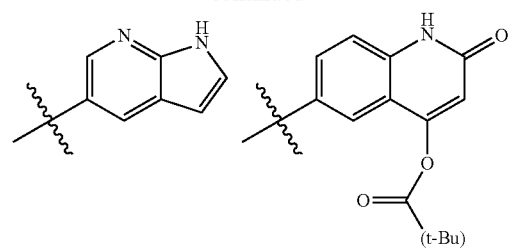
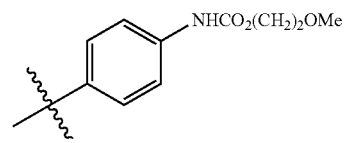
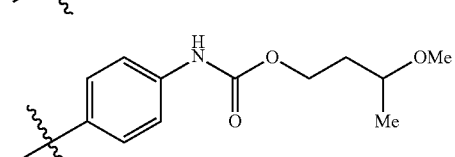
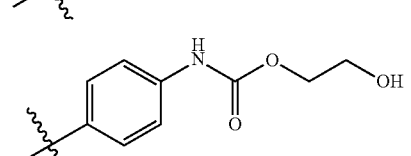
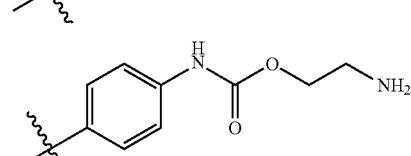
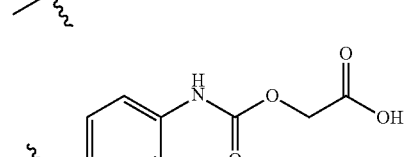
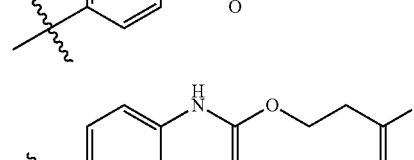
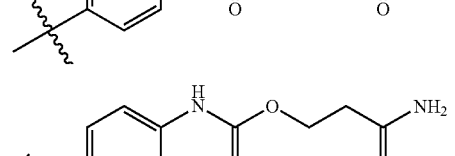
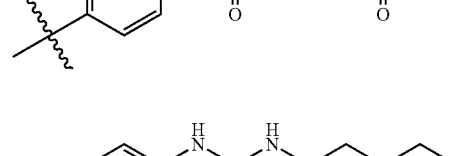
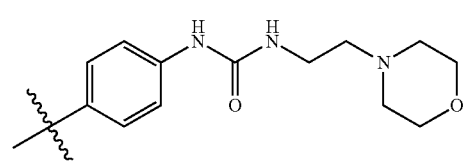
138
-continued
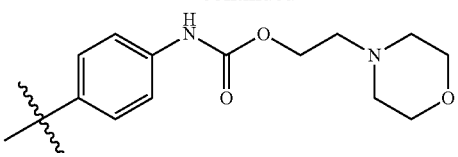
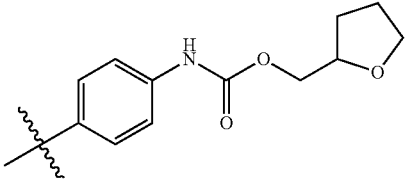
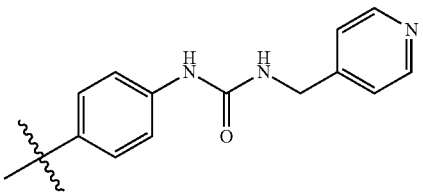
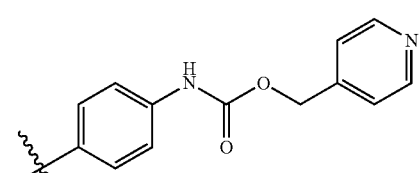
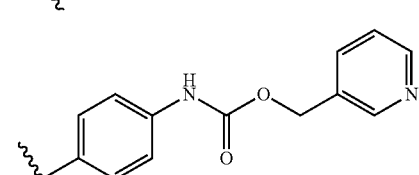
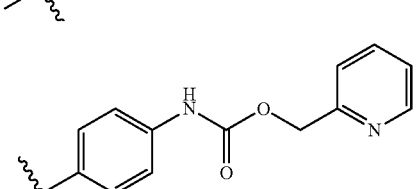
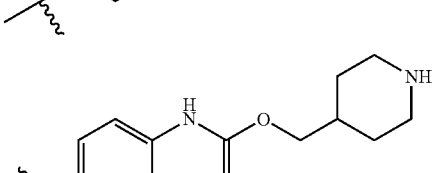
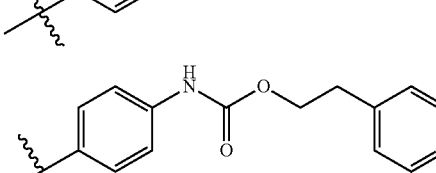
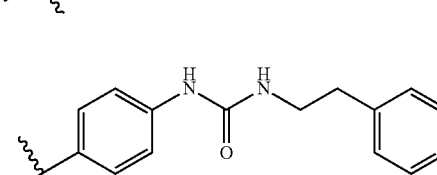

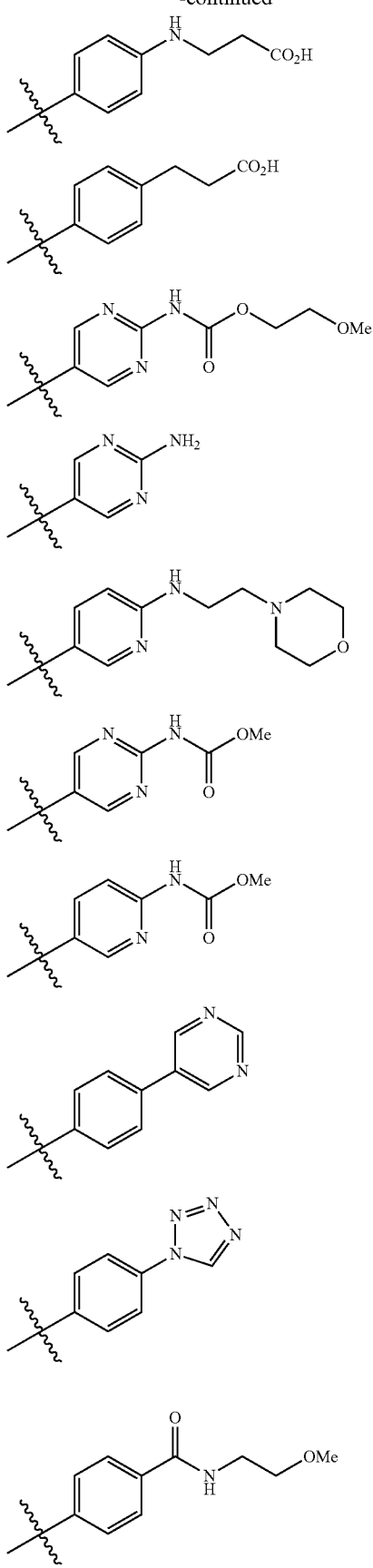

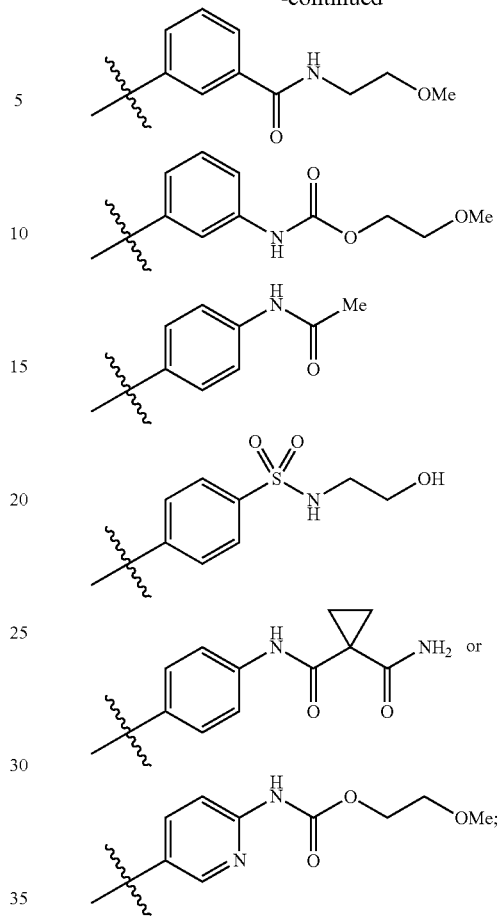

$R^4$ is H, Me, F, Br, Cl, $CF_3$, $CO_2H$, $CO_2Me$, or $CO_2Et$; and $R^{8a}$ is H or Me.

7. A compound according to claim 1, wherein:
A is 3-chlorophenyl, 3-methylphenyl, 2,5-dichlorophenyl, 5-chloro-2-fluorophenyl, 3-chloro-2-fluorophenyl, 2-methyl-5-chlorophenyl, 2-methoxy-5-chlorophenyl, 2-methylthio-5-chlorophenyl, 2-ethylthio-5-chlorophenyl, 2-propylthio-5-chlorophenyl, 2-benzylthio-5-chlorophenyl, 2-amino-5-chlorophenyl, 2-aminomethyl-5-chlorophenyl, 2,6-difluoro-3-methylphenyl, 2-chloro-6-fluoro-3-methylphenyl, 2-fluoro-6-chloro-3-methylphenyl, 2,6-difluoro-3-chlorophenyl, 2,3-dichloro-6-nitrophenyl, 5-chloro-2-thienyl, 3,4-methylenedioxyphenyl, 2-methoxycarbonyl-5-chlorophenyl, 6-chlorobenzimidazol-4-yl, 2-[(4-carboxy)-pyrazol-1-yl]-5-chlorophenyl, 2-[(4-carboxy)-pyrazol-1-yl]-5-methylphenyl, 2-(1,2,3-triazol-1-yl)-5-methylphenyl, 2-(1,2,3-triazol-1-yl)-5-chlorophenyl, 2-(1,2,4-triazol-1-yl)-5-chlorophenyl, 2-(1,2,3-triazol-2-yl)-5-chlorophenyl, 2-[(4-carboxy)-1,2,3-triazol-1-yl]-5-chlorophenyl, 2-[(4-carboxy)-1,2,3-triazol-1-yl]-5-methylphenyl, 2-[(4-ethoxycarbonyl)-1,2,3-triazol-1-yl]-5-chlorophenyl, 2-(tetrazol-1-yl)-5-methylphenyl, 2-(tetrazol-1-yl)-5-chlorophenyl, 2-(tetrazol-1-yl)-3-fluoro-5-chlorophenyl, 2-(tetrazol-1-yl)-3-fluoro-5-methylphenyl, 2-(5-methyltetrazol-1-yl)-5-chlorophenyl, 2-fluoro-3-chloro-6-(tetrazol-1-yl)phenyl, 2-fluoro-3-chloro-6-(methylcarbonyl)phenyl, or 2-methylcarbonyl-5-chlorophenyl;

141
$L_1$ is —$CH_2CH_2$—, —CH=CH—, —C(Me)=CH—, —C≡C—, or —$CH_2$NH—;
$R^3$ is
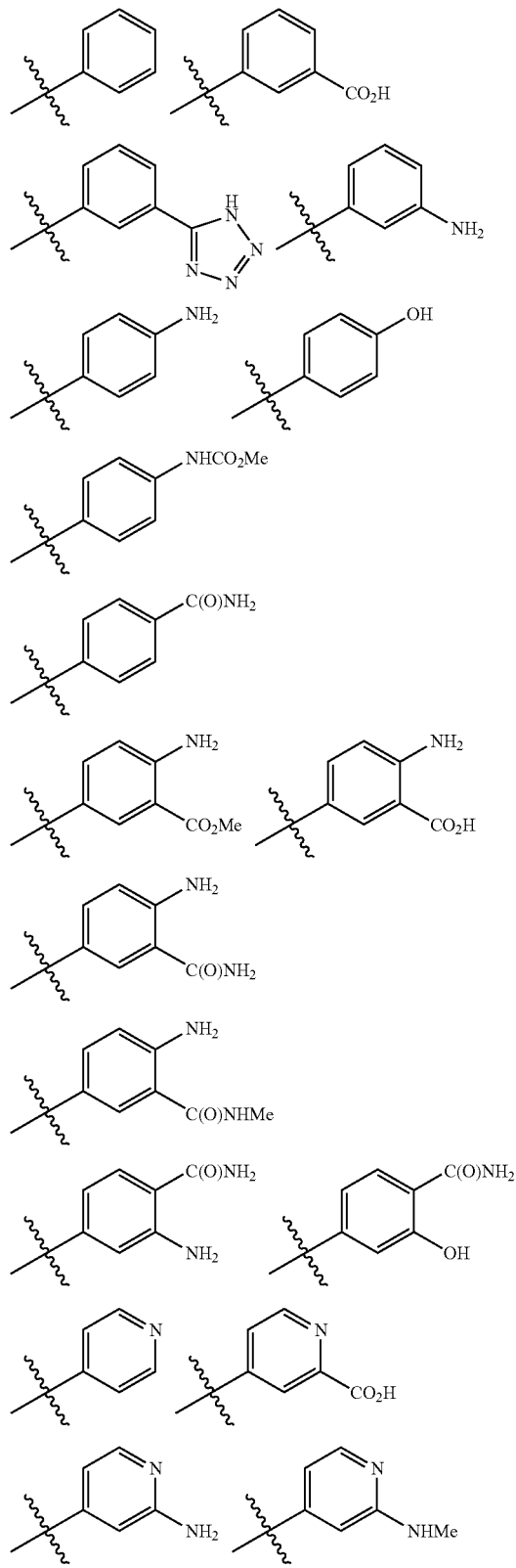
142
-continued
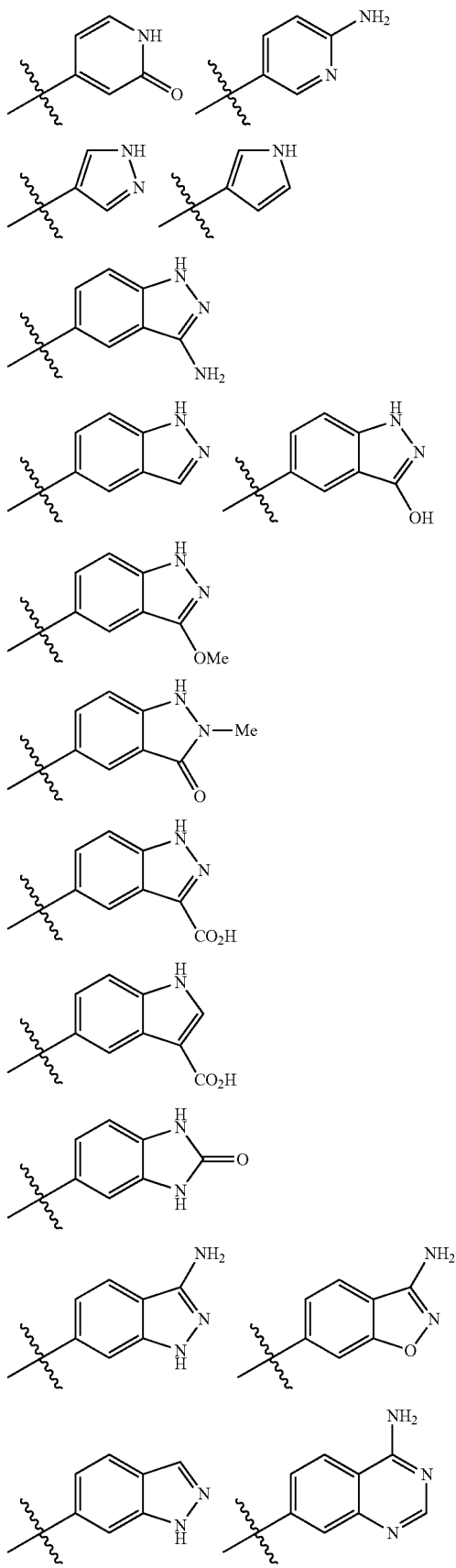

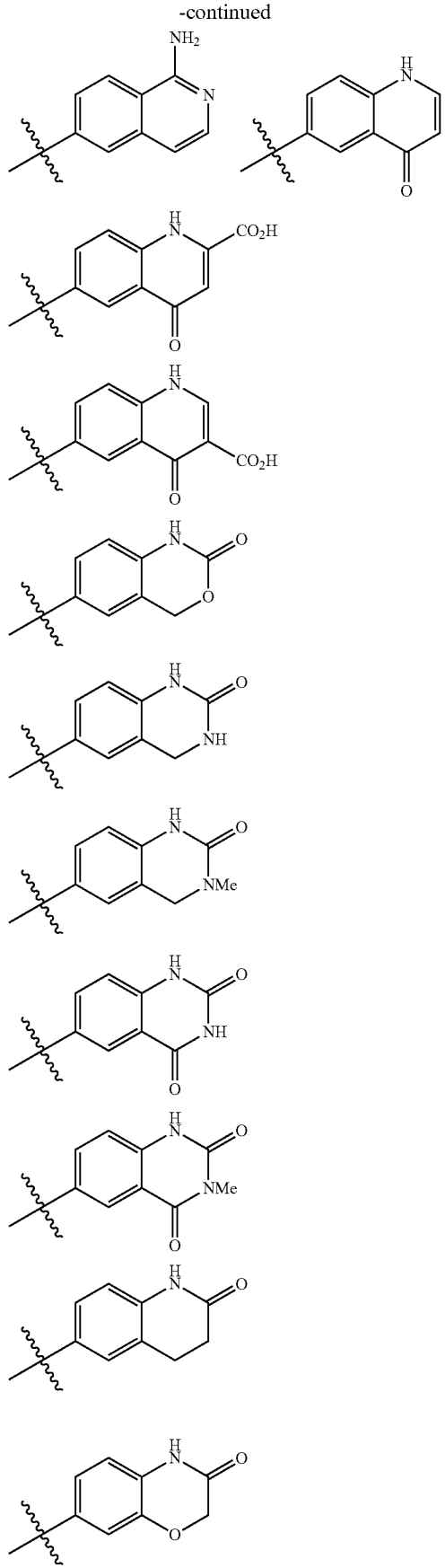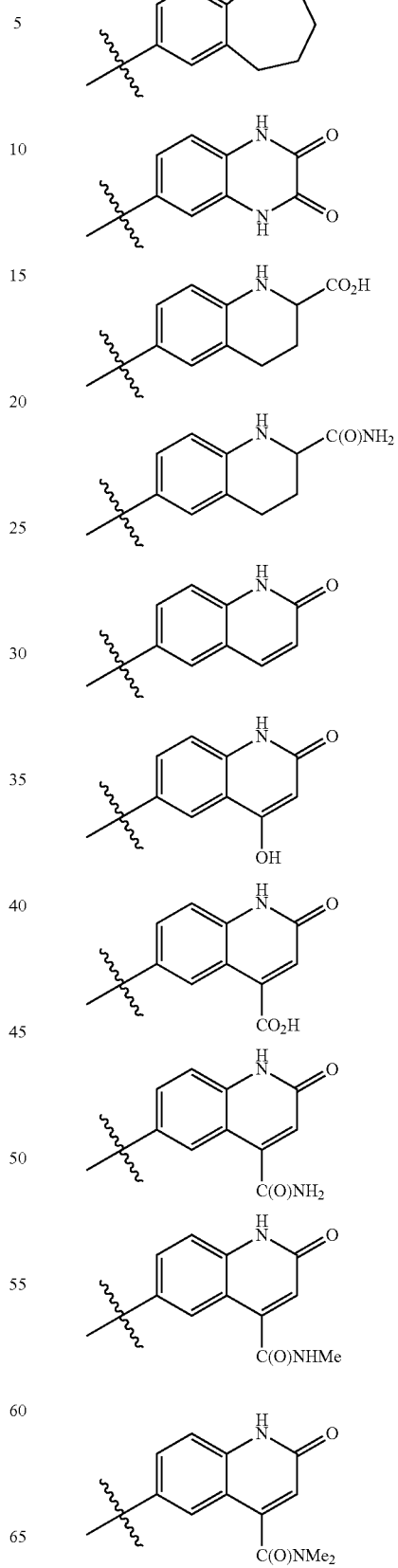

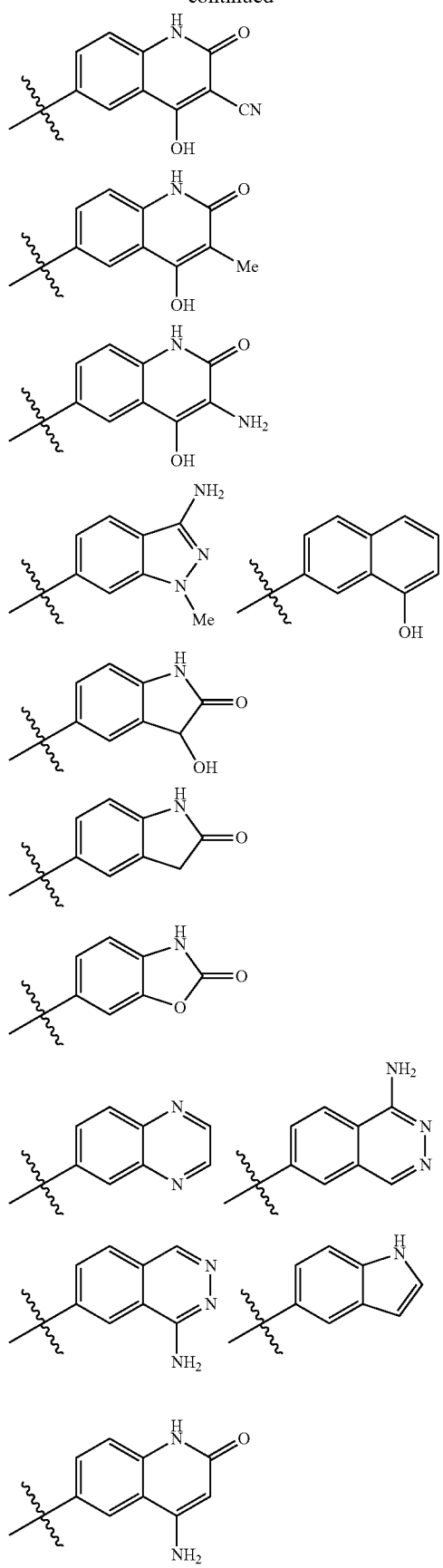
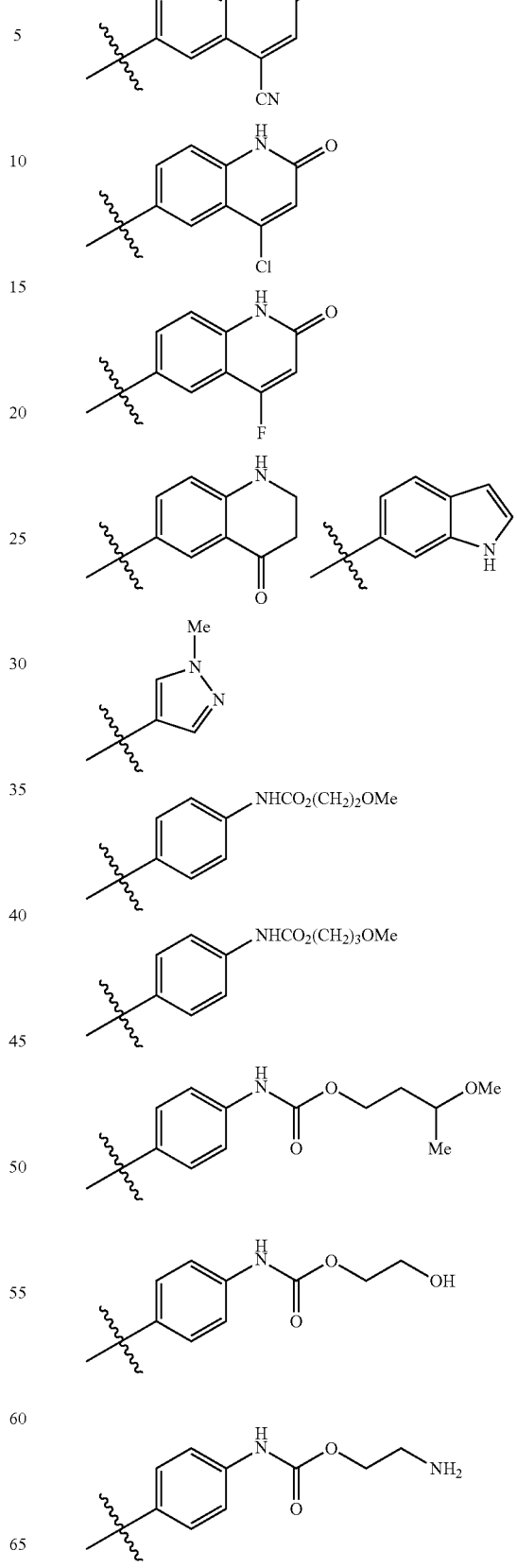

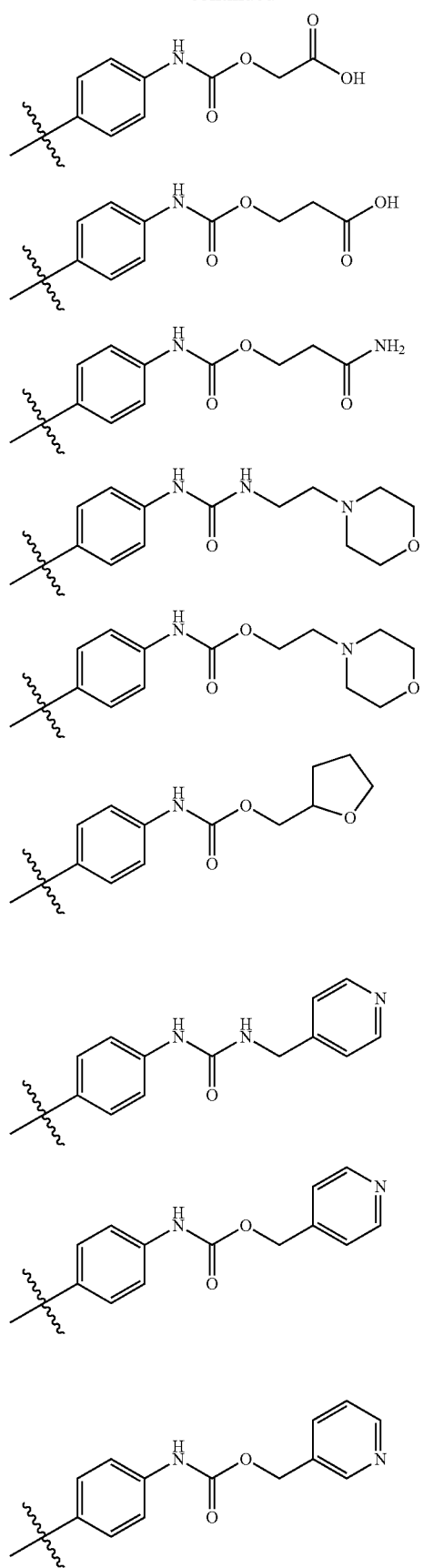
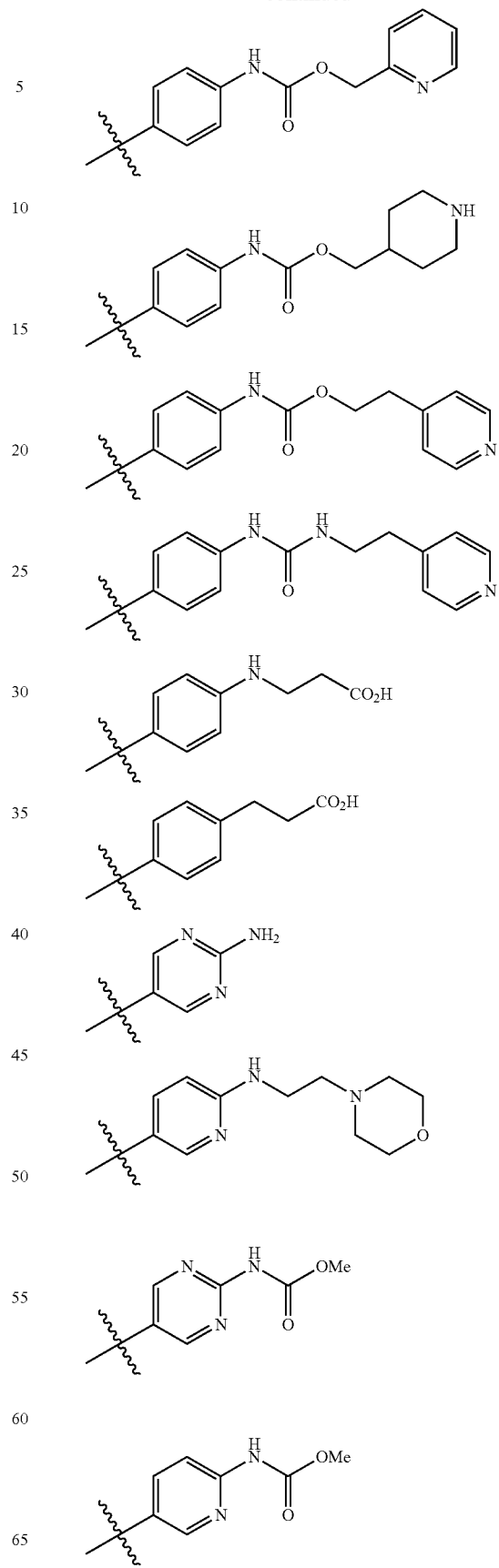

-continued

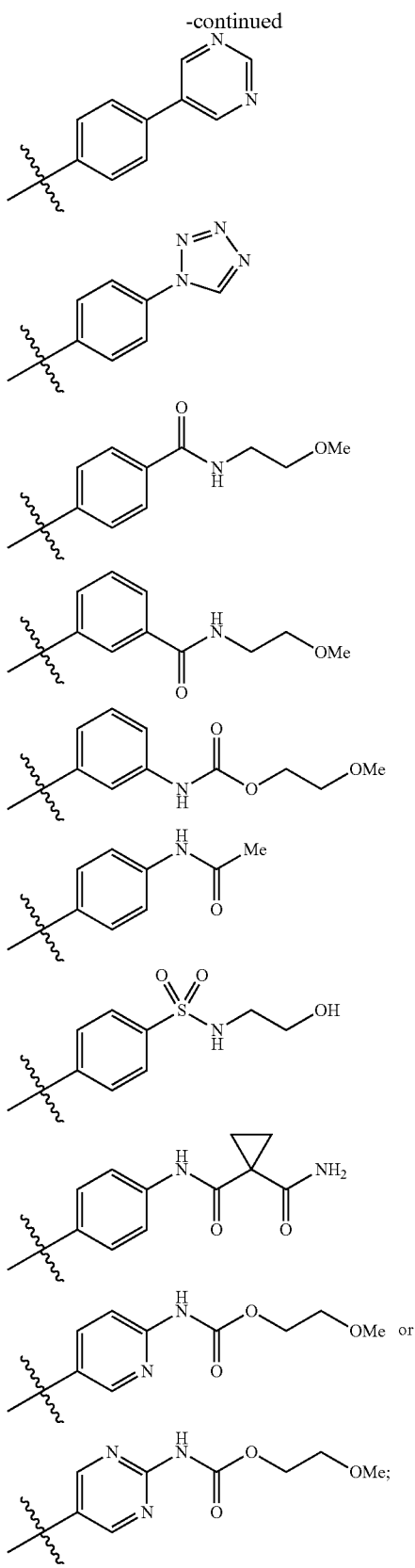

R⁴ is H, Me, or Cl;
R⁸ᵃ is H or Me; and
R¹¹ is H or benzyl.

8. A compound of Formula (II):

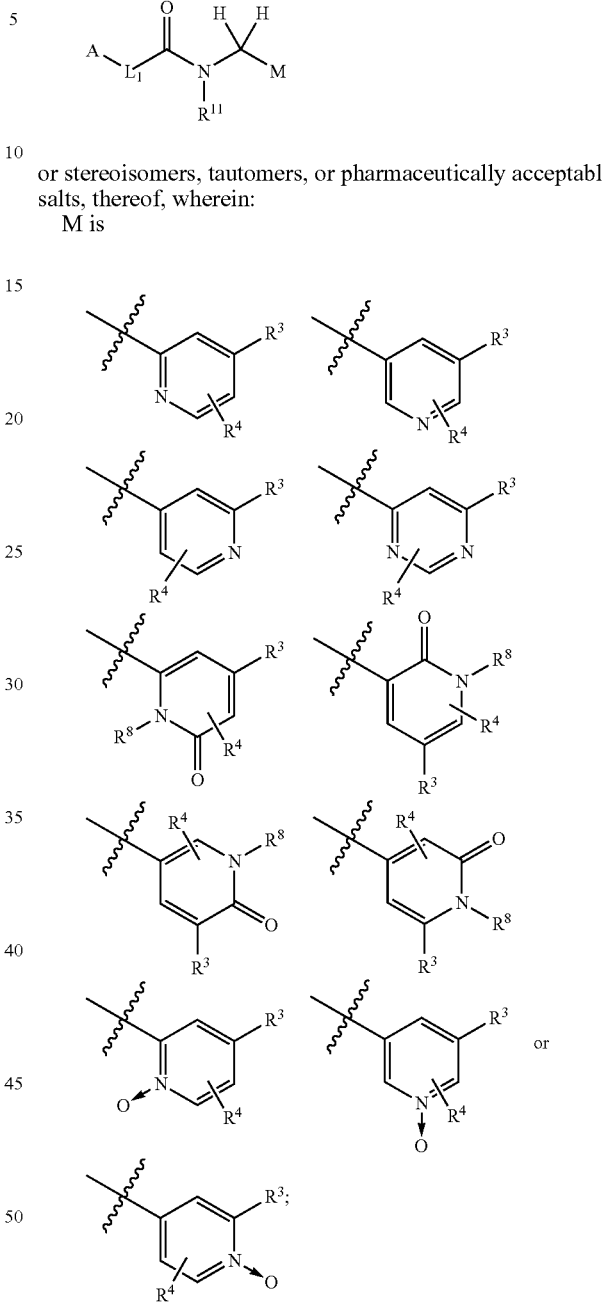

or stereoisomers, tautomers, or pharmaceutically acceptable salts, thereof, wherein:
M is A is a $C_{3-10}$ carbocycle substituted with 0-1 $R^1$ and 0-3 $R^2$, or a 5- to 12-membered heterocycle comprising: carbon atoms and 1-4 heteroatoms selected from N, O, and $S(O)_p$, wherein said heterocycle is substituted with 0-1 $R^1$ and 0-3 $R^2$; provided that when A is a heterocycle containing one or more nitrogen atoms, A is not attached to $L_1$ via any of the nitrogen atoms on the A ring;

$L_1$ is —CHR⁵CH₂—, —CH(NR⁷R⁸)CH₂—, —CR⁵=CH—, —C≡C—, —OCH₂—, —C(R⁵R⁶)NH—, —CH₂O—, —SCH₂—, —S(O)CH₂—, —SO₂CH₂—, —CH₂NR¹⁰—, or —NHNH—;

provided that when $L_1$ is —CH₂O—, then A is other than an unsubstituted phenyl;

$R^1$ is, independently at each occurrence, F, Cl, Br, I, $OCF_3$, $CF_3$, $-(CH_2)_rOR^a$, $-(CH_2)_rSR^a$, CN, $O(CH_2)_rNR^7R^8$, $-O(=NR^8)NR^8R^9$, $-C(O)NR^8R^9$, $-S(O)_pNR^8R^9$, or $C_{1-6}$ alkyl substituted with 0-1 $R^{1a}$;

$R^{1a}$ is F, $OCF_3$, $CF_3$, $OR^a$, $SR^a$, CN, $-NR^7R^8$, $-C(O)NR^8R^9$, $-NR^8C(O)R^c$, $-S(O)_pNR^8R^9$, $-NR^8SO_2R^c$, or $-(CF_2)_rCF_3$;

$R^2$ is, independently at each occurrence, =O, F, Cl, Br, $OCF_3$, $CF_3$, $CHF_2$, CN, $NO_2$, $-(CH_2)_rOR^a$, $-(CH_2)_rSR^a$, $-(CH_2)_rC(O)R^a$, $-(CH_2)_rC(O)OR^a$, $-(CH_2)_rOC(O)R^a$, $-(CH_2)_rNR^7R^8$, $-(CH_2)_rC(O)NR^8R^9$, $-(CH_2)_rNR^8C(O)R^c$, $-(CH_2)_rNR^8C(O)OR^c$, $-NR^8C(O)NR^8R^c$, $-S(O)_pNR^8R^9$, $-NR^8S(O)_pR^c$, $-S(O)R^c$, $-S(O)_2R^c$, $C_{1-6}$ alkyl substituted with 0-1 $R^{2a}$, $-(CH_2)_r$-3-7 membered carbocycle optionally substituted with 0-2 $R^{2b}$, or $-(CH_2)_r$-5-7 membered heterocycle comprising carbon atoms and 1-4 heteroatoms selected from N, O, and $S(O)_p$, wherein said heterocycle is substituted with 0-2 $R^{2b}$;

alternately, when $R^1$ and $R^2$ groups are substituents on adjacent atoms they may be taken together with the atoms to which they are attached to form a 5- to 7-membered carbocycle or heterocycle comprising carbon atoms and 0-4 heteroatoms selected from N, and $S(O)_p$ and substituted with 0-2 $R^g$;

$R^{2a}$ is F, $OCF_3$, $CF_3$, $OR^a$, $SR^a$, CN, $-NR^7R^8$, $-C(O)NR^8R^9$, $-NR^8C(O)R^c$, $-NR^8C(O)OR^c$, $-NR^8C(O)NR^8R^c$, $-S(O)_pNR^8R^9$, $-NR^8SO_2R^c$, or $-(CF_2)_rCF_3$;

$R^{2b}$ is, independently at each occurrence, =O, F, Br, Cl, $OCF_3$, $CF_3$, $-(CH_2)_rOR^a$, $-(CH_2)_rSR^a$, $-(CH_2)_rCN$, $-(CH_2)_rNR^7R^8$, $-(CH_2)_rC(O)OR^a$, $-(CH_2)_rOC(O)R^a$, $-(CH_2)_rC(O)NR^8R^9$, $-(CH_2)_rNR^8C(O)R^c$, $-(CH_2)_rNR^8C(O)OR^c$, $-(CH_2)_rS(O)_pNR^8R^9$, $-(CH_2)_rNR^8SO_2R^c$, $C_{1-4}$ alkyl or $-(CF_2)_rCF_3$;

$R^3$ is, independently at each occurrence, $-(CH_2)_r$-$C_{3-10}$ carbocycle substituted with 0-3 $R^{3a}$ and 0-1 $R^{3d}$, or $-(CH_2)_r$-5- to 12-membered heterocycle comprising: carbon atoms and 1-4 heteroatoms selected from N, O, and $S(O)_p$, wherein said heterocycle is substituted with 0-3 $R^{3a}$ and 0-1 $R^{3d}$;

$R^{3a}$ is, independently at each occurrence, =O, =$NR^8$, F, Cl, Br, I, $OCF_3$, $CF_3$, $-(CH_2)_rCN$, $NO_2$, $-(CH_2)_rOR^{3b}$, $-(CH_2)_rSR^{3b}$, $-(CH_2)_rNR^7R^8$, $-NHC(O)NR^8R^9$, $-(CH_2)_rC(O)OR^{3b}$, $-C(O)C_{1-4}$ alkyl, $-SO_2NHR^{3b}$, $-S_2NHCOR^{3c}$, $-SO_2NHCO_2R^{3c}$, $-CONHSO_2R^3$, $-(CH_2)_rNR^8C(O)R^{3b}$, $-(CH_2)_rNR^8CO_2R^{3c}$, $-(CH_2)_rS(O)_pNR^8R^9$, $-(CH_2)_rNR^8S(O)_pR^{3c}$, $-NHSO_2CF_3$, $-S(O)R^{3c}$, $-S(O)_2R^{3c}$, $(CH_2)_rOC(O)R^{3b}$, $-(CH_2)_rC(O)NR^8R^9$, $-(CH_2)_rOC(O)NR^8R^9$, $-NHCOCF_3$, $-NHSO_2R^{3c}$, $-CONHOR^{3b}$, $C_{1-4}$ haloalkyl, $C_{1-4}$ haloalkyloxy-, $C_{1-6}$ alkyl substituted by $R^{3e}$, $C_{2-6}$ alkenyl substituted by $R^{3e}$, $C_{1-6}$ alkynyl substituted by $R^3$, $C_{3-6}$ cycloalkyl substituted by 0-1 $R^{3d}$, $-(CH_2)_r$-$C_{6-10}$ carbocycle substituted by 0-3 $R^{3d}$ or $-(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

alternately, when two $R^{3a}$ groups are substituted on adjacent atoms, they can be taken together with the atoms to which they are attached to form a $C_{3-10}$ carbocycle substituted with 0-2 $R^{3d}$, or a 5- to 10-membered heterocycle comprising: carbon atoms and 1-4 heteroatoms selected from N, O, and $S(O)_p$, wherein said heterocycle is substituted with 0-2 $R^{3d}$, $R^{3b}$ is, independently at each occurrence, H, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, $-(CH_2)_r$-$C_{3-10}$ carbocycle substituted with 0-3 $R^{3d}$, or $-(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3c}$ is, independently at each occurrence, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, $-(CH_2)_r$-$C_{3-10}$ carbocycle substituted with 0-3 $R^{3d}$, or $-(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3d}$ is, independently at each occurrence, H, =O, F, Cl, Br, CN, $NO_2$, $-(CH_2)_rNR^7R^8$, $-(CH_2)_rOR^a$, $-C(O)R^a$, $-C(O)OR^a$, $-OC(O)R^a$, $-NR^8C(O)R^c$, $-C(O)NR^8R^9$, $-S(O)_2NR^8R^9$, $-NR^7R^8$, $NR^8S(O)_2NR^8R^9$, $-NR^8S(O)_2R^c$, $-S(O)_pR^c$, $-(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, $-(CH_2)_r$-$C_{3-10}$ carbocycle substituted with 0-3 $R^d$, or $-(CH_2)_r$-5- to 10-membered heterocycle comprising: carbon atoms and 1-4 heteroatoms selected from N, O, and $S(O)_p$, wherein said heterocycle is substituted with 0-3 $R^d$;

$R^{3e}$ is, independently at each occurrence, H, $-(CH_2)_rOR^a$, F, =O, CN, $NO_2$, $-(CH_2)_rNR^7R^8$, $-C(O)R^a$, $-C(O)OR^a$, $-OC(O)R^a$, $-NR^8C(O)R^c$, $-C(O)NR^8R^9$, $-S(O)_2NR^8R^9$, $-NR^8S(O)_2NR^8R^9$, $-NR^8S(O)_2R^c$, $-S(O)_pR^c$, $-(CF_2)_rCF_3$, $-(CH_2)_r$-$C_{3-10}$ carbocycle substituted with 0-3 $R^d$, or $-(CH_2)_r$-5- to 10-membered heterocycle comprising: carbon atoms and 1-4 heteroatoms selected from N, O, and $S(O)_p$, wherein said heterocycle is substituted with 0-3 $R^d$;

$R^4$ is, independently at each occurrence, H, F, Cl, Br, I, $OCF_3$, $CF_3$, CN, $NO_2$, $-(CH_2)_rOR^a$, $-(CH_2)_rSR^a$, $-(CH_2)_rC(O)R^a$, $-(CH_2)_rC(O)OR^a$, $-OC(O)R^a$, $-(CH_2)_rNR^7R^8$, $-NR^8(CH_2)_rC(O)OR^a$, $-(CH_2)_rC(O)NR^8R^9$, $-(CH_2)_rNR^8C(O)R^c$, $-(CH_2)_rNR^8C(O)_2R^b$, $-(CH_2)_rNR^8C(O)NR^8R^9$, $-S(O)_pNR^8R^9$, $-NR^8S(O)_pR^c$, $-S(O)_2R^c$, or $C_{1-4}$ alkyl substituted with 0-2 $R^{4a}$;

$R^{4a}$ is, independently at each occurrence, H, F, =O, $C_{1-6}$ alkyl, $OR^a$, $SR^a$, $CF_3$, CN, $NO_2$, $-C(O)R^a$, $-C(O)OR^a$, $-NR^7R^8$, $-C(O)NR^8R^9$, $NR^8C(O)R^c$, $-S(O)_pNR^8R^9$, $-NR^8S(O)_pR^c$, $-S(O)R^c$, or $-S(O)_2R^c$;

$R^5$ is, independently at each occurrence, H, F, $CF_3$, $-(CH_2)_rOR^a$, =O, $(CH_2)_rNR^7R^8$, $-S(O)_pNR^8R^9$, $-(CH_2)_rCO_2R^a$, $-(CH_2)_rCONR^8R^9$, or $C_{1-4}$ allyl;

$R^6$ is, independently at each occurrence, H, F, or $C_{1-4}$ alkyl;

$R^7$ is, independently at each occurrence, H, $C_{1-6}$ alkyl, $-(CH_2)_n$, $-C_{3-10}$ carbocycle, $-(CH_2)_n$-(5- to 10-membered heteroaryl), $-C(O)R^c$, $-CHO$, $-C(O)_2R^c$, $-S(O)_2R^c$, $-CONR^8R^c$, $-OCONHR^c$, $-C(O)O-(C_{1-4} \text{ alkyl})OC(O)-(C_{1-4} \text{ alkyl})$, or $-C(O)O-(C_{1-4} \text{ alkyl})OC(O)-(C_{6-10} \text{ aryl})$; wherein said alkyl, carbocycle, heteroaryl, and aryl are substituted with 0-2 $R^f$; wherein said heteroaryl comprises: carbon atoms and 1-4 heteroatoms selected from N, O, and $S(O)_p$;

$R^8$ is, independently at each occurrence, H, $C_{1-6}$ alkyl, $-(CH_2)_n$-phenyl, or $-(CH_2)_n$-5- to 10-membered heterocycle comprising: carbon atoms and 1-4 heteroatoms selected from N, O, and $S(O)_p$; wherein said alkyl, phenyl and heterocycle are optionally substituted with 0-2 $R^f$;

alternatively, $R^7$ and $R^8$, when attached to the same nitrogen, combine to form a 5- to 10-membered heterocycle comprising: carbon atoms and 0-3 additional heteroatoms selected from N, O, and $S(O)_p$, wherein said heterocycle is substituted with 0-2 $R^f$;

$R^9$ is, independently at each occurrence, H, $C_{1-6}$ alkyl, or —$(CH_2)_n$-phenyl; wherein said alkyl and phenyl are optionally substituted with 0-2 $R^f$;

alternatively, $R^8$ and $R^9$, when attached to the same nitrogen, combine to form a 5- to 12-membered heterocycle comprising: carbon atoms and 0-2 additional heteroatoms selected from N, O, and $S(O)_p$, wherein said heterocycle is substituted with 0-2 $R^d$;

$R^{10}$ is, independently at each occurrence, H or $C_{1-6}$ alkyl substituted with 0-3 $R^{10a}$;

$R^{10a}$ is, independently at each occurrence, H, =O, $C_{1-4}$ alkyl, $OR^a$, $SR^a$, F, $CF_3$, CN, $NO_2$, —$C(O)R^a$, —$C(O)OR^a$, —$C(O)NR^8R^9$, —$NR^8C(O)R^c$, —$S(O)_pNR^8R^9$, —$NR^8S(O)_pR^c$, or —$S(O)_pR^c$;

$R^{11}$ is H, $C_{1-4}$ alkyl, or benzyl;

the variables $R^a$, $R^b$, $R^c$, $R^d$, $R^e$, $R^f$, $R^g$, n, p, and r are, independently at each occurrence, the same as defined in the first aspect;

provided that:
when M is a pyridyl ring, $L_1$ is —CH=CH—, and $R^3$ is unsubstituted phenyl, then A is other than a substituted phenyl;
when M is a pyridyl ring, $L_1$ is —$CH_2O$—, and $R^3$ is carboxyl substituted pyridyl, then A is other than a 9H-fluoren-9-yl; or
when M is a pyrimidinyl ring, $L_1$ is —$CH_2CH_2$—, A is other than a nitrogen containing heterocycle.

9. A compound according to claim 8, wherein, $R^3$ is, independently at each occurrence, phenyl substituted with 0-3 $R^{3a}$ and 0-1 $R^{3d}$, naphthyl substituted with 0-3 $R^{3a}$ and 0-1 $R^{3d}$, or —$(CH_2)_r$-5- to 12-membered heterocycle comprising: carbon atoms and 1-4 heteroatoms selected from N, O, and $S(O)_p$, wherein said heterocycle is substituted with 0-3 $R^{3a}$ and 0-1 $R^{3d}$;

$R^4$ is, independently at each occurrence, H, Me, Et, Pr, F, Cl, Br, I, $OCF_3$, $CF_3$, CN, $NO_2$, $(CH_2)_rOH$, —$(CH_2)_rC(O)OR^a$, $OR^a$, $SR^a$, $C(O)R^a$, $C(O)OR^a$, —$NR^7R^8$, —$(CH_2)_rNH_2$, —$NR^8(CH_2)_rC(O)OR^a$, —$(CH_2)_rC(O)NR^8R^9$, —$NR^8C(O)R^c$, —$NR^8C(O)OR^c$, —$NR^8C(O)NR^8R^9$, —$S(O)_pNR^8R^9$, —$NR^8S(O)_pR^c$, or —$S(O)_2R^c$; and
$R^{11}$ is H.

10. A compound according to claim 8, wherein:

$R^1$ is, independently at each occurrence, F, Cl, Br, I, $OCF_3$, $CF_3$, $OCH_3$, $CH_3$, Et, $NH_2$, —C(=NH)$NH_2$, —$C(O)NH_2$, —$CH_2NH_2$ or —$SO_2NH_2$;

$R^2$ is, independently at each occurrence, F, Cl, Br, $CF_3$, $NO_2$, —$(CH_2)_rOR^a$, —$(CH_2)_rSR^a$, —$(CH_2)_rC(O)R^a$, —$C(O)OR^a$, —$C(O)NR^8R^9$, —$NR^8C(O)R^c$, —$NR^8C(O)OR^c$, —$NR^8C(O)NR^8R^c$, —$S(O)_pNR^8R^9$, —$NR^8SO_2R^c$, —$NR^7R^8$, —$S(O)R^c$, —$S(O)_2R^c$, $C_{1-6}$ alkyl substituted with 0-1 $R^{2a}$, or a 5-7 membered heterocycle comprising carbon atoms and 1-4 heteroatoms selected from N, O, and $S(O)_p$, wherein said heterocycle is substituted with 0-2 $R^{2b}$;

alternately, when $R^1$ and $R^2$ groups are substituents on adjacent atoms they may be taken together with the atoms to which they are attached to form a 5- to 7-membered carbocycle or heterocycle comprising carbon atoms and 0-4 heteroatoms selected from N, O, and $S(O)_p$ and substituted with 0-2 $R^g$;

$R^3$ is, independently at each occurrence, phenyl substituted with 0-2 $R^{3a}$ and 0-1 $R^{3d}$, naphthyl substituted with 0-2 $R^{3a}$ and 0-1 $R^{3d}$, 1,2,3,4-tetrahydronaphthyl substituted with 0-2 $R^{3a}$ and 0-1 $R^{3d}$, or a 5- to 12-membered heterocycle substituted with 0-2 $R^{3a}$ and 0-1 $R^{3d}$, wherein said heterocycle is selected from: thiophene, furan, thiazole, tetrazole, pyridine, pyridone, pyrimidine, pyrrole, pyrazole, indole, 2-oxindole, isoindoline, indazole, 7-azaindole, benzofuran, benzothiophene, benzimidazole, benzisoxazole, benzoxazole, quinazoline, quinoline, isoquinoline, quinoxaline, phthalazine, dihydrophthalazine, dihydroisoquinoline, dihydroquinoline, dihydroquinolinone, dihydroindole, dihydrobenzimidazole, dihydrobenzoxazine, dihydroquinazoline, dihydroquinoxaline, benzothiazine, benzoxazine, tetrahydrobenzazepine, dihydroazabenzocycloheptene, and tetrahydroquinoline;

$R^{3a}$ is, independently at each occurrence, =O, F, Cl, Br, Me, CN, OH, OMe, —OC(O)(t-Bu), —$CH_2$CMe, $CF_3$, COMe, $CO_2H$, $CO_2Me$, —$CH_2CO_2H$, —$(CH_2)_2CO_2H$, —$CH_2CO_2Me$, —$CH_2CO_2Et$, —$CH_2CH_2CO_2Et$, —$CH_2CN$, $NH_2$, —$CH_2NH_2$, —$CH_2NMe_2$, —NHCOMe, —$NHCO_2Me$, —$NHCO_2Et$, —$NHCH_2CH_2CO_2H$, —$NHCO_2$(i-Pr), —$NHCO_2$(i-Bu), —$NHCO_2$(t-Bu), —$NHCO_2Bn$, —$NHCO_2CH_2CH_2OMe$, —$NHCO_2CH_2CH_2CH_2OMe$, —$NHCO_2CH_2CO_2H$, —$NHCO_2CH_2CH_2CO_2H$, —$NHCO_2CH_2CH_2OH$, —$NHCO_2CH_2CH_2NH_2$, —$NHCO_2CH_2$-tetrahydrofuran-2-yl, $NHCO_2CH_2CH_2CH$(Me)OMe, —$NHCO_2CH_2CH_2C(O)NH_2$, —$NHC(O)NHCH_2CH_2$-morpholino, —$NHC(O)NHCH_2$-pyrid-4-yl, —$NHCO_2CH_2$-pyrid-4-yl, —$NHCO_2CH_2$-pyrid-3-yl, —$NHCO_2CH_2$-pyrid-2-yl, —$NHCO_2CH_2$-(piperidin-4-yl), —$NHC(O)NHCH_2CH_2$-pyrid-4-yl, —$NHCO_2CH_2CH_2$-pyrid-4-yl, —$NHCO_2CH_2CH_2$-morpholino, —$CH_2NHCO_2Me$, —NHC(O)NHMe, —$NHC(O)N(Me)_2$, —$NHC(O)NHCH_2CH_2OMe$, 4-[(1-carbamoyl-cyclopropanecarbonyl)-amino]-, —$NHSO_2Me$, —$SO_2NH_2$, —$SO_2NHMe$, —$SO_2NHCH_2CH_2OH$, —$SO_2NHCH_2CH_2OMe$, —$CONH_2$, —CONHMe, —$CON(Me)_2$, —$C(O)NHCH_2CH_2OMe$, —$CH_2CONH_2$, —CO(N-morpholino), —$NHCH_2CH_2$(N-morpholino), —$NR^7R^8$, —NH(1H-imidazol-2-yl), 1H-tetrazol-5-yl, tetrazol-1-yl, pyrimidin-5-yl, N-morpholino, or —$(CH_2)_r$-5- to 6-membered heterocycle comprising: carbon atoms and 1-4 heteroatoms selected from N, O, and $S(O)_p$, wherein said heterocycle is substituted with 0-1 $R^{3d}$;

$R^4$ is, independently at each occurrence, H, F, Cl, Br, OH, OMe, $NH_2$, Me, Et, $CF_3$, —$CH_2OH$, —$C(O)_2H$, $CO_2Me$, $CO_2Et$, —$C(O)NH_2$, —$C(O)NHMe$, —$C(O)N(Me)_2$, or —$CH_2CO_2H$;

$R^8$ is, independently at each occurrence, H, $C_{1-6}$ alkyl or —$(CH_2)_n$-phenyl; and
$R^{11}$ is H.

11. A compound according to claim 8, wherein:
A is substituted with 0-1 $R^1$ and 0-3 $R^2$ and selected from: $C_{3-7}$ cycloalkyl, phenyl, naphthyl, 1,2,3,4-tetrahydronaphthyl, pyrrolidinyl, pyridyl, indazolyl, indolyl, imidazolyl, furanyl, thienyl, benzimidazolyl, benzisoxazolyl, benzothiazolyl, benzothiophenyl, 3,4-methylenedioxy-phenyl, oxazolyl, isoxazolyl, thiazolyl, isothiazolyl, and pyrazolyl;

$L_1$ is —$CH_2CH_2$—, —$CH(NH_2)CH_2$—, —CH(NH-COMe)$CH_2$—, —CH(NHCOEt)$CH_2$—, —CH(NHCO_2(t-Bu))$CH_2$—, —CH=CH—, —C(Me)

=CH—, —C≡C—, —CH₂NH—, —CH(CH₂CO₂H)
NH—, —CH₂O—, —NHNH—, —SCH₂—, —S(O)
CH₂—, —SO₂CH2— or —OCH₂—;

R¹ is, independently at each occurrence, F, Cl, Br, CF₃, NH₂, —CH₂NH₂, —C(=NH)NH₂, —C(O)NH₂, —SO₂NH₂, SRᵃ, ORᵃ, or C₁₋₆ alkyl substituted with 0-1 R¹ᵃ;

R² is, independently at each occurrence, =O, F, Cl, Br, CF₃, Me, Et, ORᵃ, CN, NO₂, NR⁷R⁸, —CH₂OMe, —SRᵃ, —CH₂SMe, —C(O)Rᵃ, —C(O)ORᵃ, —CH₂NR⁷R⁸, —SO₂NH₂, —SO₂Me, —NHSO₂Rᶜ, —CH₂NHSO₂Rᶜ, —C(O)NR⁸R⁹, —NHC(O)Rᶜ, —CH₂NHC(O)Rᶜ, —NHC(O)ORᶜ, —CH₂NHC(O)ORᶜ, —NHC(O)NHRᶜ, —CH₂NHC(O)NHRᶜ, or a 5-7 membered heterocycle substituted with 0-2 R²ᵇ and selected from: pyrrolidinyl, 2-oxo-1-pyrrolidinyl, piperidinyl, pyrazolyl, triazolyl, imidazolyl, and tetrazolyl;

alternately, when R¹ and R² groups are substituents on adjacent atoms they may be taken together with the atoms to which they are attached to form a 5- to 6-membered heterocycle comprising carbon atoms and 0-4 heteroatoms selected from N, O, and S(O)ₚ;

R³ is, independently at each occurrence, phenyl substituted with 0-2 R³ᵃ, naphthyl substituted with 0-2 R³ᵃ, or a 5-to 12-membered heterocycle comprising: carbon atoms and 1-2 heteroatoms selected from N, O, and S(O)ₚ, wherein said heterocycle is substituted with 0-2 R³ᵃ;

R³ᵃ is, independently at each occurrence, =O, F, Cl, Br, Me, CN, OH, OMe, —OC(O)(t-Bu), CH₂OMe, CF₃, COMe, CO₂H, CO₂Me, —CH₂CO₂H, —(CH₂)₂CO₂H, —CH₂CO₂Me, —CH₂CO₂Et, —CH₂CH₂CO₂Et, —CH₂CN, NH₂, —CH₂NH₂, —CH₂NMe₂, —NHCOMe, —NHCO₂Me, —NHCO₂Et, —NHCH₂CH₂CO₂H, —NHCO₂(i-Pr), —NHCO₂(i-Bu), —NHCO₂(t-Bu), —NHCO₂Bn, —NHCO₂CH₂CH₂OMe, —NHCO₂CH₂CH₂CH₂OMe, —NHCO₂CH₂CO₂H, —NHCO₂CH₂CH₂CO₂H, —NHCO₂CH₂CH₂OH, —NHCO₂CH₂CH₂NH₂, —NHCO₂CH₂-tetrahydrofuran-₂-yl, —NHCO₂CH₂CH₂CH(Me)OMe, —NHCO₂CH₂CH₂C(O)NH₂, —NHC(O)NHCH₂CH₂-morpholino, —NHC(O)NHCH₂-pyrid-4-yl, —NHCO₂CH₂-pyrid-4-yl, —NHCO₂CH₂-pyrid-3-yl, —NHCO₂CH₂-pyrid-2-yl, —NHCO₂CH₂-(piperidin-4-yl), —NHC(O)NHCH₂CH₂-pyrid-4-yl, —NHCO₂CH₂CH₂-pyrid-4-yl, —NHCO₂CH₂CH₂-morpholino, —CH₂NHCO₂Me, —NHC(O)NHMe, —NHC(O)N(Me)₂, —NHC(O)NHCH₂CH₂OMe, 4-[(1-carbamoyl-cyclopropanecarbonyl)-amino]-, —NHSO₂Me, —SO₂NH₂, —SO₂NHMe, —SO₂NHCH₂CH₂OH, —SO₂NHCH₂CH₂OMe, —CONH₂, —CONHMe, —CON(Me)₂, —C(O)NHCH₂CH₂OMe, —CH₂CONH₂, —CO(N-morpholino), —NHCH₂Cl₂(N-morpholino), —NR⁷R⁸, —NH(1H-imidazol-2-yl), 1H-tetrazol-5-yl, tetrazol-1-yl, pyrimidin-5-yl, or N-morpholino, or —(CH₂)ᵣ-5- to 6-membered heterocycle comprising: carbon atoms and 1-4 heteroatoms selected from N, O, and S(O)ₚ, wherein said heterocycle is substituted with 0-1 R³ᵈ;

alternatively, two of R³ᵃ groups located on adjacent atoms, they can be taken together with the atoms to which they are attached to form a 5- to 10-membered heterocycle comprising: carbon atoms and 1-4 heteroatoms selected from N, O, and S(O)ₚ, wherein said heterocycle is substituted with 0-2 R³ᵈ;

R⁴ is, independently at each occurrence, H, F, Cl, Br, OMe, NH₂, CF₃, Me, Et, CO₂H, CO₂Me, or CO₂Et; and R⁸ is, independently at each occurrence, H or C₁₋₄ alkyl.

12. A compound according to claim 8, wherein:
A is substituted with 0-2 R² and selected from:

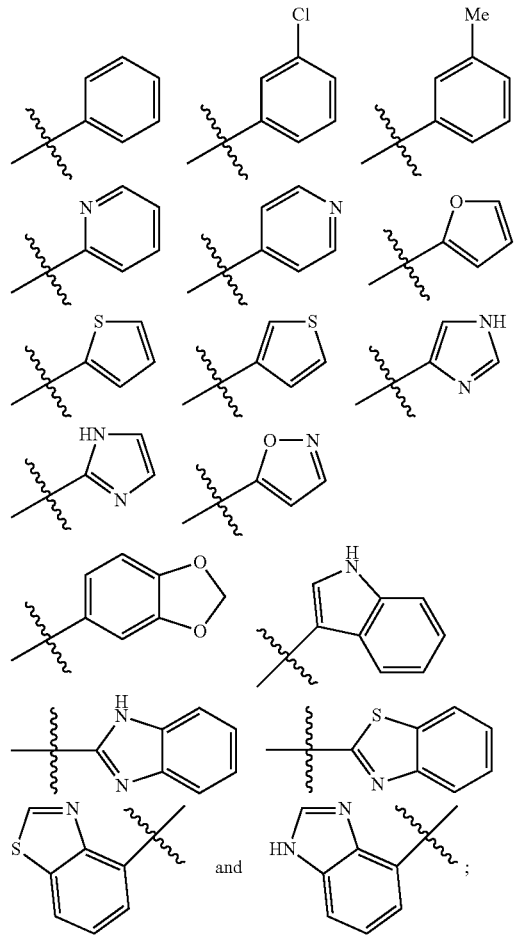

R² is, independently at each occurrence, =O, F, Cl, Br, Me, CF₃, OMe, OEt, OPh, OBn, SMe, SEt, S(n-Pr), SBn, —CH₂SMe, SO₂Me, SO₂NH₂, NH₂, —CH₂NH₂, NO₂, C(O)Me, CO₂H, CO₂Me, CONH₂, CONHMe, —CH₂NHCOPh, —NHCO₂Me, —CH₂NHCO₂Et, —CH₂₁NHCO₂(i-Pr), —CH₂NHCO₂(t-Bu), —CH₂NHCO₂Bn, —CH₂NHCO(CH₂)₂CO₂H, —CONHPh, —NHCONHMe, —CH₂NHCONHEt, —CH₂NHCONH(CH₂)₂CO₂Et, —CH₂NHCONHPh, —CH₂NHCONH(4-Cl-Ph), —CH₂NHCONHBn, —NHSO₂Me, —CH₂NHSO₂Me, —CH₂NHSO₂Et, —CH₂NHSO₂(n-Pr), —CH₂NHSO₂(i-Pr), —CH₂NHSO₂(n-pentyl), —CH₂NHSO₂Ph, —CH₂NHSO₂(4-NHCOMe-Ph), —CH₂NHSO₂(4-Cl-Bn), —CH₂NHSO₂CH₂CH₂Ph, —CH₂NHSO₂CH₂CH₂(2-Cl-Ph), —CH₂NHSO₂CH₂CH₁₂(3-Cl-Ph), —CH₂NHSO₂CH₂CH₂(4-Cl-Ph), —CH₂NHSO₂(3,4-dimethyl-isoxazol-4-yl), 1-pyrrolidinyl, 2-oxo-1-pyrrolidinyl, 3-carboxy-N-piperidinyl, pyrazol-1-yl, 4-carboxy-pyrazol-1-yl, 1,2,3-triazol-1-yl, 1,2,4-triazol-1-yl, 1,2,3-triazol-2-yl, 4-carboxy-1,2,3-triazol-1-yl, 4-(ethoxycarbonyl)-1,2,3-triazol-1-yl, tetrazol-1-yl, tetrazol-5-yl, 5-Me-tetrazol-1-yl, 5-CF$_3$-tetrazol-1-yl, or —OCH$_2$(2-tetrahydrofuranyl);

R$^3$ is, independently at each occurrence, phenyl substituted with 0-2 R$^{3a}$, naphthyl substituted with 0-2 R$^{3a}$, 1,2,3,4-tetrahydro-naphthyl substituted with 0-2 R$^{3a}$, or a 5- to 12-membered heterocycle substituted with 0-2 R$^{3a}$ and selected from: thiophene, furan, thiazole, tetrazole, pyridine, pyridinone, pyrimidine, pyrrole, pyrazole, indole, 2-oxindole, isoindolin-1-one, indazole, 1H-indazole-3-one, 7-azaindole, benzofuran, benzothiophene, benzimidazole, benzisoxazole, benzoxazole, quinazoline, quinoline, isoquinoline, 3H-quinazolin-4-one, phthalazine, 2H-phthalazin-1-one, 2H-3,4-dihydrophthalazin-1-one, 1H-quinolin-4-one, 1H-quinolin-2-one, 2H-3,4-dihydroisoquinolin-1-one, 3,4-dihydro-1H-quinolin-2-one, 1,3-dihydroindol-2-one, 3H-benzoxazol-2-one, 1,3-dihydrobenzimidazol-2-one, 1,4-dihydro-3,1-benzoxazin-2-one, 3,4-dihydro-1H-quinazolin-2-one, 1,3-dihydro-quinazoline-2,4-dione, 1,4-dihydro-quinoxaline-2,3-dione, 4H-benzo[1,4]thiazine-3-one, 2H-benzo[1,4]thiazin-3(4H)-one, 4H-1,4-benzoxazin-3-one, 1,3,4,5-tetrahydro-1-benzazepin-2-one, 1,3,4,5-tetrahydro-1,3-benzodiazepin-2-one, 8,9-dihydro-5H-7-oxa-5-aza-benzocyclohepten-6-one, benzimidazol-2-one, 1,3-dihydrobenzimidazol-2-one, 3H-benzoxazol-2-one, 3H-quinazolin-4-one, and 1,2,3,4-tetrahydroquinoline;

R$^4$ is, independently at each occurrence, H, Me, F, Br, C$_1$, CF$_3$, CO$_2$H, CO$_2$Me, or CO$_2$Et; and R$^8$ is, independently at each occurrence, H or Me.

13. A compound according to claim 8, wherein:

A is phenyl, 2-fluorophenyl, 3-fluorophenyl, 2-chlorophenyl, 3-chlorophenyl, 2-bromophenyl, 3-bromophenyl, 3-methylphenyl, 2-methoxyphenyl, 3-methoxyphenyl, 3-aminomethylphenyl, 4-aminomethylphenyl, 2-carboxy-5-chlorophenyl, 2-methoxycarbonyl-5-chlorophenyl, 2-N-(methoxycarbonyl)-amino)-5-chlorophenyl, 2-(N-(ethoxycarbonyl)-aminomethyl)-5-chlorophenyl, 2-(N-(isopropoxycarbonyl)-aminomethyl)-5-chlorophenyl, 2-(N-(tert-butoxycarbonyl)-aminomethyl)-5-chlorophenyl, 2-(N-(phenylcarbonyl)-aminomethyl)-5-chlorophenyl, 2-(N-(benzoxycarbonyl)-aminomethyl)-5-chlorophenyl, 2-((N-(3-propanoic acid)carbonyl)-aminomethyl)-5-chlorophenyl, 2-(3-methylureido)-5-chlorophenyl, 2-(3-ethylureidomethyl)-5-chlorophenyl, 2-[3-(2-ethoxycarbonyl-ethyl) -ureidomethyl]-5-chlorophenyl, 2-(3-phenylureido)methyl)-5-chlorophenyl, 2-(3-(4-chlorophenyl)ureido)methyl)-5-chlorophenyl, 2-(3-benzylureido)methyl)-5-chlorophenyl, 2-(N-(methylsulfonyl)-amino)-5-chlorophenyl, 2-(N-(methylsulfonyl)-aminomethyl)-5-chlorophenyl, 2-(N-(ethylsulfonyl)-aminomethyl)-5-chlorophenyl, 2-(N-(n-propylsulfonyl)-aminomethyl)-5-chlorophenyl, 2-(N-(isopropylsulfonyl)-aminomethyl)-5-chlorophenyl, 2-(N-(n-pentylsulfonyl)-aminomethyl)-5-chlorophenyl, 2-(N-(phenylsulfonyl)-aminomethyl)-5-chlorophenyl, 2-((N-(4-methylcarbonylaminophenyl)sulfonyl)-aminomethyl)-5-chlorophenyl, 2-(N-(4-chlorobenzylsulfonyl)-aminomethyl)-5-chlorophenyl, 2-(N-(phenethylsulfonyl)-aminomethyl)-5-chlorophenyl, 2-(N-(2-chlorophenethylsulfonyl)-aminomethyl)-5-chlorophenyl, 2-(N-(3-chlorophenethylsulfonyl)-aminomethyl)-5-chlorophenyl, 2-(N-(4-chlorophenylsulfonyl)-aminomethyl)-5-chlorophenyl, 2-(N-(3,4-dimethyl-isoxazol-4-yl)-aminomethyl)-5-chlorophenyl, 2-(N-(3,4-dimethyl-isoxazol-4-ylsulfonyl)aminomethyl)-5-chlorophenyl, 3-carbamoyl-phenyl, 2,4-difluorophenyl, 2,5-difluorophenyl, 2,5-dichlorophenyl, 3,5-dichlorophenyl, 5-chloro-2-fluorophenyl, 3-chloro-2-fluorophenyl, 3-chloro-4-methylphenyl, 2-methyl-5-chlorophenyl, 2-methoxy-5-chlorophenyl, 2-ethoxy-5-chlorophenyl, 2-benzyloxy-5-chlorophenyl, 2-methylthio-5-chlorophenyl, 2-ethylthio-5-chlorophenyl, 2-propylthio-5-chlorophenyl, 2-benzylthio-5-chlorophenyl, 2-methylthiomethyl-5-chlorophenyl, 2-(2-oxo-1-pyrrolidinyl)-5-chlorophenyl, 3-trifluoromethyl-2-fluorophenyl, 2-trifluoromethyl-5-chlorophenyl, 5-bromo-2-fluorophenyl, 2-amino-5-chlorophenyl, 2-aminomethyl-5-chlorophenyl, 2-methylsulfonyl-5-chlorophenyl, 2-methylsulfonamide-5-chlorophenyl, 2-phenylcarbamoyl-5-chlorophenyl, 2-(3-carboxy-N-piperidinyl)-5-chlorophenyl, 2,6-difluoro-3-methylphenyl, 2-chloro-6-fluoro-3-methylphenyl, 2-fluoro-6-chloro-3-methylphenyl, 2,6-difluoro-3-chlorophenyl, 2,3-dichloro-6-aminophenyl, 2,3-dichloro-6-nitrophenyl, 2-phenoxyphenyl, 2-phenoxy-5-chlorophenyl, 2-(N-pyrrolidinyl)-5-chlorophenyl, 2-(pyrazol-1-yl)-5-chlorophenyl, 2-(4-carboxy-pyrazol-1-yl)-5-chlorophenyl, 2-(1,2,3-triazol-1-yl)-5-methylphenyl, 2-(1,2,3-triazol-1-yl)-5-chlorophenyl, 2-(1,2,3-triazol-2-yl)-5-chlorophenyl, 2-(1,2,4-triazol-1-yl)-5-chlorophenyl, 2-[(4-carboxy)-1,2,3-triazol-1-yl]-5-methylphenyl, 2-[(4-carboxy)-1,2,3-triazol-1-yl]-5-chlorophenyl, 2-[(4-ethoxycarbonyl)-1,2,3-triazol-1-yl]-5-chlorophenyl, 2-(tetrazol-1-yl)-5-methylphenyl, 2-(tetrazol-1-yl)-5-chlorophenyl, 2-(tetrazol-5-yl)-5-chlorophenyl, 2-(5-methyl-tetrazol-1-yl)-5-chlorophenyl, 2-(tetrazol-1-yl)-3-fluoro-5-chlorophenyl, 2-(tetrazol-1-yl)-3-fluoro-5-methylphenyl, 2-(5-methyltetrazol-1-yl)-5-chlorophenyl, 2-(5-trifluoromethyl-tetrazol-1-yl)-5-chlorophenyl, 2-(2-tetrahydrofuranyl-methoxy)-5-chlorophenyl, 3,4-methylenedioxy-phenyl, cyclopentyl, 2-oxo-1-pyrrolidinyl, 2-furanyl, 2-thienyl, 3-thienyl, 5-chloro-2-thienyl, 5-chloro-3-thienyl, 2,5-dichloro-3-thienyl, 1-imidazolyl, 2-imidazolyl, 4-imidazolyl, 3-chloro-5-isoxazolyl, 4-pyridyl, 3-fluoro-2-pyridyl, 2(1H)-oxo-5-chloropyridin-1-yl, 1-indolyl, 3-indolyl, 2-benzimidazolyl, 6-chlorobenzimidazol-4-yl, 2-methyl-6-chlorobenzothiazol-4-yl or 2,6-dichlorobenzothiazol-4-yl, 2-[(3-carboxy)-pyrazol-1-yl]-5-chlorophenyl, 2-[(3-carboxy)-pyrazol-1-yl]-5-methylphenyl, 2-fluoro-3-chloro-6-(tetrazol-1-yl)phenyl, 2-fluoro-3-chloro-6-(methylcarbonyl)phenyl, 2-methylcarbonyl-5-chlorophenyl, 2-(aminocarbonyl)-5-chlorophenyl, 2-(methylaminocarbonyl)-5-chlorophenyl, or 2-(aminosulfonyl)-5-chlorophenyl;

L$_1$ is —CH$_2$CH$_2$—, —CH=CH—, —C(Me)=CH—, —C≡C—, —CH$_2$NH—, —CH$_2$O—, —NHNH—, —SCH$_2$—, —S(O)CH$_2$—, —SO$_2$CH$_2$— or —OCH$_2$—;

R$^3$ is, independently at each occurrence, phenyl, 3-biphenyl, 4-biphenyl, 3-aminophenyl, 4-aminophenyl, 3-N,N-dimethylaminophenyl, 4-phenoxyphenyl, 4-benzyloxyphenyl, 4-(t-butoxymethyl)-phenyl, 4-methylsulfonylphenyl, 3-cyanophenyl, 4-cyanophenyl, 3-fluorophenyl, 4-fluorophenyl, 3-chlorophenyl, 4-chlorophenyl, 3-bromophenyl, 4-bromophenyl, 3-hydroxyphenyl, 4-hydroxyphenyl, 2-methoxyphenyl, 3-methoxyphenyl, 4-methoxyphenyl, 3-trifluoromethylphenyl, 4-trifluoromethylphenyl, 3-carboxyphenyl, 4-carboxyphenyl, 3-methoxycarbonylphenyl, 4-methoxycarbonylphenyl, 3-carboxymethylphenyl, 4-carboxymethylphenyl, 4-methoxycarbonylmethylphenyl, 3-ethoxycarbonylmethylphenyl, 4-ethoxycarbonylmethylphenyl, 4-ethoxycarbonylethylphenyl, 3-carbamoylphenyl, 4-carbamoylphenyl, 3-aminocarbonylmethylphenyl, 4-aminocarbonylmethylphenyl, 4-methylaminocarbonylphenyl, 4-dimethylaminocarbonylmethylphenyl, 4-amidinophenyl, 3-methylcarbonylaminophenyl, 4-methylcarbonylaminophenyl, 4-methoxycarbonylaminophenyl, 4-aminosulfonylphenyl, 3-methylsulfonylaminophenyl, 4-methylsulfonylamino, 2,4-difluorophenyl, 3-fluoro-4-cyanophenyl, 4-amino-3-carboxyphenyl, 4-amino-3-methoxycarbonylphenyl, 2,4-dichlorophenyl, 3-cyano-5-fluorophenyl, 3-fluoro-4-carbamoylphenyl, 3-carboxy-4-cyanophenyl, 3-phenyl-4-carbamoylphenyl, 4-(2-oxo-1-piperidino)-phenyl, thiazol-2-yl, thien-2-yl, 4-methoxycarbonyl-thiazol-2-yl, 4-carbamoyl-thiazol-2-yl, 1-benzyl-pyazol-4-yl, 5-phenyl-oxazol-2-yl, 5-carbamoyl-thien-2-yl, 5-carboxy-thien-2-yl, pyrid-2-yl, pyrid-3-yl, pyrid-4-yl, 6-amino-pyrid-3-yl, benzimidazol-2-yl, 6-methoxy-pyrid-3-yl, 1-methyl-benzimidazol-2-yl, benzoxazol-2-yl, benzothiazol-2-yl, 3-amino-benzisoxazol-6-yl, 3-amino-benzisoxazol-5-yl, indazol-5-yl, indazol-6-yl, 3-amino-indazol-5-yl, 3-hydroxy-indazol-5-yl, 3-amino-indazol-6-yl, 3-amino-1-methyl-indazol-6-yl, 3-amino-4-fluoro-indazol-6-yl, 3-amino-5-fluoro-indazol-6-yl, 3-amino-7-fluoro-indazol-6-yl, 4-imino-3,4-dihydro-2H-phthalazin-1-on-7-yl, 3-(5-tetrazolyl)-phenyl, 2,3-dihydro-isoindol-1-on-6-yl, quinolin-5-yl, quinolin-6-yl, quinolin-8-yl, isoquinolin-5-yl, 2H-isoquinolin-1-on-6-yl, 2,4-diaminoquinazolin-7-yl, 4-$NH_2$-quinazolin-7-yl,

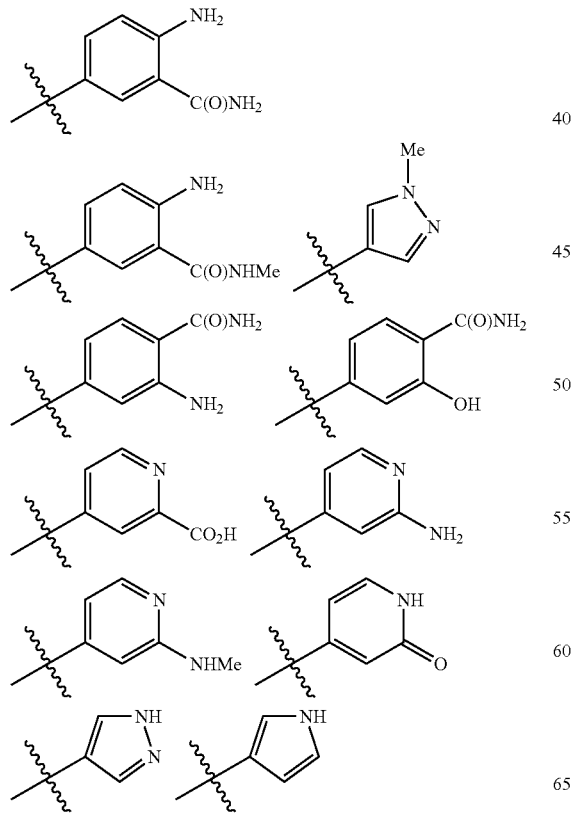

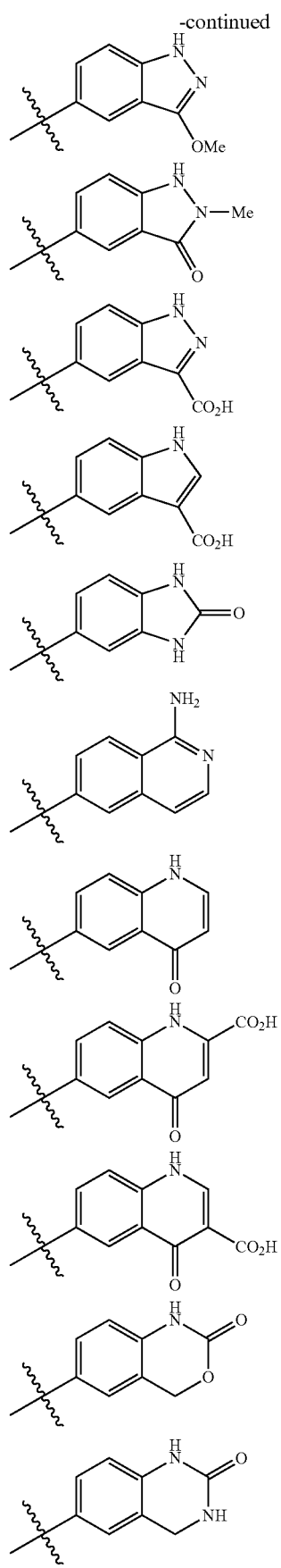

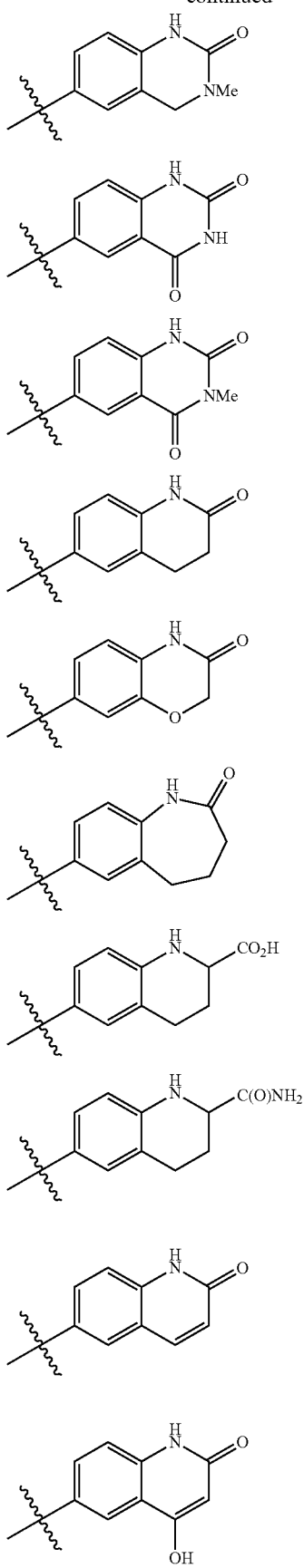
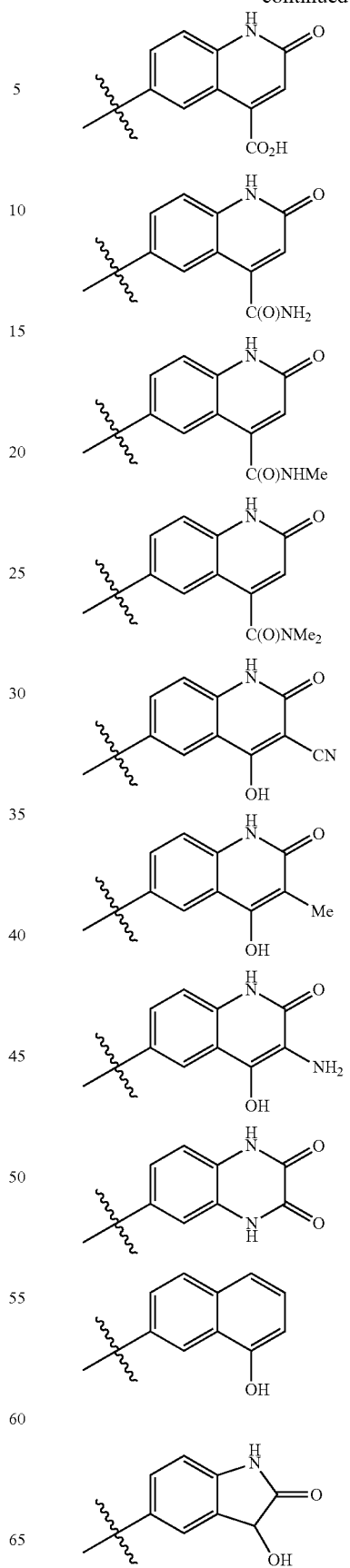

163
-continued
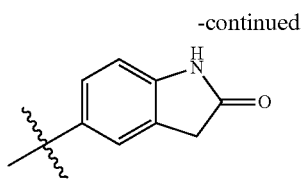
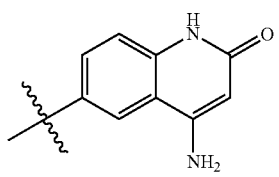
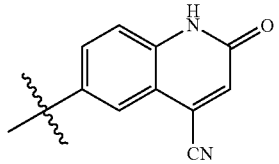
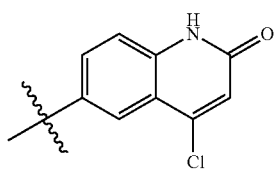
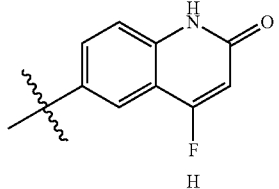
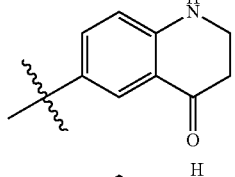
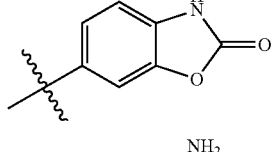
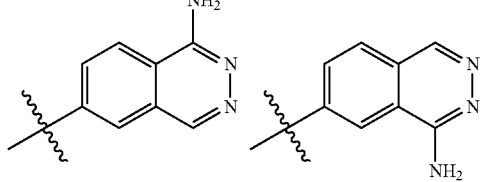
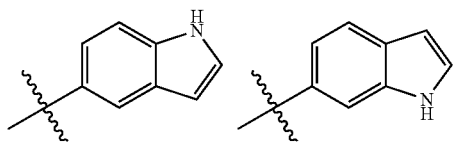
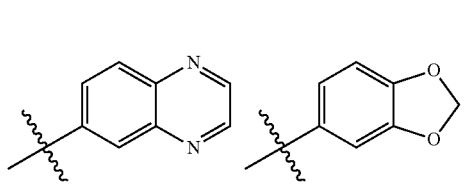
164
-continued
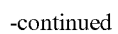
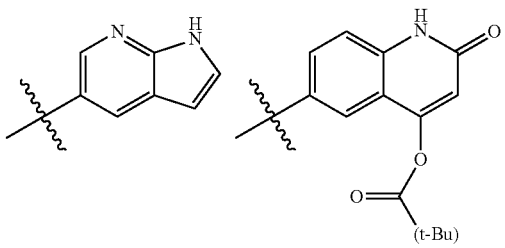
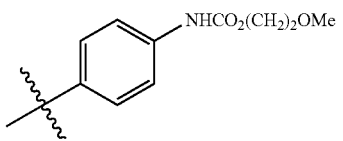
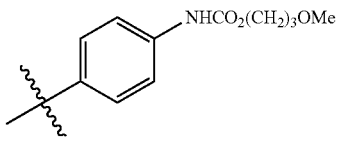
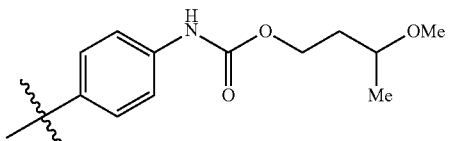
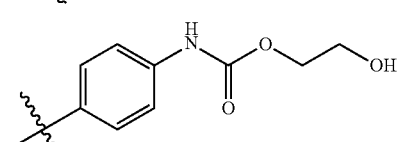
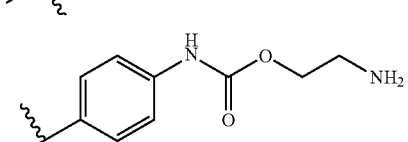
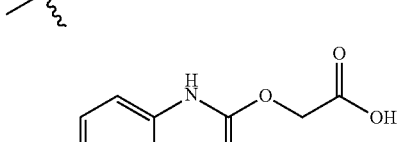
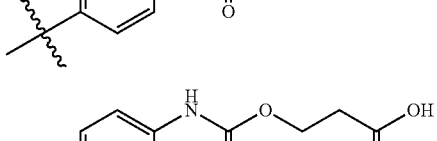
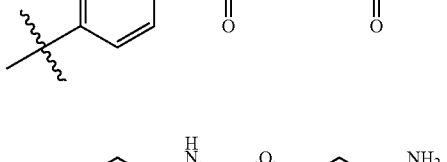
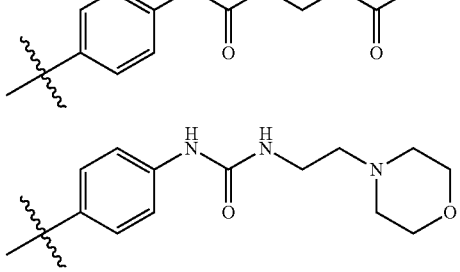

165
-continued
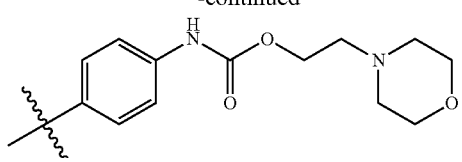
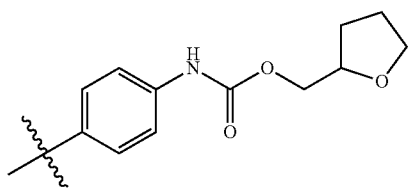
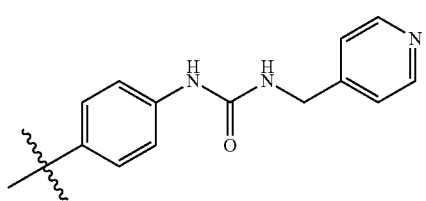
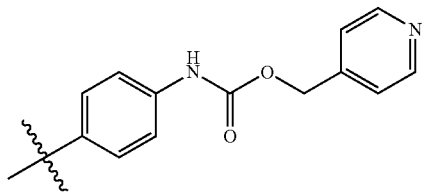
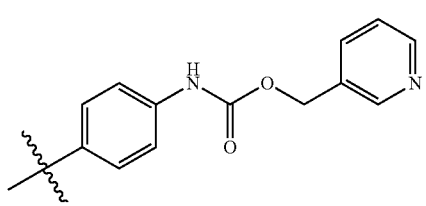
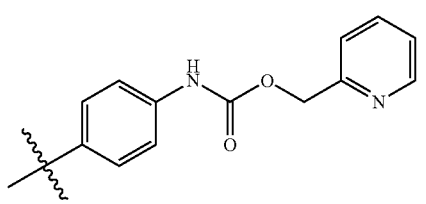
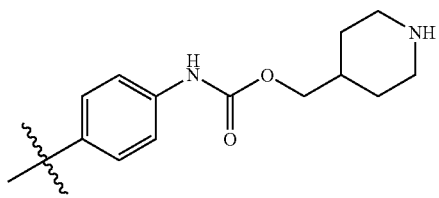
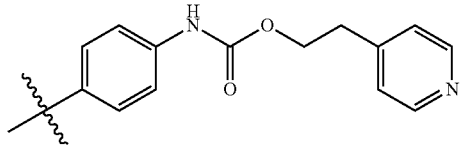
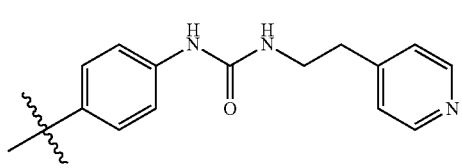
166
-continued
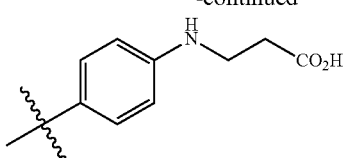
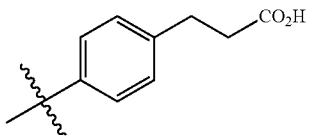
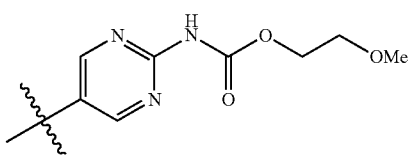
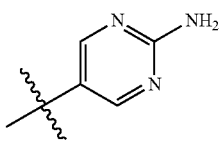
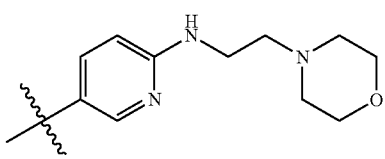
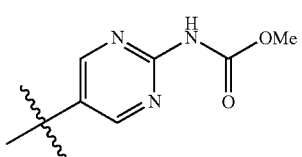
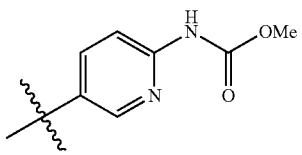
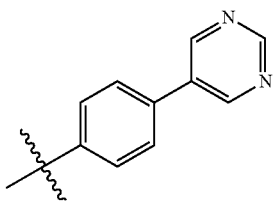
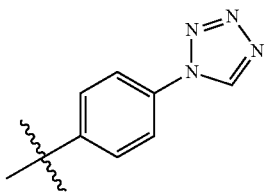
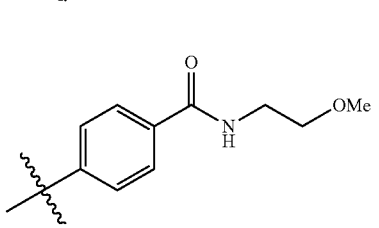

-continued

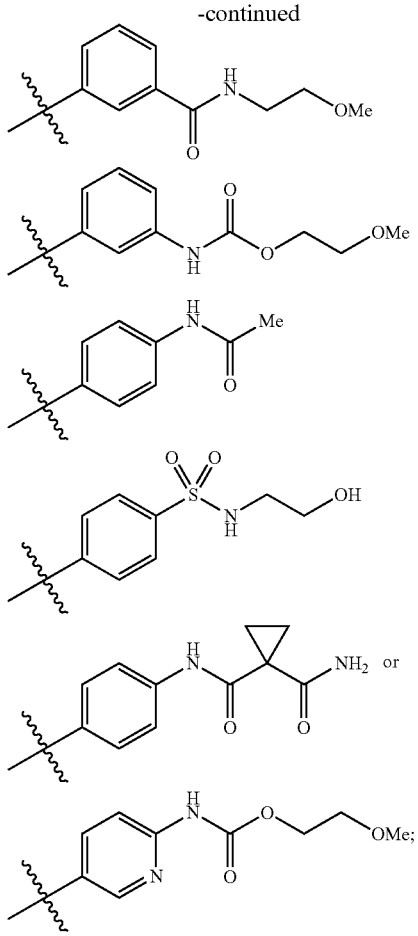

R[4] is, independently at each occurrence, H, Me, F, Br, Cl, CF$_3$, CO$_2$H, CO$_2$Me, or CO$_2$Et; and
R[8] is, independently at each occurrence, H or Me.

14. A compound according to claim 8, wherein:
A is 3-chlorophenyl, 3-methylphenyl, 2,5-dichlorophenyl, 5-chloro-2-fluorophenyl, 3-chloro-2-fluorophenyl, 2-methyl-5-chlorophenyl, 2-methoxy-5-chlorophenyl, 2-methylthio-5-chlorophenyl, 2-ethylthio-5-chlorophenyl, 2-propylthio-5-chlorophenyl, 2-benzylthio-5-chlorophenyl, 2-amino-5-chlorophenyl, 2-aminomethyl-5-chlorophenyl, 2,6-difluoro-3-methylphenyl, 2-chloro-6-fluoro-3-methylphenyl, 2-fluoro-6-chloro-3-methylphenyl, 2,6-difluoro-3-chlorophenyl, 2,3-dichloro-6-nitrophenyl, 5-chloro-2-thienyl, 3,4-methylenedioxyphenyl, 2-methoxycarbonyl-5-chlorophenyl, 6-chlorobenzimidazol-4-yl, 2-[(4-carboxy)-pyrazol-1-yl]-5-chlorophenyl, 2-[(4-carboxy)-pyrazol-1-yl]-5-methylphenyl, 2-(1,2,3-triazol-1-yl)-5-methylphenyl, 2-(1,2,3-triazol-1-yl)-5-chlorophenyl, 2-(1,2,4-triazol-1-yl)-5-chlorophenyl, 2-(1,2,3-triazol-2-yl)-5-chlorophenyl, 2-[(4-carboxy)-1,2,3-triazol-1-yl]-5-chlorophenyl, 2-[(4-carboxy)-1,2,3-triazol-1-yl]-5-methylphenyl, 2-[(4-ethoxycarbonyl)-1,2,3-triazol-1-yl]-5-chlorophenyl, 2-(tetrazol-1-yl)-5-methylphenyl, 2-(tetrazol-1-yl)-5-chlorophenyl, 2-(tetrazol-1-yl)-3-fluoro-5-chlorophenyl, 2-(tetrazol-1-yl)-3-fluoro-5-methylphenyl, 2-(5-methyltetrazol-1-yl)-5-chlorophenyl, 2-fluoro-3-chloro-6-(tetrazol-1-yl) phenyl, 2-fluoro-3-chloro-6-(methylcarbonylphenyl, or 2-methylcarbonyl-5-chlorophenyl;

L$_1$ is —CH$_2$CH$_2$—, —CH=CH—, —C(Me)=CH—, —C≡C—, or —CH$_2$NH—;

R[3] is, independently at each occurrence,

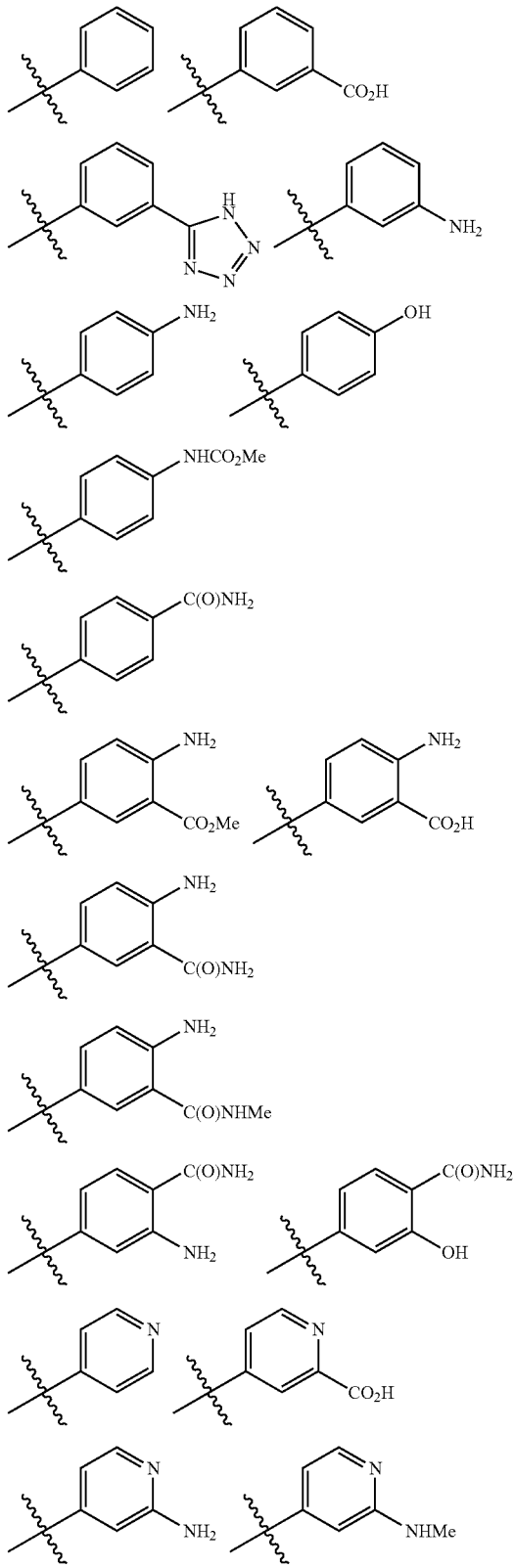

169
-continued
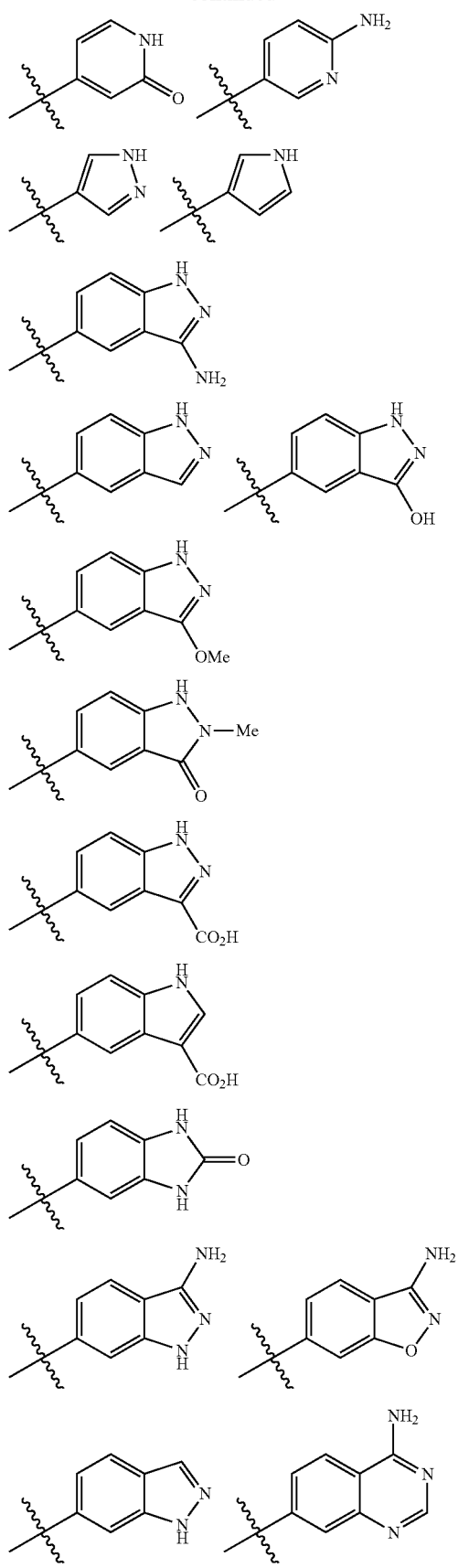
170
-continued
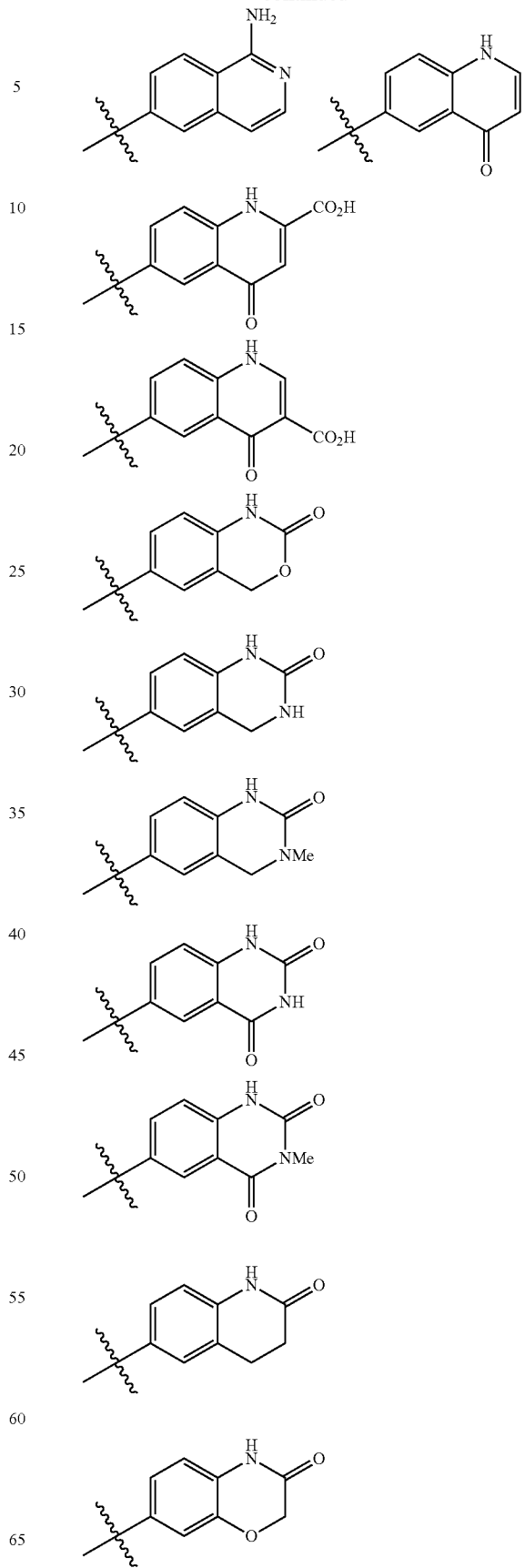

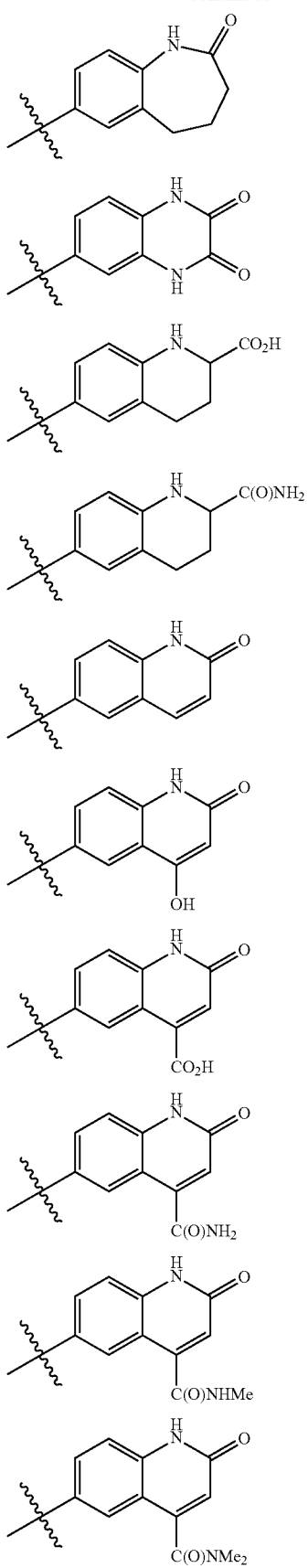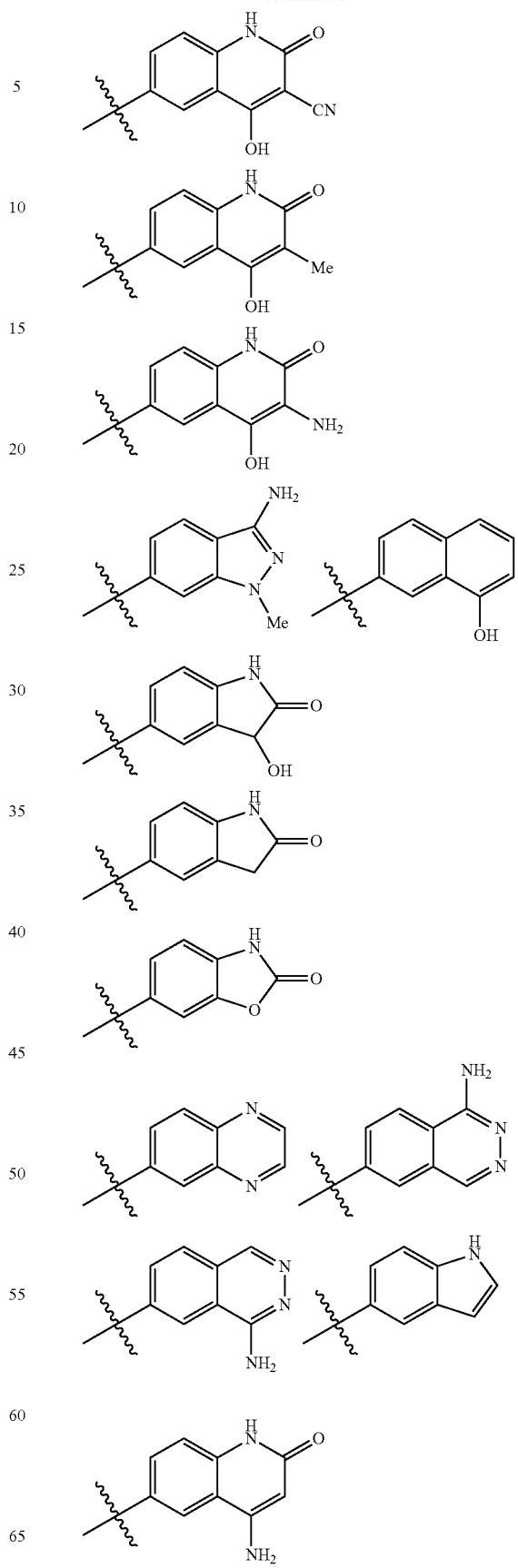

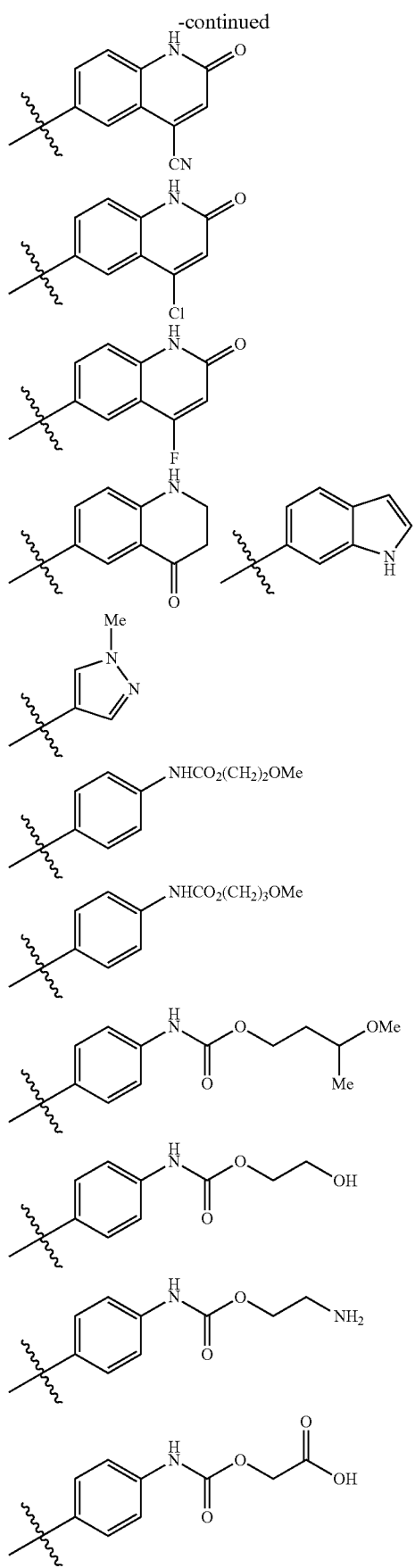
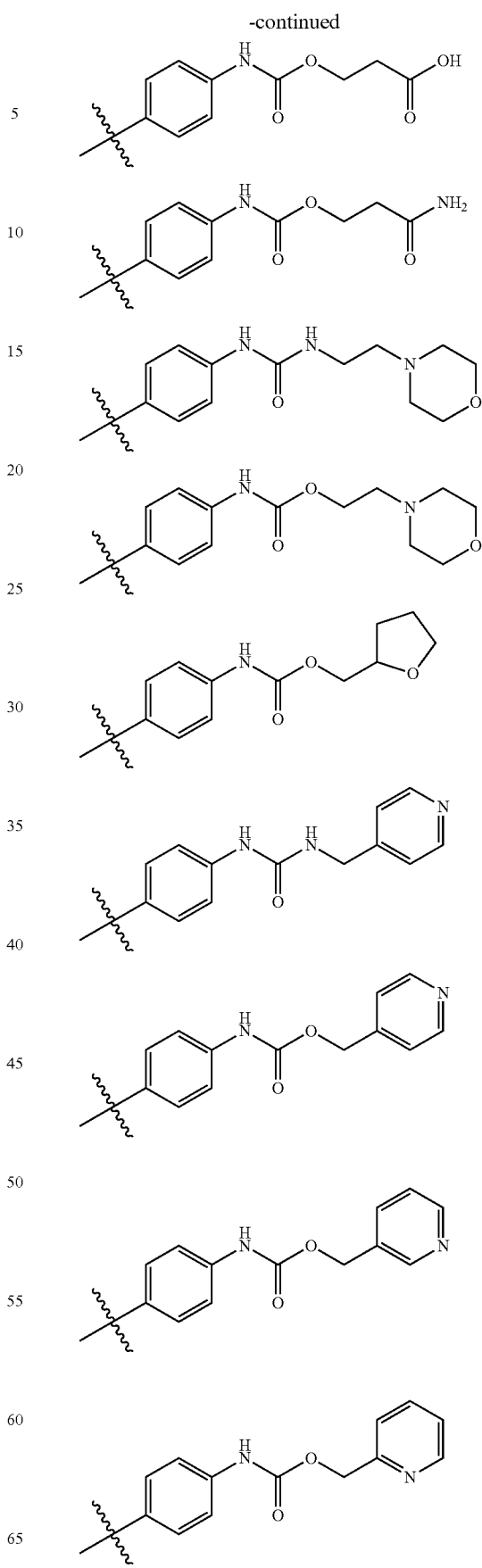

-continued
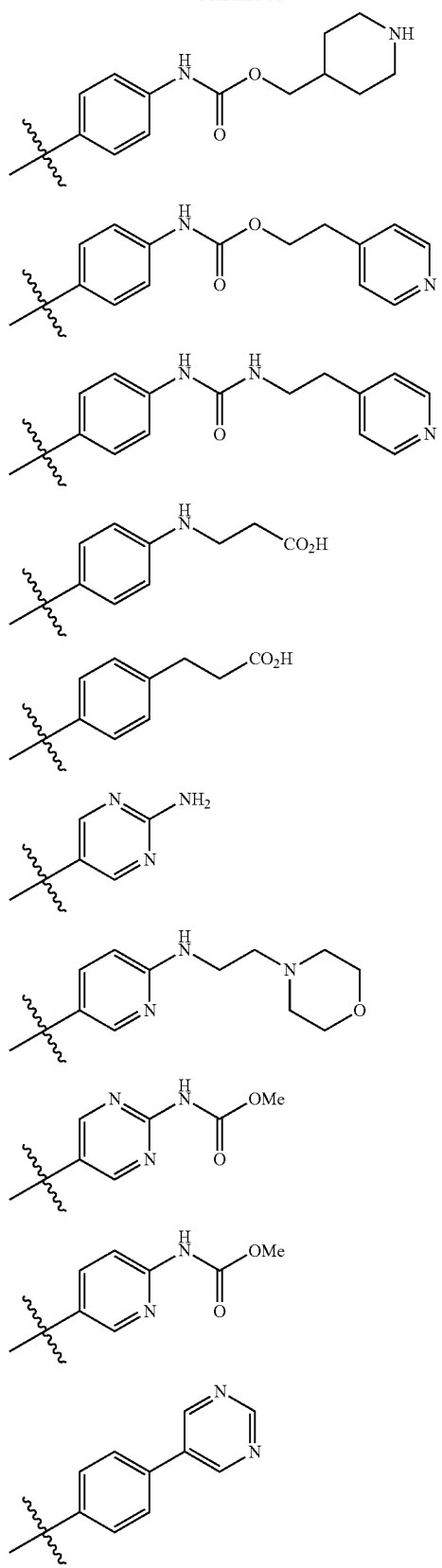
-continued
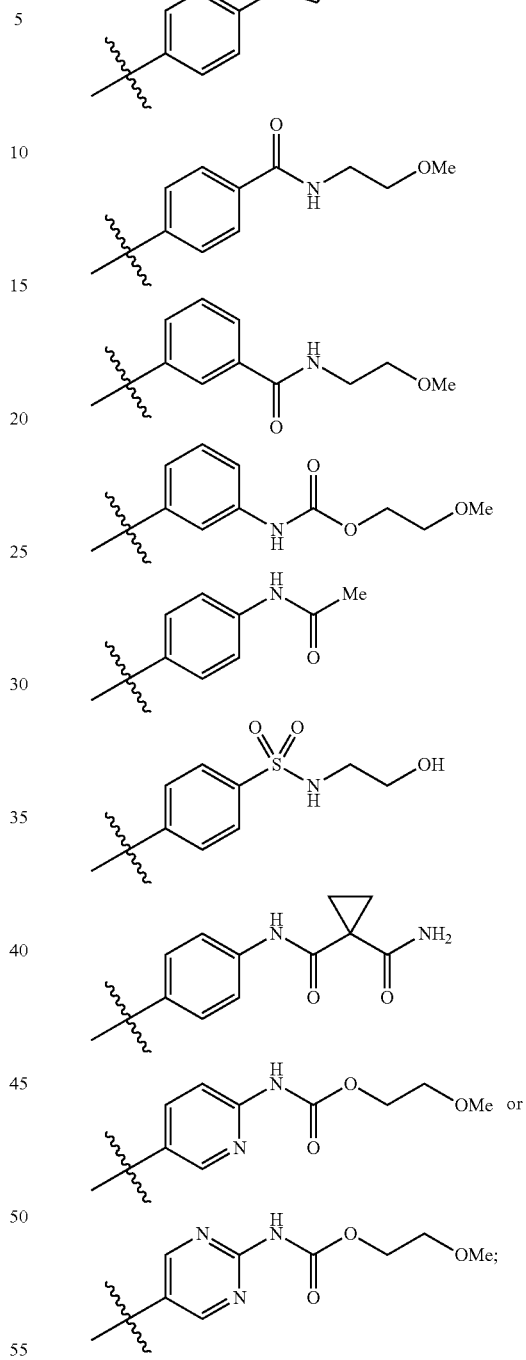
R[4] is, independently at each occurrence, H, Me, or Cl;
R[8] is, independently at each occurrence, H or Me; and
R[11] is H.
15. A pharmaceutical composition, comprising: a pharmaceutically acceptable carrier and a compound of any one of claims 1, or stereoisomers, tautomers, or pharmaceutically acceptable salts thereof.
* * * * *

UNITED STATES PATENT AND TRADEMARK OFFICE
CERTIFICATE OF CORRECTION

PATENT NO.      : 8,410,155 B2
APPLICATION NO. : 12/518111
DATED           : April 2, 2013
INVENTOR(S)     : Donald J. P. Pinto It is certified that error appears in the above-identified patent and that said Letters Patent is hereby corrected as shown below:

On the Title Page:

Item (56), References Cited, under OTHER PUBLICATIONS:

Column 2, Mederski W., et al. reference, line 1, change "*Halothiphene*" to -- *Halothiophene* --.

In the Claims:

Claim 1:

Column 123, line 51, change "–C(=NR$^8$) NR$^8$R$^9$," to -- –C(=NR$^8$)NR$^8$R$^9$, --.

Column 124, line 33, change "haloalkyloxy-," to -- haloalkyloxy, --.

Column 124, line 58, change "–(CH$_2$)$_r$-5" to -- –(CH$_2$)$_r$-5- --.

Column 125, line 10, change "NR$^8$S(O)$_2$R$^c$," to -- –NR$^8$S(O)$_2$R$^c$, --.

Column 125, line 39, change "comprises," to -- comprises: --.

Claim 2:

Column 126, line 61, change "Me" to -- Me, --.

Column 126, line 61, change "T," to -- I, --.

Column 126, line 62, change "OC(O)R$^a$," to -- –C(O)R$^a$, --.

Signed and Sealed this
Twenty-fourth Day of March, 2015

Michelle K. Lee
*Director of the United States Patent and Trademark Office*

In the Claims:

Claim 2 (continued):

Column 126, line 63, change "OC(O)OR$^a$," to -- –C(O)OR$^a$, --.

Claim 3:

Column 127, line 3, change "OCF$_3$," to -- OCH$_3$, --.

Column 127, line 7, change "–NRPC(O)R$^c$," to -- –NR$^8$C(O)R$^c$, --.

Column 127, line 49, change "NHCO$_2$CH$_2$-tetrahydrofuran-" to -- –NHCO$_2$CH$_2$-tetrahydrofuran- --.

Claim 4:

Column 128, line 27, change "C(O)R$^a$," to -- –C(O)R$^a$, --.

Column 128, line 57, change "–NHC$_2$OCH$_2$CH$_2$CH(Me)OMe," to -- –NHCO$_2$CH$_2$CH$_2$CH(Me)OMe, --.

Column 128, lines 61 and 62, change "–NHCO$_2$CH$_2$-piperidin-4-yl)," to -- –NHCO$_2$CH$_2$-(piperidin-4-yl), --.

Column 128, line 62, change "–NHC(O)NH CH$_2$CH$_2$-pyrid-4-yl," to -- –NHC(O)NHCH$_2$CH$_2$-pyrid-4-yl, --.

Claim 5:

Column 129, line 62, change "–CH$_{12}$NH$_{12}$," to -- –CH$_2$NH$_2$, --.

Column 129, line 67, change "–NHCONHME," to -- –NHCONHMe, --.

Column 130, line 20, change "S–" to -- 5- --.

Column 130, line 40, change "4," to -- H, --.

Claim 6:

Column 130, line 52, change "2-N-" to -- 2-(N- --.

Column 130, line 62, change "2-N-" to -- 2-(N- --.

CERTIFICATE OF CORRECTION (continued)

U.S. Pat. No. 8,410,155 B2

In the Claims:

Claim 6 (continued):

Column 131, line 8, change "2-N-(3,4-dimethyl-isoxazol-4-yl)-" to -- 2-(N-(3,4-dimethyl-isoxazol-4-yl)- --.

Column 132, line 12, change "4-amidinophenyl" to -- 4-amidinophenyl, --.

Column 132, lines 12 and 13, change "3-methylcarbonylaminophenyl" to -- 3-methylcarbonylaminophenyl, --.

Claim 8:

Column 150, line 12, change "salts," to -- salts --.

Column 151, line 2, change "O(CH$_2$)$_r$," to -- –(CH$_2$)$_r$ --.

Column 151, line 3, change "–O(=NR$^8$)NR$^8$R$^9$," to -- –C(=NR$^8$)NR$^8$R$^9$, --.

Column 151, line 47, change "–S$_2$NHCOR$^{3c}$," to -- –SO$_2$NHCOR$^{3c}$, --.

Column 151, line 48, change "–CONHSO$_2$R$^3$," to -- –CONHSO$_2$R$^{3c}$, --.

Column 151, line 53, change "C$_{1-4}$ haloalkyloxy-," to -- C$_{1-4}$ haloalkyloxy, --.

Column 151, line 55, change "R$^3$," to -- R$^{3e}$, --.

Column 151, line 67, change "R$^{3d}$," to -- R$^{3d}$; --.

Column 152, line 18, change "NR$^8$S(O)$_2$NR$^8$R$^9$," to -- –NR$^8$S(O)$_2$NR$^8$R$^9$, --.

Column 152, line 20, change "R$^c$," to -- R$^e$, --.

Column 152, line 45, change "NR$^8$C(O)R$^c$," to -- –NR$^8$C(O)R$^c$, --.

Column 152, line 49, change "(CH$_2$)$_r$NR$^8$R$^9$," to -- –(CH$_2$)$_r$NR$^8$R$^9$, --.

Column 152, line 50, change "C$_{1-4}$ allyl;" to -- C$_{1-4}$ alkyl; --.

Column 152, line 53, change "–(CH$_2$)$_n$, –C$_{3-10}$ carbocycle," to -- –(CH$_2$)$_n$–C$_{3-10}$ carbocycle, --.

Claim 9:

Column 153, line 34, change "wherein," to -- wherein: --.

CERTIFICATE OF CORRECTION (continued)
U.S. Pat. No. 8,410,155 B2

In the Claims:

Claim 9 (continued):

Column 153, line 42, change "(CH$_2$)$_r$OH," to -- –(CH$_2$)$_r$OH, --.

Column 153, line 43, change "C(O)R$^a$, C(O)OR$^a$," to -- –C(O)R$^a$, –C(O)OR$^a$, --.

Claim 10:

Column 154, line 19, change "–CH$_2$CMe," to -- –CH$_2$OMe, --.

Column 154, line 30, change "NHCO$_2$CH$_2$CH$_2$CH(Me)OMe," to -- –NHCO$_2$CH$_2$CH$_2$CH(Me)OMe, --.

Claim 11:

Column 155, line 3, change "–SO$_2$CH2–" to -- –SO$_2$CH$_2$– --.

Column 155, lines 41 and 42, change "tetrahydrofuran-$_2$-yl," to -- tetrahydrofuran-2-yl, --.

Column 155, line 56, change "–NHCH$_2$Cl$_2$(N-morpholino)," to -- –NHCH$_2$CH$_2$(N-morpholino), --.

Claim 12:

Column 156, line 50, change "–CH$_{21}$NHCO$_2$(i-Pr)," to -- –CH$_2$NHCO$_2$(i-Pr), --.

Column 156, line 61, change "–CH$_2$NHSO$_2$CH$_2$CH$_{12}$(3-Cl-Ph)," to -- –CH$_2$NHSO$_2$CH$_2$CH$_2$(3-Cl-Ph), --.

Column 157, line 28, change "C$_l$," to -- Cl, --.

Claim 13:

Column 157, line 37, change "2-N-(methoxycarbonyl)-" to -- 2-(N-(methoxycarbonyl)- --.

Column 157, line 47, change "ethoxycarbonyl-ethyl) -ureidomethyl]-" to -- ethoxycarbonyl-ethyl)-ureidomethyl]- --.

Column 158, line 1, change "isoxazol-4-ylsulfonyl)aminomethyl)-5-chlorophenyl, " to -- isoxazol-4-ylsulfonyl)-aminomethyl)-5-chlorophenyl, --.

Column 158, line 4, change "S-chloro-2-fluorophenyl," to -- 5-chloro-2-fluorophenyl, --.

CERTIFICATE OF CORRECTION (continued)
U.S. Pat. No. 8,410,155 B2

In the Claims:

Claim 13 (continued):

Column 159, lines 18 and 19, change "1-benzyl-pyazol-4-yl," to --1-benzyl-pyrazol-4-yl --.

Claim 14:

Column 167, line 66, change "2-fluoro-3-chloro-6-(methylcarbonylphenyl," to -- 2-fluoro-3-chloro-6-(methylcarbonyl)phenyl, --.

Claim 15:

Column 176, line 62, change "claims 1," to -- claims 1-4, --.